US009273102B2

(12) United States Patent
Møller et al.

(10) Patent No.: US 9,273,102 B2
(45) Date of Patent: Mar. 1, 2016

(54) **PEPTIDES DERIVED FROM *CAMPYLOBACTER JEJUNI* AND THEIR USE IN VACCINATION**

(71) Applicants: Niels Iversen Møller, Gilleleje (DK); Andreas Mattsson, København (DK)

(72) Inventors: Niels Iversen Møller, Gilleleje (DK); Andreas Mattsson, København (DK)

( * ) Notice: Subject to any disclaimer, the term of this patent is extended or adjusted under 35 U.S.C. 154(b) by 0 days.

(21) Appl. No.: 14/351,423

(22) PCT Filed: Oct. 12, 2012

(86) PCT No.: PCT/EP2012/070282
§ 371 (c)(1),
(2) Date: Apr. 11, 2014

(87) PCT Pub. No.: WO2013/053899
PCT Pub. Date: Apr. 18, 2013

(65) Prior Publication Data

US 2014/0255416 A1 Sep. 11, 2014

Related U.S. Application Data

(60) Provisional application No. 61/550,494, filed on Oct. 24, 2011.

(30) Foreign Application Priority Data

Oct. 12, 2011 (DK) ................................ 2011 00789

(51) Int. Cl.
*A61K 39/02* (2006.01)
*A61K 39/00* (2006.01)
*A61K 39/38* (2006.01)
*C07K 14/205* (2006.01)

(52) U.S. Cl.
CPC ............... *C07K 14/205* (2013.01); *A61K 39/02* (2013.01); *A61K 39/00* (2013.01)

(58) Field of Classification Search
CPC ... A61K 39/02; A61K 39/0208; A61K 47/00; A61K 49/00; A61K 2039/00; A61K 2039/106
USPC .................. 424/9.1, 9.2, 130.1, 139.1, 141.1, 424/150.1, 184.1, 185.1, 190.1, 192.1, 424/193.1, 197.11, 234.1, 278.1
See application file for complete search history.

(56) References Cited

U.S. PATENT DOCUMENTS 4,684,611 A 8/1987 Schilperoort et al.
4,879,236 A 11/1989 Smith et al.
4,952,500 A 8/1990 Finnerty et al.
5,302,523 A 4/1994 Coffee et al.
5,322,783 A 6/1994 Tomes et al.
5,384,253 A 1/1995 Krzyzek et al.
5,464,765 A 11/1995 Coffee et al.
5,538,877 A 7/1996 Lundquist et al.
5,538,880 A 7/1996 Lundquist et al.
5,550,318 A 8/1996 Adams et al.
5,563,055 A 10/1996 Townsend et al.
5,580,859 A 12/1996 Felgner et al.
5,589,466 A 12/1996 Felgner et al.
5,591,616 A 1/1997 Hiei et al.
5,610,042 A 3/1997 Chang et al.
5,656,610 A 8/1997 Shuler et al.
5,702,932 A 12/1997 Hoy et al.
5,736,524 A 4/1998 Content et al.
5,780,448 A 7/1998 Davis
5,789,215 A 8/1998 Berns et al.
5,843,650 A 12/1998 Segev
5,846,709 A 12/1998 Segev
5,846,783 A 12/1998 Wu et al.
5,849,497 A 12/1998 Steinman
5,849,546 A 12/1998 Sousa et al.
5,849,547 A 12/1998 Cleuziat et al.
5,858,652 A 1/1999 Laffler et al.
5,866,366 A 2/1999 Kallender
5,871,986 A 2/1999 Boyce
5,916,776 A 6/1999 Kumar
5,922,574 A 7/1999 Minter
5,928,905 A 7/1999 Stemmer et al.
5,928,906 A 7/1999 Koster et al.
5,932,451 A 8/1999 Wang et al.
5,935,825 A 8/1999 Nishimura et al.
5,939,291 A 8/1999 Loewy et al.
5,942,391 A 8/1999 Zhang et al.
5,945,100 A 8/1999 Fick
5,981,274 A 11/1999 Tyrrell et al.
5,994,624 A 11/1999 Trolinder et al.

(Continued)

FOREIGN PATENT DOCUMENTS

GB 2202328 9/1998
WO WO9820734 5/1998
WO WO0027205 5/2000

OTHER PUBLICATIONS

Parkhill, J. et al, "The genome sequence of the food-borne pathogen Campylobacter jejuni reveals hypervariable sequences", Nature, International Weekly Journal of Science, U.K., vol. 403, pp. 665-668, XP000906767, (Feb. 10, 2000).
Zhang, M. et al, "Genomic characterization of the Guillain-Barre Syndrome-Associated Campylobacter jejuni ICDCCJ07001 Isolate", Plos One, 5:11:e15060, XP0550,17335. (Jan. 1, 2010).
Strid, M, et al, "Antibody responses to Campylobacter infections determined by an enzyme-linked immunosorbert assay: 2-year follow-up study of 210 patients", Clinical and Diagnostic Laboratory Immunology, vol. 8;2:314-319, (Mar. 2001).
Garenaux, A. et al, "Role of the Cj1371 periplasmic protein and the Cj0355c two-component regulator in the Campylobacter jejuni NCTC 11168 response to oxidative stress caused by paraquat" Research in Microbiology, 159:9-10:718-726, (Nov. 2008).
Wang, Y. et al, "Natural transformation in *Campylobacter* species", Journal of Bacteriology, 72:2:949-955, (Feb. 1990).

(Continued)

*Primary Examiner* — Rodney P Swartz
(74) *Attorney, Agent, or Firm* — McHale & Slavin, P.A.

(57) ABSTRACT

Disclosed are polypeptides for *Campylobacter jejuni* that are useful as immunogenic agents for vaccine use. Also disclosed are nucleic acid fragments encoding the polypeptides as well as compositions, methods and molecular biology tools derived from or related to the proteins.

13 Claims, 3 Drawing Sheets

(56) References Cited

U.S. PATENT DOCUMENTS

Figure 1:
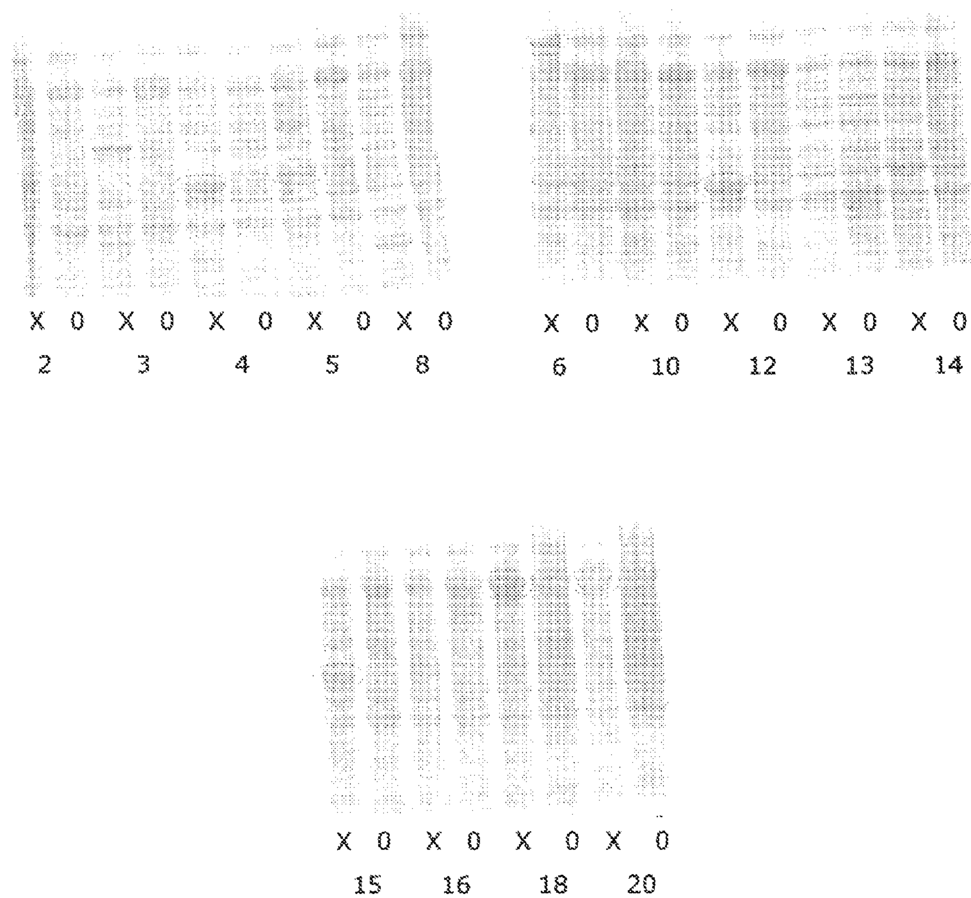

| | | | | |
|---|---|---|---|---|
| 2003/0039996 | A1 | 2/2003 | Dunlop et al. | |
| 2007/0128183 | A1* | 6/2007 | Meinke et al. | 424/130.1 |

OTHER PUBLICATIONS

Blaser, M. et al, "Susceptibility of Campylobacter isolates to the bactericidal activity of human serum", Journal of Infectious Diseases, 151:2-227-235, (Feb. 1985).

Misawa, N. et al, "Detection and characterization of autoagglutination activity by Campylobacter jejuni", Infection and Immunity, 68:11:6168-6175, (Nov. 2000).

Moller, S. et al "Evaluation of methods for the prediction of membrane spanning regions", Bioinformatics, 17:7:646-653, (Mar. 16, 2001).

Juncker, A. et al, "Prediction of lipoprotein signal peptides in Gram-negative bacteria", Protein Science, vol. 12, pp. 1652-1662, (May 19, 2003).

Parrish, J. et al, "High-throughput cloning of Campylobacter jejuni ORFs by in vivo recombination in *Escherchia coli*", Journal of Proteome Research, vol. 3, pp. 582-586. (Mar. 30, 2004).

Nielsen, L. et al, "Identification of immunogenic and virulence-associated Campylobacter jejuni proteins", Clinical and Vaccine Immunology, 19:2:113-119, (Feb. 2012).

* cited by examiner

SEQUENCE LISTING

```
<160> NUMBER OF SEQ ID NOS: 91

<210> SEQ ID NO 1
<211> LENGTH: 51
<212> TYPE: PRT
<213> ORGANISM: Campylobacter jejuni

<400> SEQUENCE: 1

Met Ala Tyr Glu Asp Glu Glu Asp Leu Asn Tyr Asp Asp Tyr Glu Asn
1               5                   10                  15

Glu Asp Glu Glu Tyr Pro Gln Asn His His Lys Asn Tyr Asn Tyr Asp
            20                  25                  30

Asp Asp Asp Tyr Glu Tyr Asp Asp Asp Asn Asn Asp Asp Asp Phe Tyr
        35                  40                  45

Glu Met Asp
    50


<210> SEQ ID NO 2
<211> LENGTH: 65
<212> TYPE: PRT
<213> ORGANISM: Campylobacter jejuni

<400> SEQUENCE: 2

Met Ile Asn Pro Ile Gln Gln Ser Tyr Val Ala Asn Thr Ala Leu Asn
1               5                   10                  15

Thr Asn Arg Ile Asp Lys Glu Thr Lys Thr Asn Asp Thr Gln Lys Thr
            20                  25                  30

Glu Asn Asp Lys Ala Ser Lys Ile Ala Glu Gln Ile Lys Asn Gly Thr
        35                  40                  45

Tyr Lys Ile Asp Thr Lys Ala Thr Ala Ala Ala Ile Ala Asp Ser Leu
```

```
    50                  55                  60

Ile
65


<210> SEQ ID NO 3
<211> LENGTH: 116
<212> TYPE: PRT
<213> ORGANISM: Campylobacter jejuni

<400> SEQUENCE: 3

Met Lys Lys Ile Leu Ile Leu Leu Thr Leu Cys Ala Phe Ala Phe Gly
1               5                   10                  15

Ala Ser Glu Cys Asp Arg Lys Ile Asp Arg Ile Asn Lys Glu Ile Ser
            20                  25                  30

Phe Ser Lys Ala His Asn Asp Thr Ala Arg Thr Leu Ser Leu Glu Leu
        35                  40                  45

Ala Leu Lys Gln Val Gln Asn Asp Cys Ala Lys Asp Pro Met Phe Tyr
    50                  55                  60

Asp Lys Lys Leu Glu Ala Lys Lys Leu Lys Glu Gln Glu Val Glu Lys
65                  70                  75                  80

Ile Glu Lys Glu Leu Asp Ala Leu Lys Glu Gln Lys Asp Tyr Met Ser
                85                  90                  95

Lys Ala Glu Tyr Lys Ala Lys Lys Glu Ala Leu Lys Glu Gln Lys Glu
            100                 105                 110

Lys Ile Lys Lys
        115


<210> SEQ ID NO 4
<211> LENGTH: 138
<212> TYPE: PRT
<213> ORGANISM: Campylobacter jejuni

<400> SEQUENCE: 4

Met Ser Phe Gly Glu Ile Ile Val Ile Leu Val Val Ala Ile Leu Val
1               5                   10                  15

Leu Gly Pro Asp Lys Leu Pro Glu Ala Ile Val Gln Ile Ala Lys Ile
            20                  25                  30

Leu Lys Ala Val Lys Arg Asn Ile Asp Asp Ala Lys Ser Ser Ile Glu
        35                  40                  45

Lys Glu Ile Arg Ile Asn Asp Leu Lys Glu Glu Ala Lys Lys Tyr Lys
    50                  55                  60

Asp Glu Phe Ser Ser Thr Asn Glu Asn Ile Arg Lys Lys Leu Ser Phe
65                  70                  75                  80

Glu Glu Phe Asp Asp Leu Lys Arg Asp Ile Leu Asp Lys Thr Lys Val
                85                  90                  95

Asp Leu Thr Phe Asp Ser Arg Asp Asp Lys Val Lys Asn Asn Leu Ser
            100                 105                 110

Gly Gln Asn Leu Asn Thr Glu Glu Lys Pro Asn Leu Ser Lys Leu Glu
        115                 120                 125

Thr Gln Asp Lys Asn Gly Lys Ile Asn Val
    130                 135


<210> SEQ ID NO 5
<211> LENGTH: 141
<212> TYPE: PRT
<213> ORGANISM: Campylobacter jejuni

<400> SEQUENCE: 5
```

```
Met Gln Lys Ala Lys Ile Leu Ile Ala Leu Ser Phe Phe Leu Leu Val
1               5                   10                  15

Leu Ser Ala Cys Ser Asn Asp Glu Lys Asn Ile Ser Lys Thr Gln Asn
            20                  25                  30

Thr Asp Gln Glu Val Val Gln Ile Glu Gln Asn Asp Glu Lys Thr Glu
        35                  40                  45

Leu Ser Asp Ser Asn Leu Pro Leu Pro Val Asp Asp Glu Ala Gln Ser
    50                  55                  60

Ser Asn Asp Glu His Glu Val Asn Pro Ser Ile Ile Asn Ser Leu Tyr
65                  70                  75                  80

Lys Gln Lys Cys Ala Thr Cys His Gly Glu Lys Gly Glu Leu Lys Pro
                85                  90                  95

Lys Asn Ser Thr Ala Ile Lys Thr Leu Ser Asn Lys Ile Phe Ile Gln
            100                 105                 110

Lys Ile Lys Thr Ile Lys Asp Lys Asn His Ser Phe Leu Ser Asp Glu
        115                 120                 125

Gln Ile Gln Asn Leu Ala Asp Phe Ile Asn Lys Gly Lys
    130                 135                 140


<210> SEQ ID NO 6
<211> LENGTH: 144
<212> TYPE: PRT
<213> ORGANISM: Campylobacter jejuni

<400> SEQUENCE: 6

Met Arg Arg Leu Ser Ile Leu Leu Ala Ile Leu Ile Val Ile Asn Ile
1               5                   10                  15

Thr Ala Cys Asp Ser Lys Thr Glu Asn Tyr Tyr Lys Asn Leu Pro Ser
            20                  25                  30

Glu Ala Lys Glu Lys Ala Lys Glu Cys Lys Glu Ser Gly Thr Leu Ser
        35                  40                  45

Glu Asp Cys Ile Asn Ala Leu Lys Val Gly Val Lys Pro Thr Asn Glu
    50                  55                  60

Glu Gly Lys Tyr Ser Pro Asn Thr Pro Lys Lys Ser Asp Asn Gln Ile
65                  70                  75                  80

Leu Glu Ala Leu Lys Gln Asn Asp Leu Lys Lys Glu Lys Thr Thr Lys
                85                  90                  95

Asp Ile Asn Gln Ser Ser Glu Asn Asn Glu Ser Ile Ile Ile Pro Pro
            100                 105                 110

Ile Ala Glu Thr Pro Ser Glu Ile Tyr Pro Ser Lys Thr Thr Glu Asn
        115                 120                 125

Asn Gln Ser Ser Ile Phe Ser Asp Asp Val Asn Met Thr Gln Glu Lys
    130                 135                 140


<210> SEQ ID NO 7
<211> LENGTH: 174
<212> TYPE: PRT
<213> ORGANISM: Campylobacter jejuni

<400> SEQUENCE: 7

Met Met Lys Lys Lys Leu Val Leu Leu Gly Ser Ala Ala Val Val Phe
1               5                   10                  15

Phe Ala Ala Cys Ala Met Asn Ser Gly Val Ser Ser Glu Gln Ile Gly
            20                  25                  30

Leu Arg Lys Ala Ser Leu Glu Asn Glu Asn Lys Val Asn Leu Val Glu
        35                  40                  45
```

```
Ala Asn Phe Thr Thr Leu Gln Pro Gly Glu Ser Thr Arg Phe Glu Arg
    50                  55                  60

Ser Tyr Glu Asn Ala Pro Pro Leu Ile Pro His Ala Ile Glu Asp Leu
65                  70                  75                  80

Leu Pro Ile Thr Lys Asp Asn Asn Met Cys Leu Ser Cys His Asp Lys
                85                  90                  95

Ala Ile Ala Ala Asp Ala Gly Ala Thr Pro Leu Pro Ala Ser His Tyr
            100                 105                 110

Tyr Asp Phe Arg His Asn Lys Thr Thr Gly Asp Met Ile Ser Asp Ser
        115                 120                 125

Arg Phe Asn Cys Thr Gln Cys His Val Pro Gln Ser Asp Ala Lys Pro
    130                 135                 140

Leu Val Gly Asn Ser Phe Lys Pro Glu Phe Lys Asn Glu Gln Leu Lys
145                 150                 155                 160

Ser Arg Ser Asn Leu Ile Asp Val Ile Asn Glu Gly Val Lys
                165                 170


<210> SEQ ID NO 8
<211> LENGTH: 201
<212> TYPE: PRT
<213> ORGANISM: Campylobacter jejuni

<400> SEQUENCE: 8

Met Lys Lys Ile Lys Lys Ile Ile Gln Ile Gly Met Ile Gly Gly Leu
1               5                   10                  15

Ala Ala Val Ala Gly Gly Ala Leu Ala Gly Cys Gly Ser Asn Asn Asp
            20                  25                  30

Asn Ala Asp Thr Leu Asn Gln Ala Ala Asn Ala Gln Gly Ala Phe Val
        35                  40                  45

Ile Ile Glu Glu Thr Ala Pro Gly Gln Tyr Lys Ile Lys Asp Gln Tyr
    50                  55                  60

Pro Ser Asp Glu Thr Arg Val Val Leu Lys Asp Leu Asn Gly Thr Glu
65                  70                  75                  80

Arg Ile Leu Ser Lys Glu Glu Met Asp Ala Leu Ile Lys Glu Glu Ala
                85                  90                  95

Ala Lys Ile Asp Asn Gly Thr Ser Asn Leu Thr Lys Asp Asn Gly Gln
            100                 105                 110

Ile Ser Ser Gly Gly Leu Ser Leu Gly Glu Thr Leu Leu Ala Ser Ala
        115                 120                 125

Ala Gly Ala Ile Leu Gly Ser Trp Ile Gly Ser Lys Leu Phe Asn Asn
    130                 135                 140

Gln Asn Phe Ala Asn Gln Gln Arg Gly Ala Phe Ser Asn Gln Ser Ala
145                 150                 155                 160

Tyr Gln Arg Ser Val Asn Ser Phe Asn Lys Ala Gly Thr Thr Ser Ser
                165                 170                 175

Ala Ser Ser Ala Lys Lys Ser Gly Phe Phe Gly Gly Gly Ser Lys Ala
            180                 185                 190

Thr Ser Ser Ser Ser Ser Phe Gly Ser
        195                 200


<210> SEQ ID NO 9
<211> LENGTH: 210
<212> TYPE: PRT
<213> ORGANISM: Campylobacter jejuni

<400> SEQUENCE: 9
```

```
Met Thr Lys Phe Leu Ser Ile Cys Ser Leu Ile Ala Met Leu Leu Ser
1               5                   10                  15

Gly Cys Gly Ser Asp Phe Pro Gly Gln Pro Ser Asp Val Ala Arg Val
            20                  25                  30

Gln Gln Asn Lys Tyr Pro Asn Gly Asn Leu Lys Lys Glu Ile Pro Tyr
        35                  40                  45

Asn Lys Asp Ser Arg Ile His Gly Leu Lys Arg Ala Phe Tyr Asp Asn
    50                  55                  60

Gly Gln Leu Arg Ala Glu Glu Asn Tyr Lys Asn Gly Lys Lys Asp Gly
65                  70                  75                  80

Ile Ser Arg Glu Tyr Ser Arg Asn Gly Gln Leu Leu Glu Glu Val His
                85                  90                  95

Phe Lys Asp Asn Arg Gly Tyr Gly Asp Phe Ala Ser Tyr Tyr Glu Asn
            100                 105                 110

Gly Asn Met Arg Ala Lys Gly Lys Leu Leu Gly Tyr Asn Glu Asp Gly
        115                 120                 125

Met Pro Glu Phe Glu Gly Asn Tyr Lys Glu Tyr Tyr Glu Asn Gly Thr
    130                 135                 140

Leu Met Cys Asp Tyr Asn Phe Asp Asn Lys Gly Lys Phe Asp Gly Val
145                 150                 155                 160

Gln Lys Arg Tyr Asp Glu Asn Gly Ala Leu Glu Asp Glu Glu Asn Tyr
                165                 170                 175

Lys Asn Gly Leu Lys Asn Gly Val Phe Arg Glu Tyr Lys Lys Gly Glu
            180                 185                 190

Ile Val Arg Glu Glu Glu Tyr Lys Asn Gly Ile Leu Val Ala Lys Pro
        195                 200                 205

Lys Asn
    210


<210> SEQ ID NO 10
<211> LENGTH: 244
<212> TYPE: PRT
<213> ORGANISM: Campylobacter jejuni

<400> SEQUENCE: 10

Met Lys Lys Ile Phe Leu Ser Val Phe Leu Val Leu Ser Leu Asn Ala
1               5                   10                  15

Gln Asn Leu Glu Ile Asp Lys Ile Arg Thr Asp Leu Tyr Ser Lys Ser
            20                  25                  30

Gly Ala Asn Val Leu Lys Lys Val Glu Ile Ser Leu Glu Phe Asp Gly
        35                  40                  45

Asn Asn Leu Lys Glu Asn Glu Asn Lys Leu Ile Asp Ala Val Asn Thr
    50                  55                  60

Val Ile Ser Gly Phe Phe Tyr Glu Asp Ile Phe Thr Glu Ile Gly Lys
65                  70                  75                  80

Asn Asn Phe Lys Lys Thr Leu Glu Lys Phe Leu Asp Lys Lys Tyr Lys
                85                  90                  95

Ile Lys Leu Asp Asp Ile Tyr Ile Ile Ser Leu Ser Gly Val Glu Lys
            100                 105                 110

Phe Asp Leu Glu Glu Phe Lys Arg Phe Leu Glu Ser Thr Glu Ala Lys
        115                 120                 125

Glu Lys Gly Met Gly Ser Glu Val Lys Lys Ala Leu Glu Asn Leu Glu
    130                 135                 140

Val Pro Lys Thr Gln Val Pro Ser Val Glu Lys Ile Pro Thr Pro Ser
```

```
145                 150                 155                 160

Val Pro Asn Leu Glu Val Lys Gln Val Glu Gln Leu Phe Lys Asp Pro
                165                 170                 175

Asp Glu Glu Asn Lys Asn Asp Asn Gly Glu Ile Asn Ile Asp Asn Leu
            180                 185                 190

Asn Thr Pro Lys Met Thr Pro Asp Ile Glu Glu Lys Ile Lys Arg Asp
        195                 200                 205

Leu Ile Ala Asn Pro Pro Gln Ile Phe Lys Glu Asn Asn Ala Ser Lys
    210                 215                 220

Pro Tyr His Leu Pro Gln Thr Gly Tyr Asp Ile Lys Leu Asp Glu Asn
225                 230                 235                 240

Ser Thr Gln Asn


<210> SEQ ID NO 11
<211> LENGTH: 259
<212> TYPE: PRT
<213> ORGANISM: Campylobacter jejuni

<400> SEQUENCE: 11

Met Lys Asn Tyr Gly Leu Ser Asn Leu Asn Ser Phe Leu Leu Ala Leu
1               5                   10                  15

Ala Ile Tyr Ile Ser Ile Val Ile Leu Val Phe Phe Arg Leu Val Ser
            20                  25                  30

Glu Val Glu Pro Ala Ile Gln Tyr Thr Asp Ile Lys Asp Ser Phe Val
        35                  40                  45

Asp Ile Glu Leu Ala Glu Pro Ser Lys Gln Val Ile Thr Gln Ser Asn
    50                  55                  60

Thr Pro Lys Glu Ile Gln Lys Pro Thr Glu Gln Ile Asp Ile Glu Lys
65                  70                  75                  80

Leu Phe Ala Gln Thr Thr Asn Lys Thr Val Lys Thr Glu Asp Ile Asp
                85                  90                  95

Gln Lys Ala Ser Asn Phe Asn Glu Leu Phe Gly Asn Ile Lys Glu Ile
            100                 105                 110

Gln Glu Glu Lys Thr Thr Lys Ile Gln Ser Ser Ala Lys Ser Gly Ile
        115                 120                 125

Ser Ser Ala Pro Lys Pro Gln Ala Ser Glu Leu Val Lys Gln Leu Asn
    130                 135                 140

Asp Ser Leu Leu Gln Glu Glu Ser Ser Thr Gln Gly Glu Ser Thr Lys
145                 150                 155                 160

Ala Gln Lys Ile Gly Ile Tyr Asp Glu Phe Leu Gly Lys Val Val Arg
                165                 170                 175

Ile Ile Thr Gln Arg Trp Thr Gln Tyr Tyr Pro Asn Ser Glu Lys Ile
            180                 185                 190

Ser Val Lys Val Lys Ile Phe Ile Asp Glu Asn Gly Lys Phe Gly Tyr
        195                 200                 205

Thr Ser Val Glu Lys Ser Gly Asn Pro Leu Tyr Asp Ala Lys Val Ala
    210                 215                 220

Glu Phe Leu Glu Ser Gln Lys Gly Lys Phe Ile Thr Tyr Pro Pro Gln
225                 230                 235                 240

Asn Lys Asn Ile Ser Ile Thr Met Asn Leu Arg Asp Glu Val Lys Val
                245                 250                 255

Lys Asn Asp


<210> SEQ ID NO 12
```

<211> LENGTH: 273
<212> TYPE: PRT
<213> ORGANISM: Campylobacter jejuni

<400> SEQUENCE: 12

```
Met Lys Lys Phe Ser Leu Val Ala Ala Thr Leu Ile Ala Gly Val Val
1               5                   10                  15

Leu Asn Val Asn Ala Ala Thr Val Ala Thr Val Asn Gly Lys Ser Ile
            20                  25                  30

Ser Asp Thr Glu Val Ser Glu Phe Phe Ala Pro Met Leu Arg Gly Gln
        35                  40                  45

Asp Phe Lys Thr Leu Pro Asp Asn Gln Lys Lys Ala Leu Ile Gln Gln
    50                  55                  60

Tyr Ile Met Gln Asp Leu Ile Leu Gln Asp Ala Lys Lys Gln Asn Leu
65                  70                  75                  80

Glu Lys Asp Pro Leu Tyr Thr Lys Glu Leu Asp Arg Ala Lys Asp Ala
                85                  90                  95

Ile Leu Val Asn Val Tyr Gln Glu Lys Ile Leu Asn Thr Ile Lys Ile
            100                 105                 110

Asp Ala Ala Lys Val Lys Ala Phe Tyr Asp Gln Asn Lys Asp Lys Tyr
        115                 120                 125

Val Lys Pro Ala Arg Val Gln Ala Lys His Ile Leu Val Ala Thr Glu
    130                 135                 140

Lys Glu Ala Lys Asp Ile Ile Asn Glu Leu Lys Gly Leu Lys Gly Lys
145                 150                 155                 160

Glu Leu Asp Ala Lys Phe Ser Glu Leu Ala Lys Glu Lys Ser Ile Asp
                165                 170                 175

Pro Gly Ser Lys Asn Gln Gly Gly Glu Leu Gly Trp Phe Asp Gln Ser
            180                 185                 190

Thr Met Val Lys Pro Phe Thr Asp Ala Ala Phe Ala Leu Lys Asn Gly
        195                 200                 205

Thr Ile Thr Thr Thr Pro Val Lys Thr Asn Phe Gly Tyr His Val Ile
    210                 215                 220

Leu Lys Glu Asn Ser Gln Ala Lys Gly Gln Ile Lys Phe Asp Glu Val
225                 230                 235                 240

Lys Gln Gly Ile Glu Asn Gly Leu Lys Phe Glu Glu Phe Lys Lys Val
                245                 250                 255

Ile Asn Gln Lys Gly Gln Asp Leu Leu Asn Ser Ala Lys Val Glu Tyr
            260                 265                 270

Lys
```

<210> SEQ ID NO 13
<211> LENGTH: 278
<212> TYPE: PRT
<213> ORGANISM: Campylobacter jejuni

<400> SEQUENCE: 13

```
Met Glu Asn Gln Lys Asn Glu Phe Asp Asp Ile Ile Leu Glu Lys Ser
1               5                   10                  15

Asn Lys Ser Glu Lys Val Lys Lys Ile Leu Leu Arg Val Ile Ala Leu
            20                  25                  30

Val Ile Leu Phe Leu Ala Ile Met Ile Val Met Lys Leu Ile Asn Gly
        35                  40                  45

Ser Gly Asp Glu Asn Thr Gln Asn Gln Ser Val Leu Pro Ser Glu Pro
    50                  55                  60
```

```
Ile Ala Thr Gln Asp Asn Asn Asn Asp Thr Ser Phe Glu Ser Met Pro
65                  70                  75                  80

Ile Thr Asp Asn Thr Ser Ala Glu Asp Gln Phe Glu Ala Leu Arg Lys
                85                  90                  95

Gln Phe Gln Asp Glu Gln Asn Thr Thr Gln Asn Thr Thr Thr Ser Ser
            100                 105                 110

Ser Asn Asn Asn Asp Thr Thr Asn Phe Ala Met Pro Asp Gln Glu Val
        115                 120                 125

Pro Ala Glu Pro Thr Ala Thr Thr Ser Ala Asn Thr Thr Pro Gln Ala
    130                 135                 140

Ser Thr Pro Lys Gln Glu Val Thr Gln Thr Ala Lys Ser Lys Glu Glu
145                 150                 155                 160

Ala Lys Lys Gln Thr Ala Val Lys Lys Glu Lys Glu Ser Ala Lys Gln
                165                 170                 175

Thr Pro Lys Lys Glu Gln Asn Ala Asn Asp Leu Phe Lys Asn Val Asp
            180                 185                 190

Ala Lys Pro Val His Pro Ser Gly Leu Ala Ser Gly Ile Tyr Val Gln
        195                 200                 205

Ile Phe Ser Val Ser Asn Leu Asp Gln Lys Ser Lys Glu Leu Ala Ser
    210                 215                 220

Val Lys Gln Lys Gly Tyr Asp Tyr Lys Leu Tyr Lys Thr Thr Val Gly
225                 230                 235                 240

Ser Lys Glu Ile Thr Lys Val Leu Ile Gly Pro Phe Glu Lys Ala Asp
                245                 250                 255

Ile Ala Ala Glu Leu Ala Lys Ile Arg Lys Asp Ile Ala Lys Asp Ala
            260                 265                 270

Phe Ser Phe Thr Leu Lys
        275


<210> SEQ ID NO 14
<211> LENGTH: 390
<212> TYPE: PRT
<213> ORGANISM: Campylobacter jejuni

<400> SEQUENCE: 14

Met Lys Lys Lys Ile Val Leu Ile Ile Leu Ile Ala Ile Leu Gly Ser
1               5                   10                  15

Val Gly Ala Tyr Phe Ile Phe Phe Asn Asn Asp Glu Lys Ile Ser Tyr
            20                  25                  30

Leu Thr Gln Lys Ile Gln Lys Lys Asp Ile Ser Gln Thr Ile Glu Ala
        35                  40                  45

Val Gly Lys Val Tyr Ala Lys Asp Gln Val Asp Val Gly Ala Gln Val
    50                  55                  60

Ser Gly Gln Ile Ile Lys Leu Tyr Val Asp Val Gly Thr His Val Lys
65                  70                  75                  80

Gln Gly Asp Leu Ile Ala Gln Ile Asp Lys Asp Lys Gln Gln Asn Asp
                85                  90                  95

Leu Asp Ile Thr Lys Ala Gln Leu Glu Ser Ala Lys Ala Asn Leu Glu
            100                 105                 110

Ser Lys Lys Val Ala Leu Glu Ile Ala Asn Lys Gln Tyr Gln Arg Glu
        115                 120                 125

Gln Lys Leu Tyr Ala Ala Lys Ala Ser Ser Leu Glu Asn Leu Glu Thr
    130                 135                 140

Gln Lys Asn Asn Tyr Tyr Thr Leu Lys Ala Asn Val Ala Glu Leu Asn
145                 150                 155                 160
```

```
Ala Gln Val Val Gln Leu Glu Ile Thr Leu Lys Asn Ala Gln Lys Asp
                165                 170                 175

Leu Gly Tyr Thr Thr Ile Thr Ala Pro Met Asp Gly Val Val Ile Asn
            180                 185                 190

Val Ala Val Asp Glu Gly Gln Thr Val Asn Ala Asn Gln Asn Thr Pro
        195                 200                 205

Thr Ile Val Arg Ile Ala Asn Leu Asp Glu Met Glu Val Arg Met Glu
    210                 215                 220

Ile Ala Glu Ala Asp Val Ser Lys Ile Lys Val Gly Thr Glu Leu Asp
225                 230                 235                 240

Phe Ser Leu Leu Asn Asp Pro Gln Lys Thr Tyr His Ala Lys Ile Ala
                245                 250                 255

Ser Ile Asp Pro Ala Asp Thr Glu Val Ser Asp Ser Ser Thr Ser Ser
            260                 265                 270

Ser Ser Ser Ser Ser Ser Ser Ser Ser Ser Ser Ser Ser Asn Ala Ile
        275                 280                 285

Tyr Tyr Tyr Ala Lys Phe Tyr Val Ala Asn Lys Asp Asp Phe Leu Arg
    290                 295                 300

Ile Gly Met Ser Ile Gln Asn Glu Ile Val Val Ala Ser Ala Lys Ala
305                 310                 315                 320

Val Leu Ala Val Pro Thr Tyr Ala Ile Lys Ser Asp Pro Lys Gly Tyr
                325                 330                 335

Tyr Val Glu Ile Leu Glu Asn Gln Lys Ala Val Lys Lys Tyr Val Lys
            340                 345                 350

Leu Gly Ile Lys Asp Ser Ile Asn Thr Gln Ile Leu Glu Gly Val Asn
        355                 360                 365

Glu Asp Glu Glu Leu Ile Val Ser Ser Ser Ala Asp Gly Leu Ala Pro
    370                 375                 380

Lys Met Lys Leu Arg Phe
385                 390


<210> SEQ ID NO 15
<211> LENGTH: 542
<212> TYPE: PRT
<213> ORGANISM: Campylobacter jejuni

<400> SEQUENCE: 15

Met Lys Ile Leu Leu Leu Asn Glu Asn Pro Val Val Ser Arg Leu Val
1               5                   10                  15

Ser Leu Ser Ala Lys Lys Met Ser Tyr Asp Phe Glu Glu Leu Asn Ala
            20                  25                  30

Tyr Ser Glu Asn Leu Gly Asn Tyr Asp Val Ile Val Val Asp Ser Asp
        35                  40                  45

Thr Pro Ala Pro Leu Lys Ile Leu Lys Glu Lys Cys Asp Arg Leu Ile
    50                  55                  60

Phe Leu Ala Pro Arg Asn Gln Asn Val Glu Asp Ile Asp Ala Gln Ile
65                  70                  75                  80

Leu Gln Lys Pro Phe Leu Pro Thr Asp Phe Leu Asn Leu Leu Asn Asn
                85                  90                  95

Lys Asp Ala Asn Lys His Thr Ser Ile Asp Leu Pro Met Leu Ser Asn
            100                 105                 110

Asp Glu Asn Pro Tyr Ala Asp Ile Ser Leu Asp Leu Asp Asn Leu Asn
        115                 120                 125

Leu Asp Asp Leu Pro Asp Glu Asn Ser Leu Asp Ile Asn Ser Glu Gly
```

```
    130                 135                 140

Met Glu Asp Leu Ser Phe Asp Asp Asp Ala Gln Asp Asp Asn Ala Asn
145                 150                 155                 160

Lys Thr Leu Glu Thr Gln Asn Leu Glu His Glu Thr Ile Lys Glu Gln
                165                 170                 175

Thr Gln Glu Asp Thr Gln Ile Asp Leu Asp Leu Thr Leu Glu Asp Gly
            180                 185                 190

Glu Ser Glu Lys Glu Asp Leu Ser Gln Glu His Thr Ala Leu Asp Thr
        195                 200                 205

Glu Pro Ser Leu Asp Glu Leu Asp Asp Lys Asn Asp Glu Asp Leu Glu
    210                 215                 220

Ile Lys Glu Asp Asp Lys Asn Glu Glu Ile Glu Lys Gln Glu Leu Leu
225                 230                 235                 240

Asp Asp Ser Lys Thr Asn Thr Leu Glu Met Gln Glu Glu Leu Ser Glu
                245                 250                 255

Ser Gln Asp Asp Asn Ser Asn Lys Thr Leu Glu Thr Gln Asn Leu Glu
            260                 265                 270

His Asp Asn Leu Glu Gln Glu Thr Ile Lys Glu Gln Thr Gln Glu Asp
        275                 280                 285

Thr Gln Ile Asp Leu Asp Leu Thr Leu Glu Asp Gly Glu Ser Glu Lys
    290                 295                 300

Glu Asp Leu Ser Gln Glu His Thr Ala Leu Asp Thr Glu Pro Ser Leu
305                 310                 315                 320

Asp Glu Leu Asp Asp Lys Asn Asp Glu Asp Leu Glu Asp Asn Lys Glu
                325                 330                 335

Leu Gln Ala Asn Ile Ser Asp Phe Asp Asp Leu Pro Glu Val Glu Glu
            340                 345                 350

Gln Glu Lys Glu Met Asp Phe Asp Asp Leu Pro Glu Asp Ala Glu Phe
        355                 360                 365

Leu Gly Gln Ala Lys Tyr Asn Glu Glu Ser Glu Glu Asn Leu Glu Glu
    370                 375                 380

Phe Ala Pro Val Val Glu Glu Asp Ile Gln Asp Glu Ile Asp Asp Phe
385                 390                 395                 400

Ala Ser Asn Leu Ser Thr Gln Asp Gln Ile Lys Glu Glu Leu Ala Gln
                405                 410                 415

Leu Asp Glu Leu Asp Tyr Gly Ile Asp Ser Asp Asn Ser Ser Lys Val
            420                 425                 430

Leu Glu Asp Phe Lys Asp Glu Pro Ile Leu Asp Asp Lys Glu Leu Gly
        435                 440                 445

Thr Asn Glu Glu Glu Val Val Val Pro Asn Leu Asn Ile Ser Asp Phe
    450                 455                 460

Asp Thr Leu Lys Glu Ser Asp Ile Gln Glu Ala Leu Gly Glu Glu Ile
465                 470                 475                 480

Leu Glu Lys Asn Glu Glu Pro Ile Val Ser Asp Val Thr Lys Asp Asp
                485                 490                 495

Asn Ser Glu Glu Ile Val Asn Glu Leu Ser Gln Ser Ile Ala Gly Ala
            500                 505                 510

Ile Thr Ser Ser Ile Lys Asp Asp Thr Leu Lys Ala Ala Leu Lys Gly
        515                 520                 525

Met Asn Met Asn Ile Asn Ile Asn Ile Ser Phe Lys Glu Asp
    530                 535                 540
```

<210> SEQ ID NO 16

```
<211> LENGTH: 610
<212> TYPE: PRT
<213> ORGANISM: Campylobacter jejuni

<400> SEQUENCE: 16

Met Lys Lys Asn Ile Leu Arg Leu Gly Ile Val Val Leu Val Leu Leu
1               5                   10                  15

Ile Ala Gly Val Leu Trp Leu Asn Asn Asp Ile Asn Gln Lys Lys Glu
            20                  25                  30

Asp Glu Ala Asn Lys Asn Ala Ile Ala Ala Asn Ala Asp Phe Ser Leu
        35                  40                  45

Leu Ser Asp Asp Asp Pro Asn Phe Glu Lys Trp Gly Lys Val Phe Pro
    50                  55                  60

Glu Gln Leu Lys Met Tyr Leu Thr Val Glu Lys Glu Glu Pro Lys Ala
65                  70                  75                  80

Thr Glu Phe Gly Gly Asn Leu Ala Tyr Ser Lys Leu Ile Arg Phe Pro
                85                  90                  95

Gln Leu Thr Ile Leu Trp Ala Gly Tyr Pro Phe Ser Leu Asp Phe Asn
            100                 105                 110

Glu Glu Arg Gly His Phe Trp Val Gln Val Asp Gln Met Lys Thr Ala
        115                 120                 125

Arg Asn Asn Lys Asp Phe Leu Asn Ala His Gly Leu Ala Ala Phe Lys
    130                 135                 140

Gly Gln Pro Ala Ala Cys Met Asn Cys His Ser Gly Trp Thr Pro Trp
145                 150                 155                 160

Leu Ile Lys Asn Val Ala Lys Gly Asp Phe Thr Ala Phe Asn Ser Thr
                165                 170                 175

Asn Tyr Trp Thr Met Ile Lys Asn Ile Pro Ala Val Asp Gly Ile Val
            180                 185                 190

Glu Asn Ser Pro Glu His Ala Gly Pro His Gly Gly Lys Arg Met Gly
        195                 200                 205

Val Thr Cys Ala Asp Cys His Asn Pro Asn Asp Met Ser Leu Arg Leu
    210                 215                 220

Thr Arg Pro Ala Ala Ile Asn Ala Leu Val Ser Arg Gly Tyr Glu Lys
225                 230                 235                 240

Asp Pro Val Gln Gly Val Lys Ala Thr Arg Glu Glu Met Arg Thr Leu
                245                 250                 255

Val Cys Ser Gln Cys His Val Glu Tyr Tyr Phe Lys Pro Thr Gly Glu
            260                 265                 270

Lys Val Lys Val Met Gly Glu Thr Ile Val Asp Asp Ser Ser Lys Lys
        275                 280                 285

Trp Trp Asn Gly Thr Gln Lys Asn Tyr Asp Glu Tyr Glu Phe Trp Arg
    290                 295                 300

Asp Gly Asn Lys Val Lys Glu Ile Glu Thr Asp Gly Ile Val Leu Thr
305                 310                 315                 320

Phe Pro Trp Ser Glu Trp Lys Lys Gly Gln Pro Phe Arg Ile Glu Met
                325                 330                 335

Leu Asp Asp Tyr Tyr Asp Lys Val Arg Gly Val Phe Gly Ala Asp Phe
            340                 345                 350

Thr His Lys Leu Thr Gly Ala Gln Ile Ile Lys Ile Gln His Pro Glu
        355                 360                 365

Ser Glu Leu Tyr Ser Gly Gly Val His Ala Ala Asn Gly Val Ser Cys
    370                 375                 380

Val Asp Cys His Met Pro Tyr Val Arg Glu Gly Ala Lys Lys Val Thr
```

```
385                 390                 395                 400

Gln His Asn Ile Thr Ser Pro Leu Arg Asp Ile Asn Ser Ala Cys Lys
                405                 410                 415

Ser Cys His Lys Gln Ser Glu Asp Tyr Leu Lys Ala Gln Val Leu Asp
            420                 425                 430

Ile Gln Asn Ser Val Ala His Asp Gln Arg Thr Ala Glu Tyr Ala Ile
        435                 440                 445

Val Ser Leu Ile Met Asp Thr Lys Lys Leu Arg Asp Glu Leu Gly Asn
    450                 455                 460

Met Glu Lys Phe Gln Ser Asp Gly Lys Ala Asp Ala Lys Lys Ile Ser
465                 470                 475                 480

Glu Glu Leu Lys Glu Val Leu Glu Leu His Arg Lys Ala Gln Met Arg
                485                 490                 495

Ala Asp Phe Val Asn Ala Glu Asn Ser Thr Gly Phe His Asn Pro Arg
            500                 505                 510

Glu Ala Ser Arg Met Leu Leu Gln Ala Val Asp Met Ala Arg Met Gly
        515                 520                 525

Gln Thr Lys Leu Val Glu Ile Ala Ala Ala Asn Gly Ile Lys Asp Phe
    530                 535                 540

Lys Thr Ser Asn Leu Gly Phe Glu Asp Ile Gln Lys Phe Asn Pro Gly
545                 550                 555                 560

Glu Leu Tyr Tyr Lys Val Asp Val Asn Asn His Lys Ala Gly Glu Arg
                565                 570                 575

Tyr Tyr Ala Asp Glu Lys Asp Val Asn Gly Asn Pro Pro Lys Glu Leu
            580                 585                 590

Leu Glu His Asp Lys Glu Leu Ala Pro Tyr Asn Tyr Gln Val Ile Asp
        595                 600                 605

Lys Lys
    610


<210> SEQ ID NO 17
<211> LENGTH: 659
<212> TYPE: PRT
<213> ORGANISM: Campylobacter jejuni

<400> SEQUENCE: 17

Met Lys Ser Val Lys Leu Lys Val Ser Leu Ile Ala Asn Leu Ile Ala
1               5                   10                  15

Val Val Cys Leu Ile Ile Leu Gly Val Val Thr Phe Ile Phe Val Lys
            20                  25                  30

Gln Ala Ile Phe His Glu Val Val Asn Ala Glu Ile Asn Tyr Val Lys
        35                  40                  45

Thr Ala Lys Asn Ser Ile Glu Ser Phe Lys Ala Arg Asn Ser Leu Ala
    50                  55                  60

Leu Glu Ser Leu Ala Lys Ser Ile Leu Lys His Pro Ile Glu Gln Leu
65                  70                  75                  80

Asp Ser Gln Asp Ala Leu Met His Tyr Val Gly Lys Asp Leu Lys Asn
                85                  90                  95

Phe Arg Asp Ala Gly Arg Phe Leu Ala Val Tyr Ile Ala Gln Pro Asn
            100                 105                 110

Gly Glu Leu Val Val Ser Asp Pro Asp Ser Asp Ala Lys Asn Leu Asp
        115                 120                 125

Phe Gly Thr Tyr Gly Lys Ala Asp Asn Tyr Asp Ala Arg Thr Arg Glu
    130                 135                 140
```

```
Tyr Tyr Ile Glu Ala Val Lys Thr Asn Lys Leu Tyr Ile Thr Pro Ser
145                 150                 155                 160

Tyr Ile Asp Val Thr Thr Asn Leu Pro Cys Phe Thr Tyr Ser Ile Pro
                165                 170                 175

Leu Tyr Lys Asp Gly Lys Phe Ile Gly Val Leu Ala Val Asp Ile Leu
            180                 185                 190

Ala Ala Asp Leu Gln Ala Glu Phe Glu Asn Leu Pro Gly Arg Thr Phe
        195                 200                 205

Val Phe Asp Glu Glu Asn Lys Val Phe Val Ser Thr Asp Lys Ala Leu
    210                 215                 220

Leu Gln Lys Gly Tyr Asp Ile Ser Ala Ile Ala Asn Leu Ala Lys Thr
225                 230                 235                 240

Lys Glu Asp Leu Glu Pro Phe Glu Tyr Thr Arg Pro Lys Asp Gly Asn
                245                 250                 255

Glu Arg Phe Ala Val Cys Thr Lys Val Ser Gly Ile Tyr Thr Ala Cys
            260                 265                 270

Val Gly Glu Pro Ile Glu Gln Ile Glu Ala Pro Val Tyr Lys Ile Ala
        275                 280                 285

Phe Ile Gln Thr Ala Ile Val Ile Phe Thr Ser Ile Ile Ser Val Ile
    290                 295                 300

Leu Leu Tyr Phe Ile Val Ser Lys Tyr Leu Ser Pro Leu Ala Ala Ile
305                 310                 315                 320

Gln Thr Gly Leu Thr Ser Phe Phe Asp Phe Ile Asn Tyr Lys Thr Lys
                325                 330                 335

Asn Val Ser Thr Ile Glu Val Lys Ser Asn Asp Glu Phe Gly Gln Ile
            340                 345                 350

Ser Asn Ala Ile Asn Glu Asn Ile Leu Ala Thr Lys Arg Gly Leu Glu
        355                 360                 365

Gln Asp Asn Gln Ala Val Lys Glu Ser Val Gln Thr Val Ser Val Val
    370                 375                 380

Glu Gly Gly Asn Leu Thr Ala Arg Ile Thr Ala Asn Pro Arg Asn Pro
385                 390                 395                 400

Gln Leu Ile Glu Leu Lys Asn Val Leu Asn Lys Leu Leu Asp Val Leu
                405                 410                 415

Gln Ala Arg Val Gly Ser Asp Met Asn Ala Ile His Lys Ile Phe Glu
            420                 425                 430

Glu Tyr Lys Ser Leu Asp Phe Arg Asn Lys Leu Glu Asn Ala Ser Gly
        435                 440                 445

Ser Val Glu Leu Thr Thr Asn Ala Leu Gly Asp Glu Ile Val Lys Met
    450                 455                 460

Leu Lys Gln Ser Ser Asp Phe Ala Asn Ala Leu Ala Asn Glu Ser Gly
465                 470                 475                 480

Lys Leu Gln Thr Ala Val Gln Ser Leu Thr Thr Ser Ser Asn Ser Gln
                485                 490                 495

Ala Gln Ser Leu Glu Glu Thr Ala Ala Ala Leu Glu Glu Ile Thr Ser
            500                 505                 510

Ser Met Gln Asn Val Ser Val Lys Thr Ser Asp Val Ile Thr Gln Ser
        515                 520                 525

Glu Glu Ile Lys Asn Val Thr Gly Ile Ile Gly Asp Ile Ala Asp Gln
    530                 535                 540

Ile Asn Leu Leu Ala Leu Asn Ala Ala Ile Glu Ala Ala Arg Ala Gly
545                 550                 555                 560

Glu His Gly Arg Gly Phe Ala Val Val Ala Asp Glu Val Arg Lys Leu
```

```
                565                 570                 575

Ala Glu Arg Thr Gln Lys Ser Leu Ser Glu Ile Glu Ala Asn Thr Asn
            580                 585                 590

Leu Leu Val Gln Ser Ile Asn Asp Met Ala Glu Ser Ile Lys Glu Gln
        595                 600                 605

Thr Ala Gly Ile Thr Gln Ile Asn Asp Ser Val Ala Gln Ile Asp Gln
    610                 615                 620

Thr Thr Lys Asp Asn Val Glu Ile Ala Asn Glu Ser Ala Ile Ile Ser
625                 630                 635                 640

Ser Thr Val Ser Asp Ile Ala Asn Asn Ile Leu Glu Asp Val Lys Lys
                645                 650                 655

Lys Arg Phe


<210> SEQ ID NO 18
<211> LENGTH: 665
<212> TYPE: PRT
<213> ORGANISM: Campylobacter jejuni

<400> SEQUENCE: 18

Met Gln Ser Ile Asn Ser Gly Lys Ser Val Gly Ile Ser Ala Lys Leu
1               5                   10                  15

Thr Leu Trp Val Gly Ile Leu Val Val Leu Ile Leu Ala Ile Thr Ser
            20                  25                  30

Ala Ile Ser Tyr Phe Asp Ser Arg Asn Asn Thr Tyr Glu Leu Leu Lys
        35                  40                  45

Asp Thr Gln Leu Lys Thr Met Gln Asp Val Asp Ala Phe Phe Lys Ser
    50                  55                  60

Tyr Ala Met Ser Lys Arg Asn Gly Ile Gln Ile Leu Ala Asn Glu Leu
65                  70                  75                  80

Thr Asn Arg Pro Asp Met Ser Asp Glu Glu Leu Ile Asn Leu Ile Lys
                85                  90                  95

Val Ile Lys Lys Val Asn Asp Tyr Asp Leu Val Tyr Val Gly Phe Asp
            100                 105                 110

Asn Thr Gly Lys Asn Tyr Gln Ser Asp Asp Gln Ile Leu Asp Leu Ser
        115                 120                 125

Lys Gly Tyr Asp Thr Lys Asn Arg Pro Trp Tyr Lys Ala Ala Lys Glu
    130                 135                 140

Ala Lys Lys Leu Ile Val Thr Glu Pro Tyr Lys Ser Ala Ala Ser Gly
145                 150                 155                 160

Glu Val Gly Leu Thr Tyr Ala Ala Pro Phe Tyr Asp Arg Asn Gly Asn
                165                 170                 175

Phe Arg Gly Val Val Gly Gly Asp Tyr Asp Leu Ala Asn Phe Ser Thr
            180                 185                 190

Asn Val Leu Thr Val Gly Lys Ser Asp Asn Thr Phe Thr Glu Val Leu
        195                 200                 205

Asp Ser Glu Gly Thr Ile Leu Phe Asn Asp Glu Val Ala Lys Ile Leu
    210                 215                 220

Thr Lys Thr Glu Leu Ser Ile Asn Ile Ala Asn Ala Ile Lys Ala Asn
225                 230                 235                 240

Pro Ala Leu Ile Asp Pro Arg Asn Gln Asp Thr Leu Phe Thr Ala Lys
                245                 250                 255

Asp His Gln Gly Val Asp Tyr Ala Ile Met Cys Asn Ser Ala Phe Asn
            260                 265                 270

Pro Leu Phe Arg Ile Cys Thr Ile Thr Glu Asn Lys Val Tyr Thr Glu
```

-continued

```
        275                 280                 285

Ala Val Asn Ser Ile Leu Met Lys Gln Val Ile Val Gly Ile Ile Ala
    290                 295                 300

Ile Ile Ile Ala Leu Ile Leu Ile Arg Phe Leu Ile Ser Arg Ser Leu
305                 310                 315                 320

Ser Pro Leu Ala Ala Ile Gln Thr Gly Leu Thr Ser Phe Phe Asp Phe
                325                 330                 335

Ile Asn Tyr Lys Thr Lys Asn Val Ser Thr Ile Glu Val Lys Ser Asn
            340                 345                 350

Asp Glu Phe Gly Gln Ile Ser Asn Ala Ile Asn Glu Asn Ile Leu Ala
        355                 360                 365

Thr Lys Arg Gly Leu Glu Gln Asp Asn Gln Ala Val Lys Glu Ser Val
    370                 375                 380

Gln Thr Val Ser Val Val Glu Gly Gly Asn Leu Thr Ala Arg Ile Thr
385                 390                 395                 400

Ala Asn Pro Arg Asn Pro Gln Leu Ile Glu Leu Lys Asn Val Leu Asn
                405                 410                 415

Lys Leu Leu Asp Val Leu Gln Ala Arg Val Gly Ser Asp Met Asn Ala
            420                 425                 430

Ile His Lys Ile Phe Glu Glu Tyr Lys Ser Leu Asp Phe Arg Asn Lys
        435                 440                 445

Leu Glu Asn Ala Ser Gly Ser Val Glu Leu Thr Thr Asn Ala Leu Gly
    450                 455                 460

Asp Glu Ile Val Lys Met Leu Lys Gln Ser Ser Asp Phe Ala Asn Ala
465                 470                 475                 480

Leu Ala Asn Glu Ser Gly Lys Leu Gln Thr Ala Val Gln Ser Leu Thr
                485                 490                 495

Thr Ser Ser Asn Ser Gln Ala Gln Ser Leu Glu Glu Thr Ala Ala Ala
            500                 505                 510

Leu Glu Glu Ile Thr Ser Ser Met Gln Asn Val Ser Val Lys Thr Ser
        515                 520                 525

Asp Val Ile Thr Gln Ser Glu Glu Ile Lys Asn Val Thr Gly Ile Ile
    530                 535                 540

Gly Asp Ile Ala Asp Gln Ile Asn Leu Leu Ala Leu Asn Ala Ala Ile
545                 550                 555                 560

Glu Ala Ala Arg Ala Gly Glu His Gly Arg Gly Phe Ala Val Val Ala
                565                 570                 575

Asp Glu Val Arg Lys Leu Ala Glu Arg Thr Gln Lys Ser Leu Ser Glu
            580                 585                 590

Ile Glu Ala Asn Thr Asn Leu Leu Val Gln Ser Ile Asn Asp Met Ala
        595                 600                 605

Glu Ser Ile Lys Glu Gln Thr Ala Gly Ile Thr Gln Ile Asn Asp Ser
    610                 615                 620

Val Ala Gln Ile Asp Gln Thr Thr Lys Asp Asn Val Glu Ile Ala Asn
625                 630                 635                 640

Glu Ser Ala Ile Ile Ser Ser Thr Val Ser Asp Ile Ala Asn Asn Ile
                645                 650                 655

Leu Glu Asp Val Lys Lys Lys Arg Phe
            660                 665
```

<210> SEQ ID NO 19
<211> LENGTH: 750
<212> TYPE: PRT
<213> ORGANISM: Campylobacter jejuni

<400> SEQUENCE: 19

```
Met Arg Ile Thr Asn Lys Leu Asn Phe Thr Asn Ser Val Asn Asn Ser
1               5                   10                  15

Met Gly Gly Gln Ser Ala Leu Tyr Gln Ile Ser Gln Gln Leu Ala Ser
            20                  25                  30

Gly Leu Lys Ile Gln Asn Ser Tyr Glu Asp Ala Ser Thr Tyr Ile Asp
        35                  40                  45

Asn Thr Arg Leu Glu Tyr Glu Ile Lys Thr Leu Glu Gln Val Lys Glu
    50                  55                  60

Ser Thr Ser Arg Ala Gln Glu Met Thr Gln Asn Ser Met Lys Ala Leu
65                  70                  75                  80

Gln Asp Met Val Lys Leu Leu Glu Asp Phe Lys Val Lys Val Thr Gln
                85                  90                  95

Ala Ala Ser Asp Ser Asn Ser Gln Thr Ser Arg Glu Ala Ile Ala Lys
            100                 105                 110

Glu Leu Glu Arg Ile Lys Glu Ser Ile Val Gln Leu Ala Asn Thr Ser
        115                 120                 125

Val Asn Gly Gln Tyr Leu Phe Ala Gly Ser Gln Val Ala Asn Lys Pro
    130                 135                 140

Phe Asp Ser Asn Gly Asn Tyr Tyr Gly Asp Lys Asn Asn Ile Asn Val
145                 150                 155                 160

Val Thr Gly Ala Gly Thr Glu Ser Pro Tyr Asn Ile Pro Gly Trp Asp
                165                 170                 175

Leu Phe Phe Lys Ala Asp Gly Asp Tyr Lys Lys Gln Ile Ser Thr Asn
            180                 185                 190

Val Ser Phe Thr Asp Asn Arg Trp Asp Leu Asn Lys Asp Pro Asp Lys
        195                 200                 205

Thr Lys Tyr Leu Thr Gly Asp Ser Lys Trp Gln Gln Leu Ile Gly Gln
    210                 215                 220

Ser Tyr Val Lys Asp Asn Ser Leu Asp Ala Asp Lys Asp Phe Glu Tyr
225                 230                 235                 240

Asp Asp Ser Lys Leu Asp Phe Pro Pro Thr Thr Leu Tyr Val Gln Gly
                245                 250                 255

Thr Arg Pro Asp Gly Thr Ser Phe Lys Ser Ala Val Leu Val Lys Pro
            260                 265                 270

Glu Asp Thr Leu Glu Asp Val Met Glu Asn Ile Gly Ala Leu Tyr Gly
        275                 280                 285

Asn Thr Pro Asn Asn Lys Val Val Glu Val Ser Met Asn Asp Ser Gly
    290                 295                 300

Gln Ile Gln Ile Thr Asp Leu Lys Gln Gly Asn Asn Lys Leu Asp Phe
305                 310                 315                 320

His Ala Val Ala Phe Thr Pro Gln Ala Asp Asp Lys Thr Glu Leu Asn
                325                 330                 335

Asn Ile Ile Gln Ala Ala Gln Asp Glu Gly Ile Thr Met Glu Asp Val
            340                 345                 350

Thr Asn Arg Val Met Thr Ala Ala Leu Gly Asn Pro Asn Asn Gly Asp
        355                 360                 365

Ile Thr Asn Leu Asn Asn Pro Val Thr Ile Gln Ile Asn Gly Gln Asn
    370                 375                 380

Phe Glu Ile Asp Leu Lys Gln Thr Asp Phe Ile Lys Ser Lys Met Thr
385                 390                 395                 400

Asp Thr Asp Gly Asn Ala Ala Asn Gly Ala Asp Tyr Asp Asn Val Tyr
```

```
                405                 410                 415

Phe Glu Lys Asn Gly Asn Thr Val Tyr Gly Asn Val Ser Gln Val Ile
            420                 425                 430

Lys Gly Ser Asn Ala Tyr Ala Thr Asp Ser Thr Lys Leu Ser Glu Val
        435                 440                 445

Met Ala Gly Asp Ser Leu Asn Gly Thr Thr Leu Asn Leu Lys Val Asn
    450                 455                 460

Ser Lys Gly Gly Asn Ser Tyr Asp Val Thr Ile Asn Leu Gln Thr Ser
465                 470                 475                 480

Thr Val Ser Tyr Pro Asp Pro Asn Asn Pro Gly Gln Thr Ile Ser Phe
                485                 490                 495

Pro Ile Met His Thr Asn Pro Ala Thr Gly Asn Ser Gly Val Val Thr
            500                 505                 510

Gly Ser Asn Asp Ile Thr Tyr Gly Gln Ile Asn Asp Ile Ile Gly Met
        515                 520                 525

Phe Ala Ala Asp Lys Ile Pro Thr Thr Thr Ile Gln Ala Asn Asn Gly
    530                 535                 540

Gln Ile Asn Asn Ala Asp Tyr Thr Gln Ile Gln Gln Leu Met Lys Asp
545                 550                 555                 560

Ser Gln Ala Thr Val Asp Val Ser Met Asp Tyr Lys Gly Arg Ile Ser
                565                 570                 575

Val Thr Asp Lys Leu Ser Ser Gly Thr Asn Ile Glu Ile Ser Leu Ser
            580                 585                 590

Asp Ser Gln Ser Gly Gln Phe Pro Ala Pro Pro Phe Thr Thr Thr Ser
        595                 600                 605

Thr Val Gln Asn Gly Pro Asn Phe Ser Phe Ser Ala Asn Asn Ser Leu
    610                 615                 620

Thr Ile Asp Glu Pro Asn Val Asp Ile Ile Lys Asp Leu Asp Ser Met
625                 630                 635                 640

Ile Asp Ala Val Leu Lys Gly Asn Met Arg Ala Asp Ser Glu Ser Glu
                645                 650                 655

Asn Pro Arg Asn Thr Gly Met Gln Gly Ala Leu Glu Arg Leu Asp His
            660                 665                 670

Leu Ala Asp His Val Ser Lys Leu Asn Thr Thr Met Gly Ala Tyr His
        675                 680                 685

Asn Thr Ile Glu Gly Val Asn Thr Arg Thr Ser Phe Leu Ser Val Asn
    690                 695                 700

Val Gln Ser Ile Lys Ser Asn Val Ile Asp Val Asp Tyr Gly Glu Ala
705                 710                 715                 720

Met Met Asn Leu Met Gln Val Gln Leu Ala Tyr Gln Ala Ser Leu Lys
                725                 730                 735

Ala Ser Thr Thr Ile Ser Gln Leu Ser Leu Leu Asn Tyr Met
            740                 745                 750


<210> SEQ ID NO 20
<211> LENGTH: 865
<212> TYPE: PRT
<213> ORGANISM: Campylobacter jejuni

<400> SEQUENCE: 20

Met Met Arg Ser Leu Trp Ser Gly Val Ser Gly Leu Gln Ala His Gln
1               5                   10                  15

Val Ala Met Asp Val Glu Gly Asn Asn Ile Ser Asn Val Asn Thr Thr
            20                  25                  30
```

```
Gly Phe Lys Tyr Ser Arg Ala Asp Phe Gly Thr Met Phe Ser Gln Thr
        35                  40                  45

Val Lys Ile Ala Thr Ala Pro Thr Asp Gly Arg Gly Gly Ser Asn Pro
    50                  55                  60

Leu Gln Ile Gly Leu Gly Val Ser Val Ser Ser Thr Thr Arg Ile His
65                  70                  75                  80

Ser Gln Gly Ser Val Gln Thr Thr Asp Lys Asn Thr Asp Val Ala Ile
                85                  90                  95

Asn Gly Asp Gly Phe Phe Met Val Ser Asp Asp Gly Gly Leu Thr Asn
            100                 105                 110

Tyr Leu Thr Arg Ser Gly Asp Phe Lys Leu Asp Ala Tyr Gly Asn Phe
        115                 120                 125

Val Asn Asn Ala Gly Phe Val Val Gln Gly Trp Asn Ile Asn Trp Asp
    130                 135                 140

Asp Gln Thr Ile Asp Ser Ser Arg Thr Pro Gln Asn Ile Phe Ile Asp
145                 150                 155                 160

Pro Gly Met His Ile Pro Ala Ala Lys Ser Thr Glu Val Ala Ile Lys
                165                 170                 175

Ala Asn Leu Asn Ser Gly Leu Asn Ile Gly Thr Ser Ser Arg Asn Leu
            180                 185                 190

Tyr Ala Leu Asp Ser Val His Gly Trp Asn Thr Lys Thr Gln Arg Ala
        195                 200                 205

Glu Asp Glu Asn Asp Thr Gly Thr Thr Gln Phe Tyr Thr Thr Ser Lys
    210                 215                 220

Asn Ser Val Glu Val Thr Glu Lys Gly Val Asp Ala Gly Ser Leu Phe
225                 230                 235                 240

Asn Ala Lys Gly Gln Gly Leu Asn Leu Arg Asp Gly Gln Gly Ile Trp
                245                 250                 255

Val Ser Tyr Ala Asp Ala Thr Tyr Ser Thr Asn Lys Val Gly Val Asn
            260                 265                 270

Ala Phe Asp Pro Asn Leu Gln Gln Asn Gln Thr Ala Ala Phe Trp Gly
        275                 280                 285

Thr Ala Asn Gln Lys Val Asn Leu Asp Ile Thr Leu Asn Gly Val Arg
    290                 295                 300

Ile Gln Asn Ala Asp Ile Gln Ser Ile Asp Asp Ala Ile Ala Tyr Ile
305                 310                 315                 320

Asn Thr Phe Thr Ala Pro Thr Asp Thr Arg Asp Gly Thr Gly Val Lys
                325                 330                 335

Ala Val Lys Asn Lys Asp Gly Ser Gly Ile Asp Phe Val Asn Asp Asn
            340                 345                 350

Ala Asp Gly Thr Thr Asp Asn Met Lys Asn Ile Asn Leu Val Val Ala
        355                 360                 365

Asn Thr Asn Thr Ala Gly Glu Leu Trp Asn Ala Val Trp Asn Asn Asn
    370                 375                 380

Asn Gln Thr Phe Thr Phe Asn Asn Asn Gly Asn Gly Gln Ala Gly Thr
385                 390                 395                 400

Pro Thr Ile Asn Lys Asn Gly Ser Ser Leu Trp Thr Ala Thr Asn Ile
                405                 410                 415

Thr Phe Thr Pro Gln Pro Pro Gln Ala Ala Thr Asn Val Gln Leu Thr
            420                 425                 430

Gly Gly Leu Asn Ala Gln Ile Ile Thr Ala His Lys Tyr Ile Tyr Ser
        435                 440                 445

Ser Asn Pro Val Asp Ile Gly Pro Met Tyr Asn Pro Asp Gly Gly Pro
```

```
    450                 455                 460

Ala Phe Gln Pro Gly Ala Asn Ala Thr Thr Arg Pro Thr Glu Pro Gly
465                 470                 475                 480

Ser Ala Ala Tyr Trp Asp Ala Val Asn Gly Gly Leu Leu Asn Thr Asn
                485                 490                 495

Val Arg Thr Phe Arg Thr Thr Glu Asp Leu Arg Glu Leu Leu Gln Arg
            500                 505                 510

Asp Ala Arg Tyr Gly Val Asp Tyr Asp Gly Ser Gly Thr Phe Ala Ala
        515                 520                 525

Ala Asp Ile Asn Gln Asn Ile Lys Val Val Val Thr Ala Asp Gly His
    530                 535                 540

Phe Ala Ile Ser Asn Ala Asn Glu Gln Ser Thr Val Pro Pro Asn Ala
545                 550                 555                 560

Ile Asn Gly Val Gly Asn Ala Thr Thr Thr Asp Pro Lys Asn Met Ser
                565                 570                 575

Phe Asn Ile Thr Ala Tyr Ser Asn Lys Gln Gly Thr Val Ser Thr Asn
            580                 585                 590

Asp Ala Phe Thr Ala Ile Phe Lys Ala Phe Asp Gly Pro Leu Val Ile
        595                 600                 605

Gly Asn Gln Ile Lys Glu Ser Glu Gln Leu Lys Leu Ser Ala Phe Ser
    610                 615                 620

Ala Gly Leu Glu Ile Tyr Asp Ser Leu Gly Ser Lys His Thr Leu Glu
625                 630                 635                 640

Val Gln Phe Val Lys Gln Ser Thr Thr Gln Asp Gly Gly Asn Glu Trp
                645                 650                 655

Gln Met Ile Ile Arg Val Pro Glu Pro Ala Glu Ile Asn Thr Thr Gly
            660                 665                 670

Glu Gly Pro Asn Asn Ile Ile Val Gly Thr Ala Arg Phe Asn Asn Asp
        675                 680                 685

Gly Ser Leu Ala Ser Tyr Thr Pro Arg Thr Ile Asn Phe Ser Pro Asn
    690                 695                 700

Asn Gly Ala Ala Pro Asn Gln Gln Ile Lys Leu Ser Phe Gly Thr Ser
705                 710                 715                 720

Gly Ser Asn Asp Gly Leu Val Ser Ser Asn Ser Ala Ser Thr Leu Thr
                725                 730                 735

Gly Gln Ala Thr Asp Gly Tyr Thr Ser Gly Asn Leu Lys Pro Asp Ala
            740                 745                 750

Ile Arg Val Asp Asp Lys Gly Asn Ile Leu Gly Glu Phe Thr Asn Gly
        755                 760                 765

Lys Thr Phe Ala Val Ala Lys Ile Ala Met Ala Ser Val Ala Asn Asn
    770                 775                 780

Ser Gly Leu Glu Glu Ile Gly Gly Asn Leu Phe Lys Val Thr Ala Asn
785                 790                 795                 800

Ser Gly Asn Ile Val Val Gly Glu Ala Gly Thr Gly Gly Arg Gly Glu
                805                 810                 815

Met Lys Thr Ser Ala Leu Glu Met Ser Asn Val Asp Leu Ser Arg Ser
            820                 825                 830

Leu Thr Glu Leu Ile Ile Ile Gln Arg Gly Tyr Gln Ala Asn Ser Lys
        835                 840                 845

Thr Ile Ser Thr Ser Asp Gln Met Leu Gln Thr Leu Ile Gln Leu Lys
    850                 855                 860

Gln
865
```

<210> SEQ ID NO 21
<211> LENGTH: 871
<212> TYPE: PRT
<213> ORGANISM: Campylobacter jejuni

<400> SEQUENCE: 21

```
Met Ala Lys Ile Arg Ile His Glu Ile Ala Lys Glu Leu Gly Tyr Asp
1               5                   10                  15

Ser Lys Glu Ile Ile Glu Lys Ala Asn Glu Leu Gly Leu Gly Ile Lys
            20                  25                  30

Thr Ala Ser Asn Ala Val Glu Pro Glu Ile Ala Ala Ala Ile Tyr Glu
        35                  40                  45

Tyr Ile Gln Thr Arg Glu Ile Pro Glu Ala Phe Lys Lys Asn Ile Lys
    50                  55                  60

Thr Pro Thr Ala Lys Lys Pro Lys Lys Glu Asn Ile Lys Glu Gln Glu
65                  70                  75                  80

Lys Leu Asn Glu Ser Glu Lys Lys Glu Pro Lys Lys Glu Glu Lys Leu
                85                  90                  95

Lys Gln Glu Val Lys Lys Glu Glu Leu Lys Ile Glu Lys Glu Asn Ala
            100                 105                 110

Lys Glu Glu Glu Lys Gln Glu Ile Ile Asp Ala His Lys Pro Gln Ser
        115                 120                 125

Leu Ala Ser Ala Thr Leu Ala Lys Arg Arg Gly Leu Val Ile Val Lys
    130                 135                 140

Lys Lys Lys Asp Glu Glu Glu Ile Gln Val Lys Lys Glu Glu Val Lys
145                 150                 155                 160

Asn Ser Asn Asp Ile Ser Ile Asn Asn Glu Glu Arg Leu Ser Leu Lys
                165                 170                 175

Thr Met Phe Ser Asn Ala Asp Glu Ser Leu Lys Lys Lys Lys Lys Glu
            180                 185                 190

Lys Lys Ser Phe Val Ala Ser Lys Lys Glu Ser Thr Glu Lys Met Asn
        195                 200                 205

Phe Leu Asp Glu His Asp Phe Gly Asp Ile Ser Leu Asp Asp Glu Asp
    210                 215                 220

Glu Val Val Leu Pro Asp Phe Ser Val Lys Glu Gln Glu Lys Pro Gln
225                 230                 235                 240

Asn Ile Asn Lys Lys Gln Pro Asn Phe Ile Arg Gln Ala Val Gly Asn
                245                 250                 255

Ser Ala Gly Phe Gly Phe Glu Gly Gly Ile Gln Arg Arg Ser Arg Lys
            260                 265                 270

Lys Pro Ser Lys Lys Ile Glu Lys Lys Glu Val Glu Glu Val Gly Ser
        275                 280                 285

Val Ala Ile Ser Lys Glu Ile Arg Val Tyr Glu Phe Ala Asp Lys Ile
    290                 295                 300

Gly Lys Ser Thr Ser Glu Val Ile Ser Lys Leu Phe Met Leu Gly Met
305                 310                 315                 320

Met Thr Thr Lys Asn Asp Phe Leu Asp Glu Asp Ala Ile Glu Ile Leu
                325                 330                 335

Ala Ala Glu Phe Gly Ile Glu Ile Asn Ile Ile Asn Glu Ala Asp Glu
            340                 345                 350

Phe Asp Tyr Val Lys Asp Tyr Glu Glu Glu Thr Asp Glu Lys Asp Leu
        355                 360                 365

Val Thr Arg Ala Pro Val Ile Thr Ile Met Gly His Val Asp His Gly
```

```
    370                 375                 380

Lys Thr Ser Leu Leu Asp Tyr Ile Arg Lys Ser Arg Val Ala Ser Gly
385                 390                 395                 400

Glu Ala Gly Gly Ile Thr Gln His Val Gly Ala Tyr Met Val Glu Lys
                405                 410                 415

Asn Gly Arg Lys Ile Thr Phe Ile Asp Thr Pro Gly His Glu Ala Phe
            420                 425                 430

Thr Ala Met Arg Ala Arg Gly Ala Ser Ile Thr Asp Ile Val Ile Ile
        435                 440                 445

Val Val Ala Ala Asp Asp Gly Val Lys Pro Gln Thr Lys Glu Ala Ile
    450                 455                 460

Asn His Ala Lys Ala Ala Gly Val Pro Ile Ile Ile Ala Ile Asn Lys
465                 470                 475                 480

Met Asp Lys Glu Ala Ala Asn Pro Asp Met Val Lys Thr Gln Leu Ala
                485                 490                 495

Glu Met Glu Ile Met Pro Val Glu Trp Gly Gly Ser Tyr Glu Phe Val
            500                 505                 510

Gly Val Ser Ala Lys Thr Gly Met Gly Ile Glu Asp Leu Leu Glu Ile
        515                 520                 525

Val Leu Leu Gln Ala Asp Ile Leu Glu Leu Lys Ala Asn Pro Lys Ser
    530                 535                 540

Phe Ala Lys Ala Ser Ile Ile Glu Ser Ser Val Gln Lys Gly Arg Gly
545                 550                 555                 560

Ala Val Ala Thr Val Ile Val Gln Asn Gly Thr Leu Thr Val Gly Ser
                565                 570                 575

Thr Val Val Ala Gly Glu Ala Tyr Gly Lys Val Arg Ala Met Ser Asp
            580                 585                 590

Asp Gln Gly Lys Ala Leu Lys Glu Ile Lys Pro Gly Glu Cys Gly Val
        595                 600                 605

Ile Val Gly Leu Ser Glu Val Ala Asp Ala Gly Glu Ile Leu Ile Ala
    610                 615                 620

Val Lys Thr Asp Lys Glu Ala Arg Glu Tyr Ala Asn Lys Arg His Glu
625                 630                 635                 640

Tyr Asn Arg Gln Lys Glu Leu Ser Lys Ser Thr Lys Val Ser Ile Asp
                645                 650                 655

Glu Leu Gly Ala Lys Ile Lys Glu Gly Asn Leu Lys Ala Leu Pro Val
            660                 665                 670

Ile Leu Lys Ala Asp Val Gln Gly Ser Leu Glu Ala Leu Lys Ala Ser
        675                 680                 685

Leu Glu Lys Leu Arg Asn Asp Glu Ile Lys Val Asn Ile Ile His Ser
    690                 695                 700

Gly Val Gly Gly Ile Thr Gln Ser Asp Ile Glu Leu Ala Ser Ala Ser
705                 710                 715                 720

Glu Asn Ser Ile Val Leu Gly Phe Asn Ile Arg Pro Thr Gly Glu Val
                725                 730                 735

Lys Glu Arg Ala Lys Asp Lys Gly Val Glu Ile Lys Thr Tyr Asn Val
            740                 745                 750

Ile Tyr Asn Leu Leu Asp Asp Val Lys Ala Leu Leu Gly Gly Met Met
        755                 760                 765

Ser Pro Ile Ile Ser Glu Glu Gln Leu Gly Gln Ala Glu Ile Arg Gln
    770                 775                 780

Val Ile Asn Val Pro Lys Ile Gly Gln Ile Ala Gly Cys Met Val Thr
785                 790                 795                 800
```

```
Glu Gly Val Ile Asn Arg Gly Ala Lys Ile Arg Leu Ile Arg Asp Gly
                805                 810                 815

Val Val Val Tyr Glu Gly Asn Val Ser Ser Leu Lys Arg Phe Lys Asp
            820                 825                 830

Asp Ala Lys Glu Val Ala Lys Gly Tyr Glu Cys Gly Val Gly Ile Glu
        835                 840                 845

Gly Cys Asp Asp Met Arg Val Gly Asp Tyr Ile Glu Ser Tyr Lys Glu
    850                 855                 860

Val Glu Glu Gln Ala Ser Leu
865                 870


<210> SEQ ID NO 22
<211> LENGTH: 946
<212> TYPE: PRT
<213> ORGANISM: Campylobacter jejuni

<400> SEQUENCE: 22

Met Leu Ala Pro Gly Met Gly Glu Trp Val Tyr Lys Ala Asn Leu Phe
1               5                   10                  15

Leu Phe Gly Glu Phe Ala Tyr Tyr Tyr Pro Phe Phe Leu Phe Ile Leu
            20                  25                  30

Asn Tyr Val Tyr Tyr Lys Arg Asn Tyr Lys Leu Ala Asn Phe Thr Arg
        35                  40                  45

Arg Glu Leu Phe Gly Ile Gly Phe Ala Phe Phe Ser Ser Leu Leu Leu
    50                  55                  60

Phe Ala Val Phe Tyr Pro Asn Ser Gly Tyr Ile Leu Glu Leu Ala Tyr
65                  70                  75                  80

Ala Ile Phe Ser Thr Ile Leu Gly His Thr Gly Ser Gly Ile Phe Ala
                85                  90                  95

Leu Leu Leu Leu Leu Phe Ser Leu Val Leu Leu Phe Pro Lys Phe Ala
            100                 105                 110

Lys Glu Ile Leu Lys Ile Glu Leu Asp Phe Thr Tyr Leu Leu Lys Val
        115                 120                 125

Glu Gln Ala Phe Lys Ser Leu Leu Met Arg Val Phe Gly Gly Glu Asn
    130                 135                 140

Glu Lys Glu Asp Val Gly Lys Se Glu Pro Ile Val Pro Lys Leu Asn
145                 150                 155                 160

Ile Leu Gln Asp Ser Ile Tyr Gly Asn Leu Gln Ile Asn Lys Lys Gly
                165                 170                 175

Glu Thr Asn Asn Leu Glu Gln Ile Ile Lys Asp Ser Asn Ile Asn Ala
            180                 185                 190

Ser Lys Asn Ser Ile Thr Thr Ala Lys Glu Asn Phe Glu Lys Leu Lys
        195                 200                 205

Asn Gln Ile Leu Asp Glu Thr Ile Glu Ile Asp Lys Gln Ser Leu Lys
    210                 215                 220

Glu Ser Arg Ser Phe Val His Glu His Ser Gln Gln Val Arg Asn Phe
225                 230                 235                 240

Ala Gln Lys Ala Ser Lys Met Ser Ile Ser Leu Asp Glu Asp Phe Asn
                245                 250                 255

Phe Ile Ser Glu Glu Glu Val Asp Met Ile Pro Glu Arg Phe Leu Lys
            260                 265                 270

Pro Lys Lys Leu Glu Asp Ile Lys Gln Ile Asp Thr Asn Lys Asn Leu
        275                 280                 285

Asp Glu Pro Ser Tyr Lys Arg Lys Asn Ile Glu Ile Pro Val Ser Asn
```

```
    290                 295                 300

Gln Glu Val Lys Pro Lys Ile Phe Thr Lys Glu Leu Glu Leu Arg Glu
305                 310                 315                 320

Asn Leu Ile Lys Lys Glu Lys Leu Glu Gln Glu Tyr Lys Ala Tyr Gln
                325                 330                 335

Asn Glu Ile Leu Glu Asn Lys Val Lys Gln Glu Ile Lys Lys Leu Glu
            340                 345                 350

Glu Tyr Asp Ala Ile Asn Ser Ser Asp Ile Ile Glu Gly Asn Lys Tyr
        355                 360                 365

Ser Phe Asn Ser Pro Lys Thr Ile Lys Thr Glu Thr Glu Glu Ser Asp
    370                 375                 380

Lys Ile Asn Glu Asn Lys Asn Leu Asp Lys Ala Asp Asn Ile Phe Glu
385                 390                 395                 400

Phe Ala Pro Ile Val Glu Glu Leu Asn His Pro Tyr Ile Glu Pro Thr
                405                 410                 415

Pro Ile Lys Asn Ile Asn Glu Ile Val Ile Glu Glu Lys Asn Thr Leu
            420                 425                 430

Asp Phe Ile Gln Asn Thr Glu Thr Lys Ile Asp Asn Glu Lys Thr Asn
        435                 440                 445

Asp Gln Glu Ile Lys Leu Gln Lys Ala Val Leu Ala Lys Glu Ile Ala
    450                 455                 460

Ile Asn Gln Ala Leu Leu Arg Glu Ile Glu Gln Gly Glu Ile Glu Lys
465                 470                 475                 480

Pro Lys Asp Phe Thr Leu Pro Pro Leu Asp Phe Leu Ala Asn Pro Lys
                485                 490                 495

Glu His Lys Gln Glu Ile Asn Glu Ser Glu Ile Asp Lys Lys Ile Tyr
            500                 505                 510

Asn Leu Leu Glu Lys Leu Arg Arg Phe Lys Ile Gly Gly Asp Val Ile
        515                 520                 525

Ser Thr Tyr Val Gly Pro Val Val Thr Thr Phe Glu Phe Arg Pro Ser
    530                 535                 540

Ala Asp Val Lys Val Ser Arg Ile Leu Asn Leu Gln Asp Asp Leu Thr
545                 550                 555                 560

Met Ala Leu Met Ala Lys Ser Ile Arg Ile Gln Ala Pro Ile Pro Gly
                565                 570                 575

Lys Asp Val Val Gly Ile Glu Val Pro Asn Asp Glu Ile Gln Thr Ile
            580                 585                 590

Tyr Leu Arg Glu Ile Leu Gln Ser Glu Val Phe Lys Asn Ala Lys Ser
        595                 600                 605

Pro Leu Thr Ile Ala Leu Gly Lys Asp Ile Val Gly Asn Ala Phe Val
    610                 615                 620

Thr Asp Leu Lys Lys Leu Pro His Leu Leu Ile Ala Gly Thr Thr Gly
625                 630                 635                 640

Ser Gly Lys Ser Val Gly Ile Asn Ser Met Leu Leu Ser Leu Leu Tyr
                645                 650                 655

Arg Asn Ser Pro Lys Thr Leu Arg Leu Met Met Ile Asp Pro Lys Met
            660                 665                 670

Leu Glu Phe Ser Ile Tyr Asn Asp Ile Pro His Leu Leu Thr Pro Val
        675                 680                 685

Ile Thr Asp Pro Lys Lys Ala Val Asn Ala Leu Ser Asn Met Val Ala
    690                 695                 700

Glu Met Glu Arg Arg Tyr Arg Leu Met Ala Asp Ala Lys Thr Lys Asn
705                 710                 715                 720
```

```
Ile Glu Asn Tyr Asn Glu Lys Met Lys Glu Leu Gly Gly Glu Lys Leu
                725                 730                 735

Pro Phe Ile Val Val Ile Ile Asp Glu Leu Ala Asp Leu Met Met Thr
            740                 745                 750

Ala Gly Lys Asp Val Glu Phe Tyr Ile Gly Arg Leu Ala Gln Met Ala
        755                 760                 765

Arg Ala Ser Gly Ile His Leu Ile Val Ala Thr Gln Arg Pro Ser Val
    770                 775                 780

Asp Val Val Thr Gly Leu Ile Lys Ala Asn Leu Pro Ser Arg Ile Ser
785                 790                 795                 800

Tyr Lys Val Gly Gln Lys Ile Asp Ser Lys Val Ile Leu Asp Ala Met
                805                 810                 815

Gly Ala Glu Ser Leu Leu Gly Arg Gly Asp Cys Leu Phe Thr Pro Pro
            820                 825                 830

Gly Thr Ser Ser Ile Val Arg Leu His Ala Pro Phe Ala Ser Glu Phe
        835                 840                 845

Glu Ile Glu Lys Ile Val Asp Phe Leu Lys Asp Gln Gln Ser Val Glu
    850                 855                 860

Tyr Asp Glu Ser Phe Leu Lys Asp Gln Gln Ser Val Gly Val Thr Thr
865                 870                 875                 880

Asn Glu Ser Phe Asp Gly Glu Ala Asp Glu Leu Tyr Glu Glu Ala Lys
                885                 890                 895

Arg Val Ile Leu Glu Asp Gly Lys Thr Ser Ile Ser Tyr Leu Gln Arg
            900                 905                 910

Arg Leu Lys Ile Gly Tyr Asn Arg Ser Ala Asn Ile Ile Glu Gln Leu
        915                 920                 925

Thr Gln Asn Gly Ile Leu Ser Glu Pro Asp Ala Lys Gly Gln Arg Glu
    930                 935                 940

Ile Leu
945


<210> SEQ ID NO 23
<211> LENGTH: 1041
<212> TYPE: PRT
<213> ORGANISM: Campylobacter jejuni

<400> SEQUENCE: 23

Met Lys Lys Phe Phe Cys Leu Thr Leu Val Cys Lys Leu Phe Ala Leu
1               5                   10                  15

Ser Glu Phe Glu Leu His His Ile Asp Lys Val His Lys Leu Gly Tyr
            20                  25                  30

Ser Gly Asp Thr Ile Ile Ile Gly Val Ala Asp Asp Ala Phe Asn Gln
        35                  40                  45

Asp His Ile Ser Leu Lys Asp Lys Ile Leu Lys Ser Thr Tyr Pro Thr
    50                  55                  60

Asp Thr Ala Gly Lys Gln Leu Ile Pro Asp Leu Lys Lys Ser Thr His
65                  70                  75                  80

Gly Ser His Val Ala Gly Ile Ala Val Gly Ala Lys Ile Gly Asp Ser
                85                  90                  95

Lys Pro Tyr Gly Val Ala Tyr Gly Ala Lys Phe Tyr Gly Ala Gly Val
            100                 105                 110

Phe Pro Asn Gly Ser Tyr Thr Gln Ile Pro Asp Ile Tyr Asn Phe Phe
        115                 120                 125

Lys Asp Val Ser Ile Ile Asn Asn Ser Trp Gly Ile Asn Phe Tyr Pro
```

```
    130                 135                 140

Tyr Phe Asn Leu Lys Ala Ser Asn Ser Gly Leu Val Asp Cys Thr Gln
145                 150                 155                 160

Thr Asn Gln Gly Thr Ser Tyr Asn Ile Cys Asn Thr Pro Leu Glu Tyr
                165                 170                 175

Val Met Lys Ala Asp Lys Val Ala Asn Asp Met Met Arg Leu Ser Lys
            180                 185                 190

Asp Lys Gly Val Leu Asn Val Phe Ala Ala Gly Asn Glu Gly Ile Leu
        195                 200                 205

Ser Pro Ala Leu His Ala Ile Leu Pro Ser Tyr Asp Glu Ser Leu Arg
    210                 215                 220

Ala Trp Leu Ala Val Gly Ala Leu Asp Ala Asn Glu Ile Thr Leu Glu
225                 230                 235                 240

Ser Asp Gly Thr Leu Ile Ile Lys Ser Gln Gly Leu Ala Asp Phe Ser
                245                 250                 255

Asn Gly Phe Lys Gly Ala Thr Asn Phe Ser Leu Val Ala Ala Gly Val
            260                 265                 270

Asn Ile Asn Asn Val Asp Ser Ser Thr Asn Asp Lys Phe Thr Lys Lys
        275                 280                 285

Ser Gly Thr Ser Met Ala Ala Pro Met Val Ser Gly Thr Ala Ala Leu
    290                 295                 300

Val Lys Gln Asn Phe Pro Phe Leu Asp Gly Lys Gln Ile Ala Asp Ile
305                 310                 315                 320

Leu Leu Ser Thr Ala Asn Lys Asn Tyr Lys Ala Pro Lys Phe Thr Val
                325                 330                 335

Lys Gln Val Thr Asp Gly Thr Asn Gln Pro Lys Phe Leu Ile Val Tyr
            340                 345                 350

Ile Ser Gln Asp Pro Pro Gly Ile Glu Asp Glu Ile Lys Arg Asp Leu
        355                 360                 365

Lys Gln Leu Tyr Asn Gly Ile Gln Val Gln Val Asn Gly Gln Trp Ile
    370                 375                 380

Asp Tyr Ser Asp Tyr Ile Trp Asp Asn Arg Asp Ser Ala Gln Ser Gln
385                 390                 395                 400

Lys Leu Asn Thr Ser Thr Ile Ser Ser Ile Asn Gly Val Val Arg Val
                405                 410                 415

Glu Lys Glu Glu Leu Phe Gly Gln Gly Ile Leu Asp Ala Gln Lys Ala
            420                 425                 430

Leu Lys Gly Leu Ser Ile Leu Asp Ala Asn Arg Leu Ser Asp Gln Asp
        435                 440                 445

Val Leu Lys Tyr Glu Gln Glu Pro Asn Thr Ala Tyr Tyr Thr Ile Asn
    450                 455                 460

Thr Ala Gly Tyr Asp Ala Glu Phe Ser Asn Asp Ile Ser Gln Arg Lys
465                 470                 475                 480

Trp Asp Glu Ser Thr His Leu Ser Ser Ala Ile Asn Lys Pro Thr His
                485                 490                 495

Leu Ala Asn Leu Asn Ile Gly Leu Ser Lys Glu Gly Glu Gly Ile Leu
            500                 505                 510

Ile Ile Ser Gly Gln Asn Thr Tyr Glu Gly Ala Thr Leu Ile Lys Gln
        515                 520                 525

Gly Glu Leu Lys Leu Lys Gly Lys Val Lys Asn Asn Ala Tyr Val Glu
    530                 535                 540

Gln Lys Ala Ile Leu Ser Gly Asn Gly Ile Val Gly Gln Asn Leu Asn
545                 550                 555                 560
```

```
Asn Lys Gly Ile Val Arg Pro Gly Asn Glu Asp Leu Asn Asp Leu Thr
                565                 570                 575

Val Gln Gly Thr Tyr Thr Gln Glu Gly Val Asp Ser Lys Leu Gln Leu
            580                 585                 590

Asp Phe Gly Asn Tyr Lys Asn Ser Lys Leu Ile Ala Lys Thr Tyr Asp
        595                 600                 605

Ile Lys Ser Gly Asn Leu Glu Tyr Ile Pro Leu Pro Lys Tyr Tyr Ile
    610                 615                 620

Leu Asn Lys Pro Val Lys Ile Asn Leu Gly Asp Leu Glu Lys Ser Leu
625                 630                 635                 640

Ser Ser Phe Asn His Val Leu Ile Gln Asn Thr Tyr Ala Leu Asn Phe
                645                 650                 655

Asp Phe Val Leu Ser Asp Asp Leu Val Ser Ile Asn Lys Thr Leu Ile
            660                 665                 670

Lys Pro Asn Leu Lys Pro Asn Ala Tyr Glu Ile Pro Asn Thr Ser Leu
        675                 680                 685

Gly Asn Ala Leu Arg Gln Leu Arg Ser Arg Ala Asp Leu Ser Gln Thr
    690                 695                 700

Tyr Gln Glu Phe Phe Ala Ser Leu Asp Asn Gly Ile Asp Val Lys Thr
705                 710                 715                 720

Lys Leu Asn Arg Ile Glu Gly Ser Gly Tyr Leu Ser Thr Phe Ser Asn
                725                 730                 735

His Asn Gln Ser Asn Leu Met Gln Asn Asn Met Leu Phe Thr Leu His
            740                 745                 750

Pro Leu Asn Ile Asn Asn Phe Ala Gln Asn Asn Asn Ile Leu Leu Ala
        755                 760                 765

Ser Thr Tyr Leu Pro Arg Ile Phe Ser Asn Glu Glu Tyr Phe Trp His
    770                 775                 780

Leu Thr Pro Ser Tyr Lys Tyr Tyr Lys Asp Lys Asp Phe Ser Gly Gln
785                 790                 795                 800

Lys Thr Gly Ala Asn Ile Ser Leu Gly Glu Asn Phe Ser Ser Gly Phe
                805                 810                 815

Leu Ala Tyr Ala Leu Ser Leu Ser Ser Ala Lys Phe Asn Phe Asn Asn
            820                 825                 830

Gly Ser Asp Leu Lys Ser Tyr Asn Met Asp Leu Leu Leu Asn Tyr Asn
        835                 840                 845

His Asp Leu Asp Phe Ile Lys Ile Leu Ser Gly Leu Gly Ile Gly Val
    850                 855                 860

Gly Phe Asn Thr Leu Asn Arg Phe Val Val Glu Gln Pro Ile Glu Gly
865                 870                 875                 880

Lys Tyr Lys Thr Leu Gln Thr Ser Ala Gln Leu Gly Val Thr Lys Asp
                885                 890                 895

Ile Ile Leu Gly Gln Asp Phe Ile Phe Asn Pro Leu Met Tyr Phe Thr
            900                 905                 910

His Ser Phe Phe Tyr Gln Glu Asp Phe Lys Glu Asn Lys Ser Pro Phe
        915                 920                 925

Ala Lys Asn Tyr Glu Ser Leu Lys His His Ser Ile Asn Ala Asn Leu
    930                 935                 940

Gly Phe Asn Leu Ala Lys Asn Ile Glu Gln Asp Asp Tyr Gln Ala Ser
945                 950                 955                 960

Phe Ser Thr Phe Val Ile Phe Glu Lys Arg Ile Tyr Gly Arg Thr Leu
                965                 970                 975
```

```
Glu Asn Lys Ala Ser Phe Val Asp Phe Pro Ile Ala Phe Ile Gln Lys
            980                 985                 990

Tyr Lys Leu Lys Asp Asn Ile Leu  Ser Gln Gly Phe Asn  Ser Glu Phe
        995                 1000                1005

Leu Tyr  Lys Asn Asn Val Phe  Trp Gln Phe Met Leu  Met Asn Arg
    1010                 1015                 1020

Phe Ser  His Asn Ala Tyr Glu  Leu His Leu Met Ser  Ser Val Gly
    1025                 1030                 1035

Lys Arg  Phe
    1040


<210> SEQ ID NO 24
<211> LENGTH: 1089
<212> TYPE: PRT
<213> ORGANISM: Campylobacter jejuni

<400> SEQUENCE: 24

Met Pro Lys Arg Thr Asp Ile Lys Ser Ile Leu Leu Ile Gly Ser Gly
1               5                   10                  15

Pro Ile Val Ile Gly Gln Ala Cys Glu Phe Asp Tyr Ser Gly Thr Gln
            20                  25                  30

Ala Ala Lys Thr Leu Lys Glu Leu Gly Tyr Arg Val Val Leu Ile Asn
        35                  40                  45

Ser Asn Pro Ala Thr Ile Met Thr Asp Pro Glu Phe Ala Asp Ala Thr
    50                  55                  60

Tyr Ile Glu Pro Ile Thr Lys Glu Ser Ile Leu Ser Ile Ile Lys Lys
65                  70                  75                  80

Glu Lys Ile Asp Ala Ile Leu Pro Thr Met Gly Gly Gln Val Ala Leu
                85                  90                  95

Asn Val Ala Met Glu Val Tyr Glu Ser Gly Leu Leu Gly Asp Val Lys
            100                 105                 110

Phe Leu Gly Ala Asn Pro Glu Ala Ile Lys Lys Gly Glu Asp Arg Gln
        115                 120                 125

Val Phe Lys Glu Cys Met Lys Lys Ile Gly Met Asp Leu Pro Lys Ser
    130                 135                 140

Met Tyr Ala Tyr Asn Tyr Asp Glu Ala Leu Lys Ala Val Asp Glu Ile
145                 150                 155                 160

Asp Phe Pro Leu Met Ile Arg Ala Ser Tyr Thr Leu Gly Gly Ala Gly
                165                 170                 175

Ser Gly Val Val Tyr Asn Met Asp Glu Phe Lys Glu Leu Thr Asn Thr
            180                 185                 190

Ala Leu Ala Leu Ser Pro Ile His Glu Ile Leu Ile Glu Glu Ser Leu
        195                 200                 205

Leu Gly Trp Lys Glu Tyr Glu Met Glu Val Ile Arg Asp Arg Ala Asp
    210                 215                 220

Asn Cys Ile Ile Val Cys Ser Ile Glu Asn Ile Asp Pro Met Gly Val
225                 230                 235                 240

His Thr Gly Asp Ser Ile Thr Ile Ala Pro Ala Leu Thr Leu Thr Asp
                245                 250                 255

Lys Glu Tyr Gln Val Met Arg Asn Ala Ser Phe Ala Ile Leu Arg Glu
            260                 265                 270

Ile Gly Val Asp Thr Gly Gly Ser Asn Val Gln Phe Ala Ile Asn Pro
        275                 280                 285

Lys Asn Gly Arg Met Ile Val Ile Glu Met Asn Pro Arg Val Ser Arg
    290                 295                 300
```

```
Ser Ser Ala Leu Ala Ser Lys Ala Thr Gly Tyr Pro Ile Ala Lys Val
305                 310                 315                 320

Ala Thr Leu Leu Ala Val Gly Phe Ser Leu Asp Glu Ile Lys Asn Asp
                325                 330                 335

Ile Thr Gly Thr Pro Ala Ser Phe Glu Pro Val Ile Asp Tyr Ile Val
            340                 345                 350

Thr Lys Ile Pro Arg Phe Thr Phe Glu Lys Phe Pro Gly Ala Asn Thr
        355                 360                 365

Thr Leu Gly Thr Ala Met Lys Ser Val Gly Glu Val Met Ala Ile Gly
    370                 375                 380

Arg Thr Phe Lys Glu Ser Ile Gln Lys Ala Leu Cys Ser Leu Glu Arg
385                 390                 395                 400

Ser Leu Ser Gly Phe Asp Arg Val Lys Phe Glu Asp Arg Asn Asp Leu
                405                 410                 415

Val Phe Lys Ile Arg Asn Ala Asn Glu Lys Arg Leu Leu Tyr Val Ala
            420                 425                 430

Gln Ala Phe Arg Glu Gly Phe Ser Val Glu Glu Leu Tyr Glu Leu Cys
        435                 440                 445

Lys Ile Asp Pro Trp Phe Leu Thr Gln Ile Lys Glu Ile Val Asp Phe
    450                 455                 460

Glu Glu Gln Ile Asp Met Asp Ile Leu Asn Asn Lys Ala Leu Leu Arg
465                 470                 475                 480

Lys Ala Lys Thr Met Gly Phe Ser Asp Lys Met Ile Ala Leu Leu Val
                485                 490                 495

Asn Leu Lys Asp Asn Leu Glu Leu Ser Gln Asn Asp Ile Tyr Tyr Val
            500                 505                 510

Arg Met Lys Gln Lys Ile Ile Ala Glu Phe Ser Glu Val Asp Thr Cys
        515                 520                 525

Ala Gly Glu Phe Glu Ala Leu Thr Pro Tyr Leu Tyr Ser Ser Ile Asn
    530                 535                 540

Val Ser Glu Leu Thr Gln Ser Lys Asn Asp Ala Lys Asp Lys Lys Glu
545                 550                 555                 560

Lys Lys Val Met Ile Ile Gly Gly Gly Pro Asn Arg Ile Gly Gln Gly
                565                 570                 575

Ile Glu Phe Asp Tyr Ala Cys Val His Ala Ser Phe Ala Leu Lys Asp
            580                 585                 590

Met Gly Ile Lys Thr Ile Met Tyr Asn Cys Asn Pro Glu Thr Val Ser
        595                 600                 605

Thr Asp Tyr Asp Thr Ser Asp Ile Leu Tyr Phe Glu Pro Ile Asp Phe
    610                 615                 620

Glu His Leu Arg Ala Val Ile Glu Arg Glu Lys Pro Asp Gly Val Ile
625                 630                 635                 640

Val His Phe Gly Gly Gln Thr Pro Leu Lys Phe Ala Lys Arg Leu Ser
                645                 650                 655

Ala Phe Gly Ala Lys Ile Ile Gly Thr Ser Ala Arg Val Ile Asp Met
            660                 665                 670

Ala Glu Asp Arg Lys Lys Phe Ala Glu Phe Ile Thr Lys Leu Gly Ile
        675                 680                 685

Asn Gln Pro Lys Asn Ser Thr Ala Thr Ser Val Glu Glu Ala Val Leu
    690                 695                 700

Lys Ala Ser Asp Ile Gly Tyr Pro Val Leu Val Arg Pro Ser Tyr Val
705                 710                 715                 720
```

```
Leu Gly Gly Arg Ala Met Arg Val Val Asn Asp Glu Ala Glu Leu Arg
                725                 730                 735

Leu Tyr Met Gln Glu Ala Val Asp Val Ser Asp Lys Ser Pro Val Leu
            740                 745                 750

Ile Asp Gln Phe Leu Asp Asn Ala Thr Glu Ile Asp Val Asp Ala Ile
        755                 760                 765

Cys Asp Gly Lys Asp Val Tyr Val Ala Gly Ile Met Glu His Ile Glu
    770                 775                 780

Glu Ala Gly Ile His Ser Gly Asp Ser Ala Cys Ser Leu Pro Pro Cys
785                 790                 795                 800

Asn Ile Asp Glu Lys Met Gln Glu Phe Ile Ala Gln Lys Thr Ala Asp
                805                 810                 815

Ile Ala Leu Asn Leu Gly Val Val Gly Leu Leu Asn Ile Gln Phe Ala
            820                 825                 830

Leu His Asn Asn Glu Leu Tyr Met Ile Glu Val Asn Pro Arg Ala Ser
        835                 840                 845

Arg Thr Ile Pro Phe Val Ser Lys Ala Thr Gly Ile Pro Leu Ala Lys
    850                 855                 860

Val Ala Thr Arg Val Met Trp Gln Gly Asn Leu Lys Glu Ala Leu Lys
865                 870                 875                 880

Phe Tyr Asp Thr Phe Lys Val Val Asn Phe Asp Thr Lys Ile Leu Arg
                885                 890                 895

Pro Lys Thr Pro Lys Tyr Met Ser Val Lys Glu Ala Val Phe Pro Phe
            900                 905                 910

Ala Lys Leu Ser Gly Ser Asp Leu Glu Leu Gly Pro Glu Met Arg Ser
        915                 920                 925

Thr Gly Glu Val Met Gly Ile Ser Lys Asp Phe Ala Asn Ser Tyr Ala
    930                 935                 940

Lys Ser Gln Ile Ala Ser Phe Asn His Leu Pro Glu Gln Gly Val Val
945                 950                 955                 960

Phe Ile Ser Leu Lys Asp Lys Asp Lys Lys Tyr Thr Lys Lys Ile Ala
                965                 970                 975

Ala Glu Tyr Val Lys Leu Gly Phe Lys Leu Met Ala Thr Gly Gly Thr
            980                 985                 990

Cys Lys Glu Ile Leu Glu Ser Gly  Phe Glu Cys Glu Leu  Val His Lys
        995                 1000                1005

Ile Ser  Glu Gly Arg Pro Asn  Val Glu Asp Lys Leu  Lys Asn Gly
    1010                1015                1020

Glu Ile  His Leu Val Ile Asn  Thr Ser Asp Ser His  Ser Phe Lys
    1025                1030                1035

Gly Asp  Thr Lys Lys Ile Arg  Glu Asn Ile Ile Arg  Phe Lys Ile
    1040                1045                1050

Pro Tyr  Phe Thr Asn Leu Arg  Ser Ala Leu Ala Gly  Ala Lys Ser
    1055                1060                1065

Ile Lys  Ala Ile Gln Ser Lys  Ser Cys Leu Asp Val  Lys Ser Leu
    1070                1075                1080

Gln Glu  Trp Leu Lys Ser
    1085


<210> SEQ ID NO 25
<211> LENGTH: 1120
<212> TYPE: PRT
<213> ORGANISM: Campylobacter jejuni

<400> SEQUENCE: 25
```

```
Met Lys Asn Ile Thr Leu Thr Lys Ile Pro Ile Gly Glu Gly Lys Glu
1               5                   10                  15

Pro Cys Leu Asn Ser Lys Lys Ile Val Leu Ser Leu Ala Thr Ile Ser
            20                  25                  30

Phe Leu Ala Ser Cys Ala Asn Ala Lys Leu Asn Ser Glu Ile Lys Thr
        35                  40                  45

Tyr Asp Glu Val Asn Lys Asn Val Lys Thr Arg Ser Ala Ser Val Tyr
    50                  55                  60

Ser Pro Gln Ala Lys Ile Asn Thr Thr Ile Asn Ser Leu His Asn Gln
65                  70                  75                  80

Gln Val Thr Ile Thr Gly Asn Gly Thr Ser Asn Ser Leu Thr Ile Gly
                85                  90                  95

Ser Ser Gly Thr Leu Gly Ser Ile Gly Asn Thr Gly Lys Ile Ile Tyr
            100                 105                 110

Ala His Ala Asn Gly Ser Asn Thr Leu Thr Leu Ala Asn Leu Thr Asn
        115                 120                 125

Asn Arg Thr Ile Asn Gly Lys Ile Gly Ile Glu Asn Asn Gly Asn Phe
    130                 135                 140

Thr Gly Thr Ile Ala Val Asn Thr Phe Glu Asn Thr Gly Gln Ile Asn
145                 150                 155                 160

Gly Gln Ile Tyr Met Gly Ile Trp Gly Asn Asn Ser Gly Thr Leu Asn
                165                 170                 175

Ile Asp Lys Phe Asp Asn Ser Gly Thr Ile Ile Asp Asn Asn Lys Gly
            180                 185                 190

Val Phe Glu Gly Lys Asn Thr Asn Ile Gln Thr Phe Asn Asn Ser Gly
        195                 200                 205

Phe Ile Ser Ala Asn Lys Gly Val Asp Ile Gly Asn Ile Gly Thr Ile
    210                 215                 220

Lys Asn Phe Asn Asn Asn Gly Thr Ile Gln Gly Ser Glu Val Gly Val
225                 230                 235                 240

Ala Ile Asn Thr Lys Ile Asp Thr Phe Thr Asn Asn Gly Phe Ile Asn
                245                 250                 255

Ser Pro Gly Ser Gly Gln Trp Asn Asn Gly Ile Trp Ile Ser Ser Asn
            260                 265                 270

Ala Thr Ile Glu Lys Leu Val Asn Asn Gly Thr Ile Lys Gly Gly His
        275                 280                 285

Ser Ala Ile Met Val Thr Ser Gln His Ile Lys Thr Val Glu Asn Thr
    290                 295                 300

Gly Ile Ile His Ala Glu Gly Glu Trp Gly Ser Ser Ile Leu Leu Glu
305                 310                 315                 320

Tyr Gly Gly Phe Ile Glu His Ile Ile Asn Thr Gly Thr Ile Ser Asn
                325                 330                 335

Asn Asn Val Gly Ile Gly Ser Ala Tyr Gly Val Phe Gly Thr Leu Thr
            340                 345                 350

Ile Lys Asp Gly Gly Met Val Tyr Gly Lys Tyr Ser Ala Ile Gly Val
        355                 360                 365

Gly Arg Ser Gln Thr Leu Gly Asp Leu Tyr Ile Asp Gly Arg Ser Asn
    370                 375                 380

Asn Gly Thr Val Ser Gly Ile Tyr Ser Glu Glu His Gly Ile Leu Leu
385                 390                 395                 400

Glu Asn Asn Ser Arg Thr Gln Lys Ile Glu Leu Lys Asn Gly Gly Ile
                405                 410                 415
```

```
Ile Lys Gly Asn Ile Asp Gly Ile Arg Leu Ile Asn Ser Ala Ser Leu
            420                 425                 430

Ser Gly Glu Met Ile Leu Ser Gly Glu Gly Ser Arg Val Glu Gly Gly
        435                 440                 445

Arg Gly Val Gly Ile Leu Asn Arg Ser Gly Lys Ile Glu Gly Ser Ile
    450                 455                 460

Lys Val Glu Asp Gly Ala Thr Val Thr Ala Thr Ser Asn Arg Ala Ile
465                 470                 475                 480

Ala Asn Ser Gly Ser Gly Ser Ile Thr Gly Gly Ile Thr Val Ser Gly
                485                 490                 495

Lys Asn Thr Lys Leu Glu Gly Asn Ile Ile Asn Thr Gly Asn Ala Ser
            500                 505                 510

Ile Gly Ser Asp Ile Lys Ile Glu Gly Gly Ala Lys Val Glu Gly Gly
        515                 520                 525

Leu Val Asn Gln Gly Asn Gly Ser Ile Ser Gly Ser Val Gln Val Ser
    530                 535                 540

Gly Gly Ser Ser Ile Asp Ser Ile Thr Asn Glu Gly Asn Gly Ala Ile
545                 550                 555                 560

Ser Gly Ser Ile Thr Val Tyr Lys Asp Ser Lys Leu Asp Ser Ile Thr
                565                 570                 575

Asn Thr Ser Thr Ser Ser Thr Gly Ile Ser Gly Ser Ile Thr Asn Asn
            580                 585                 590

Ser Asp Asn Lys Leu Glu Ile Ser Asn Ser Gly Asn Ile Gly Gly Lys
        595                 600                 605

Ile Glu Ser Thr Gly Ser Ala Asp Met Val Ile Ser Asn Ser Asn Gly
    610                 615                 620

Gly Thr Ile Ser Gly Gly Ile Ser Ser Ser Gly Ser Gly Ser Thr Ser
625                 630                 635                 640

Ile Ser Asn Ser Gln Gly Ser Thr Ile Asn Asn Gly Ile Thr Val Ser
                645                 650                 655

Gly Ser Ala Gln Val Glu Ile Ser Asn Gln Gly Ser Val Gly Lys Asp
            660                 665                 670

Glu Asn Gly Asn Thr Val Thr Asn Asn Gly Ser Gly Ser Val Gly Ile
        675                 680                 685

Lys Asp Trp Leu Val Ser Thr Asp Lys Asn Thr Gly Lys Leu Asn Thr
    690                 695                 700

Val Val Ile Gly Gly Ser Arg Ala Phe Asn Val Lys Val Glu Asn Ile
705                 710                 715                 720

Thr Val Asp Gln Ser Asn Val Asp Leu Glu Glu Leu Asn Asp Ile Asn
                725                 730                 735

Asn Ile Ile Ser Gly Val Asn Gln Asn Asn Ile Gly Asn Ile Gly Thr
            740                 745                 750

Asn Gly Ser Gly Glu Ile Ser Leu Ser Phe Asp Pro Ile Thr Gly Lys
        755                 760                 765

Leu Thr Thr Asp Phe Asn Leu Asn Ala Ser Ile Ser Gly Ala Thr Phe
    770                 775                 780

Arg Ser Leu Ile Ser Thr Thr Ser Arg Arg Ser Thr Phe Ile Asp Asn
785                 790                 795                 800

Val Met Gly Asn Ser Met Gln Ser Phe Ala Leu Ala Ser Ser Ser Lys
                805                 810                 815

Ser Gln Ser Ile Ala Met Ser Glu Lys Gly Asn Leu Tyr Ala Asp Ala
            820                 825                 830

Ser Asp Tyr Ile Lys Ser Asp Leu Asn Asn Gly Ser Tyr Gly Ser Asn
```

835 840 845

Lys Glu His Ser Leu Phe Ile Leu Pro Tyr Thr Ser Ser Gln Asn Val
850 855 860

Glu Leu Ser Leu Asn Glu Glu Ser Lys Gly His Thr Lys Gly Thr Ile
865 870 875 880

Ile Gly Tyr Ser Thr Leu Lys Asp Ser Gly Ile Tyr Gly Val Tyr Ala
885 890 895

Gly Tyr Glu Asp Thr Lys Met Gly Ser Thr Tyr Phe Asp Ile Asn Asn
900 905 910

Arg Thr Tyr Tyr Ala Gly Leu Lys Tyr Phe Asn Thr Leu Phe Thr Thr
915 920 925

Glu Lys Gly Gln Glu Val Tyr Ile Lys Ala Gln Gly Lys Ala Ala Leu
930 935 940

Ile Lys Asn Asp Leu Thr Glu Lys Ile Gly Asn Asn Glu Ala Lys Ala
945 950 955 960

Glu Pro Asn Ser Tyr Ala Tyr Gly Val Asn Thr Ala Leu Gly Met Asn
965 970 975

Phe Ile Ser Asn Lys Asp Ile Phe Ser Pro Glu Ile Gly Leu Ala Tyr
980 985 990

Glu Gly Gly Tyr Thr Glu Ala Phe Ser Met Lys Asp Thr Ile Gly Gln
995 1000 1005

Ala Thr Val Lys Gly Gly Glu Arg Thr Tyr Ala Asn Tyr Leu Asn
1010 1015 1020

Leu Phe Ser Thr Lys Thr Ser Leu Thr Trp Phe Arg Asp Trp Leu
1025 1030 1035

Pro Asn Leu Lys Thr Ser Val Glu Leu Gly Ala Lys Phe Asn Ile
1040 1045 1050

Asn Pro Lys Val Glu Ala Glu Ala Arg Phe Gly Asn Ile Lys Val
1055 1060 1065

Ser Asp Glu Phe Asp Leu Pro Arg Val Gln Lys Phe Val Ser Thr
1070 1075 1080

Ser Phe Ile Val Pro Val Asn Glu Ala Phe Tyr Phe Ser Leu Asn
1085 1090 1095

Tyr Asn Gly Met Phe Asp Lys Asp Gly Asn Thr His Thr Gly Phe
1100 1105 1110

Ala Gln Phe Asn Tyr Leu Trp
1115 1120

<210> SEQ ID NO 26
<211> LENGTH: 1144
<212> TYPE: PRT
<213> ORGANISM: Campylobacter jejuni

<400> SEQUENCE: 26

Met Asn Lys Thr Ala Leu Thr Lys Thr Tyr Thr Lys Asp Ile Gln Asn
1 5 10 15

Ser Cys Leu Asn Ser Lys Lys Ile Val Leu Ser Leu Ala Thr Ile Ser
20 25 30

Phe Leu Ala Ser Cys Thr His Ala Thr Leu Thr Pro Glu Ile Lys Thr
35 40 45

Tyr Glu Glu Thr Asn Arg His Ala Lys Ala Arg Ser Gly Leu Gln Ser
50 55 60

Arg Asn Ser Asn Asn Glu Thr Ile Asn Asn Leu Gln Thr Leu Thr Lys
65 70 75 80

```
Thr Ile Ser Asp Thr Gly Asn Thr Leu Val Ile Glu Ser Ser Gly Thr
                85                  90                  95

Ile Thr Ile Ser Asn Asp Gly Gln Gln Ala Val Asn Phe Gln Pro Asn
            100                 105                 110

Ser Ser Thr Ser Thr Phe Leu Asn Lys Gly Thr Leu Ile Gly Gly Asn
        115                 120                 125

Asn Thr Ala Ser Val Gln Leu Gly Ala Ala Asn Gly Asn Asn Gly Val
    130                 135                 140

Ser Ile Glu Thr Phe Asn Asn Gln Gly Ile Ile Gly Asn Gly Ser Ser
145                 150                 155                 160

Lys Phe Gly Val Thr Val Phe Gly Gly Gly Ser Lys Asp Asn Pro Lys
                165                 170                 175

Ser Ile Ile Asn Asn Phe Ser Asn Ser Gly Thr Ile His Ser Asn Thr
            180                 185                 190

Gly Glu Ser Ile Tyr Phe Gly Asn Ala Lys Ile Ser Ser Phe Val Asn
        195                 200                 205

Ser Gly Thr Ile Lys Ser Lys Gln Gly Ala Gly Val Asn Ile Ser Gln
    210                 215                 220

Gly Thr Ser Ile Glu Asn Phe Asn Asn Thr Gly Thr Gly Ile Ile Glu
225                 230                 235                 240

Gly Lys Arg Met Gly Val Asn Val Arg Ser Thr Ile Asn Thr Phe Val
                245                 250                 255

Asn Asp Gly Leu Ile Ala Ala Thr Asn Asp Gly Ile Gln Ile Asn Ala
            260                 265                 270

Asn Val Lys Thr Leu Ile Asn Lys Gly Thr Ile Lys Gly Asp Ala Ile
        275                 280                 285

Ser Ile Arg Ser Leu Gly Gly Thr Ile Glu Thr Leu Thr Asn Glu Gly
    290                 295                 300

Ile Met Tyr Gly Lys Ser Ala Gly Ile Tyr Met Asn Arg Ser Leu Val
305                 310                 315                 320

Lys Thr Leu Thr Asn Ser Gly Thr Ile Asn Gln Asn Asn Ser Ala Thr
                325                 330                 335

Trp Ser Ala Gly Ile Lys Leu Glu Asn Gly Ser Ile Ile Glu Asn Ile
            340                 345                 350

Ile Asn Thr Gly Ser Ile Arg Ser Asn Ala Phe Gly Ile Ser Val Thr
        355                 360                 365

Gly Gly Lys Phe Gly Thr Leu Thr Ile Lys Asp Gly Gly Met Val Tyr
    370                 375                 380

Gly Lys Tyr Ser Ala Ile Gly Val Gly Arg Ser Gln Thr Leu Gly Asp
385                 390                 395                 400

Leu Tyr Ile Asp Gly Arg Ser Asn Asn Gly Thr Val Ser Gly Ile Tyr
                405                 410                 415

Ser Glu Glu His Gly Ile Leu Leu Glu Asn Asn Ser Arg Thr Gln Lys
            420                 425                 430

Ile Glu Leu Lys Asn Gly Gly Ile Ile Lys Gly Asn Ile Asp Gly Ile
        435                 440                 445

Arg Leu Ile Asn Ser Ala Ser Leu Ser Gly Glu Met Ile Leu Ser Gly
    450                 455                 460

Glu Gly Ser Arg Val Glu Gly Gly Arg Gly Val Gly Ile Leu Asn Arg
465                 470                 475                 480

Ser Gly Lys Ile Glu Gly Ser Ile Lys Val Glu Asp Gly Ala Thr Val
                485                 490                 495

Thr Ala Thr Ser Asn Arg Ala Ile Ala Asn Ser Gly Ser Gly Ser Ile
```

```
            500                 505                 510

Thr Gly Gly Ile Thr Val Ser Gly Lys Asn Thr Lys Leu Glu Gly Asn
        515                 520                 525

Ile Ile Asn Thr Gly Asn Ala Ser Ile Gly Ser Asp Ile Lys Ile Glu
    530                 535                 540

Gly Gly Ala Lys Val Glu Gly Gly Leu Val Asn Gln Gly Asn Gly Ser
545                 550                 555                 560

Ile Ser Gly Ser Val Gln Val Ser Gly Gly Ser Ser Ile Asp Ser Ile
                565                 570                 575

Thr Asn Glu Gly Asn Gly Ala Ile Ser Gly Ser Ile Thr Val Tyr Lys
            580                 585                 590

Asp Ser Lys Leu Asp Ser Ile Thr Asn Thr Ser Thr Ser Ser Thr Gly
        595                 600                 605

Ile Ser Gly Ser Ile Thr Asn Asn Ser Asp Asn Lys Leu Glu Ile Ser
    610                 615                 620

Asn Ser Gly Asn Ile Gly Gly Lys Ile Glu Ser Thr Gly Ser Ala Asp
625                 630                 635                 640

Met Val Ile Ser Asn Ser Asn Gly Gly Thr Ile Ser Gly Gly Ile Ser
                645                 650                 655

Ser Ser Gly Ser Gly Ser Thr Ser Ile Ser Asn Ser Gln Gly Ser Thr
            660                 665                 670

Ile Asn Asn Gly Ile Thr Val Ser Gly Ser Ala Gln Val Glu Ile Ser
        675                 680                 685

Asn Gln Gly Ser Val Gly Lys Asp Glu Asn Gly Asn Thr Val Thr Asn
    690                 695                 700

Asn Gly Ser Gly Ser Val Gly Ile Lys Asp Trp Leu Val Ser Thr Asp
705                 710                 715                 720

Lys Asn Thr Gly Lys Leu Asn Thr Val Val Ile Gly Gly Ser Arg Ala
                725                 730                 735

Phe Asn Val Lys Val Glu Asn Ile Thr Val Asp Gln Ser Asn Val Asp
            740                 745                 750

Leu Glu Glu Leu Asn Asp Ile Asn Asn Ile Ile Ser Gly Val Asn Gln
        755                 760                 765

Asn Asn Ile Gly Asn Ile Gly Thr Asn Gly Ser Gly Glu Ile Ser Leu
    770                 775                 780

Ser Phe Asp Pro Ile Thr Gly Lys Leu Thr Thr Asp Phe Asn Leu Asn
785                 790                 795                 800

Ala Ser Ile Ser Gly Ala Thr Phe Arg Ser Leu Ile Ser Thr Thr Ser
                805                 810                 815

Arg Arg Ser Thr Phe Ile Asp Asn Val Met Gly Asn Ser Met Gln Ser
            820                 825                 830

Phe Ala Leu Ala Ser Ser Ser Lys Ser Gln Ser Ile Ala Met Ser Glu
        835                 840                 845

Lys Gly Asn Leu Tyr Ala Asp Ala Ser Asp Tyr Ile Lys Ser Asp Leu
    850                 855                 860

Asn Asn Gly Ser Tyr Gly Ser Asn Lys Glu His Ser Leu Phe Ile Leu
865                 870                 875                 880

Pro Tyr Thr Ser Ser Gln Asn Val Glu Leu Ser Leu Asn Glu Glu Ser
                885                 890                 895

Lys Gly His Thr Lys Gly Thr Ile Ile Gly Tyr Ser Thr Leu Lys Asp
            900                 905                 910

Ser Gly Ile Tyr Gly Val Tyr Ala Gly Tyr Glu Asp Thr Lys Met Gly
        915                 920                 925
```

```
Ser Thr Tyr Phe Asp Ile Asn Asn Arg Thr Tyr Tyr Ala Gly Leu Lys
    930                 935                 940

Tyr Phe Asn Thr Leu Phe Thr Thr Glu Lys Gly Gln Glu Val Tyr Ile
945                 950                 955                 960

Lys Ala Gln Gly Lys Ala Ala Leu Ile Lys Asn Asp Leu Thr Glu Lys
                965                 970                 975

Ile Gly Asn Asn Glu Ala Lys Ala Glu Pro Asn Ser Tyr Ala Tyr Gly
            980                 985                 990

Val Asn Thr Ala Leu Gly Met Asn  Phe Ile Ser Asn Lys  Asp Ile Phe
        995                 1000                 1005

Ser Pro  Glu Ile Gly Leu Ala  Tyr Glu Gly Gly Tyr  Thr Glu Ala
    1010                 1015                 1020

Phe Ser  Met Lys Asp Thr Ile  Gly Gln Ala Thr Val  Lys Gly Gly
    1025                 1030                 1035

Glu Arg  Thr Tyr Ala Asn Tyr  Leu Asn Leu Phe Ser  Thr Lys Thr
    1040                 1045                 1050

Ser Leu  Thr Trp Phe Arg Asp  Trp Leu Pro Asn Leu  Lys Thr Ser
    1055                 1060                 1065

Val Glu  Leu Gly Ala Lys Phe  Asn Ile Asn Pro Lys  Val Glu Ala
    1070                 1075                 1080

Glu Ala  Arg Phe Gly Asn Ile  Lys Val Ser Asp Glu  Phe Asp Leu
    1085                 1090                 1095

Pro Arg  Val Gln Lys Phe Val  Ser Thr Ser Phe Ile  Val Pro Val
    1100                 1105                 1110

Asn Glu  Ala Phe Tyr Phe Ser  Leu Asn Tyr Asn Gly  Met Phe Asp
    1115                 1120                 1125

Lys Asp  Gly Asn Thr His Thr  Gly Phe Ala Gln Phe  Asn Tyr Leu
    1130                 1135                 1140

Trp


<210> SEQ ID NO 27
<211> LENGTH: 1186
<212> TYPE: PRT
<213> ORGANISM: Campylobacter jejuni

<400> SEQUENCE: 27

Met Gly Lys Ile Met Lys Thr Met Asp Gly Asn Glu Ala Ala Ala Tyr
1               5                   10                  15

Ala Ala Tyr Ala Phe Thr Glu Val Ala Gly Ile Tyr Pro Ile Thr Pro
            20                  25                  30

Ser Ser Pro Met Ala Asp Tyr Thr Asp Met Trp Ala Ala Ala Gly Lys
        35                  40                  45

Lys Asn Leu Phe Gly Val Pro Val Lys Ile Val Glu Met Gln Ser Glu
    50                  55                  60

Ala Gly Ala Ala Gly Ser Val His Gly Ser Leu Gln Ala Gly Ala Leu
65                  70                  75                  80

Thr Thr Thr Tyr Thr Ala Ser Gln Gly Leu Leu Leu Lys Ile Pro Asn
                85                  90                  95

Met Tyr Lys Ile Ala Gly Gln Leu Leu Pro Cys Val Ile His Val Ala
            100                 105                 110

Ala Arg Ser Leu Ala Ala Gln Ala Leu Ser Ile Phe Gly Asp His Gln
        115                 120                 125

Asp Ile Tyr Ala Ala Arg Gln Ile Gly Phe Ala Met Leu Cys Ser His
    130                 135                 140
```

```
Ser Val Gln Glu Thr Met Asp Leu Ala Gly Val Ala His Leu Ala Ala
145                 150                 155                 160

Ile Lys Gly Arg Val Pro Phe Leu His Phe Phe Asp Gly Phe Arg Thr
                165                 170                 175

Ser His Glu Ile Gln Lys Val Glu Val Met Asp Tyr Ala His Phe Asp
            180                 185                 190

Arg Leu Leu Asp Arg Glu Ala Leu Leu Glu Phe Arg Asn Asn Ala Leu
        195                 200                 205

Asn Pro Glu Asn Pro Lys Thr Arg Gly Thr Ala Gln Asn Asp Asp Ile
    210                 215                 220

Tyr Phe Gln Thr Arg Glu Val Ser Asn Arg Phe Tyr Asp Ala Leu Pro
225                 230                 235                 240

Asp Val Val Asn Glu Tyr Met Gln Glu Ile Ser Lys Ile Thr Gly Arg
                245                 250                 255

Glu Tyr Lys Pro Phe Thr Tyr Tyr Gly His Lys Glu Pro Glu Cys Val
            260                 265                 270

Ile Val Ala Met Gly Ser Val Thr Gln Ala Leu Glu Glu Val Val Asp
        275                 280                 285

Tyr Leu Asn Ala Lys Gly Glu Lys Val Gly Ile Leu Lys Val Tyr Leu
    290                 295                 300

Tyr Arg Pro Phe Ser Leu Lys Tyr Phe Phe Asp Val Met Pro Lys Ser
305                 310                 315                 320

Val Lys Lys Ile Ala Val Leu Asp Arg Thr Lys Glu Pro Gly Ser Leu
                325                 330                 335

Gly Glu Pro Leu Tyr Leu Asp Val Lys Ser Ala Phe Tyr Gly Arg Glu
            340                 345                 350

Asn Ala Pro Val Ile Val Gly Gly Arg Tyr Gly Leu Ser Ser Lys Asp
        355                 360                 365

Val Asp Pro Ala Gln Met Ile Ala Val Phe Glu Asn Leu Lys Leu Asp
    370                 375                 380

Asn Pro Lys Asp Gly Phe Thr Val Gly Ile Ile Asp Asp Val Thr His
385                 390                 395                 400

Thr Ser Leu Ser Thr Gly Glu Lys Ile Ser Leu Gly Asp Glu Ser Thr
                405                 410                 415

Ile Glu Cys Leu Phe Tyr Gly Leu Gly Ala Asp Gly Thr Val Gly Ala
            420                 425                 430

Asn Lys Asn Ser Ile Lys Ile Ile Gly Asp Lys Thr Asp Phe Tyr Ala
        435                 440                 445

Gln Ala Tyr Phe Ala Tyr Asp Ser Lys Lys Ser Gly Gly Tyr Thr Arg
    450                 455                 460

Ser His Leu Arg Phe Ser Lys Lys Pro Ile Arg Ser Thr Tyr Leu Val
465                 470                 475                 480

Ser Thr Pro His Phe Ile Ala Cys Ser Val Ala Ala Tyr Leu Glu Ile
                485                 490                 495

Tyr Asp Val Leu Ala Gly Ile Arg Lys Gly Gly Thr Phe Leu Leu Asn
            500                 505                 510

Ser Ile Trp Asn Ala Glu Glu Thr Ile Arg Gln Leu Pro Asp Ala Val
        515                 520                 525

Lys Lys Thr Leu Ala Glu Lys Glu Val Asn Phe Tyr Ile Ile Asn Ala
    530                 535                 540

Thr Lys Leu Ala Arg Asp Ile Gly Leu Gly Asn Arg Thr Asn Thr Ile
545                 550                 555                 560
```

```
Met Gln Ser Ala Phe Phe Lys Leu Ala Lys Ile Ile Pro Tyr Glu Asp
                565                 570                 575

Ala Gln Lys Tyr Met Lys Glu Leu Ala Tyr Lys Ser Tyr Ser Lys Lys
            580                 585                 590

Gly Asp Ala Ile Val Glu Met Asn Tyr Lys Ala Ile Asp Val Gly Ala
        595                 600                 605

Asp Gly Leu Val Lys Val Glu Val Asp Pro Asn Trp Lys Asn Leu Glu
    610                 615                 620

Leu Lys Glu Lys Glu Gln Thr Asn Ala Tyr Lys Gly Thr Glu Phe Val
625                 630                 635                 640

Glu Lys Ile Val Lys Pro Met Asn Ala Ala Lys Gly Asp Asp Leu Pro
                645                 650                 655

Val Ser Ala Phe Leu Gly Tyr Glu Asp Gly Ser Phe Glu His Gly Thr
            660                 665                 670

Thr Glu Tyr Glu Lys Arg Gly Val Gly Val Met Val Pro Arg Trp Ile
        675                 680                 685

Glu Ala Asn Cys Ile Gln Cys Asn Gln Cys Ala Ser Val Cys Pro His
    690                 695                 700

Ala Val Ile Arg Pro Phe Leu Ile Asn Asp Glu Glu Met Ala Asn Ala
705                 710                 715                 720

Pro Arg Gly Val Lys Asp His Ala Leu Glu Ala Lys Gly Thr Lys Gly
                725                 730                 735

Glu Lys Leu Ser Phe Lys Ile Gln Val Ser Pro Leu Asp Cys Thr Gly
            740                 745                 750

Cys Glu Leu Cys Val His Glu Cys Pro Thr Lys Glu Lys Ser Leu Val
        755                 760                 765

Met Val Pro Leu Gln Glu Glu Met Asp Phe Gly Glu Gln Glu Asn Ala
    770                 775                 780

Asp Tyr Leu Phe Lys Glu Ile Thr Tyr Lys Asp Asp Ile Leu Asn Lys
785                 790                 795                 800

Glu Thr Thr Lys Gly Ala Gln Phe Ala Gln Pro Leu Phe Glu Phe His
                805                 810                 815

Gly Ala Cys Pro Gly Cys Gly Glu Thr Pro Tyr Ile Thr Leu Ile Thr
            820                 825                 830

Arg Leu Phe Gly Glu Arg Met Ile Val Ala Asn Ala Thr Gly Cys Ser
        835                 840                 845

Ser Ile Tyr Gly Gly Ser Ala Pro Ser Thr Pro Tyr Arg Lys Ser Val
    850                 855                 860

Lys Asn Gly His Gly Pro Ala Trp Gly Asn Ser Leu Phe Glu Asp Asn
865                 870                 875                 880

Ala Glu Phe Gly Leu Gly Met Lys Ile Ala Thr Glu Asn Thr Arg His
                885                 890                 895

Arg Ile Glu His Ile Met Asn Glu Ser Met Gln Glu Val Pro Asn Ala
            900                 905                 910

Leu Ser Ala Leu Phe Lys Asp Trp Ile Ala Asn Lys Asp Asn Gly Ala
        915                 920                 925

Met Ser Val Glu Ile Lys Asp Lys Met Ile Pro Ile Leu Glu Gln Asn
    930                 935                 940

Lys Asn Ile Lys Ala Val Gln Asp Ile Leu Glu Leu Lys Gln Tyr Leu
945                 950                 955                 960

Ser Lys Lys Ser His Trp Ile Phe Gly Gly Asp Gly Trp Ala Tyr Asp
                965                 970                 975

Ile Gly Tyr Gly Gly Leu Asp His Val Leu Ala Ser Gly Glu Asn Val
```

```
            980                 985                 990

Asn Ile Leu Val Leu Asp Thr Glu  Val Tyr Ser Asn Thr  Gly Gly Gln
        995                 1000                1005

Ser Ser  Lys Ser Ser Arg Thr  Gly Ala Val Ala Gln  Phe Ala Ala
    1010                1015                1020

Ala Gly  Lys Pro Ile Gln Lys  Lys Asp Leu Gly Gln  Ile Ala Met
    1025                1030                1035

Thr Tyr  Gly Tyr Ile Phe Val  Ala Gln Val Asn Ser  Thr Ala Asn
    1040                1045                1050

Tyr Thr  His Leu Ile Lys Ala  Ile Thr Ala Ala Glu  Ala Tyr Asp
    1055                1060                1065

Gly Pro  Ser Leu Val Ile Cys  Tyr Ser Pro Cys Ile  Ala His Gly
    1070                1075                1080

Ile Lys  Gly Gly Leu Gly Tyr  Ser Gly Glu Gln Gly  Glu Leu Ala
    1085                1090                1095

Thr Lys  Cys Gly Tyr Trp Pro  Leu Tyr Thr Phe Asp  Pro Arg Leu
    1100                1105                1110

Glu Glu  Gln Gly Lys Asn Pro  Leu Thr Leu Thr Gly  Lys Glu Pro
    1115                1120                1125

Asp Trp  Asp Leu Tyr Glu Gln  Phe Leu Met Asn Glu  Val Arg Tyr
    1130                1135                1140

Asn Ser  Leu Lys Lys Ala Asn  Pro Glu His Ala Ala  Glu Leu Phe
    1145                1150                1155

Glu Arg  Asn Lys Lys Asp Ala  Gln Arg Arg Tyr Arg  Gln Leu Lys
    1160                1165                1170

Arg Ile  Ala Met Ala Asp Tyr  Ser Asn Glu Val Glu  Ser
    1175                1180                1185


<210> SEQ ID NO 28
<211> LENGTH: 1378
<212> TYPE: PRT
<213> ORGANISM: Campylobacter jejuni

<400> SEQUENCE: 28

Met Cys Asp Met Leu Asp Asn Lys Leu Gly Asn Arg Leu Arg Val Asp
1               5                   10                  15

Phe Ser Asn Ile Ser Lys Gln Ile Glu Ile Pro Asn Leu Leu Gln Leu
            20                  25                  30

Gln Lys Lys Ser Phe Asp Tyr Phe Leu Asn Leu Asp Asn Gly Glu Ser
        35                  40                  45

Gly Ile Glu Lys Val Phe Lys Ser Ile Phe Pro Ile His Asp Pro Gln
    50                  55                  60

Asn Arg Leu Ser Leu Glu Tyr Val Ser Ser Glu Ile Gly Lys Pro Lys
65                  70                  75                  80

Tyr Thr Ile Arg Glu Cys Met Glu Arg Gly Leu Thr Tyr Ser Val Asn
                85                  90                  95

Leu Lys Met Lys Ile Arg Leu Thr Leu His Glu Lys Asp Glu Lys Thr
            100                 105                 110

Gly Glu Lys Val Gly Val Lys Asp Ile Lys Glu Gln Glu Ile Tyr Ile
        115                 120                 125

Arg Glu Ile Pro Leu Met Thr Asp Arg Val Ser Phe Ile Ile Asn Gly
    130                 135                 140

Val Glu Arg Val Val Val Asn Gln Leu His Arg Ser Pro Gly Val Ile
145                 150                 155                 160
```

```
Phe Lys Glu Glu Glu Ser Ser Thr Val Ala Asn Lys Leu Val Tyr Thr
                165                 170                 175

Ala Gln Ile Ile Pro Asp Arg Gly Ser Trp Leu Tyr Phe Glu Tyr Asp
            180                 185                 190

Ala Lys Asp Val Leu Tyr Val Arg Ile Asn Lys Arg Arg Lys Val Pro
        195                 200                 205

Val Thr Met Leu Phe Arg Ala Leu Gly Tyr Lys Lys Gln Asp Ile Ile
    210                 215                 220

Lys Leu Phe Tyr Pro Ile Gln Thr Ile His Val Lys Lys Asp Lys Phe
225                 230                 235                 240

Leu Thr Glu Phe Asn Pro Asn Asp Phe Met Asp Arg Ile Glu Tyr Asp
                245                 250                 255

Ile Lys Asp Glu Lys Gly Lys Ile Val His Gln Ala Gly Lys Arg Leu
            260                 265                 270

Thr Lys Lys Lys Ala Glu Gln Leu Ile Lys Asp Gly Leu Lys Trp Ile
        275                 280                 285

Glu Tyr Pro Val Glu Ile Leu Leu Asn Arg Tyr Leu Ala Asn Pro Ile
    290                 295                 300

Ile Asp Lys Glu Ser Gly Glu Val Leu Phe Asp Ser Leu Thr Leu Leu
305                 310                 315                 320

Asp Glu Ser Lys Leu Ala Lys Ile Lys Glu Gln Lys Ser Phe Asp Ile
                325                 330                 335

Ala Asn Asp Leu Ala Asn Gly Val Asp Ala Ala Ile Ile Asn Ser Phe
            340                 345                 350

Ala Gln Asp Gly Glu Thr Leu Lys Leu Leu Lys Gln Ser Glu Asn Ile
        355                 360                 365

Asp Asp Glu Asn Asp Leu Ala Ala Ile Arg Ile Tyr Lys Val Met Arg
    370                 375                 380

Pro Gly Glu Pro Val Val Lys Asp Ala Ala Lys Ala Phe Val Asn Asp
385                 390                 395                 400

Leu Phe Phe Asn Pro Glu Arg Tyr Asp Leu Thr Lys Val Gly Arg Met
                405                 410                 415

Lys Met Asn His Lys Leu Gly Leu Glu Val Pro Glu Tyr Val Thr Val
            420                 425                 430

Leu Thr Asn Glu Asp Ile Ile Lys Thr Ala Lys Tyr Leu Ile Lys Val
        435                 440                 445

Lys Asn Gly Lys Gly His Ile Asp Asp Arg Asp His Leu Gly Asn Arg
    450                 455                 460

Arg Ile Arg Ser Ile Gly Glu Leu Leu Ala Asn Glu Leu His Leu Gly
465                 470                 475                 480

Leu Ala Lys Met Gln Lys Ala Ile Arg Asp Lys Phe Thr Ser Leu Asn
                485                 490                 495

Ala Asp Leu Asp Lys Val Met Pro Tyr Asp Leu Ile Asn Pro Lys Met
            500                 505                 510

Ile Thr Thr Thr Ile Ile Glu Phe Phe Thr Gly Gly Gln Leu Ser Gln
        515                 520                 525

Phe Met Asp Gln Thr Asn Pro Leu Ser Glu Val Thr His Lys Arg Arg
    530                 535                 540

Leu Ser Ala Leu Gly Glu Gly Gly Leu Val Lys Glu Arg Ala Gly Phe
545                 550                 555                 560

Glu Val Arg Asp Val His Ala Thr His Tyr Gly Arg Ile Cys Pro Val
                565                 570                 575

Glu Thr Pro Glu Gly Gln Asn Ile Gly Leu Ile Asn Thr Leu Ser Thr
```

```
            580                 585                 590

Tyr Ala Lys Val Asn Glu Leu Gly Phe Val Glu Ala Pro Tyr Arg Lys
        595                 600                 605

Val Val Asn Gly Lys Val Thr Asn Glu Val Val Tyr Leu Thr Ala Thr
    610                 615                 620

Gln Glu Glu Gly Leu Phe Ile Ala Pro Ala Ser Thr Lys Val Asp Ala
625                 630                 635                 640

Lys Gly Asn Ile Val Glu Glu Phe Val Glu Ala Arg Gln Asp Gly Glu
                645                 650                 655

Thr Ile Leu Ala Arg Arg Glu Glu Val Gln Leu Ile Asp Leu Cys Ser
            660                 665                 670

Gly Met Val Val Gly Val Ala Ala Ser Leu Ile Pro Phe Leu Glu His
        675                 680                 685

Asp Asp Ala Asn Arg Ala Leu Met Gly Ser Asn Met Gln Arg Gln Ala
    690                 695                 700

Val Pro Leu Leu Thr Ala Ser Ala Pro Ile Val Gly Thr Gly Met Glu
705                 710                 715                 720

Gln Ile Ile Ala Arg Asp Ala Trp Glu Ala Val Lys Ala Lys Arg Gly
                725                 730                 735

Gly Val Val Glu Lys Val Asp Asn Lys Ser Ile Phe Ile Leu Gly Glu
            740                 745                 750

Asp Asp Lys Gly Pro Phe Ile Asp His Tyr Thr Met Glu Lys Asn Leu
        755                 760                 765

Arg Thr Asn Gln Asn Thr Asn Tyr Ile Gln His Pro Ile Val Lys Lys
    770                 775                 780

Gly Asp Ile Val Lys Ala Gly Gln Ile Ile Ala Asp Gly Pro Ser Met
785                 790                 795                 800

Asp Gln Gly Glu Leu Ala Ile Gly Lys Asn Ala Leu Ile Ala Phe Met
                805                 810                 815

Pro Trp Asn Gly Tyr Asn Tyr Glu Asp Ala Ile Val Val Ser Glu Arg
            820                 825                 830

Ile Ile Arg Glu Asp Thr Phe Thr Ser Val His Ile Tyr Glu Lys Glu
        835                 840                 845

Ile Glu Ala Arg Glu Leu Lys Asp Gly Ile Glu Glu Ile Thr Lys Asp
    850                 855                 860

Ile Pro Asn Val Lys Glu Glu Asp Val Ala His Leu Asp Glu Ser Gly
865                 870                 875                 880

Ile Ala Lys Ile Gly Thr His Ile Lys Pro Gly Met Ile Leu Val Gly
                885                 890                 895

Lys Val Ser Pro Lys Gly Glu Val Lys Pro Thr Pro Glu Glu Arg Leu
            900                 905                 910

Leu Arg Ala Ile Phe Gly Glu Lys Ala Gly His Val Val Asn Lys Ser
        915                 920                 925

Leu Tyr Ala Thr Ala Ser Leu Glu Gly Val Val Val Asp Val Lys Ile
    930                 935                 940

Phe Thr Lys Lys Gly Tyr Glu Lys Asp Asp Arg Ala Ile Lys Ser Tyr
945                 950                 955                 960

Asp Lys Glu Lys Met Ala Leu Glu Lys Glu His His Asp Arg Leu Leu
                965                 970                 975

Met Met Asp Arg Glu Glu Met Leu Arg Val Cys Ala Leu Leu Ser Lys
            980                 985                 990

Ala Ser Leu Asn Ser Asp Gln Lys  Ile Gly Asp Lys Asn  Tyr Lys Lys
        995                 1000                1005
```

```
Gly Gln  Thr Ala Asp Ile Ser  Glu Leu Glu Lys Ile  Asn Arg Phe
    1010                 1015                 1020

Thr Leu  Thr Thr Leu Ile Lys  Ala Tyr Ser Lys Glu  Ile Gln Lys
    1025                 1030                 1035

Glu Tyr  Asp Asp Leu Lys Asn  His Phe Gln Asn Glu  Lys Lys Lys
    1040                 1045                 1050

Leu Lys  Ala Glu His Asp Glu  Lys Leu Glu Ile Leu  Glu Lys Asp
    1055                 1060                 1065

Asp Ile  Leu Pro Ser Gly Val  Ile Lys Leu Val Lys  Val Tyr Ile
    1070                 1075                 1080

Ala Thr  Lys Arg Lys Leu Lys  Val Gly Asp Lys Met  Ala Gly Arg
    1085                 1090                 1095

His Gly  Asn Lys Gly Ile Val  Ser Thr Ile Val Pro  Glu Val Asp
    1100                 1105                 1110

Met Pro  Tyr Leu Pro Asn Gly  Lys Ser Val Asp Ile  Ala Leu Asn
    1115                 1120                 1125

Pro Leu  Gly Val Pro Ser Arg  Met Asn Ile Gly Gln  Ile Leu Glu
    1130                 1135                 1140

Ser His  Leu Gly Leu Val Gly  Leu Arg Leu Gly Asp  Gln Ile Gln
    1145                 1150                 1155

Glu Ile  Phe Asp Arg Lys Gln  Lys Asp Phe Leu Lys  Glu Leu Arg
    1160                 1165                 1170

Ala Lys  Ile Leu Glu Ile Cys  Ser Ile Pro Arg Leu  Ala Asn Glu
    1175                 1180                 1185

Lys Glu  Phe Ile Lys Ser Leu  Ser Asp Glu Glu Leu  Leu Asn Tyr
    1190                 1195                 1200

Ala Arg  Asp Trp Ser Lys Gly  Val Lys Phe Ser Thr  Pro Val Phe
    1205                 1210                 1215

Glu Gly  Val Asn Ile Glu Glu  Phe Ser Lys Leu Phe  Lys Met Ala
    1220                 1225                 1230

Lys Ile  Asp Met Asp Gly Lys  Thr Glu Leu Tyr Asp  Gly Arg Thr
    1235                 1240                 1245

Gly Glu  Lys Ile Ala Glu Arg  Val His Val Gly Cys  Met Tyr Met
    1250                 1255                 1260

Leu Lys  Leu His His Leu Val  Asp Glu Lys Val His  Ala Arg Ser
    1265                 1270                 1275

Thr Gly  Pro Tyr Ser Leu Val  Thr Gln Gln Pro Val  Gly Gly Lys
    1280                 1285                 1290

Ala Leu  Phe Gly Gly Gln Arg  Phe Gly Glu Met Glu  Val Trp Ala
    1295                 1300                 1305

Leu Glu  Ala Tyr Gly Ala Ala  His Thr Leu Arg Glu  Met Leu Thr
    1310                 1315                 1320

Ile Lys  Ser Asp Asp Val Glu  Gly Arg Phe Ser Ala  Tyr Lys Ala
    1325                     1330                 1335

Leu Thr  Lys Gly Glu Asn Val  Pro Ala Thr Gly Ile  Pro Glu Thr
    1340                 1345                 1350

Phe Phe  Val Leu Thr Asn Glu  Leu Lys Ser Leu Ala  Leu Asp Val
    1355                 1360                 1365

Glu Ile  Phe Asp Lys Asp Glu  Asp Asn Glu
    1370                 1375

<210> SEQ ID NO 29
<211> LENGTH: 1496
```

<212> TYPE: PRT
<213> ORGANISM: Campylobacter jejuni

<400> SEQUENCE: 29

```
Met Asp Leu Glu Asn Ile Leu Glu Asn Asn Gln Ser Ile Gly Leu Tyr
1               5                   10                  15

His Pro Lys Asn Glu His Asp Ala Cys Gly Ile Ala Ala Val Ala Asn
            20                  25                  30

Ile Arg Gly Ile Ala Ser Tyr Lys Val Ile Cys Asp Ala Leu Glu Ile
        35                  40                  45

Leu Met Asn Leu Glu His Arg Gly Gly Thr Gly Ala Glu Glu Asn Ser
    50                  55                  60

Gly Asp Gly Ala Gly Ile Leu Ile Gln Ile Pro His Asp Phe Phe Lys
65                  70                  75                  80

Thr Gln Glu Leu Gly Phe Glu Leu Pro Lys Lys Gly Asp Tyr Ala Val
                85                  90                  95

Ala Gln Met Phe Leu Ser Pro Asn Thr Asp Ala Lys Glu Glu Ala Lys
            100                 105                 110

Glu Ile Phe Leu Gln Gly Leu Lys Asp Lys Lys Leu Glu Phe Leu Gly
        115                 120                 125

Phe Arg Glu Val Pro Phe Asn Pro Ser Asp Ile Gly Ala Ser Ala Leu
    130                 135                 140

Lys Ala Met Pro Tyr Phe Leu Gln Ala Phe Val Lys Lys Pro Ser Lys
145                 150                 155                 160

Ile Ser Ala Gly Leu Glu Phe Glu Arg Val Leu Tyr Ser Thr Arg Arg
                165                 170                 175

Leu Ile Glu Lys Arg Ala Ile Asn Val Pro Lys Phe Tyr Phe Ser Ser
            180                 185                 190

Phe Ser Ser Arg Thr Ile Val Tyr Lys Gly Met Leu Leu Ser Thr Gln
        195                 200                 205

Leu Ser Asp Phe Tyr Leu Asp Phe Lys Asp Val Asn Met Lys Ser Ala
    210                 215                 220

Ile Ala Leu Val His Ser Arg Phe Ser Thr Asn Thr Phe Pro Ser Trp
225                 230                 235                 240

Glu Arg Ala His Pro Asn Arg Tyr Met Val His Asn Gly Glu Ile Asn
                245                 250                 255

Thr Ile Arg Gly Asn Val Asp Ser Ile Arg Ala Arg Glu Gly Leu Met
            260                 265                 270

Gln Ser Glu Tyr Phe Glu Asn Leu Asp Glu Ile Phe Pro Ile Ile Ala
        275                 280                 285

Lys Leu Ser Ser Asp Ser Ala Met Phe Asp Asn Thr Leu Glu Phe Leu
    290                 295                 300

Ala Leu Asn Gly Arg Thr Leu Glu Glu Ala Phe Met Met Met Val Pro
305                 310                 315                 320

Glu Pro Trp His Lys Asn Glu Asn Met Glu Ser Lys Lys Arg Ala Phe
                325                 330                 335

Tyr Glu Tyr His Ser Leu Leu Met Glu Pro Trp Asp Gly Pro Ala Ala
            340                 345                 350

Ile Val Phe Thr Asp Gly Val Ile Met Gly Ala Ser Leu Asp Arg Asn
        355                 360                 365

Gly Phe Arg Pro Ser Arg Tyr Tyr Leu Thr Lys Asp Asp Met Leu Ile
    370                 375                 380

Leu Ser Ser Glu Thr Gly Ala Leu Lys Leu Asp Glu Lys Asn Ile Lys
385                 390                 395                 400
```

```
Ala Lys Lys Arg Leu Glu Pro Gly Lys Leu Leu Leu Val Asp Thr Ala
                405                 410                 415

Arg Gly Arg Val Ile Ala Asp Asn Glu Ile Lys Glu His Tyr Ala Asn
            420                 425                 430

Ala Lys Pro Tyr Lys Lys Trp Leu Lys Asn Leu Val Glu Leu Glu Lys
        435                 440                 445

Gln Lys Ser Gly Val Tyr Lys His Gln Phe Leu Lys Glu Asp Glu Val
    450                 455                 460

Leu Lys Leu Gln Lys Ala Phe Gly Trp Ser Tyr Asp Glu Leu Lys Met
465                 470                 475                 480

Ser Val Ala Ala Met Ala Gln Asn Gly Lys Glu Ala Ile Ala Ala Met
                485                 490                 495

Gly Val Asp Thr Pro Leu Ala Ile Leu Ser Lys Thr Tyr Gln Pro Leu
            500                 505                 510

Tyr Asn Tyr Phe Lys Gln Leu Phe Ala Gln Val Thr Asn Pro Pro Leu
        515                 520                 525

Asp Ala Ile Arg Glu Glu Ile Val Thr Ser Thr Arg Ile Tyr Leu Gly
    530                 535                 540

Ser Glu Gly Asn Leu Leu Lys Pro Asp Glu Asn Asn Ala Lys Arg Val
545                 550                 555                 560

Lys Ile Ala Leu Pro Val Ile Ser Asn Glu Glu Leu Phe Glu Val Lys
                565                 570                 575

Ala Leu Asn Lys Phe Gln Val Lys Glu Phe Ser Ile Leu Tyr Asp Tyr
            580                 585                 590

Ser Lys Lys Thr Leu Glu Lys Ala Leu Asp Glu Leu Cys Val Lys Ile
        595                 600                 605

Glu Asp Glu Val Lys Lys Gly Val Ser Ile Ile Ile Leu Ser Asp Lys
    610                 615                 620

Gly Val Asp Glu Lys Asn Ala Tyr Ile Pro Ala Leu Leu Ala Val Ser
625                 630                 635                 640

Gly Val His Asn His Leu Val Arg Lys Asn Leu Arg Thr His Thr Ser
                645                 650                 655

Leu Ile Ile Glu Ser Gly Glu Pro Arg Glu Ile His His Phe Ala Cys
            660                 665                 670

Leu Leu Gly Tyr Gly Ala Thr Val Ile Asn Pro Tyr Leu Val Tyr Glu
        675                 680                 685

Ser Ile Gln Lys Leu Ile Ala Asn Lys Asp Leu Asn Leu Ser Tyr Glu
    690                 695                 700

Lys Ala Val Glu Asn Phe Ile Lys Ala Ser Ser Ser Gly Ile Val Lys
705                 710                 715                 720

Ile Ala Ser Lys Met Gly Val Ser Thr Leu Gln Ser Tyr Asn Gly Ser
                725                 730                 735

Ala Leu Phe Glu Cys Leu Gly Leu Ser Ser Lys Val Ile Asp Lys Tyr
            740                 745                 750

Phe Thr Ser Thr Thr Ser Arg Ile Glu Gly Met Asp Leu Glu Asp Phe
        755                 760                 765

Glu Lys Glu Leu Ile Ala Leu His Lys His Ala Phe Asn Asp Thr His
    770                 775                 780

Lys Ala Leu Asp Ser Lys Gly Ile His Gly Phe Arg Ser Ala Lys Glu
785                 790                 795                 800

Glu His Leu Ile Asp Pro Leu Val Ile Phe Asn Leu Gln Gln Ala Cys
                805                 810                 815
```

```
Arg Asn Lys Asp Tyr Lys Ser Phe Lys Lys Tyr Ser Ala Leu Val Asp
            820                 825                 830

Glu Lys Gln Val Asn Leu Arg Ser Leu Met Glu Phe Asp Phe Ser Glu
        835                 840                 845

Ala Ile Ser Ile Asp Lys Val Glu Ser Val Glu Ser Ile Val Lys Arg
    850                 855                 860

Phe Arg Thr Gly Ala Met Ser Tyr Gly Ser Ile Ser Lys Glu Ala His
865                 870                 875                 880

Glu Cys Leu Ala Gln Ala Met Asn Lys Ile Gly Ala Lys Ser Asn Ser
                885                 890                 895

Gly Glu Gly Gly Glu Asp Glu Glu Arg Tyr Glu Ile Lys Glu Gly Val
            900                 905                 910

Asp Lys Asn Ser Ala Ile Lys Gln Val Ala Ser Gly Arg Phe Gly Val
        915                 920                 925

Asp Leu Asn Tyr Leu Ser His Ala Lys Glu Ile Gln Ile Lys Val Ala
    930                 935                 940

Gln Gly Ala Lys Pro Gly Glu Gly Gly Gln Leu Met Gly Phe Lys Val
945                 950                 955                 960

Tyr Pro Trp Ile Ala Lys Ala Arg His Ser Thr Ala Gly Val Thr Leu
                965                 970                 975

Ile Ser Pro Pro Pro His His Asp Ile Tyr Ser Ile Glu Asp Leu Ala
            980                 985                 990

Gln Leu Ile Tyr Asp Leu Lys His  Ala Asn Lys Asp Ala  Lys Ile Ser
        995                 1000                 1005

Val Lys  Leu Val Ser Glu Asn  Gly Ile Gly Thr Val  Ala Ala Gly
    1010                 1015                 1020

Val Ala  Lys Ala Gly Ala Asn  Leu Ile Leu Val Ser  Gly Tyr Asp
    1025                 1030                 1035

Gly Gly  Thr Gly Ala Ser Pro  Arg Thr Ser Ile Pro  His Ala Gly
    1040                 1045                 1050

Ile Pro  Trp Glu Leu Gly Leu  Ala Glu Thr His Gln  Thr Leu Ile
    1055                 1060                 1065

Leu Asn  Lys Leu Arg Asp Arg  Val Arg Leu Glu Thr  Asp Gly Lys
    1070                 1075                 1080

Leu Met  Asn Gly Arg Asp Leu  Ala Ile Ala Ala Leu  Leu Gly Ala
    1085                 1090                 1095

Glu Glu  Phe Gly Phe Ala Thr  Ala Pro Leu Ile Val  Leu Gly Cys
    1100                 1105                 1110

Thr Met  Met Arg Val Cys His  Leu Asn Thr Cys Pro  Phe Gly Ile
    1115                 1120                 1125

Ala Thr  Gln Asp Thr Glu Leu  Arg Asp Arg Phe Lys  Gly Lys Val
    1130                 1135                 1140

Asp Asp  Val Ile Asn Phe Met  Tyr Phe Ile Ala Glu  Glu Leu Arg
    1145                 1150                 1155

Glu Tyr  Met Ala Arg Leu Gly  Phe Glu Arg Leu Asp  Asp Met Ile
    1160                 1165                 1170

Gly Arg  Val Asp Lys Leu Arg  Gln Lys Ser Val Gln  Gly Lys Ala
    1175                 1180                 1185

Gly Lys  Leu Asn Leu Asp Lys  Ile Leu Lys Ser Leu  Pro Thr Tyr
    1190                 1195                 1200

Asn Arg  Thr Ala Val His Phe  Lys Asp Tyr Lys Asp  Asn Lys Leu
    1205                 1210                 1215

Glu Lys  Thr Ile Asp Tyr Arg  Ile Leu Leu Pro Leu  Cys Lys Asn
```

```
    1220                1225                1230

Ala Val  Glu Lys Lys Glu Pro  Ile Lys Leu Ser Leu  Glu Val Gly
    1235                1240                1245

Asn Gln  Ser Arg Thr Phe Ala  Thr Met Leu Ser Ser  Glu Ile Leu
    1250                1255                1260

Lys Thr  Tyr Gly Lys Asp Ala  Leu Asp Glu Asp Ser  Ile His Ile
    1265                1270                1275

Lys Ala  Ile Gly Asn Ala Gly  Asn Ser Phe Gly Ala  Phe Leu Leu
    1280                1285                1290

Lys Gly  Ile Lys Leu Glu Ile  Ile Gly Asp Ser Asn  Asp Tyr Leu
    1295                1300                1305

Gly Lys  Gly Leu Ser Gly Gly  Lys Ile Ile Ala Lys  Ile Ser Asn
    1310                1315                1320

Glu Ala  Thr Phe Ser Pro Glu  Glu Asn Ile Ile Ala  Gly Asn Ala
    1325                1330                1335

Cys Leu  Tyr Gly Ala Thr Lys  Gly Glu Val Tyr Leu  Asp Gly Ile
    1340                1345                1350

Ala Gly  Glu Arg Phe Cys Val  Arg Asn Ser Gly Ala  Leu Ala Val
    1355                1360                1365

Val Leu  Gly Thr Gly Val His  Gly Cys Glu Tyr Met  Thr Gly Gly
    1370                1375                1380

Gln Val  Val Val Leu Gly Asp  Val Gly Ala Asn Phe  Ala Ala Gly
    1385                1390                1395

Met Ser  Gly Gly Val Val Tyr  Ile Phe Gly Arg His  Asn Glu Ala
    1400                1405                1410

His Val  Asn Thr Glu Leu Val  Asp Ile Lys Asp Leu  Asn Ala Lys
    1415                1420                1425

Asp Glu  Lys Glu Leu Lys Ala  Val Ile Glu Lys His  Ile Thr Tyr
    1430                1435                1440

Thr Asp  Ser Lys Lys Ala Lys  Asp Ile Leu Glu Lys  Phe Asp Lys
    1445                1450                1455

Lys Asp  Phe Phe Lys Val Met  Pro Arg Asp Tyr Glu  Lys Met Leu
    1460                1465                1470

Lys Met  Leu Asp Leu Cys Lys  Asn Glu Lys Asp Pro  Asn Leu Ala
    1475                1480                1485

Ala Phe  Leu Lys Ile Thr Gln  Lys
    1490                1495


<210> SEQ ID NO 30
<211> LENGTH: 1517
<212> TYPE: PRT
<213> ORGANISM: Campylobacter jejuni

<400> SEQUENCE: 30

Met Ser Lys Phe Lys Val Ile Glu Ile Lys Glu Asp Ala Arg Pro Arg
1               5                   10                  15

Asp Phe Glu Ala Phe Gln Leu Arg Leu Ala Ser Pro Glu Lys Ile Lys
            20                  25                  30

Ser Trp Ser Tyr Gly Glu Val Lys Lys Pro Glu Thr Ile Asn Tyr Arg
        35                  40                  45

Thr Leu Lys Pro Glu Arg Asp Gly Leu Phe Cys Ala Lys Ile Phe Gly
    50                  55                  60

Pro Ile Arg Asp Tyr Glu Cys Leu Cys Gly Lys Tyr Lys Lys Met Arg
65                  70                  75                  80
```

```
Phe Lys Gly Val Lys Cys Glu Lys Cys Gly Val Glu Val Ala Asn Ser
                85                  90                  95

Lys Val Arg Arg Ser Arg Met Gly His Ile Glu Leu Val Thr Pro Val
            100                 105                 110

Ala His Ile Trp Tyr Val Asn Ser Leu Pro Ser Arg Ile Gly Thr Leu
        115                 120                 125

Leu Gly Val Lys Met Lys Asp Leu Glu Arg Val Leu Tyr Tyr Glu Ala
    130                 135                 140

Tyr Ile Val Glu Asn Pro Gly Asp Ala Phe Tyr Asp Asn Glu Ser Thr
145                 150                 155                 160

Lys Lys Val Glu Tyr Cys Asp Val Leu Asn Glu Glu Gln Tyr Gln Asn
                165                 170                 175

Leu Met Gln Arg Tyr Glu Asn Ser Gly Phe Lys Ala Arg Met Gly Gly
            180                 185                 190

Glu Val Val Arg Asp Leu Leu Ala Asn Leu Asp Leu Val Ala Leu Leu
        195                 200                 205

Asn Gln Leu Lys Glu Glu Met Gly Ala Thr Asn Ser Glu Ala Lys Lys
    210                 215                 220

Lys Thr Ile Ile Lys Arg Leu Lys Val Val Glu Asn Phe Leu Asn Ser
225                 230                 235                 240

Asn Leu Asn Ala Asn Thr Asp Ser Asp Glu Ala Val Pro Asn Arg Pro
                245                 250                 255

Glu Trp Met Met Ile Thr Asn Leu Pro Val Leu Pro Pro Asp Leu Arg
            260                 265                 270

Pro Leu Val Ala Leu Asp Gly Gly Lys Phe Ala Val Ser Asp Val Asn
        275                 280                 285

Asp Leu Tyr Arg Arg Val Ile Asn Arg Asn Thr Arg Leu Lys Lys Leu
    290                 295                 300

Met Glu Leu Asp Ala Pro Glu Ile Ile Ile Arg Asn Glu Lys Arg Met
305                 310                 315                 320

Leu Gln Glu Ala Val Asp Ala Leu Phe Asp Asn Gly Arg Arg Ala Asn
                325                 330                 335

Ala Val Lys Gly Ala Asn Lys Arg Pro Leu Lys Ser Leu Ser Glu Ile
            340                 345                 350

Ile Lys Gly Lys Gln Gly Arg Phe Arg Gln Asn Leu Leu Gly Lys Arg
        355                 360                 365

Val Asp Phe Ser Gly Arg Ser Val Ile Val Val Gly Pro Lys Leu Arg
    370                 375                 380

Met Asp Gln Cys Gly Leu Pro Lys Lys Met Ala Leu Glu Leu Phe Lys
385                 390                 395                 400

Pro His Leu Leu Ala Lys Leu Glu Glu Lys Gly Tyr Ala Thr Thr Val
                405                 410                 415

Lys Gln Ala Lys Lys Met Ile Glu Asn Lys Thr Asn Glu Val Trp Glu
            420                 425                 430

Cys Leu Glu Glu Val Val Lys Gly His Pro Val Met Leu Asn Arg Ala
        435                 440                 445

Pro Thr Leu His Lys Leu Ser Ile Gln Ala Phe His Pro Val Leu Val
    450                 455                 460

Glu Gly Lys Ala Ile Gln Leu His Pro Leu Val Cys Ala Ala Phe Asn
465                 470                 475                 480

Ala Asp Phe Asp Gly Asp Gln Met Ala Val His Val Pro Leu Ser Gln
                485                 490                 495

Glu Ala Ile Ala Glu Cys Lys Val Leu Met Leu Ser Ser Met Asn Ile
```

```
            500                 505                 510

Leu Leu Pro Ala Ser Gly Lys Ser Val Thr Val Pro Ser Gln Asp Met
        515                 520                 525

Val Leu Gly Ile Tyr Tyr Leu Ser Leu Glu Lys Ala Gly Ala Lys Gly
    530                 535                 540

Ser His Lys Ile Cys Thr Gly Ile Asp Glu Val Met Met Ala Leu Glu
545                 550                 555                 560

Ser Lys Cys Leu Asp Ile His Ala Ser Ile Gln Thr Met Val Asp Gly
                565                 570                 575

Arg Lys Ile Thr Thr Thr Ala Gly Arg Leu Ile Val Lys Ser Ile Leu
            580                 585                 590

Pro Asp Phe Val Pro Glu Asn Ser Trp Asn Lys Val Leu Lys Lys Lys
        595                 600                 605

Asp Ile Ala Ala Leu Val Asp Tyr Val Tyr Lys Gln Gly Gly Leu Glu
    610                 615                 620

Ile Thr Ala Ser Phe Leu Asp Arg Leu Lys Asn Leu Gly Phe Glu Tyr
625                 630                 635                 640

Ala Thr Lys Ala Gly Ile Ser Ile Ser Ile Ala Asp Ile Ile Val Pro
                645                 650                 655

Asn Asp Lys Gln Lys Ala Ile Asp Glu Ala Lys Lys Gln Val Arg Glu
            660                 665                 670

Ile Gln Asn Ser Tyr Asn Leu Gly Leu Ile Thr Ser Gly Glu Arg Tyr
        675                 680                 685

Asn Lys Ile Ile Asp Ile Trp Lys Ser Thr Asn Asn Val Leu Ser Lys
    690                 695                 700

Glu Met Met Lys Leu Val Glu Lys Asp Lys Glu Gly Phe Asn Ser Ile
705                 710                 715                 720

Tyr Met Met Ala Asp Ser Gly Ala Arg Gly Ser Ala Ala Gln Ile Ser
                725                 730                 735

Gln Leu Ala Ala Met Arg Gly Leu Met Thr Lys Pro Asp Gly Ser Ile
            740                 745                 750

Ile Glu Thr Pro Ile Ile Ser Asn Phe Arg Glu Gly Leu Asn Val Leu
        755                 760                 765

Glu Tyr Phe Ile Ser Thr His Gly Ala Arg Lys Gly Leu Ala Asp Thr
    770                 775                 780

Ala Leu Lys Thr Ala Asn Ala Gly Tyr Leu Thr Arg Lys Leu Ile Asp
785                 790                 795                 800

Val Ala Gln Asn Val Lys Ile Thr Ile Glu Asp Cys Gly Thr His Glu
                805                 810                 815

Gly Val Glu Ile Asn Glu Ile Thr Ala Asp Ser Ser Ile Ile Glu Thr
            820                 825                 830

Leu Glu Glu Arg Ile Leu Gly Arg Val Leu Ala Glu Asp Val Ile Asp
        835                 840                 845

Pro Ile Thr Asn Ser Val Leu Phe Ala Glu Gly Thr Leu Met Asp Glu
    850                 855                 860

Glu Lys Ala Lys Ile Leu Gly Glu Ser Gly Ile Lys Ser Val Asn Ile
865                 870                 875                 880

Arg Thr Pro Ile Thr Cys Lys Ala Lys Lys Gly Ile Cys Ala Lys Cys
                885                 890                 895

Tyr Gly Ile Asn Leu Gly Glu Gly Lys Leu Val Lys Pro Gly Glu Ala
            900                 905                 910

Val Gly Ile Ile Ser Ala Gln Ser Ile Gly Glu Pro Gly Thr Gln Leu
        915                 920                 925
```

```
Thr Leu Arg Thr Phe His Ser Gly Gly Thr Ala Ser Thr Asp Leu Gln
    930                 935                 940

Asp Arg Gln Val Ser Ala Gln Lys Glu Gly Phe Ile Arg Phe Tyr Asn
945                 950                 955                 960

Leu Lys Thr Tyr Lys Asn Lys Glu Gly Lys Asn Ile Val Ala Asn Arg
                965                 970                 975

Arg Asn Ala Ala Val Leu Leu Val Glu Pro Lys Ile Lys Thr Pro Phe
            980                 985                 990

Lys Gly Val Ile Asn Ile Glu Asn  Ile His Glu Asp Val  Ile Val Ser
        995                 1000                1005

Ile Lys  Asp Lys Lys Gln Glu  Val Lys Tyr Ile Leu  Arg Lys Tyr
    1010                 1015                 1020

Asp Leu  Ala Lys Pro Asn Glu  Leu Ala Gly Val Ser  Gly Ser Ile
    1025                 1030                 1035

Asp Gly  Lys Leu Tyr Leu Pro  Tyr Gln Ser Gly Met  Gln Val Glu
    1040                 1045                 1050

Glu Asn  Glu Ser Ile Val Glu  Val Ile Lys Glu Gly  Trp Asn Val
    1055                 1060                 1065

Pro Asn  Arg Ile Pro Phe Ala  Ser Glu Ile Leu Val  Glu Asp Gly
    1070                 1075                 1080

Glu Pro  Val Val Gln Asn Ile  Lys Ala Gly Glu Lys  Gly Thr Leu
    1085                 1090                 1095

Lys Phe  Tyr Ile Leu Lys Gly  Asp Gly Leu Asp Arg  Val Lys Asn
    1100                 1105                 1110

Val Lys  Lys Gly Asp Ile Val  Lys Glu Lys Gly Phe  Phe Val Val
    1115                 1120                 1125

Ile Ala  Asp Glu Asn Asp Arg  Glu Ala Lys Arg His  Tyr Ile Pro
    1130                 1135                 1140

Arg Glu  Ser Lys Ile Glu Phe  Asn Asp Ser Glu Lys  Ile Asp Asp
    1145                 1150                 1155

Ala Asn  Thr Ile Ile Ala Ser  Ala Pro Lys Lys Glu  Arg Lys Val
    1160                 1165                 1170

Ile Ala  Glu Trp Asp Ala Tyr  Asn Asn Thr Ile Ile  Ala Glu Ile
    1175                 1180                 1185

Asp Gly  Val Val Ser Phe Glu  Asp Ile Glu Ala Gly  Tyr Ser Ala
    1190                 1195                 1200

Asp Glu  Gln Ile Asp Glu Ala  Thr Gly Lys Arg Ser  Leu Val Ile
    1205                 1210                 1215

Asn Glu  Tyr Leu Pro Ser Gly  Val Arg Pro Thr Leu  Val Ile Ala
    1220                 1225                 1230

Gly Lys  Gly Asp Lys Ala Val  Arg Tyr His Leu Glu  Pro Lys Thr
    1235                 1240                 1245

Val Ile  Phe Val His Asp Gly  Asp Lys Ile Ala Gln  Ala Asp Ile
    1250                 1255                 1260

Leu Ala  Lys Thr Pro Lys Ala  Ala Ala Lys Ser Lys  Asp Ile Thr
    1265                 1270                 1275

Gly Gly  Leu Pro Arg Val Ser  Glu Leu Phe Glu Ala  Arg Lys Pro
    1280                 1285                 1290

Lys Asn  Ala Ala Val Ile Ala  Glu Ile Asp Gly Val  Val Arg Phe
    1295                 1300                 1305

Asp Lys  Pro Leu Arg Ser Lys  Glu Arg Ile Ile Ile  Gln Ala Glu
    1310                 1315                 1320
```

```
Asp Gly  Thr Ser Ala Glu Tyr  Leu Ile Asp Lys Ser  Lys His Ile
    1325                 1330                 1335

Gln Val  Arg Asp Gly Glu Phe  Ile His Ala Gly Glu  Lys Leu Thr
    1340                 1345                 1350

Asp Gly  Val Val Ser Ser His  Asp Val Leu Lys Ile  Leu Gly Glu
    1355                 1360                 1365

Lys Ala  Leu His Tyr Tyr Leu  Ile Ser Glu Ile Gln  Gln Val Tyr
    1370                 1375                 1380

Arg Gly  Gln Gly Val Val Ile  Ser Asp Lys His Ile  Glu Val Ile
    1385                 1390                 1395

Val Ser  Gln Met Leu Arg Gln  Val Lys Val Val Asp  Ser Gly His
    1400                 1405                 1410

Thr Lys  Phe Ile Glu Gly Asp  Leu Val Ser Arg Arg  Lys Phe Arg
    1415                 1420                 1425

Glu Glu  Asn Glu Arg Ile Ile  Arg Met Gly Gly Glu  Pro Ala Ile
    1430                 1435                 1440

Ala Glu  Pro Val Leu Leu Gly  Val Thr Arg Ala Ala  Ile Gly Ser
    1445                 1450                 1455

Asp Ser  Val Ile Ser Ala Ala  Ser Phe Gln Glu Thr  Thr Lys Val
    1460                 1465                 1470

Leu Thr  Glu Ala Ser Ile Ala  Gly Lys Phe Asp Tyr  Leu Glu Asp
    1475                 1480                 1485

Leu Lys  Glu Asn Val Ile Leu  Gly Arg Met Ile Pro  Val Gly Thr
    1490                 1495                 1500

Gly Leu  Tyr Gly Glu Gln Asn  Leu Lys Leu Lys Glu  Gln Glu
    1505                 1510                 1515


<210> SEQ ID NO 31
<211> LENGTH: 156
<212> TYPE: DNA
<213> ORGANISM: Campylobacter jejuni

<400> SEQUENCE: 31

atggcttatg aagatgaaga agatttaaat tacgatgatt atgaaaacga agatgaagaa      60

tatccacaaa atcaccataa aaattataat tacgatgatg atgattatga atacgatgat     120

gataacaatg atgatgattt ttatgagatg gattaa                               156


<210> SEQ ID NO 32
<211> LENGTH: 198
<212> TYPE: DNA
<213> ORGANISM: Campylobacter jejuni

<400> SEQUENCE: 32

atgatcaatc ctatacaaca aagttatgtg gcaaataccg cattaaatac aaatagaata      60

gataaagaaa ctaaaacaaa cgatactcaa aaaacggaaa atgataaagc gagtaaaatc     120

gcagagcaga ttaaaaacgg tacttataaa atcgatacaa aagctacagc tgctgcgatt     180

gctgactctt taatctaa                                                   198


<210> SEQ ID NO 33
<211> LENGTH: 351
<212> TYPE: DNA
<213> ORGANISM: Campylobacter jejuni

<400> SEQUENCE: 33

atgaaaaaaa tacttattct acttacacta tgtgcttttg cttttggtgc aagtgaatgt      60
```

```
gatagaaaaa tcgatcgtat caataaagaa atcagttttt ctaaagcgca taatgataca    120

gctagaactt taagcttaga gcttgcttta aaacaagtac aaaatgattg tgctaaagat    180

cctatgtttt atgataaaaa gttagaagct aaaaaactta aagaacaaga agtggaaaaa    240

atcgaaaaag aacttgatgc tttaaaagaa caaaaagatt atatgagcaa ggctgagtat    300

aaagctaaaa aagaagcttt aaaagaacaa aaagagaaaa tcaaaaaata a             351


<210> SEQ ID NO 34
<211> LENGTH: 417
<212> TYPE: DNA
<213> ORGANISM: Campylobacter jejuni

<400> SEQUENCE: 34

atgagttttg gtgaaattat agttatttta gttgtagcga ttttagtctt aggacctgat     60

aaacttccag aagctatagt acaaatagca aaaattctaa aggctgtaaa acgcaacata    120

gatgatgcaa aatcaagcat agaaaaagaa atacgcatca atgacttaaa agaagaagct    180

aagaaataca aagatgaatt ttcaagcact aatgaaaata tacgcaaaaa actcagcttt    240

gaagaatttg atgaccttaa gagagatatt ttagataaaa caaaggtaga tttaaccttt    300

gatagcagag atgataaagt aaaaaataac cttagcggac aaaatttaaa tacagaagaa    360

aaaccaaatc ttagcaaatt agaaacacaa gataaaaacg gaaaaataaa tgtttga       417


<210> SEQ ID NO 35
<211> LENGTH: 426
<212> TYPE: DNA
<213> ORGANISM: Campylobacter jejuni

<400> SEQUENCE: 35

atgcaaaaag ctaaaatttt aattgcctta agtttttttt tattagtttt atctgcctgt     60

tctaatgatg aaaaaaatat ttccaagact caaaatacag atcaagaagt agtccaaata    120

gaacaaaacg atgaaaaaac agaattaagt gactccaacc tgcctttacc tgtagatgat    180

gaagcacaaa gttcaaatga tgaacatgaa gtcaatccta gtattatcaa ctctttatat    240

aaacaaaaat gcgccacttg tcatggagaa aaaggggaat taaaacctaa aaacagcacg    300

gccattaaaa ccttgagcaa taaaattttt atacaaaaaa taaaaacgat aaaagataaa    360

aaccatagtt ttttaagtga tgaacaaatt caaaatttag ctgattttat aaacaaagga    420

aaataa                                                               426


<210> SEQ ID NO 36
<211> LENGTH: 435
<212> TYPE: DNA
<213> ORGANISM: Campylobacter jejuni

<400> SEQUENCE: 36

atgcgaagac taagtatttt acttgcaatt ttaatagtta ttaatataac agcttgtgat     60

agtaaaacag aaaattacta caaaaatctt cctagcgaag caaaagaaaa agcgaaagaa    120

tgcaaagaaa gcggaactct tagcgaagat tgtattaatg cattaaaagt tggtgttaaa    180

ccaacaaatg aagagggtaa atacagtcca aacacaccga aaaaatctga taatcaaata    240

ttagaagctt taaaacaaaa tgatttaaaa aaagaaaaaa ccacaaaaga tattaaccaa    300

agttcagaaa ataatgaaag tattataata ccacctatag cagaaacacc ttctgaaatt    360

tatccttcca aaacaacaga aaacaatcaa agttctatct ttagcgatga tgttaatatg    420

acacaggaaa aatga                                                     435
```

<210> SEQ ID NO 37
<211> LENGTH: 525
<212> TYPE: DNA
<213> ORGANISM: Campylobacter jejuni

<400> SEQUENCE: 37
atgatgaaga agaaattggt tttattagga agtgctgcag tggtattttt tgccgcttgt 60
gcaatgaata gtggggtaag ttcagaacaa attggactta gaaaagcaag tttagaaaat 120
gaaaataaag taaatttagt ggaggcaaat ttcacaactt tacagcctgg ggaatctact 180
cgttttgagc gttcttatga aaatgcacca ccattaattc cgcatgctat tgaagatttg 240
ttacctataa ctaaagataa caatatgtgc ttaagctgcc atgataaggc tatagcagca 300
gatgctggtg caactccact tcctgctagt cattattatg attttagaca caataaaacc 360
acaggagata tgattagcga tagtcgtttt aattgcactc agtgtcatgt tccacaaagt 420
gatgcaaaac ctttagtggg aaatagcttt aaacctgaat ttaaaaatga acaattaaaa 480
agtcgttcaa atttaattga tgtgattaat gagggtgtaa agtaa 525

<210> SEQ ID NO 38
<211> LENGTH: 606
<212> TYPE: DNA
<213> ORGANISM: Campylobacter jejuni

<400> SEQUENCE: 38
atgaaaaaaa tcaaaaaaat cattcaaatt ggtatgatag gtggtttagc agctgttgct 60
ggaggtgctt tagcaggttg tggaagtaat aatgacaatg cagatacttt aaatcaagcg 120
gctaatgctc aaggagcttt tgtaattatc gaagaaacag ctccagggca gtataaaatc 180
aaagatcaat atccaagtga tgaaacaagg gtagttttaa aagatcttaa tggtacagaa 240
agaattttat ccaaagaaga aatggatgct ttgattaaag aagaagcagc taaaattgat 300
aatggaactt caaatttaac taaagacaat ggacaaatca gtagtggggg attgagttta 360
ggggaaactt tactcgcaag tgctgcaggt gctattttag gaagttggat aggttcaaaa 420
cttttcaata atcaaaattt tgccaaccaa caacgcggtg ctttttcaaa tcaaagtgct 480
tatcaaagga gtgttaatag ttttaataaa gcaggcacaa caagctctgc ttcaagtgct 540
aaaaaatcag gtttttttgg tggaggctct aaagccacaa gttctagttc ttcttttggc 600
tcttaa 606

<210> SEQ ID NO 39
<211> LENGTH: 633
<212> TYPE: DNA
<213> ORGANISM: Campylobacter jejuni

<400> SEQUENCE: 39
atgacaaaat ttttaagcat ttgtagttta attgcgatgt tgttaagtgg ttgtggaagt 60
gattttcctg gacaacctag cgatgtggct agagttcagc aaaacaaata tccaaatgga 120
aatttaaaaa aagaaattcc ctataataaa gattcaagaa tacatgggtt aaaaagagct 180
ttttatgaca atggtcagct aagagctgaa gaaaattata aaaatggaaa aaaagatgga 240
attagcaggg aatattctag aaatgggcaa ttacttgagg aggtgcattt taaagataat 300
cgcggatatg gtgattttgc aagctattat gagaatggaa atatgagagc aaagggaaaa 360
ctacttggct ataatgaaga tggtatgcca gaatttgaag gtaattacaa ggaatattat 420

```
gaaaatggaa ctttaatgtg tgattataat tttgataata aaggtaaatt tgatggagta    480

caaaagcgtt atgatgaaaa tggcgcctta gaagacgaag aaaattataa aaatggactt    540

aaaaatggag tctttagaga atataaaaaa ggggagattg taagagaaga agaatataaa    600

aatggtattt tagtagcaaa acctaaaaat tag                                 633
```

<210> SEQ ID NO 40
<211> LENGTH: 735
<212> TYPE: DNA
<213> ORGANISM: Campylobacter jejuni

<400> SEQUENCE: 40

```
atgaaaaaaa tatttttaag tgttttttg gttttgagtt taaatgctca aaatcttgaa      60

atagataaaa taagaacaga tttgtattct aaaagtggag caaatgttct taaaaaagtt    120

gaaatttctt tggaatttga tgggaataat ttaaaagaaa atgaaaataa gttaattgat    180

gctgtaaata cagtaatttc agggtttttt tatgaagata tttttacaga aattggaaaa    240

aataatttta aaaaaacttt agaaaaattt ttagataaga aatataagat taaactagat    300

gatatatata tcatatcttt aagtggagtg gaaaaatttg atttagagga gtttaaacgc    360

tttttagaaa gtactgaggc taaagagaag ggtatgggta gcgaggtaaa aaaagcactt    420

gaaaacttag aagttcctaa aactcaagtt cctagtgttg aaaagatccc aactcctagt    480

gttccaaatt tagaagtcaa gcaagttgaa cagcttttca aagatccaga tgaagaaaat    540

aaaaatgaca atggagaaat caatatagat aatttaaata cacctaaaat gactccagat    600

atagaagaaa aaattaaaag agatttaatc gccaatcctc cacaaatatt caaagaaaat    660

aacgcaagca agccttatca tttgccacaa acaggctatg atataaagct tgatgagaat    720

tcaacgcaaa attag                                                     735
```

<210> SEQ ID NO 41
<211> LENGTH: 780
<212> TYPE: DNA
<213> ORGANISM: Campylobacter jejuni

<400> SEQUENCE: 41

```
atgaaaaatt atggtttgag taatttaaat tcgtttttac ttgctttagc aatatatatt     60

agtatagtaa ttcttgtttt ttttagactt gtaagcgagg ttgaacctgc tatacaatat    120

actgatataa aagatagttt tgtagatatt gaacttgctg aaccatcaaa acaagttatt    180

actcaaagca acactcctaa agaaatacaa aaaccaacag agcaaattga tatagaaaag    240

ctttttgctc agactacaaa taaaacagtt aaaactgaag atattgacca aaaggcaagt    300

aattttaatg agctttttgg aaatattaaa gaaatacaag aagaaaagac tacaaaaatt    360

caatcaagtg ctaaatcagg aatttctagt gccccaaaac ctcaagcttc tgaacttgta    420

aaacaactta atgatagttt acttcaagaa gaaagttcaa cgcaaggcga aagcacaaag    480

gcgcaaaaga ttggaattta tgatgaattt ttagggaaag ttgtgcgtat tatcactcaa    540

agatggactc agtattatcc aaatagtgaa aaaatttctg ttaaggtaaa aatttttatt    600

gatgaaaatg gaaaatttgg ctatacttca gttgaaaaaa gtgggaatcc tttatatgat    660

gctaaagtgg ctgaattttt agaaagtcaa aaaggtaaat ttattactta tcctccgcaa    720

aataaaaata taagcattac catgaattta agagatgaag taaaagttaa aaatgattag    780
```

<210> SEQ ID NO 42
<211> LENGTH: 822

<212> TYPE: DNA
<213> ORGANISM: Campylobacter jejuni

<400> SEQUENCE: 42

```
atgaaaaaat tttctttagt cgcagcaact ttgattgcag gtgtagtttt aaatgtaaat     60
gcagctacag tagctactgt taatggcaag agcattagcg atacagaagt aagtgaattt    120
tttgcccccta tgcttagagg acaggatttt aaaactttgc cagataatca aaaaaaagct   180
cttattcagc aatatattat gcaagattta attttgcaag atgctaaaaa acaaaattta    240
gaaaaagacc ctttatacac aaaagaactt gatcgtgcaa aagatgcaat acttgttaat    300
gtttatcaag agaaaatttt aaatactatt aaaattgatg cggctaaagt taaagctttt    360
tatgatcaaa ataaagacaa atatgtaaaa cctgcaagag tgcaagcaaa acatatctta    420
gtagcgacag aaaaagaagc taaggatatt attaacgaac ttaaaggttt aaaaggtaaa    480
gaactagatg ctaaatttag cgagcttgct aaagagaaat caattgatcc aggttcaaaa    540
aaccaaggtg gtgagcttgg ttggtttgat caatcaacta tggtaaagcc ttttacagat    600
gctgctttcg cgcttaaaaa tggtactatt actacaactc cggtaaaaac gaattttggt    660
tatcatgtaa tcttaaaaga aaattcgcaa gctaaaggtc aaatcaaatt tgatgaagta    720
aaacaaggta ttgaaaacgg acttaaattt gaagaattta aaaaagttat caatcaaaaa    780
ggccaagatc tcttaaatag tgctaaagtg gaatataaat aa                       822
```

<210> SEQ ID NO 43
<211> LENGTH: 837
<212> TYPE: DNA
<213> ORGANISM: Campylobacter jejuni

<400> SEQUENCE: 43

```
atggaaaatc aaaaaaatga atttgatgat attattttag aaaaaagtaa taaaagtgaa     60
aaagtaaaaa aaattctttt acgagttatt gctttagtta ttttgttttt agctatcatg    120
atagttatga agcttattaa tggtagtggt gatgaaaata cgcaaaatca aagtgtattg    180
ccaagtgaac ctatagcaac tcaagacaat aacaatgata cttcttttga aagtatgcca    240
attacagata atacttcagc agaagatcaa tttgaggcat taagaaaaca atttcaagat    300
gaacaaaata caactcaaaa tacaacaacc tctagttcaa ataacaatga tactacaaat    360
tttgctatgc ctgatcaaga agttccagca gaaccaacag caactacttc agcaaatacc    420
actccacaag caagtactcc taaacaagaa gtaacacaaa ctgcaaaatc taaagaagaa    480
gcaaaaaaac aaacagctgt aaaaaaagaa aaagaaagtg caaaacaaac ccctaaaaaa    540
gaacaaaatg caaatgattt atttaaaaat gttgatgcta aacctgtaca tccaagtggt    600
ttagcatcgg gtatttatgt gcaaattttc tcagtaagta atttggatca aaaatcaaaa    660
gaacttgctt ctgtaaagca aaaaggttat gattataaac tttataaaac tacagttgga    720
agtaaagaaa ttaccaaggt tttaatagga ccatttgaaa aggcagatat tgcagcagaa    780
cttgctaaaa tccgtaagga tattgcaaaa gatgcttttt cttttacttt aaaatga       837
```

<210> SEQ ID NO 44
<211> LENGTH: 1173
<212> TYPE: DNA
<213> ORGANISM: Campylobacter jejuni

<400> SEQUENCE: 44

```
atgaaaaaga agattgtttt aatcatttta attgcaatac ttggaagtgt tggggcttat     60
```

```
tttatttttt ttaataatga tgaaaaaatc agctatttaa ctcaaaaaat acaaaaaaaa    120

gatatatctc aaaccataga ggcagtagga aaggtatatg ccaaagatca agtcgatgtg    180

ggtgctcaag ttagtggaca aattataaaa ctttatgttg atgtgggaac tcatgtaaag    240

caaggtgatt tgatcgctca aattgataaa gataaacaac aaaacgattt agatattaca    300

aaagctcagc ttgaaagtgc taaggctaat ttagagagta aaaaagttgc ccttgagatt    360

gcgaataagc aatatcaaag agagcaaaaa ctttatgcag ctaaagcaag ttctcttgaa    420

aatttagaaa ctcaaaaaaa taattattat actttaaaag ccaatgttgc agagcttaat    480

gctcaagtag ttcagcttga aatcactctt aaaaatgcac aaaaagattt aggttataca    540

accattactg ctcctatgga tggtgttgtg attaatgtag ctgtagatga aggacaaaca    600

gttaatgcta atcaaaacac tcctactata gtccgtatag ctaatttaga cgaaatggaa    660

gtaagaatgg aaatagcaga ggctgatgtg agtaagataa aagtaggaac agagcttgat    720

ttttctttgc ttaatgatcc tcaaaaaact tatcatgcta agattgcaag tatagatcca    780

gctgatactg aagtgagtga ttctagtaca agctcaagct catcaagttc gagttcttca    840

agctcaagct catcaaatgc tatttattat tacgcaaaat tttatgtagc caataaagat    900

gatttttgc gtattggtat gagtatacaa aatgaaattg tcgtagcaag tgcaaaggct    960

gttttagcag tgccaactta tgcaattaaa agcgatccaa aaggctatta tgttgaaatt   1020

ttggaaaatc aaaaagctgt taaaaaatat gtcaaacttg gcattaaaga ttctatcaat   1080

actcaaattt tagaaggtgt aaatgaagat gaagaattga tagtaagctc aagtgctgat   1140

ggtttagctc ctaaaatgaa gttgagattt taa                                1173
```

<210> SEQ ID NO 45
<211> LENGTH: 1629
<212> TYPE: DNA
<213> ORGANISM: Campylobacter jejuni

<400> SEQUENCE: 45

```
atgaaaattt tacttttaaa tgaaaaccct gtagtttcaa gacttgtaag ccttagtgct     60

aaaaaaatgt cttatgattt tgaagaactt aatgcttata gtgaaaattt gggtaattat    120

gatgtgattg ttgtagatag tgatactcca gcacctttaa aaattcttaa agaaaaatgc    180

gataggttga tttttttagc cccgcgaaat caaaatgtag aagatataga tgcgcaaatt    240

ttacaaaaac ctttttttacc tacagatttt ttaaatttac ttaataataa agatgcgaac    300

aagcatacat ctattgattt gccaatgtta agcaatgatg aaaatcctta tgctgatata    360

agcttggatt tagataattt aaatttagat gatttgcctg atgaaaattc tttagatata    420

aattcagagg gaatggaaga tttgagtttt gatgatgatg ctcaagatga taatgcaaac    480

aaaactttag aaactcaaaa tttagaacat gaaacaatta aagaacagac tcaagaagac    540

actcaaattg atttagattt aactttagaa gatggcgaaa gtgaaaaaga agacttaagc    600

caagaacata cagctttgga tactgagcct agtttagatg agctagatga taaaaatgat    660

gaagatttag aaatcaaaga agatgataaa aatgaagaaa tagaaaagca agaattatta    720

gacgattcta aaacaaatac attagaaatg caagaagagc ttagcgaatc tcaagatgat    780

aattcaaaca aaactttaga aactcaaaat ttagaacatg acaatttaga acaagaaaca    840

attaaagaac agactcaaga agacactcaa attgatttag atttaacttt agaagatggc    900

gaaagtgaaa aagaagactt aagccaagaa catacagctt tggatactga gcctagttta    960

gatgagctag atgataaaaa tgatgaagat ttagaagata ataaagaatt acaagctaat   1020
```

```
ataagcgatt ttgatgatct tcctgaggtt gaagagcaag aaaaagaaat ggattttgat   1080

gatcttcctg aggatgctga atttttaggt caagcaaaat ataatgaaga atcagaggaa   1140

aatttagagg agtttgctcc tgttgtggaa gaagatattc aagatgaaat agatgatttt   1200

gcttcaaatt tgagtactca agatcaaatc aaagaagaac tagctcaact tgatgagctt   1260

gattatggta ttgatagtga caatagtagc aaggtcttag aagattttaa agatgaacca   1320

attttagacg ataaagaatt aggaacaaat gaagaggaag tggttgtgcc aaatttaaat   1380

ataagtgatt ttgatacatt gaaagaaagt gatatacaag aagctcttgg agaggaaatc   1440

ttagaaaaaa atgaagagcc tatagtaagt gatgtaacta aagatgataa tagcgaagag   1500

atagttaatg agcttagcca aagcatagca ggagcgatca cttcaagtat taaagatgat   1560

accttaaaag ctgctcttaa gggtatgaat atgaatataa atataaacat tagttttaaa   1620

gaggattga                                                           1629
```

<210> SEQ ID NO 46
<211> LENGTH: 1833
<212> TYPE: DNA
<213> ORGANISM: Campylobacter jejuni

<400> SEQUENCE: 46

```
atgaaaaaaa atattttacg cttaggtatt gtcgttttgg ttttacttat agcgggagtt     60

ttatggctaa ataatgatat caatcaaaaa aaagaagatg aagcaaataa aaatgccatt    120

gcagcaaatg ctgatttttc tttgcttagc gatgatgatc caaattttga aaaatggggt    180

aaggtttttc cagagcaact aaaaatgtat ttaacggttg aaaaagaaga gcctaaggct    240

actgaatttg gtggtaattt agcttattca aaattaattc gctttcctca attaaccata    300

ctttgggcag gatatccttt tagtcttgat ttcaatgaag aaagagggca tttttgggtt    360

caagtagatc aaatgaaaac agcaagaaac aacaaagatt ttcttaatgc ccatggactt    420

gctgctttta aggtcaaccc tgcagcttgt atgaattgtc atagtggatg gactccatgg    480

cttataaaaa atgttgctaa aggagatttt actgctttta actctacaaa ttattggact    540

atgattaaaa atatcccagc tgttgatggt atagtagaaa attcacctga acatgcaggc    600

ccacatggtg gtaaaagaat gggtgtaact tgtgcagatt gtcacaatcc aaatgatatg    660

agtttaagac ttactcgtcc agcagctatt aatgctttag tttctagagg atatgaaaaa    720

gatccagtac aaggcgtaaa agctacaaga gaagaaatga gaactttagt ttgctctcaa    780

tgtcatgttg aatactattt taaaccaaca ggggaaaaag taaaagtaat gggtgaaact    840

attgtagatg atagttctaa aaaatggtgg aatggaactc agaaaaatta tgatgagtat    900

gagttttgga gagatggcaa taaagttaaa gagattgaaa ccgatggtat agttttaact    960

tttccttgga gtgagtggaa aaaaggacaa ccatttagaa ttgaaatgct agatgattat   1020

tatgataaag ttcgtggagt atttggagct gattttactc ataaattaac aggagcgcaa   1080

attattaaaa ttcaacatcc agaaagtgaa ctttatagtg gcggtgtgca tgctgcaaat   1140

ggagtaagtt gcgtggattg tcatatgcct tatgttagag aaggagctaa aaaggttact   1200

caacacaata tcacttctcc tttaagagat attaactctg cttgtaagtc ttgtcataaa   1260

caaagtgaag attatttaaa agctcaagtg cttgacatac aaaacagcgt tgcacatgat   1320

caaagaactg cagagtatgc aattgttagt ttgattatgg atactaaaaa attacgcgat   1380

gaactaggca atatggaaaa attccaaagc gatggaaaag ctgatgcgaa aaaaattagc   1440
```

```
gaagagctaa aagaagtttt agaacttcat cgtaaagctc aaatgagagc ggattttgtt   1500

aatgctgaaa actcaactgg tttccataat cctcgcgaag cttcaagaat gttattgcaa   1560

gctgttgata tggcaagaat gggacaaact aaacttgtag aaattgcagc ggcaaatgga   1620

attaaagatt ttaaaacttc aaatttaggt tttgaagata ttcaaaaatt taatccagga   1680

gagctttatt ataaagtaga tgttaataat cataaagctg gagagcgtta ctatgcagat   1740

gaaaaagatg ttaatggcaa tcctccaaaa gaacttttag agcatgataa agagcttgct   1800

ccttataatt atcaagtgat tgataaaaaa taa                                1833
```

<210> SEQ ID NO 47
<211> LENGTH: 1980
<212> TYPE: DNA
<213> ORGANISM: Campylobacter jejuni

<400> SEQUENCE: 47

```
atgaaaagcg taaaattgaa ggtttcgctg attgcaaatt taatcgcagt agtgtgtttg     60

ataattttag gtgttgtaac atttatattt gtaaagcaag caatttttca tgaagttgtg    120

aatgctgaaa taaattatgt taaaacggct aaaaattcta tagagtcttt taaggcaaga    180

aattctttag ctcttgaaag tttagctaaa agtattttaa agcatcctat agaacagtta    240

gatagtcaag atgctttaat gcattatgtt ggaaaagatt taaagaattt tagagatgct    300

ggaagattct tagcagttta tattgctcaa ccaaatggcg aacttgttgt aagcgatcca    360

gactctgatg ctaaaaattt agattttgga acttatggaa aagctgataa ttatgatgct    420

agaacaagag agtattatat agaagcagtt aaaacaaata aactttatat taccccatct    480

tatattgatg taactacaaa tttaccttgc tttacatatt ctattccgct ttataaagat    540

ggtaaattta taggggtttt ggctgtagat attcttgcgg cagatttgca agctgaattt    600

gaaaatttac caggtagaac ttttgtattt gatgaagaaa ataaagtatt tgtttctaca    660

gacaaagctc ttttacaaaa aggttatgat attagtgcaa ttgcaaatct tgctaaaact    720

aaagaggatc ttgaaccttt tgagtatact agaccaaaag atggtaatga aagatttgct    780

gtatgcacaa aggtttctgg aatttatact gcttgcgttg gagagccaat agaacaaata    840

gaagctccag tttataaaat tgcatttata caaactgcga ttgttatttt tacaagtatt    900

attagcgtca tcctccttta tttcatcgta tcaaaatacc tctccccact tgcagctatc    960

caaacaggtt taacttcatt ctttgatttt atcaactata aaacaaaaaa tgtttccact   1020

atagaagtaa aaagcaatga tgaatttgga caaatctcaa atgctatcaa tgaaaacatt   1080

cttgctacta aaagaggctt agaacaagac aatcaagccg ttaaagaatc agttcaaacc   1140

gtatcagttg tagaaggtgg taatttaaca gcaagaatta ctgctaatcc aagaaaccca   1200

cagcttattg aacttaaaaa tgttctaaat aaacttcttg atgttttaca agctagagta   1260

ggttctgata tgaatgctat tcataaaatt tttgaagaat acaaaagctt agactttaga   1320

aataaattag aaaatgctag cggtagtgta gaattaacta ctaatgcttt aggtgatgaa   1380

atagttaaaa tgctaaaaca aagttcagac tttgctaatg ctttagctaa tgaaagtgga   1440

aaattacaaa ctgctgttca aagcttaacc acttcttcaa attctcaagc tcaatcttta   1500

gaagaaactg cagcagcttt agaagagatc acttcttcta tgcaaaatgt ttcagttaaa   1560

actagtgatg ttatcactca atctgaagag attaaaaatg ttacaggtat tataggtgat   1620

attgcagatc aaatcaatct tttagcttta aatgcagcta ttgaagcagc tcgtgctgga   1680

gaacatggta gaggctttgc agtggtagct gatgaagtta gaaagttagc tgaaagaact   1740
```

```
caaaagtctt tatcagaaat tgaagctaat actaatttac ttgttcaatc tatcaatgat   1800

atggcagaaa gtattaaaga acaaactgca ggtatcactc aaatcaatga tagcgtagct   1860

caaattgatc aaactactaa agataatgtt gaaattgcta atgaatcagc tattatttct   1920

agtacagtaa gtgatatagc taataatatc ttagaagatg ttaagaagaa gaggttttaa   1980
```

<210> SEQ ID NO 48
<211> LENGTH: 1998
<212> TYPE: DNA
<213> ORGANISM: Campylobacter jejuni

<400> SEQUENCE: 48

```
atgcaatcaa taaattcagg caaatccgtt ggaatttcag ctaagcttac gctatgggtt     60

ggaattttag ttgtattaat tttagcaatc acaagtgcta ttagttactt tgattcgaga    120

aacaatacat atgaattgct aaaagacact cagttaaaaa ctatgcaaga tgtggatgct    180

ttctttaaaa gctatgctat gtcaaaaaga aatggtattc aaatactagc caatgagcta    240

acaaatcgtc ctgatatgag cgatgaagag ctaatcaatc ttatcaaagt aattaaaaaa    300

gttaatgact acgatctagt ttatgtagga tttgataata caggaaaaaa ttatcaatct    360

gatgatcaaa ttttagatct atcaaaaggt tatgatacta aaaatcgtcc ttggtataaa    420

gctgccaaag aagcaaaaaa gcttatagta acagaacctt ataaatccgc cgctagcgga    480

gaggttggtt taacttacgc tgctccattt tatgatagaa atggaaattt tagaggtgtt    540

gtaggtggag attatgatct agcaaatttt tcaaccaatg ttttaactgt aggaaaatca    600

gacaatacct ttactgaagt acttgattca gaaggaacaa tactttttaa tgatgaagtt    660

gctaaaatac taacaaaaac agaattaagt atcaatatcg ccaatgcaat caaagcaaat    720

cctgctctta ttgatccaag aaaccaagat actttattta ccgctaaaga tcaccaaggc    780

gtagattatg cgattatgtg taattctgct tttaatcctt tatttagaat ttgtacaata    840

acagaaaaca aagtttatac cgaagctgtt aattctattt taatgaaaca agttatagtt    900

ggtattatag ctataatcat agctttaatc ttgattagat tttaatcag cagaagtctc    960

tccccacttg cagctatcca aacaggttta acttcattct ttgattttat caactataaa   1020

acaaaaaatg tttccactat agaagtaaaa agcaatgatg aatttggaca aatctcaaat   1080

gctatcaatg aaaacattct tgctactaaa agaggcttag aacaagacaa tcaagccgtt   1140

aaagaatcag ttcaaaccgt atcagttgta gaaggtggta atttaacagc aagaattact   1200

gctaatccaa gaaacccaca gcttattgaa cttaaaaatg ttctaaataa acttcttgat   1260

gttttacaag ctagagtagg ttctgatatg aatgctattc ataaaatttt tgaagaatac   1320

aaaagcttag actttagaaa taaattagaa aatgctagcg gtagtgtaga attaactact   1380

aatgctttag gtgatgaaat agttaaaatg ctaaaacaaa gttcagactt tgctaatgct   1440

ttagctaatg aaagtggaaa attacaaact gctgttcaaa gcttaaccac ttcttcaaat   1500

tctcaagctc aatctttaga agaaactgca gcagctttag aagagatcac ttcttctatg   1560

caaaatgttt cagttaaaac tagtgatgtt atcactcaat ctgaagagat taaaaatgtt   1620

acaggtatta taggtgatat tgcagatcaa atcaatcttt tagctttaaa tgcagctatt   1680

gaagcagctc gtgctggaga acatggtaga ggctttgcag tggtagctga tgaagttaga   1740

aagttagctg aaagaactca aaagtcttta tcagaaattg aagctaatac taatttactt   1800

gttcaatcta tcaatgatat ggcagaaagt attaaagaac aaactgcagg tatcactcaa   1860
```

```
atcaatgata gcgtagctca aattgatcaa actactaaag ataatgttga aattgctaat   1920

gaatcagcta ttatttctag tacagtaagt gatatagcta ataatatctt agaagatgtt   1980

aagaagaaga ggttttaa                                                 1998
```

<210> SEQ ID NO 49
<211> LENGTH: 2253
<212> TYPE: DNA
<213> ORGANISM: Campylobacter jejuni

<400> SEQUENCE: 49

```
atgagaatta caaataaact taacttcaca aatagtgtga ataattctat gggcggtcaa     60

agtgctttat atcagatatc tcaacaactt gcttcaggtt tgaaaataca aaattcatat    120

gaagatgcaa gcacttatat agataatacg cgtcttgaat atgaaattaa aacgttagaa    180

caagtaaaag aatcaacaag tagagctcaa gaaatgactc aaaatagtat gaaagcttta    240

caagatatgg ttaaacttct tgaagatttt aaagttaaag taacccaagc tgcaagcgat    300

agcaattctc aaacctcaag agaagctata gcaaaagaac tagaacgtat aaaagaaagc    360

atagttcagc ttgcaaatac cagtgttaat ggtcagtatc tttttgcggg ttctcaagtt    420

gcaaacaaac cttttgattc taatggaaat tattatggag ataaaaaataa tattaatgta    480

gtaactggag ctggaactga aagcccatac aatataccag gttgggattt attttttaaa    540

gcagatggag actataaaaa acaaataagc actaatgtta gttttacaga taatcgttgg    600

gatttaaata aagaccctga taaaactaaa tatctcacag gagattctaa atggcaacaa    660

cttatcggac aaagttatgt aaaagataat agcttagatg ctgacaaaga ctttgagtat    720

gatgatagca aactagattt tcctccaaca actctttatg ttcaaggtac aagacccgat    780

ggaacaagtt ttaaaagtgc tgtactcgtc aaacccgaag atactttaga agatgtaatg    840

gaaaatattg gagctcttta tggtaatact ccaaataata aagtagtaga agtaagtatg    900

aatgatagtg gtcaaattca aattacagat ctaaagcaag gtaataataa actcgatttt    960

catgctgtag ctttcacacc acaagctgat gataaaactg aattaaataa tattatccaa   1020

gcagcacagg atgaaggcat tacaatggaa gatgttacaa acagggttat gactgctgca   1080

ctaggaaatc ccaataatgg agatattaca aatttaaata atcctgtaac cattcaaatt   1140

aacggacaaa actttgaaat tgatttaaaa caaactgatt ttatcaaaag taaaatgaca   1200

gatacagatg gaaatgctgc taatggagct gattacgata atgtgtattt tgaaaaaaat   1260

ggcaatactg tttatggtaa tgtttctcaa gttatcaaag gaagcaatgc ttatgccact   1320

gattcaacca aacttagcga ggtaatggca ggagatagcc taaatggtac tactttaaat   1380

ttaaaagtca attccaaagg tggaaattct tacgatgtta ctataaattt acaaacttca   1440

actgtaagct atcctgatcc taataatcca ggtcaaacca taagctttcc tattatgcat   1500

actaatcctg caactggaaa tagtggggtt gttacaggat caaatgatat tacttatggt   1560

caaattaatg atattatagg tatgtttgct gcagataaaa ttcctacaac aaccatacaa   1620

gccaataatg gtcaaattaa taatgcagat tatacccaaa tacaacaact catgaaagat   1680

tcacaagcta ctgttgatgt aagtatggat tataaaggtc gtattagtgt tactgataaa   1740

ctttcatcag gaaccaatat agaaatttct cttagtgatt ctcaaagtgg ccaatttcca   1800

gcacctcctt ttaccacaac ttctactgta caaaatggtc caaattttag ttttagcgcg   1860

aataattctt taactataga tgagccaaat gtggatatta ttaaagattt agattcaatg   1920

attgatgctg ttttaaaagg caatatgaga gcagactccg aaagtgaaaa ccctagaaat   1980
```

```
acaggtatgc aaggagcttt agaaagactt gatcatttag cagatcatgt tagcaagctt   2040

aatacaacta tgggagcata tcataatact atcgaaggtg ttaatacacg cacatcattt   2100

ttaagcgtta atgtccaaag tataaaatca aatgtgattg atgtagatta tggtgaggca   2160

atgatgaatt taatgcaagt tcaacttgca tatcaagctt ctcttaaagc tagtacaaca   2220

atttctcaac ttagcttatt aaattatatg taa                                2253
```

<210> SEQ ID NO 50
<211> LENGTH: 2598
<212> TYPE: DNA
<213> ORGANISM: Campylobacter jejuni

<400> SEQUENCE: 50

```
atgatgagat cactttggtc tggcgtaagc ggactacaag cacatcaagt tgcgatggat     60

gttgaaggta ataacatttc aaatgttaat accactggtt ttaaatattc tcgtgcagat    120

tttgggacta tgtttagcca aactgtgaaa atcgctacag ctccaactga tggaagaggc    180

ggatctaatc cacttcaaat cggtcttggc gtttcagtaa gttctacaac tagaattcat    240

tctcaaggtt cagttcaaac cacagataaa aacactgacg ttgctataaa tggcgatggt    300

ttttttatgg taagcgatga tggtggtctt acaaactatc ttacaaggag cggggatttt    360

aaactagatg cttatggaaa ttttgttaat aatgcaggtt ttgttgtcca agggtggaat    420

atcaactggg atgatcaaac tatagatagt tcaagaactc cacaaaatat tttatcgat     480

ccaggtatgc atatccctgc agcaaaatct actgaagttg ctatcaaagc gaatttaaat    540

agtggtttaa atataggaac ttcaagtaga aatctttatg cacttgattc tgttcatgga    600

tggaatacta aaacccaaag agcagaagat gaaaatgata caggaactac tcagttttat    660

acgacttcta agaattctgt agaagtgaca gaaaagggtg tggatgcggg atcacttttt    720

aacgcgaaag gacaaggact taatcttaga gatggacaag gaatttgggt atcttatgca    780

gatgcaacat attctaccaa taaagtagga gtaaatgctt ttgatccaaa tttacagcaa    840

aatcaaactg ctgcttttgg gggaacagct aatcaaaaag tgaatttaga tataacttta    900

aatggggtta gaattcaaaa tgctgatatt caaagtattg atgatgctat tgcttatatc    960

aataccttta ctgcaccaac ggatacaagg gatggaacag gtgtaaaagc ggttaaaaat   1020

aaggatggta gtggaattga ttttgtcaat gataatgccg atggtactac agataatatg   1080

aaaaatatca atcttgtggt tgccaatacc aatacagcag gtgagctttg gaatgctgta   1140

tggaataaca acaatcaaac atttacattt aataataatg gtaatggaca ggctggaaca   1200

ccgactatta ataaaaatgg ttcttctttg tggacagcta caaatattac atttacacca   1260

caacctcctc aagcagctac gaatgttcag cttactggtg gactaaatgc acaaataata   1320

acagcacata aatatattta tagttcaaac cctgtggata taggtcctat gtataatcct   1380

gacggtggac cagcattcca gcctggtgct aatgcaacta caagaccaac tgaaccaggt   1440

tcagcagctt attgggatgc tgttaatggt ggacttttaa atactaatgt aagaactttt   1500

agaaccacag aagatttaag agaactttta caaagggatg ctagatatgg ggttgattat   1560

gatggaagtg gaacttttgc tgcagctgat attaatcaaa atataaaagt agtagtaacg   1620

gcagatggac attttgctat ttccaatgct aatgaacaat caactgttcc accaaatgct   1680

attaatggtg taggaaatgc cactacaaca gatccaaaaa atatgagttt taatataaca   1740

gcttatagta acaaacaagg aactgtaagt actaatgatg ctttcactgc tatttttaaa   1800
```

```
gctttcgatg gtcctttggt tataggaaat cagatcaaag aaagcgaaca acttaagctt   1860

tctgcttttt cggcggggct tgaaatttat gattctttag gttcaaaaca cactttagaa   1920

gtgcagtttg ttaagcaaag taccactcaa gatgggggta atgaatggca aatgatcatc   1980

cgtgtacctg aacctgcaga gattaacact acaggcgaag gaccaaacaa tatcatcgta   2040

ggaacagcta gatttaacaa tgacggctct ttagctagtt atacaccaag aacgataaat   2100

ttctcaccaa acaatggtgc cgcaccaaat caacaaatca aactttcctt tggaacaagt   2160

ggaagcaatg acggccttgt aagctcaaat tctgcttcaa ctctaacagg acaggcaact   2220

gatggttata cttcaggtaa cttaaaacct gatgctatcc gtgtggatga taaaggtaat   2280

atcttaggtg aatttactaa tggcaaaacc tttgctgtag caaaaatcgc aatggcttca   2340

gtggcaaata actcaggtct tgaggaaatt ggtggaaatc tttttaaagt tactgcaaat   2400

agtggtaata tcgtggtagg tgaagcagga acaggaggtc gtggtgagat gaaaacctca   2460

gctcttgaaa tgtcaaatgt ggatttaagt cgttctttaa cagagcttat tatcattcaa   2520

agaggttatc aagcaaactc aaaaaccatt tcaacgagtg atcaaatgct ccaaactcta   2580

atccagctta aacaataa                                                 2598
```

<210> SEQ ID NO 51
<211> LENGTH: 2616
<212> TYPE: DNA
<213> ORGANISM: Campylobacter jejuni

<400> SEQUENCE: 51

```
atggcaaaga ttagaattca tgaaatcgca aaagaattag gttatgatag taaggaaatt     60

attgaaaagg caaatgaatt aggacttgga attaaaacag catcaaatgc tgtagaacct    120

gagattgcgg cagctattta tgagtatata caaacaagag aaattccaga agcttttaag    180

aaaaatatca aaactcctac agcaaaaaag cctaaaaaag aaaatataaa agaacaagaa    240

aagctaaatg aatctgaaaa aaaagaacct aaaaaagaag aaaagcttaa acaagaagtt    300

aaaaaagaag aattaaaaat tgaaaaagaa aatgcaaaag aggaagaaaa acaagaaatt    360

attgatgctc ataagccaca aagccttgct agtgcaactt tagccaaaag acgcggactt    420

gttattgtta aaaagaaaaa agacgaagaa gaaattcaag ttaaaaaaga agaagtaaaa    480

aattcaaatg atatatctat caataatgaa gagcgcttaa gtttaaaaac tatgttttca    540

aatgctgatg agagtttaaa gaaaaagaaa aaagaaaaaa aatcttttgt tgcgagtaaa    600

aaagaaagta ccgaaaaaat gaattttttta gatgaacatg attttggtga tatttcttta    660

gatgatgaag atgaggtagt attacctgat tttagtgtaa aagaacaaga aaaaccacaa    720

aatatcaata aaaaacaacc taattttata agacaagctg ttggaaattc tgcgggtttt    780

gggtttgaag gtggaattca aagaagaagt cgtaaaaaac catctaaaaa gattgaaaaa    840

aaggaagtag aagaagtagg tagcgttgct atttctaaag aaattcgtgt gtatgaattc    900

gctgataaga taggaaaaag cactagtgaa gtgatttcaa aactttttcat gcttggaatg    960

atgacaacaa aaaatgattt cttagatgaa gatgcgattg aaattttggc tgctgaattt   1020

ggtatagaga tcaatatcat taacgaggct gatgagtttg attatgtaaa agactatgaa   1080

gaagagactg atgaaaaaga tttagtgact agagcacctg tgattaccat catggggcat   1140

gttgatcatg gtaaaacttc tttgttagat tatattagaa aatcacgcgt tgcaagtggt   1200

gaagcagggg gtattactca gcacgtgggt gcttatatgg tagaaaaaaa cgggcgtaaa   1260

attactttta tcgatactcc aggtcacgaa gcttttactg ctatgcgtgc aaggggtgca   1320
```

```
agtatcactg atattgtaat catcgttgta gccgcagatg atggggtaaa accacaaacc   1380
aaagaagcga taaatcatgc taaagcagca ggtgtgccta ttattattgc tattaataaa   1440
atggataaag aagcagcaaa tcccgatatg gtaaaaactc aactcgcaga aatggaaatc   1500
atgccagtag aatggggcgg atcttatgaa tttgtaggag tttcggctaa aacaggaatg   1560
gggattgaag atttgcttga aatcgtgctt ttacaagctg atattttaga acttaaagcc   1620
aatccaaaaa gttttgctaa agcaagcatt atagaaagtt ctgtgcaaaa agggcgtggt   1680
gcggtggcta ctgtcatcgt gcaaaatgga acacttactg taggaagtac cgtggttgca   1740
ggcgaggctt atggaaaagt gcgtgcgatg agcgatgatc aaggtaaagc cttaaaagaa   1800
attaaaccag gcgaatgtgg ggttatcgta gggcttagtg aagtagcaga tgcaggtgaa   1860
attttaatcg cagtaaaaac cgataaagaa gcaagagaat atgctaataa acgccacgaa   1920
tacaatcgcc aaaaagaact tagcaaatcc actaaagtta gcattgatga gcttggagct   1980
aagatcaaag aaggtaatct aaaagccttg cctgttattt taaaagctga tgtgcaagga   2040
tctttagaag ccttaaaggc aagtttagaa aaacttagaa atgatgagat taaagtgaat   2100
atcattcata gtggagtagg aggaatcacg caaagtgata tagagcttgc aagtgcgagt   2160
gaaaactcta tagtactagg ttttaacata cgcccaacag ggaagttaa agagcgtgct   2220
aaggataaag gcgtagaaat taaaacttat aatgtaattt ataatctttt agacgatgta   2280
aaagccttac ttggtggtat gatgagcccg attatttctg aagagcaatt aggacaagca   2340
gagattagac aagtgatcaa tgtgccaaaa atcggacaaa tcgcaggttg tatggtaact   2400
gaagggtga ttaatcgtgg agccaaaatt cgccttatcc gtgatggagt tgtggtttat   2460
gaaggaaatg taagttcgct taaacgcttt aaagatgatg ctaaagaagt ggcaaaaggc   2520
tatgagtgtg gcgtaggtat agaagggtgc gatgatatga gagtgggtga ttatatagaa   2580
agctataaag aagtagagga acaagcaagt ctatga                            2616
```

<210> SEQ ID NO 52
<211> LENGTH: 2841
<212> TYPE: DNA
<213> ORGANISM: Campylobacter jejuni

<400> SEQUENCE: 52

```
atgctagcac ctggcatggg agaatgggtt tacaaggcta atttattttt atttggagaa     60
tttgcgtatt attatccttt tttcttattt attttaaatt atgtttatta taaaagaaat    120
tacaaattag ctaattttac aagaagagag ctttttggta taggatttgc ctttttctcg    180
agtttgcttt tatttgcagt tttttatcct aattcaggct atatactaga gcttgcttat    240
gcgatttttt ctactatttt ggggcatact gggagcggaa ttttcgctct tttacttcta    300
ctattttctt tggttttatt gtttccaaaa tttgcaaaag aaattttaaa aatagaatta    360
gattttactt atttattaaa agtagagcaa gcttttaaat ctttacttat gcgtgtattt    420
ggtggagaaa acgagaaaga agatgtaggt aaatcagaac ctatagttcc aaaattaaat    480
attttgcaag atagtattta tggaaattta caaataaaca aaaaagggga aaccaataac    540
ttagaacaga taattaaaga tagcaatatc aatgcaagta aaaattcaat taccacggcc    600
aaggaaaatt ttgaaaaact aaaaaatcaa attttagatg aaaccataga gattgataaa    660
caaagtttaa aagaatcaag aagttttgtt catgagcatt ctcaacaagt gcgaaatttc    720
gcacaaaagg ctagtaaaat gagcattagt cttgatgaag attttaattt tatttcagaa    780
```

```
gaagaggtag atatgattcc tgaacgtttt ttaaaaccta aaaaacttga agatataaag    840
caaatagata caaataaaaa tttagatgag ccaagttata aacgtaaaaa tattgaaatt    900
ccagtttcta atcaagaagt taaaccaaaa atttttacaa aagagcttga acttagagag    960
aatttgataa aaaaagaaaa actagaacaa gaatacaaag cctatcaaaa tgaaatttta   1020
gaaaataaag taaaacaaga aattaaaaaa ttagaagaat atgatgcgat aaattcaagc   1080
gatattatag aagggaataa atatagtttt aatagcccaa aaacaattaa aacagaaaca   1140
gaagaatcag acaaaataaa tgaaaataaa aatctagata aagcagacaa tatctttgaa   1200
tttgctccca ttgtagaaga gttaaatcat ccttatatag aacctactcc tataaaaaat   1260
ataaatgaaa tagttataga agaaaaaaat acactcgatt ttatccaaaa tacagaaact   1320
aaaatcgata atgaaaaaac aaatgatcaa gaaattaaac ttcaaaaagc agttttagcc   1380
aaagaaattg ctattaacca agctttattg cgtgaaatag agcagggcga aatagaaaaa   1440
ccaaaagatt tcaccttgcc gccattagat tttttagcta atccaaaaga acacaaacaa   1500
gaaatcaatg aaagtgaaat agataaaaaa atttataatc ttcttgaaaa attgcgtcgt   1560
tttaaaatag gcggcgatgt tataagcact tatgttggtc ctgtggtaac tacttttgaa   1620
tttcgtccta gtgcagatgt gaaagtaagt cgtattttaa atttacaaga tgatttaact   1680
atggctttaa tggcaaaatc aatccgtatt caagctccaa taccaggaaa agatgttgta   1740
ggtatagaag ttccaaatga tgaaattcaa accatttatt taagagaaat tttacaaagt   1800
gaagttttta aaaacgctaa aagtccttta accatagctt taggtaaaga tatagtaggc   1860
aatgcttttg taaccgatct taaaaaactt ccgcatttac tcatcgcagg aacgacaggt   1920
agtggtaaaa gtgtggggat aaattctatg cttttaagtc ttttatatcg caactctcca   1980
aaaaccttgc gtttgatgat gatagatcct aagatgcttg aatttagcat ttataatgac   2040
attcctcatc ttttaactcc tgttatcaca gatccaaaaa aagcagtcaa tgcgctttca   2100
aatatggtag ctgaaatgga aagacgctat cgcttaatgg ctgatgcaaa aaccaaaaat   2160
atagaaaatt acaatgaaaa aatgaaagaa ttaggcggag aaaaacttcc ttttattgta   2220
gtaattatcg atgaacttgc tgatttgatg atgactgcgg gtaaagatgt agaattttat   2280
ataggaagac ttgcgcaaat ggcaagagca agtggaatcc acttgattgt agctacacaa   2340
cgaccttctg ttgatgttgt aacaggacta attaaagcga atttaccaag tagaatttct   2400
tataaagtag ggcaaaaaat tgactctaaa gttattttag atgctatggg tgctgaaagt   2460
ttacttggaa gaggggattg tttatttact cctcctggaa caagctctat agtgcgtttg   2520
catgcgcctt ttgcaagcga atttgaaata gaaaaaatcg tggattttct aaaggatcaa   2580
caaagcgtag aatatgatga aagcttttta aaggatcagc aaagcgtagg tgttacaaca   2640
aatgaaagct ttgatgggga agcagatgag ctttatgaag aagctaaaag agtaatctta   2700
gaagatggaa aaacaagcat ttcttattta caacgccgtt taaaaatcgg ctataaccgc   2760
tctgcaaata ttattgaaca acttacgcaa aacgggattt taagcgaacc tgatgccaaa   2820
ggacaaaggg aaatcttgta a                                             2841
```

<210> SEQ ID NO 53
<211> LENGTH: 3126
<212> TYPE: DNA
<213> ORGANISM: Campylobacter jejuni

<400> SEQUENCE: 53

```
atgaaaaaat ttttttgttt aactttagtt tgtaaacttt ttgctttaag cgaatttgaa     60
```

```
cttcatcata ttgataaagt acataagcta gggtatagcg gagatactat tataataggt    120

gtagccgatg atgcttttaa tcaagatcat attagtttaa aggataagat tttaaagtct    180

acttatccta ctgatacagc tgggaaacag cttatacctg atttgaaaaa atcaacacac    240

ggaagtcatg tagcaggtat agctgttgga gcaaagatag gcgatagcaa accttatgga    300

gtggcttatg ggcaaaattt ttatggagct ggggtgtttc caaatggctc ttacactcaa    360

attcctgata tttataattt tttcaaagat gtgagtatta ttaataatag ctggggtatt    420

aatttttatc cttattttaa tcttaaggct tcaaattctg gattagtaga ttgtactcaa    480

actaatcaag ggacaagcta taatatctgt aatactcctt tggaatatgt tatgaaagca    540

gataaggttg ctaatgatat gatgaggctt agcaaggaca agggagtatt aaatgtattt    600

gctgctggta atgaaggaat tcttagccct gctttgcatg cgattttacc aagttatgat    660

gaatctttaa gagcttggtt ggctgttgga gctttggatg caaatgagat tactttagaa    720

tcagatggga ctttaataat taaaagtcaa ggtttggctg attttagtaa tggttttaag    780

ggagctacga atttttcttt agttgctgct ggagtaaata ttaataatgt tgattcaagc    840

actaatgata agtttacaaa aaaaagtgga acttctatgg cagcacctat ggtaagtgga    900

acagcggcac tggtcaagca aaatttcccc tttttggatg gtaagcaaat tgctgatata    960

ctattaagta cagcaaataa aaattataag gctccaaaat ttactgttaa acaagtaacc   1020

gatggaacaa atcaacctaa atttcttatt gtgtatattt cgcaagatcc acctgggata   1080

gaagatgaaa taaaacggga tttaaaacag ctttacaatg gaatacaagt tcaagttaat   1140

ggacaatgga ttgattatag tgattatatt tgggataata gagatagtgc gcagtcacaa   1200

aaacttaata cttccactat tagttctatt aatggagtag ttagagttga gaaagaagaa   1260

ttatttggac aaggaatttt agatgcacaa aaggcgttaa aaggactgag tattttagat   1320

gcaaacagac tcagtgatca ggatgtatta aaatatgagc aagaacctaa tacagcttat   1380

tatactataa acactgcagg ttatgatgct gaattttcta atgatattag tcaaagaaaa   1440

tgggatgaaa gtactcattt atcaagtgct attaataaac ctacacattt agctaatctt   1500

aacatagggt tatctaaaga aggtgaaggt attttgatta tcagtggtca aaatacttat   1560

gagggcgcaa ctttaatcaa acaaggagaa ttaaagctta aggaaaagt taaaaataat   1620

gcttatgtag aacaaaaagc aatattaagc ggtaatggta ttgtagggca aaatttaaac   1680

aataaaggca tagttagacc tggaaatgaa gatttgaatg atttaaccgt gcaaggaact   1740

tatactcaag aaggagttga ttctaaattg caacttgatt ttggtaatta taaaaattct   1800

aaactgattg caaaaactta tgatattaag agcgggaatt tagaatatat tcctttacct   1860

aaatactata tcttaaataa gccagtgaaa attaatttgg gagatttgga aaaaagttta   1920

tcatctttta atcatgtttt gatacaaaat acctatgctt taaattttga ttttgtttta   1980

agtgatgatt tagtgagtat taataaaacc ttaataaaac ctaatttaaa gccaaatgct   2040

tacgaaattc ctaatacaag cttgggaaat gctttaagac aattgcgatc tagggcagac   2100

ttgagtcaga cttatcagga attttttgct tctttagata atggaataga tgtaaagact   2160

aaattaaata gaatagaagg ttcagggtat ttaagcactt ttagtaatca taatcaatct   2220

aatttaatgc aaaataatat gttatttacc cttcatcctc ttaatattaa taattttgca   2280

caaaacaata atatcttact tgctagtact tatttaccta gaatttttag caatgaagaa   2340

tatttttggc atcttactcc aagttataaa tactataaag ataaagattt ttcaggtcaa   2400
```

```
aaaacaggtg ctaatatctc tttaggagaa aatttctcat caggcttttt agcttatgct   2460
ttatctcttt ctagcgctaa atttaatttt aataatggta gtgatttgaa gagttataac   2520
atggatttat tgcttaatta taaccatgat ttagatttta taaaaatatt aagtggatta   2580
ggtataggtg taggatttaa tactcttaat cgttttgtag tagagcagcc aattgaaggc   2640
aaatataaaa cattgcaaac ttcagcccag cttggtgtaa ctaaagatat tattttaggt   2700
caagatttta tttttaatcc tttaatgtat tttacacata gtttttttta tcaagaagat   2760
tttaaagaaa ataaaagtcc ttttgctaaa aattatgaaa gtttaaaaca tcatagcata   2820
aatgcaaatt taggttttaa tcttgctaaa aatatagagc aagatgatta tcaagcttct   2880
ttttctactt ttgtaatttt tgaaaaaaga atttatggaa gaactttaga aaataaggct   2940
agttttgttg attttcctat tgcttttatt caaaaatata aattaaaaga taatatttta   3000
agtcaaggtt ttaattcaga atttttatat aaaaacaatg tattttggca gtttatgtta   3060
atgaatagat tttctcataa tgcctatgaa ttgcatttaa tgagttcagt aggaaaacgt   3120
ttttga                                                              3126
```

<210> SEQ ID NO 54
<211> LENGTH: 3270
<212> TYPE: DNA
<213> ORGANISM: Campylobacter jejuni

<400> SEQUENCE: 54

```
atgccaaaac gaacagatat taaaagcatt ttacttatag gaagtggtcc tattgtgata     60
ggacaagctt gtgaatttga ttattctgga actcaagccg caaagacttt aaaagaatta    120
ggatatcgtg tagtattaat caactcaaat cctgcaacca tcatgacaga tcccgaattt    180
gcagatgcga cttatataga acccataaca aaagaaagta ttttaagtat tattaaaaaa    240
gaaaaaattg atgcaatttt gccaactatg ggtggacaag tagcgttaaa tgttgctatg    300
gaagtttatg aaagcggact tttaggagat gtgaaatttt taggcgcaaa tcctgaggcg    360
attaaaaaag gcgaagatcg tcaggttttt aaagaatgta tgaaaaaaat tggcatggat    420
ttgccaaaat cgatgtatgc gtataattat gacgaagctt taaaagccgt agatgaaatc    480
gactttcctt tgatgatccg tgcttcttat actttagggg gtgctggaag tggtgtggtt    540
tacaatatgg acgaatttaa agaacttacc aatactgctt tagctttatc acctattcat    600
gaaattttga ttgaagaaag tttgttaggt tggaaagaat atgaaatgga agttatacgc    660
gatagagcgg ataattgtat catagtttgt agcatagaaa atatcgatcc tatgggagtt    720
catacaggag atagtattac aatagctcca gcattaactt tgacagataa agaatatcaa    780
gttatgcgta atgcttcttt tgctattttg cgtgaaattg gtgtagatac aggcggaagt    840
aatgtgcaat ttgctatcaa cccaaaaaat ggaagaatga tagttataga aatgaatcca    900
agagtttcaa gatcaagtgc tttagcttct aaggcaacgg gttatcctat agcaaaggtt    960
gcgacacttt tggcagtagg ttttagctta gatgagatta aaaatgatat tacaggaact   1020
cctgcatctt tcgagcctgt gattgattat attgtaacaa aaattcctcg ctttaccttt   1080
gaaaaatttc caggagcaaa tacaacttta ggtacagcta tgaaaagtgt gggtgaggta   1140
atggctatag gacgcacttt taaagaaagt atacaaaaag cactttgttc gcttgagcgt   1200
tctttaagtg gttttgatag ggtaaaattt gaagatagaa atgatcttgt ttttaaaatt   1260
cgcaatgcca atgaaaagcg tttactttat gttgctcaag cttttaggga aggttttagc   1320
gtagaagaac tttatgagct ttgtaaaata gatccttggt ttttaacaca gattaaagaa   1380
```

attgtagatt ttgaagaaca aattgatatg gatattttaa acaataaggc tcttttgaga 1440
aaagcaaaaa ctatgggctt ttcagataaa atgatagcct tgcttgtaaa tttgaaagat 1500
aatttagaat taagccaaaa tgatatttat tatgtaagaa tgaagcaaaa aatcatcgca 1560
gaatttagtg aagtggatac ttgtgcgggt gaatttgaag ccttaactcc ttatctttat 1620
tcaagtatca atgtaagcga actcactcaa agtaaaaacg atgctaagga taaaaaagaa 1680
aaaaaagtga tgattatagg tggggggcca aaccgtatag gacaaggtat agaatttgac 1740
tatgcttgcg tacatgcttc ttttgcgctt aaagatatgg gtattaaaac tattatgtat 1800
aattgtaatc ctgaaaccgt ttcgactgac tatgatacaa gtgatatttt gtatttcgag 1860
cctattgatt tcgaacattt aagagcggtg attgagcgtg aaaaacctga tggagtgatt 1920
gtgcattttg gtggacaaac tcctttgaaa tttgctaagc gtttaagtgc ttttggagct 1980
aagattatag gtactagcgc aagagtaatt gatatggcag aagatagaaa gaaatttgcc 2040
gaatttatta caaagctagg tatcaatcag ccaaaaaatt ctactgcaac aagcgtagaa 2100
gaagcggttc ttaaggctag tgatataggg tatcctgtgc ttgtaagacc aagttatgtt 2160
ttaggtgggc gtgcgatgcg cgtggtaaat gatgaggctg aacttagact ctatatgcaa 2220
gaagctgtgg atgtaagcga taaaagccct gttttgatcg atcagttttt agacaatgct 2280
acagaaattg atgttgatgc gatttgtgat ggcaaagatg tttatgttgc aggaattatg 2340
gagcacatag aagaagcagg aattcattcg ggtgacagtg cttgttcttt gccgccttgc 2400
aatatcgatg aaaaaatgca agaatttatt gcacaaaaaa ccgcagatat tgctttaaat 2460
ttgggagttg taggactttt aaatatacaa tttgctttac ataataatga gctttatatg 2520
atagaggtaa atcctagagc tagtcgtacc ataccttttg ttagtaaagc tacgggtatt 2580
cctttagcaa aagtggcaac gcgtgtgatg tggcaaggaa atttaaaaga agctttaaaa 2640
ttttatgata cttttaaagt ggttaatttt gatactaaaa ttttacgccc taaaactcca 2700
aaatatatga gcgtgaaaga agcagtattt ccatttgcaa aacttagtgg aagtgattta 2760
gaattaggtc ctgaaatgcg ttcaacgggt gaagttatgg gtataagcaa ggattttgca 2820
aattcttatg cgaaaagtca aattgcatcg tttaatcatc ttccagagca aggcgtggta 2880
tttatctcct taaaagataa ggataaaaaa tataccaaaa aaatcgctgc agaatatgta 2940
aagcttggct ttaagcttat ggcaacaggg ggaacttgca aggaaatttt agaaagtggt 3000
tttgagtgcg aacttgtaca taaaatttca gaaggacgcc ccaatgttga agataaattg 3060
aaaaatggag aaattcactt agttatcaat acaagcgata gtcacagttt taaaggcgat 3120
acgaaaaaaa ttcgtgaaaa tattattcgt tttaaaatac cttattttac aaatttacga 3180
tcagctttag caggtgcaaa atcgattaaa gctatacaga gtaaatcttg cctagatgta 3240
aagagtttgc aagagtggct taaatcttga 3270

<210> SEQ ID NO 55
<211> LENGTH: 3365
<212> TYPE: DNA
<213> ORGANISM: Campylobacter jejuni

<400> SEQUENCE: 55
atgaaaaata tcacattaac taaaatacct ataggagagg gcaaagaacc ctgtttaaat 60
tctaaaaaga tagttttatc tttagctact atttcttttt tggcaagttg tgctaatgct 120
aaattaaatt ctgaaataaa aacttatgat gaagttaata aaaatgttaa aactagatca 180

```
gcaagtgttt atagccctca agctaagatc aatacgacta taaattcttt acacaatcaa    240
caagtaacta ttactggaaa tggaacatca aattctttaa caatcggatc aagtggaact    300
ctaggtagca taggcaatac aggtaaaatc atctatgccc atgctaatgg tagcaacact    360
cttactcttg caaatcttac taataataga actattaatg gtaagattgg tatagaaaac    420
aatggtaatt ttacaggaac tattgctgtc aacacctttg aaaatacagg tcaaattaat    480
ggacaaattt acatgggaat ttggggtaac aactcaggaa ctcttaatat agataaattt    540
gacaatagtg gaaccataat tgacaacaat aaaggagttt ttttgaagga aagaatacca    600
acatacaaac ctttaataac agtggtttta ttagtgcaaa taagggtgta gatataggca    660
acataggaac cataaaaaat tttaataaca acggaactat acaaggctca gaagtgggag    720
tggctataaa tacaaaaata gatactttta ctaataatgg ttttattaat tcccctggta    780
gtggacaatg gaataatggt atatggataa gtagcaatgc taccatagaa aagcttgtta    840
acaatggcac aataaaagga ggacattctg ctataatggt aacatctcag catataaaaa    900
ctgttgaaaa tacaggaatt atacatgctg aaggagaatg ggttctagt atattattag    960
aatatggtgg ttttatagag catataatca atactggaac cataagtaat aataatgttg   1020
gtataggttc agcttatgga gtatttggaa cacttaccat aaaagatgga ggtatggttt   1080
atggaaaata ctcggcaata ggagtgggtc gatcgcaaac tctaggagat ttatatatag   1140
atggacgttc aaataatggc acagtaagtg gaatttatag tgaagaacat ggaattttat   1200
tagagaataa ctcacgaact caaaaaatag aacttaaaaa tggcggcatt ataaaaggta   1260
atatcgatgg tataagattg ataaactcgg cctctttaag tggagaaatg attttatctg   1320
gcgaaggttc tagggtagaa ggtggaagag gtgttggtat attgaatcga agtggaaaaa   1380
tagaaggctc tataaaagta gaagatggag caactgttac ggctacttcg aatcgagcca   1440
tagctaactc tggctcagga agtataacag gtggtattac tgttagtggg aaaaacacta   1500
aacttgaagg aaatataatc aatacaggta atgcttctat aggtagtgat atcaagatag   1560
aaggtggagc taaggtagaa ggtggtcttg ttaatcaagg taatggaagt atctcaggaa   1620
gtgttcaagt aagtggtggt agtagtattg attccattac caatgagggt aatggagcta   1680
tttctggttc aattactgta tataaagata gtaaacttga ttctatcact aacacttcta   1740
catcatctac aggtataagt ggttctatta ctaacaatag tgataataaa cttgaaattt   1800
ctaattcagg taatatcggt ggtaagattg aaagtacagg tagtgctgat atggtgatta   1860
gcaatagtaa tggtggaact attagtggcg gtattagttc ttcaggaagt ggaagcacta   1920
gtatttccaa ttcacaaggc tcaaccataa ataacggcat cactgtttca ggatcagcac   1980
aagttgaaat ctccaatcaa ggctcagtag gtaaagatga aaatggtaat acagtaacta   2040
acaatggtag tggtagtgtt ggaatcaaag attggcttgt ttctacagat aaaaacacag   2100
gtaaattaaa cactgtggtt ataggtggaa gtagagcttt taatgtaaaa gtagaaaaca   2160
tcaccgtaga tcaaagcaat gttgatcttg aagagctaaa cgatataaac aacatcatct   2220
caggtgttaa tcaaaacaat attggcaata taggaaccaa tggaagtgga gaaatatctt   2280
taagctttga tccaataaca ggaaagctta ctacagattt taatcttaat gcttccatat   2340
caggtgcaac ctttagatct ttaatctcta ctacttcaag aagatcaacc tttatagata   2400
atgttatggg taattctatg caaagctttg ctttagcttc ttcaagtaaa tctcaaagca   2460
tcgctatgtc tgaaaagggt aatttatatg cagatgcaag tgattatata aagagtgatt   2520
taaataatgg aagctatggt tctaataaag aacattcttt attcatcctt ccttatactt   2580
```

```
cttcacagaa tgttgaactt tctttaaatg aagaaagtaa aggacacact aaaggaacca   2640

ttataggtta ttctacttta aaagacagtg gaatatatgg tgtgtatgca ggttatgaag   2700

atacaaaaat gggttcaact tattttgata ttaataatag aacctattat gcaggtttaa   2760

aatactttaa taccttattt actacagaaa aaggtcaaga agtttatatc aaagctcaag   2820

gtaaagctgc tttgattaaa aatgatttaa ctgaaaaaat aggaaataat gaagctaaag   2880

ctgaacctaa ttcttatgct tatggagtca atacagcctt aggtatgaat tttatttcta   2940

ataaagatat attctctcct gaaataggtc ttgcttatga aggaggttat actgaagctt   3000

tttctatgaa agacaccata ggacaagcaa cagttaaagg tggagaaaga acctatgcaa   3060

actatttaaa tcttttctct actaaaacaa gtcttacttg gtttagagat tggttgccta   3120

atttaaaaac ttcagtagaa cttggagcta agtttaatat caatcctaaa gtagaagctg   3180

aggctagatt tggtaatata aaagtaagtg atgagtttga tttaccaaga gtacaaaaat   3240

ttgtaagcac ttcttttatc gttcctgtta atgaagcttt ctattttagt ttaaactata   3300

atggaatgtt tgataaagat ggcaataccc atacaggatt tgctcagttt aattatcttt   3360

ggtaa                                                              3365
```

<210> SEQ ID NO 56
<211> LENGTH: 3436
<212> TYPE: DNA
<213> ORGANISM: Campylobacter jejuni

<400> SEQUENCE: 56

```
atgaataaaa ctgcattaac taaaacatac acaaaagata tacaaaattc ctgtttaaat     60

tctaaaaaga tagttttatc tttagctact atttcttttt tggcaagttg tactcatgct    120

acacttactc ctgaaataaa aacttacgaa gagacaaata gacatgctaa agctaggtca    180

ggtcttcaat ctagaaattc gaataatgag actataaata atttacaaac tttaactaaa    240

actataagtg acaccggcaa tactctagtt atagaaagta gtggaactat tactatttct    300

aatgatgggc aacaagcagt aaactttcaa ccaaattctt caacttctac ctttttaaat    360

aaaggaactc ttataggtgg aaataatact gctagtgttc aactaggagc agcaaatgga    420

aataacggtg ttagcataga aacctttaat aatcaaggta tcataggtaa tggttcttct    480

aaatttggag taacagtttt tgggggggg gagtaaagat aaccctaaat ctataatcaa     540

taattttagt aatagtggaa ctattcactc taatactggt gaaagtattt attttggtaa    600

cgccaaaata tcaagttttg ttaatagtgg gactattaag agtaaacaag gtgcaggagt    660

aaatatatct caaggaacaa gtatagagaa ttttaacaat accggaaccg gaattattga    720

aggcaagaga atgggtgtaa atgttcgttc aacaataaat accttcgtca atgacggttt    780

aattgctgca acgaacgatg gaatacagat aaatgctaat gtaaaaacat taataaataa    840

gggaaccata aaaggagatg ctatatctat aagatcatta ggtggaacta tagaaacatt    900

gaccaatgaa ggcattatgt atggtaaaag tgctggtatt tacatgaaca gaagtcttgt    960

taaaactctt acaaatagcg gtaccattaa tcaaaacaat tcggcaactt ggtctgctgg   1020

tataaaactc gaaaatggta gtatcataga aaatatcatc aacacaggat ctatccgttc   1080

taatgctttt ggaatatctg taactggtgg taaatttgga acacttacca taaaagatgg   1140

aggtatggtt tatggaaaat actcggcaat aggagtgggt cgatcgcaaa ctctaggaga   1200

tttatatata gatggacgtt caaataatgg cacagtaagt ggaatttata gtgaagaaca   1260
```

```
tggaatttta ttagagaata actcacgaac tcaaaaaata gaacttaaaa atggcggcat   1320
tataaaaggt aatatcgatg gtataagatt gataaactcg gcctctttaa gtggagaaat   1380
gattttatct ggcgaaggtt ctagggtaga aggtggaaga ggtgttggta tattgaatcg   1440
aagtggaaaa atagaaggct ctataaaagt agaagatgga gcaactgtta cggctacttc   1500
gaatcgagcc atagctaact ctggctcagg aagtataaca ggtggtatta ctgttagtgg   1560
gaaaaacact aaacttgaag gaaatataat caatacaggt aatgcttcta taggtagtga   1620
tatcaagata gaaggtggag ctaaggtaga aggtggtctt gttaatcaag gtaatggaag   1680
tatctcagga agtgttcaag taagtggtgg tagtagtatt gattccatta ccaatgaggg   1740
taatggagct atttctggtt caattactgt atataaagat agtaaacttg attctatcac   1800
taacacttct acatcatcta caggtataag tggttctatt actaacaata gtgataataa   1860
acttgaaatt tctaattcag gtaatatcgg tggtaagatt gaaagtacag gtagtgctga   1920
tatggtgatt agcaatagta atggtggaac tattagtggc ggtattagtt cttcaggaag   1980
tggaagcact agtatttcca attcacaagg ctcaaccata aataacggca tcactgtttc   2040
aggatcagca caagttgaaa tctccaatca aggctcagta ggtaaagatg aaaatggtaa   2100
tacagtaact aacaatggta gtggtagtgt tggaatcaaa gattggcttg tttctacaga   2160
taaaaacaca ggtaaattaa acactgtggt tataggtgga agtagagctt ttaatgtaaa   2220
agtagaaaac atcaccgtag atcaaagcaa tgttgatctt gaagagctaa acgatataaa   2280
caacatcatc tcaggtgtta atcaaaacaa tattggcaat ataggaacca atggaagtgg   2340
agaaatatct ttaagctttg atccaataac aggaaagctt actacagatt ttaatcttaa   2400
tgcttccata tcaggtgcaa cctttagatc tttaatctct actacttcaa gaagatcaac   2460
ctttatagat aatgttatgg gtaattctat gcaaagcttt gctttagctt cttcaagtaa   2520
atctcaaagc atcgctatgt ctgaaaaggg taatttatat gcagatgcaa gtgattatat   2580
aaagagtgat ttaaataatg gaagctatgg ttctaataaa gaacattctt tattcatcct   2640
tccttatact tcttcacaga atgttgaact ttctttaaat gaagaaagta aaggacacac   2700
taaaggaacc attataggtt attctacttt aaaagacagt ggaatatatg gtgtgtatgc   2760
aggttatgaa gatacaaaaa tgggttcaac ttattttgat attaataata gaacctatta   2820
tgcaggttta aaatacttta ataccttatt tactacagaa aaaggtcaag aagtttatat   2880
caaagctcaa ggtaaagctg ctttgattaa aaatgattta actgaaaaaa taggaaataa   2940
tgaagctaaa gctgaaccta attcttatgc ttatggagtc aatacagcct taggtatgaa   3000
ttttatttct aataaagata tattctctcc tgaaataggt cttgcttatg aaggaggtta   3060
tactgaagct tttctatga aagacaccat aggacaagca acagttaaag gtggagaaag   3120
aacctatgca aactatttaa atcttttctc tactaaaaca agtcttactt ggtttagaga   3180
ttggttgcct aatttaaaaa cttcagtaga acttggagct aagtttaata tcaatcctaa   3240
agtagaagct gaggctagat ttggtaatat aaaagtaagt gatgagtttg atttaccaag   3300
agtacaaaaa tttgtaagca cttcttttat cgttcctgtt aatgaagctt tctattttag   3360
tttaaactat aatggaatgt ttgataaaga tggcaatacc catacaggat ttgctcagtt   3420
taattatctt tggtaa                                                   3436
```

<210> SEQ ID NO 57
<211> LENGTH: 3561
<212> TYPE: DNA
<213> ORGANISM: Campylobacter jejuni

<400> SEQUENCE: 57

```
atgggtaaaa ttatgaaaac tatggacgga aatgaggctg ctgcatacgc tgcgtatgct     60
tttactgaag ttgctggaat ttatcctatt acacctagtt ctcctatggc tgattatacc    120
gatatgtggg cagctgcagg aaaaaaaaat ctttttggag ttcctgtaaa aatcgtagaa    180
atgcaaagtg aagcaggagc tgcaggtagt gtgcatggat ctttacaagc tggggctttg    240
actacaactt atacggcttc tcaaggatta ctccttaaaa ttccaaatat gtataaaata    300
gcaggtcaat tactcccctg tgtaatccat gtagcagcgc gttctttggc tgctcaagct    360
ttgtctatct ttggtgatca tcaagatatt tatgcagcaa gacaaattgg ttttgctatg    420
ctttgttcgc attctgtgca agaaaccatg gacttagctg gtgtagcaca tttagctgca    480
attaagggaa gagtgccatt tttacatttt tttgatggtt ttagaacaag ccatgaaatt    540
caaaaagttg aagtaatgga ttatgcgcat tttgatagat tattagatag agaagctttg    600
cttgaattta gaaataatgc tttaaatcca gaaaatccaa aaacacgtgg aacagcacaa    660
aatgatgata tttattttca aactagagaa gtaagcaatc gtttttacga tgctttacct    720
gatgttgtta atgaatatat gcaagaaatt tcaaaaatta caggtagaga atacaaacca    780
tttacttatt atggtcacaa agagccagag tgtgtgattg ttgctatggg ttctgtaact    840
caagcacttg aagaagtggt ggactatctt aatgccaagg gtgaaaaggt agggatttta    900
aaagtttatc tttatcgccc atttagttta aaatatttct ttgatgttat gccaaaatca    960
gtgaaaaaaa tcgcggtttt agatagaacc aaagaaccag gaagtctcgg agaaccactt   1020
tatcttgatg taaaatcagc tttctatgga agagaaaatg ctcctgttat agtgggtgga   1080
agatacggac tttcttcaaa ggatgttgat cctgctcaaa tgatagcagt atttgaaaat   1140
cttaaacttg ataatccaaa agatggcttt actgtaggta taattgatga tgtaactcat   1200
acttcactga gtactggaga gaaaatttca cttggagatg aaagtacgat cgaatgttta   1260
ttttacggac ttggtgctga tggaactgtg ggtgcaaata aaaactcgat taaaatcatc   1320
ggagataaaa cggattttta cgctcaagct tattttgctt atgattctaa aaaatcaggg   1380
ggttatacaa gaagccattt aagattttct aaaaaaccta tccgttcaac ttatcttgtt   1440
tcaactccgc attttatcgc ttgttcggta gcggcttatt tggaaattta tgatgtttta   1500
gcaggaattc gcaaaggagg aactttcctt ttaaatagta tttggaatgc tgaagaaacc   1560
ataagacaac ttccagatgc agtaaagaaa actttagctg aaaaagaagt aaatttttat   1620
atcatcaatg caaccaaact agctcgtgat ataggtttgg gaaatcgtac aaataccatt   1680
atgcaatcag cctttttcaa acttgcaaaa atcattcctt atgaagacgc acaaaaatac   1740
atgaaagagc ttgcgtataa atcttatagt aaaaaaggcg atgctattgt agaaatgaat   1800
tacaaggcta ttgatgtggg tgctgatgga cttgtaaaag ttgaagtgga tccaaattgg   1860
aaaaatttag agcttaaaga aaaagaacaa accaatgcct ataaaggtac tgaatttgtt   1920
gaaaaaatcg taaaacctat gaatgcggct aagggtgatg atttacctgt ttcagccttt   1980
ttaggttatg aagatggaag ttttgaacac ggcacaaccg aatacgaaaa acgcggtgtt   2040
ggggttatgg taccaagatg gatagaggca aattgtattc aatgcaatca atgtgcttca   2100
gtttgtccgc atgctgttat caggccattt ttgattaatg atgaagaaat ggcaaatgca   2160
cctcgcggtg taaaagatca tgctttagaa gctaaaggaa ccaaaggaga aaaattaagc   2220
tttaaaattc aagtttctcc acttgattgt acaggctgtg agctttgtgt tcatgagtgt   2280
```

```
cctactaaag aaaaatcttt ggttatggta ccacttcaag aagagatgga ttttggtgag   2340

caagaaaatg cggattattt atttaaagaa attacttata aagatgatat tttaaataaa   2400

gaaaccacaa aaggagcgca atttgcccaa cctttatttg aattccatgg ggcatgtcct   2460

ggatgtgggg aaactcctta tattacttta attacaagat tgttcggtga aagaatgatt   2520

gtggctaatg ctacaggttg tagttctatt tatgggggtt cagctccatc aactccttat   2580

agaaaaagtg tgaaaaatgg acacggtcct gcttggggaa attcactttt tgaagacaat   2640

gctgagtttg gtttgggtat gaaaattgca actgaaaata caagacaccg cattgaacat   2700

atcatgaatg aaagtatgca agaagttcca aatgctttat cagctctttt taaagattgg   2760

attgcaaata aagacaatgg tgctatgtct gtggaaatta aagataaaat gatccctatt   2820

ttagagcaaa ataaaaatat taaagctgta caagatatat tagagcttaa acagtattta   2880

agtaaaaaat ctcactggat ttttggtggt gatggttggg cttatgatat aggctatggc   2940

ggacttgatc atgttttagc aagtggagaa aatgtaaata ttttagtgct tgatacagaa   3000

gtttattcta atacaggcgg tcaaagttca aaatcttcta gaacaggagc tgtagcacag   3060

tttgcagcag caggcaaacc tatacagaaa aaagatctag gtcaaattgc tatgacttat   3120

ggttatattt ttgtagcaca agtaaattca acggcaaatt atactcatct tatcaaagct   3180

atcactgcag ctgaggccta tgatggacca tctttggtga tttgttattc tccttgtata   3240

gctcatggta ttaaaggtgg gctgggttac tcaggagagc aaggtgagct tgctacaaaa   3300

tgtggttatt ggccacttta tacctttgat cctcgtttag aagagcaagg aaaaaatcct   3360

ttaactctaa caggaaaaga acctgattgg gatttatatg agcaattttt gatgaatgaa   3420

gtgcgttata attcacttaa aaaagcaaat cctgaacacg ctgctgagct tttgaacgc   3480

aataaaaaag acgctcaacg tcgctataga cagcttaagc gtattgctat ggctgattat   3540

agcaatgagg tcgaaagctg a                                             3561
```

<210> SEQ ID NO 58
<211> LENGTH: 4137
<212> TYPE: DNA
<213> ORGANISM: Campylobacter jejuni

<400> SEQUENCE: 58

```
atgtgcgata tgttagataa taaattagga aatcgtttaa gagtagactt ctcaaacatt     60

tcaaaacaaa tagaaatccc aaatcttcta caattacaaa aaaagagttt tgattatttt    120

ttaaatcttg ataatggtga aagtggtata gaaaaagttt ttaaatcaat ttttcctatt    180

catgatccgc aaaatagatt gagtcttgaa tatgttagta gtgaaatagg caagccaaaa    240

tataccattc gcgaatgcat ggaaagaggt ttgacttatt ctgtaaattt aaaaatgaaa    300

atccgtctta ctctgcatga aaaagatgaa aaaacagggg aaaaagttgg cgtaaaagat    360

attaaagaac aagaaattta tatccgcgaa attcctttaa tgacagatcg tgtatctttt    420

atcattaacg gggttgagag agtggttgta aatcaattac atagaagccc tggtgttatt    480

tttaaagaag aagaaagttc aacggttgca aataagcttg tttatacagc acaaattatt    540

cctgatcgtg gttcgtggct ttattttgaa tacgatgcca aagatgtttt gtatgtaaga    600

atcaataagc gtagaaaagt tcctgtaact atgcttttta gagctttagg gtataaaaaa    660

caagatatta ttaagttgtt ttatcctatt cagactatac atgtgaaaaa agataaattt    720

ttaacagaat ttaatccaaa tgattttatg gatagaatag aatatgatat taaagatgaa    780

aaaggaaaaa tcgttcatca agctggaaaa agacttacaa agaaaaaagc agaacagctt    840
```

```
attaaagacg gtttaaaatg gatagaatat cctgtagaaa ttttacttaa tcgttattta    900
gcaaatccta ttattgataa agaaagtgga gaggttttat ttgattcttt aactttgtta    960
gatgagagta agcttgctaa gattaaagag caaaaaagtt ttgatatagc aaatgacttg   1020
gctaatggcg ttgatgcagc gattattaac tcctttgccc aagatggaga aactctaaaa   1080
cttcttaaac aaagtgaaaa tatcgatgat gaaaatgatt tagctgcgat tagaatttac   1140
aaagttatgc gcccaggtga acctgtggta aaagatgcag cgaaggcttt tgtaaatgat   1200
ttattcttca atcctgaaag atacgatctt accaaggtag gtcgtatgaa aatgaaccat   1260
aaattaggtc ttgaagtacc tgagtatgtt actgttttga ctaatgaaga tattattaaa   1320
actgcaaaat atttaattaa agtaaaaaat ggtaaaggac atattgatga tagagatcat   1380
ttaggaaatc gtcgtatccg ttctataggt gaacttttag ccaatgaact tcatttaggt   1440
cttgcaaaaa tgcaaaaggc gatcagagat aaatttactt ctttaaatgc ggatcttgat   1500
aaagtaatgc cttatgattt aatcaatcct aaaatgatta ctacaactat cattgaattt   1560
tttacaggag gtcagctttc gcaatttatg gatcaaacca accctttaag cgaggttact   1620
cataagcgtc gtttgtcagc gcttggtgaa ggtggacttg taaaagaaag agcaggtttt   1680
gaagtgcgtg atgttcacgc gacacattat ggtagaattt gtccagttga aacacctgaa   1740
ggtcaaaata ttggtttgat taacactctt tctacttatg caaaagtaaa tgaacttggc   1800
tttgttgaag cgccatatag aaaagttgta aatggtaaag tgactaatga agttgtttat   1860
cttacagcga cacaagaaga aggcttgttt atcgcaccag cttcaactaa ggttgatgct   1920
aaaggcaata tagtagaaga atttgttgag gctaggcaag atggtgaaac tatacttgca   1980
agacgcgaag aagtgcaatt aatcgatctt tgctcaggta tggttgttgg agttgcagct   2040
tctttgattc cgtttttaga gcacgatgat gcaaacagag cgctaatggg ttcaaacatg   2100
caacgtcaag ctgtgccact tcttactgct tcagctccga tagtaggaac aggtatggaa   2160
caaattattg cgcgtgatgc ttgggaagct gttaaagcaa agcgtggcgg tgtggttgag   2220
aaagtggata ataaaagcat tttcatttta ggtgaagatg ataaaggtcc atttattgac   2280
cattacacta tggagaaaaa tttaagaacc aatcaaaata caaattatat tcaacaccct   2340
attgttaaaa aaggtgatat agtaaaagca ggacaaatta tcgcagatgg tccttctatg   2400
gatcaaggcg aacttgctat aggtaaaaat gctttaatcg cttttatgcc ttggaatggt   2460
tataactatg aggatgctat agttgtaagt gagagaatta ttcgtgaaga tacttttaca   2520
agcgtgcaca tttatgaaaa agaaattgaa gcaagagaac taaaagacgg tatagaagaa   2580
attaccaaag atattccaaa tgtaaaagaa gaagatgttg cgcatcttga tgagagcggt   2640
attgcaaaaa ttggtaccca tatcaaacca ggtatgattt tggtgggtaa ggtttctcca   2700
aaaggtgagg ttaaaccaac tcctgaagaa agacttttaa gagcgatttt tggagaaaaa   2760
gcaggacatg ttgtgaataa atccctttat gcaaccgctt ctttagaggg tgttgttgtg   2820
gatgttaaaa ttttcactaa aaaaggctat gaaaaagatg atcgcgcaat aaaatcttat   2880
gataaagaaa aaatggcttt agaaaaagag catcatgata gacttttgat gatggataga   2940
gaagaaatgc ttcgtgtttg tgctcttctt tccaaagcct ctttaaatag cgatcaaaaa   3000
attggagata aaaattataa aaaaggacaa actgcagata ttagcgaact tgaaaaaatc   3060
aatcgtttta ctttaacaac tttgattaaa gcttattcta aagagattca aaaagaatac   3120
gatgatttaa aaaatcattt ccaaaatgag aagaaaaaat taaaagcaga acacgatgaa   3180
```

-continued

```
aagcttgaaa ttttagaaaa agatgatatt ttaccaagtg gggtaattaa gcttgttaaa   3240

gtttatattg ctacaaaaag aaagcttaaa gtcggtgata aaatggcagg acgtcatgga   3300

aataaaggta tagtttcaac tatagttcct gaagtagata tgccttattt gccaaatggt   3360

aagagcgtgg atattgcgct taatccactt ggcgttccaa gtcgtatgaa tataggtcaa   3420

attttagaaa gtcatttagg tttagttgga cttagacttg gggatcaaat tcaagaaatt   3480

tttgatagaa agcaaaaaga ttttcttaaa gaattaagag cgaaaatact tgaaatttgt   3540

tctattccaa gacttgcaaa cgaaaaagaa tttattaaaa gcttaagcga tgaagagctt   3600

ttaaactatg ctagagactg gagtaaagga gttaaatttt ctactcctgt tttgaaggt   3660

gtaaatatag aagaatttag caagcttttt aaaatggcta agatagatat ggatggcaaa   3720

acagaacttt atgatggacg cacgggggaa aaaattgcag agcgtgttca tgtaggatgt   3780

atgtatatgc taaaactcca tcacttggtt gatgaaaaag ttcatgcaag aagtacagga   3840

ccttatagct tggttaccca acaacctgtg ggtggtaaag cactctttgg gggacaaaga   3900

tttggagaaa tggaagtttg ggcacttgaa gcttatggag cggctcacac tttaagagaa   3960

atgttaacca taaaatcaga tgatgtagaa ggtagattta gtgcctataa agcattgaca   4020

aaaggtgaaa atgttccagc aacaggaatt cctgaaacat tttttgtatt aaccaatgag   4080

cttaaatctc ttgctttaga tgttgagatt tttgataagg atgaagataa tgagtaa      4137
```

<210> SEQ ID NO 59
<211> LENGTH: 4491
<212> TYPE: DNA
<213> ORGANISM: Campylobacter jejuni

<400> SEQUENCE: 59

```
atggatttag aaaatatcct agaaaataat caaagcatag gtttatatca cccaaagaac     60

gaacacgatg cctgtggtat cgctgcagtt gctaatatac gcggtattgc ttcttataag    120

gttatttgtg atgctttaga aattttgatg aatcttgaac accgaggtgg tacaggagct    180

gaagaaaatt caggtgatgg ggcggggatt ttaatccaaa ttccacatga ttttttttaaa    240

actcaagaat tgggttttga acttcctaaa aagggtgatt atgctgtagc acagatgttt    300

ttatcaccca atactgatgc aaaagaagaa gcaaaagaaa tatttttaca aggtttaaag    360

gataaaaaac ttgaattttt aggttttaga gaagtgcctt ttaatcctag cgatataggt    420

gcaagtgctt taaaagctat gccttatttt ttacaagcct ttgtaaaaaa accaagtaaa    480

ataagtgcag gacttgagtt tgaaagagtg ctttatagta cgcgtcgact tatagaaaaa    540

agagctatta atgtgccaaa attttatttt tcaagttttt cttcacgcac catagtttat    600

aaaggaatgc ttctttcaac tcaattgagc gatttttatc ttgattttaa agatgtcaat    660

atgaaatcag ccatcgcttt ggtgcattct cgcttttcga ctaatacctt cccaagttgg    720

gaaagagccc atccaaaccg ttatatggtg cataatggag agattaatac catacgcgga    780

aatgttgata gcataagagc tagagaaggc ttgatgcaaa gtgagtattt tgaaaattta    840

gatgaaattt ttcctatcat agctaagctt agcagtgatt ctgcaatgtt tgataatact    900

ttagaatttt tagctctaaa tggtcgtact ttagaagaag cttttatgat gatggtgcca    960

gaaccttggc ataaaaatga aaatatggaa agcaaaaagc gtgcttttta tgaatatcat   1020

tctttattga tggagccttg ggatggacct gctgctatag tttttactga tggagtgatt   1080

atgggggcga gtttggatag aaatggtttt cgtccttcaa ggtattatct tacaaaagat   1140

gatatgctca tactttcaag tgaaacaggg gctttaaaac ttgatgaaaa aaatatcaaa   1200
```

```
gctaaaaaac gcttagaacc tggaaaactt ttactcgttg atacagcaag aggtagggtt   1260
atagctgata atgaaatcaa agagcattat gctaatgcta agccttataa aaaatggctt   1320
aaaaatttag ttgaacttga aaaacaaaaa agcggagttt ataaacatca gtttttaaaa   1380
gaagatgagg ttttaaaact tcaaaaagct tttggttgga gttatgatga gcttaaaatg   1440
agcgtggctg ctatggctca aaatggtaaa gaagctatag cagctatggg tgtagatact   1500
cctttggcta tactttctaa aacttatcaa cctttgtata attattttaa acaacttttt   1560
gcacaagtaa ctaatcctcc tcttgatgcc ataagagaag agattgttac ttctacaagg   1620
atttatctag gaagcgaagg caatttatta aaacccgatg aaaacaatgc aaaacgcgta   1680
aaaatagcct tgcctgtgat aagcaatgaa gaactttttg aagttaaggc tttaaataaa   1740
tttcaagtta aagaattttc tatactttat gattattcta aaaaaacttt agaaaaggct   1800
ttagatgaac tttgcgttaa gatagaagat gaggttaaaa aaggtgtttc tattatcatt   1860
ttaagcgata aaggagtgga tgaaaaaaac gcttatatcc ctgctttgct tgctgtttct   1920
ggagtgcata atcatctagt aagaaaaaat ttaagaacac atacaagtct tatcatcgaa   1980
agtggtgaac ctagagaaat tcatcatttt gcatgtcttt taggttatgg tgcgactgtt   2040
attaatcctt atttggttta tgagagtata caaaaactca ttgccaataa agatttaaat   2100
ttaagttatg aaaaggcggt agaaaatttc atcaaggcaa gttcaagtgg tatagtcaaa   2160
attgcttcta aaatgggggt ttctaccttg caaagttata atggctctgc actttttgaa   2220
tgtctgggct taagctctaa ggtgattgat aaatacttca cttctacaac ttcacgcatt   2280
gaaggtatgg atttagaaga ttttgaaaaa gaactcattg ctttacacaa acatgctttt   2340
aacgatacac ataaggcttt agattctaaa ggaattcatg gttttagaag tgctaaagaa   2400
gaacatttaa tcgatccgct tgtgattttt aatcttcagc aagcctgtcg caacaaagac   2460
tataaaagct ttaaaaaata ctcggcttta gtagatgaaa aacaagttaa tttgcgttct   2520
ttgatggaat ttgattttag tgaagctatc agtatagata aggttgaaag tgtagaaagt   2580
atagttaaac gctttagaac aggggcgatg agttatggtt ctatttctaa agaagcacac   2640
gagtgtttag cacaggctat gaataaaata ggtgctaaat caaattcagg tgaaggtggt   2700
gaggatgaag aacgctatga aatcaaagag ggtgtggata aaaactcagc cattaagcaa   2760
gtagcaagtg ggcgttttgg cgtggattta aactacttaa gtcatgcaaa agaaattcaa   2820
atcaaagtcg ctcaaggtgc aaaaccaggt gagggcggac aattaatggg ctttaaagtc   2880
tatccttgga tagctaaggc tagacattct actgcaggtg tgacgcttat ttccccacct   2940
cctcatcatg atatttattc tattgaggat ttggctcaac tcatttatga tttaaaacat   3000
gcgaacaaag acgctaaaat ttcagtaaaa cttgtaagcg aaaatggcat aggaacggtt   3060
gctgcaggtg tggctaaggc aggcgcgaat ttaatccttg tttcaggtta tgatggaggt   3120
acgggtgcaa gtcctagaac ttctataccg catgctggaa ttccttggga gttaggctta   3180
gctgaaacgc atcaaacttt gatcttaaat aagcttagag atagggtaag attagaaact   3240
gatggaaagc ttatgaatgg gcgtgattta gccatagcag cacttttagg agctgaagaa   3300
tttggttttg caaccgctcc tttgattgtt ttaggttgta caatgatgag agtttgtcat   3360
ctaaatacct gtccttttgg tatagccact caagatacag aacttagaga tcgtttcaaa   3420
ggcaaagtag atgatgtgat taatttcatg tattttatag ctgaggagct tagagaatac   3480
atggcaaggc ttggttttga acgcctagat gatatgatag gtcgcgtgga taaactccgc   3540
```

-continued

```
caaaaaagtg tgcaaggtaa agcaggaaag ctaaatttag ataaaatttt aaaatccttg   3600

cctacttata atagaaccgc tgtgcatttt aaagattata aagacaataa acttgaaaaa   3660

acgattgatt atagaatttt actaccactt tgtaaaaatg ctgtggagaa aaaagagcct   3720

atcaaacttt ctttagaagt aggaaatcaa agtcgtactt ttgcaactat gctttcaagt   3780

gaaattttaa aaacttatgg aaaagatgct ttagatgaag atagtatcca tatcaaagct   3840

ataggcaatg caggcaatag ctttggagcg tttttgttaa agggtattaa acttgagatt   3900

ataggcgata gcaatgatta tttaggcaag ggtttaagtg gtggtaaaat catagcaaaa   3960

atttcaaatg aagccacttt ttcacctgaa gaaaatatca tcgcaggaaa tgcttgttta   4020

tacggagcta caaaaggtga agtgtattta gatggtatag caggggaaag attttgtgta   4080

agaaattcag ggctttggc tgtggtttta ggaacaggcg tgcatggttg tgaatatatg   4140

acaggtggac aagttgtagt tcttggagat gtgggtgcga atttcgctgc tggtatgagt   4200

gggggcgttg tttatatctt tggaagacac aatgaagctc atgtaaatac cgagcttgtg   4260

gatattaaag atcttaatgc taaggatgaa aaagaattaa aagctgtgat agaaaaacat   4320

atcacttata cagattctaa aaaggctaaa gatattttag aaaaattcga taaaaaagac   4380

ttttttaaag tcatgccaag agattatgaa aagatgttaa aaatgcttga tctttgtaaa   4440

aatgaaaaag atccaaattt agcagcattt ttgaaaatca cacaaaaata a            4491
```

<210> SEQ ID NO 60
<211> LENGTH: 4554
<212> TYPE: DNA
<213> ORGANISM: Campylobacter jejuni

<400> SEQUENCE: 60

```
atgagtaaat ttaaagtaat agaaattaaa gaagatgcaa gacctagaga ttttgaagca     60

tttcaactaa gacttgcaag tcctgaaaaa atcaaatcat ggtcttatgg agaagtaaaa    120

aaaccagaaa ctattaatta tagaacctta aagcctgaaa gagatgggct tttttgtgca    180

aagatttttg gacctataag agattatgag tgtctttgtg gtaaatacaa aaaaatgcgt    240

tttaaaggcg ttaagtgtga aaaatgtggt gttgaagtag caaattcaaa agtgcgtcgt    300

tctagaatgg ggcatatcga gcttgtaact cctgtggctc atatttggta tgttaattct    360

cttccaagcc gtataggaac gcttttgggt gttaagatga aagatcttga gcgcgtgctt    420

tattatgaag cttatattgt tgaaaaccca ggtgatgctt tctatgataa tgaaagtact    480

aaaaaagtgg aatattgcga tgttttgaac gaagagcaat atcaaaattt aatgcaacgc    540

tatgaaaata gcggctttaa agcaagaatg ggtggagaag ttgttcgtga tttacttgca    600

aatttagatc ttgtagcgct tttaaatcag cttaaagaag aaatgggggc tacaaattca    660

gaggctaaga aaaaaactat cattaaacgc ttaaaagttg tagaaaattt cttaaattca    720

aatttaaacg ccaataccga tagcgacgaa gctgtaccaa atcgtcctga atggatgatg    780

attacaaatc ttccagtttt accgccagat ttgcgtcctt tagtggcttt agatggtggg    840

aaatttgcag tttctgatgt gaatgactta tatcgtcgtg ttatcaatag aaatacacgt    900

cttaaaaaac ttatggaact tgatgcacct gaaatcatta tcagaaatga aaaaagaatg    960

cttcaagagg ctgttgatgc gctttttgac aacggtcgtc gtgctaatgc tgtaaaagga   1020

gcaaataaac gcccattgaa atctttaagt gaaatcatca aagggaaaca aggacgtttt   1080

agacaaaatc tactaggtaa aagggtggat ttctcaggtc gtagcgttat tgttgtaggt   1140

ccaaaactta gaatggatca atgcggttta cctaaaaaaa tggctttaga gctttttaag   1200
```

```
ccacatcttt tagctaagct tgaagaaaaa ggttatgcaa ccacagtaaa acaagctaaa   1260
aaaatgatag aaaataaaac caatgaagtt tgggaatgtt tagaagaggt agtaaaggga   1320
catcctgtta tgctaaaccg tgcacctact ttgcataagc tttctatcca agcttttcat   1380
cctgttttag tggaaggtaa ggctatacaa cttcatcctt tggtttgtgc agcatttaac   1440
gcagactttg atggggatca aatggcagtg catgtaccgc tttctcaaga ggctattgca   1500
gaatgtaaag tgcttatgct ttcatcaatg aatattcttt taccagcaag cggtaagtct   1560
gtaaccgttc catcgcaaga tatggtttta ggaatttatt atctttcgtt ggaaaaagca   1620
ggtgctaaag gttcgcataa aatttgtaca ggcattgatg aagtgatgat ggcacttgaa   1680
agcaagtgtt tggatattca tgcgagcata caaactatgg tagatggtag aaagattacc   1740
actacagcag gaagattgat tgttaaatcc atcttgcctg attttgtgcc tgaaaatagt   1800
tggaataaag tcttaaagaa aaaagacatt gctgcgcttg tagattatgt ttataaacaa   1860
ggtggtttag agattacagc aagtttctta gatagactta aaaatttagg ttttgaatat   1920
gcaactaaag caggtatttc aatttcgatt gcagatatta ttgttcctaa tgataaacaa   1980
aaagctatcg atgaagcaaa aaaacaagta agagaaattc aaaattctta taatctcggt   2040
ttgattactt caggggaaag atacaataaa atcattgata tttggaaaag tacaaacaat   2100
gttctttcaa aagaaatgat gaagcttgta gaaaaagata aagaaggttt taactctatt   2160
tatatgatgg cagattctgg tgctaggggt agtgcagctc aaatttctca gcttgctgcg   2220
atgagaggac ttatgaccaa acctgatggt tctattatcg aaacgcctat tatttcaaat   2280
ttccgtgaag ggctaaatgt tcttgaatac tttatttcaa ctcacggtgc tagaaaaggt   2340
cttgcagata ccgctcttaa aacagcaaat gcgggttatt tgacaagaaa actcatcgat   2400
gttgcacaaa atgtaaaaat taccattgaa gattgtggaa cacatgaggg tgttgaaatc   2460
aatgaaatta ccgcagatag ttctattata gaaactttag aagaaagaat tttaggcagg   2520
gttttagctg aggatgtgat tgatcctatt acaaattctg tgctttttgc ggaaggtact   2580
ttaatggatg aggaaaaagc aaaaattctt ggcgaaagcg gtataaaaag tgtcaatatc   2640
cgcactccta ttacctgcaa agctaaaaaa ggaatttgtg caaaatgtta tggtatcaat   2700
cttggtgaag gtaaattagt aaaaccaggc gaagcagtgg gaattatttc cgctcaatct   2760
atcggtgaac caggaacgca gctaactcta agaactttcc atagcggggg aactgcaagt   2820
acggatttac aagatagaca agtaagcgca caaaaagaag gttttataag attttataat   2880
cttaaaactt ataaaaacaa agaaggtaaa aatatcgtag caaatcgtag aaatgcggcg   2940
gttttacttg tggagccaaa aatcaaaact ccatttaaag gtgtgattaa tatagaaaat   3000
attcatgaag atgtgattgt ttctattaaa gataaaaaac aagaagtaaa atacatatta   3060
agaaaatacg atcttgctaa accaaatgaa ttagcaggtg taagtggcag tatagatgga   3120
aaactttatt tgccatatca aagcggcatg caagtagaag aaaatgaaag tatcgtagaa   3180
gtgattaaag agggttggaa tgtaccaaat cgtattcctt ttgcgagtga aattttagta   3240
gaagatggcg agcctgtagt tcaaaatatc aaagcaggcg aaaaaggaac actcaaattt   3300
tacatcctta aaggcgatgg tttagataga gtaaaaaatg ttaaaaaagg tgatattgtt   3360
aaagaaaaag gattctttgt agtgattgct gatgaaaatg atagagaagc aaaaagacac   3420
tatatcccaa gagaatctaa gatagaattt aacgatagtg aaaaaatcga tgacgcaaat   3480
actatcattg caagtgctcc taaaaaagaa agaaaagtga ttgcagaatg ggatgcttat   3540
```

```
aataatacta tcattgcaga aattgatggt gttgtaagct ttgaggatat tgaagcaggt   3600

tatagtgccg atgagcaaat tgatgaagct acaggtaagc gttctttagt aattaatgag   3660

tatttaccta gcggagttag accaactttg gtaattgcag gaaaaggtga taaagctgtg   3720

cgttatcacc ttgaaccaaa aaccgttatt tttgttcatg atggcgataa aattgctcaa   3780

gcagatattt tagcaaaaac tccaaaagca gcagctaaat caaaggatat tacaggaggt   3840

cttccaagag tttctgaact tttgaagca agaaaaccaa aaaatgcggc tgtgattgca   3900

gaaattgatg gtgttgttcg ttttgataag cctttgcgtt ctaaagaaag aattattatc   3960

caagcagaag atggaacaag tgctgagtat ttaatcgaca aatcaaaaca tattcaagta   4020

agagatggag agtttattca tgcaggtgaa aaacttacag atggagttgt ttcgagtcat   4080

gatgtgctta aaattttagg tgaaaaagcc ttgcattatt atttgatttc tgaaattcag   4140

caagtttatc gcggacaagg tgttgtgatt tctgataaac atatagaagt tatcgtttct   4200

caaatgctaa gacaagtaaa agttgtagat agtggacata cgaaatttat tgaaggtgat   4260

ttggtttcaa gacgtaaatt ccgtgaagaa aatgaaagaa tcattagaat gggtggagaa   4320

ccagctattg ccgagcctgt gcttttaggt gtaacaagag cagcgattgg aagtgatagt   4380

gtgatttctg cggcttcatt ccaagaaact accaaagttt taactgaagc aagtatagca   4440

ggtaaatttg actacttaga agatttaaaa gaaaatgtta ttctaggtag aatgattcct   4500

gttggaacag ggctttatgg cgaacaaaat ttaaaactta aagaacaaga ataa         4554
```

<210> SEQ ID NO 61
<211> LENGTH: 156
<212> TYPE: RNA
<213> ORGANISM: Campylobacter jejuni

<400> SEQUENCE: 61

```
auggcuuaug aagaugaaga agauuuaaau uacgaugauu augaaaacga agaugaagaa     60

uauccacaaa aucaccauaa aaauuauaau uacgaugaug augauuauga auacgaugau    120

gauaacaaug augaugauuu uuaugagaug gauuaa                              156
```

<210> SEQ ID NO 62
<211> LENGTH: 198
<212> TYPE: RNA
<213> ORGANISM: Campylobacter jejuni

<400> SEQUENCE: 62

```
augaucaauc cuauacaaca aaguuaugug gcaaauaccg cauuaaauac aaauagaaua     60

gauaaagaaa cuaaaacaaa cgauacucaa aaaacggaaa augauaaagc gaguaaaauc    120

gcagagcaga uuaaaaaacgg uacuuauaaa aucgauacaa aagcuacagc ugcugcgauu    180

gcugacucuu uaaucuaa                                                  198
```

<210> SEQ ID NO 63
<211> LENGTH: 351
<212> TYPE: RNA
<213> ORGANISM: Campylobacter jejuni

<400> SEQUENCE: 63

```
augaaaaaaa uacuuauucu acuuacacua ugugcuuuug cuuuuggugc aagugaaugu     60

gauagaaaaa ucgaucguau caauaaagaa aucaguuuuu cuaaagcgca uaaugauaca    120

gcuagaacuu uaagcuuaga gcuugcuuua aacaaguac aaaaugauug ugcuaaagau    180

ccuauguuuu augauaaaaa guuagaagcu aaaaaacuua aagaacaaga aguggaaaaa    240
```

```
aucgaaaaag aacuugaugc uuuaaaagaa caaaaagauu auaugagcaa ggcugaguau    300

aaagcuaaaa aagaagcuuu aaaagaacaa aaagagaaaa ucaaaaaaua a             351
```

<210> SEQ ID NO 64
<211> LENGTH: 417
<212> TYPE: RNA
<213> ORGANISM: Campylobacter jejuni

<400> SEQUENCE: 64

```
augaguuuug gugaaauuau aguuauuuua guuguagcga uuuuagucuu aggaccugau     60

aaacuuccag aagcuauagu acaaauagca aaaauucuaa aggcuguaaa acgcaacaua    120

gaugaugcaa aaucaagcau agaaaaagaa auacgcauca augacuuaaa agaagaagcu    180

aagaaauaca aagaugaauu uucaagcacu aaugaaaaua uacgcaaaaa acucagcuuu    240

gaagaauuug augaccuuaa gagagauauu uuagauaaaa caaagguaga uuuaaccuuu    300

gauagcagag augauaaagu aaaaaauaac cuuagcggac aaaauuuaaa uacagaagaa    360

aaaccaaauc uuagcaaauu agaaacacaa gauaaaaacg gaaaaauaaa uguuuga       417
```

<210> SEQ ID NO 65
<211> LENGTH: 426
<212> TYPE: RNA
<213> ORGANISM: Campylobacter jejuni

<400> SEQUENCE: 65

```
augcaaaaag cuaaaauuuu aauugccuua aguuuuuuuu uauuaguuuu aucugccugu     60

ucuaaugaug aaaaaaauau uuccaagacu caaaauacag aucaagaagu aguccaaaua    120

gaacaaaacg augaaaaaac agaauuaagu gacuccaacc ugccuuuacc uguagaugau    180

gaagcacaaa guucaaauga ugaacaugaa gucaauccua guauuaucaa cucuuuauau    240

aaacaaaaau gcgccacuug ucauggagaa aaaggggaau uaaaaccuaa aaacagcacg    300

gccauuaaaa ccuugagcaa uaaaaauuuu auacaaaaaa uaaaaacgau aaaagauaaa    360

aaccauaguu uuuuaaguga ugaacaaauu caaaauuuag cugauuuuau aaacaaagga    420

aaauaa                                                               426
```

<210> SEQ ID NO 66
<211> LENGTH: 435
<212> TYPE: RNA
<213> ORGANISM: Campylobacter jejuni

<400> SEQUENCE: 66

```
augcgaagac uaaguauuuu acuugcaauu uuaauaguua uuaauauaac agcuugugau     60

aguaaaacag aaaauuacua caaaaaucuu ccuagcgaag caaaagaaaa agcgaaagaa    120

ugcaaagaaa gcggaacucu uagcgaagau uguauuaaug cauuaaaagu ugguguuaaa    180

ccaacaaaug aagaggguaa auacagucca aacacaccga aaaaaucuga uaaucaaaua    240

uuagaagcuu uaaaacaaaa ugauuuaaaa aaagaaaaaa ccacaaaaga uauuaaccaa    300

aguucagaaa auaaugaaag uauuauaaua ccaccuauag cagaaacacc uucugaaauu    360

uauccuucca aaacaacaga aaacaaucaa aguucuaucu uuagcgauga uguuaauaug    420

acacaggaaa aauga                                                     435
```

<210> SEQ ID NO 67
<211> LENGTH: 525
<212> TYPE: RNA

<213> ORGANISM: Campylobacter jejuni

<400> SEQUENCE: 67
augaugaaga agaaauuggu uuuauuagga agugcugcag ugguauuuuu ugccgcuugu 60
gcaaugaaua gugggguaag uucagaacaa auuggacuua gaaaagcaag uuuagaaaau 120
gaaaauaaag uaaauuuagu ggaggcaaau uucacaacuu uacagccugg ggaaucuacu 180
cguuuugagc guucuuauga aaaugcacca ccauuaauuc cgcaugcuau ugaagauuug 240
uuaccuauaa cuaaagauaa caauaugugc uuaagcugcc augauaaggc uauagcagca 300
gaugcuggug caacuccacu uccugcuagu cauuauuaug auuuuagaca caauaaaacc 360
acaggagaua ugauuagcga uagucguuuu aauugcacuc agugucaugu uccacaaagu 420
gaugcaaaac cuuuaguggg aaauagcuuu aaaccugaau uuaaaaauga acaauuaaaa 480
agucguucaa auuuaauuga ugugauuaau gaggguguaa aguaa 525

<210> SEQ ID NO 68
<211> LENGTH: 606
<212> TYPE: RNA
<213> ORGANISM: Campylobacter jejuni

<400> SEQUENCE: 68
augaaaaaaa ucaaaaaaau cauucaaauu gguaugauag gugguuuagc agcuguugcu 60
ggaggugcuu uagcagguug uggaaguaau aaugacaaug cagauacuuu aaaucaagcg 120
gcuaaugcuc aaggagcuuu uguaauuauc gaagaaacag cuccagggca guauaaaauc 180
aaagaucaau auccaaguga ugaaacaagg guaguuuuaa aagaucuuaa ugguacagaa 240
agaauuuuau ccaaagaaga aauggaugcu uugauuaaag aagaagcagc uaaaauugau 300
aauggaacuu caaauuuaac uaaagacaau ggacaaauca guaguggggg auugaguuua 360
ggggaaacuu uacucgcaag ugcugcaggu gcuauuuuag gaaguuggau agguucaaaa 420
cuuuucaaua aucaaaauuu ugccaaccaa caacgcggug cuuuuucaaa ucaaagugcu 480
uaucaaagga guguuaauag uuuuaauaaa gcaggcacaa caagcucugc uucaagugcu 540
aaaaaaucag guuuuuuugg uggaggcucu aaagccacaa guucuaguuc uucuuuuggc 600
ucuuaa 606

<210> SEQ ID NO 69
<211> LENGTH: 633
<212> TYPE: RNA
<213> ORGANISM: Campylobacter jejuni

<400> SEQUENCE: 69
augacaaaau uuuuaagcau uuguaguuua auugcgaugu uguuaagugg uuguggaagu 60
gauuuuccug gacaaccuag cgauguggcu agaguucagc aaaacaaaua uccaaaugga 120
aauuuaaaaa aagaaauucc cuauaauaaa gauucaagaa uacauggguu aaaaagagcu 180
uuuuaugaca auggucagcu aagagcugaa gaaaauuaua aaaauggaaa aaaagaugga 240
auuagcaggg aauauucuag aaaugggcaa uuacuugagg aggugcauuu uaaagauaau 300
cgcggauaug gugauuuugc aagcuauuau gagaauggaa auaugagagc aaagggaaaa 360
cuacuuggcu auaaaugaaga ugguaugcca gaauuugaag guaauuacaa ggaauauuau 420
gaaaauggaa cuuuaaugug ugauuauaau uuugauaaua aagguaaauu ugauggagua 480
caaaagcguu augaugaaaa uggcgccuua gaagacgaag aaaauuauaa aaauggacuu 540
aaaaauggag ucuuuagaga auauaaaaaa ggggagauug uaagagaaga agaauauaaa 600
aaugguauuu uaguagcaaa accuaaaaau uag 633

<210> SEQ ID NO 70
<211> LENGTH: 735
<212> TYPE: RNA
<213> ORGANISM: Campylobacter jejuni

<400> SEQUENCE: 70
augaaaaaaa uauuuuuaag uguuuuuuug guuuugaguu uaaaugcuca aaaucuugaa 60
auagauaaaa uaagaacaga uuuguauucu aaaaguggag caaauguucu uaaaaaaguu 120
gaaauuucuu uggaauuuga ugggaauaau uuaaaagaaa augaaaauaa guuaauugau 180
gcuguaaaua caguaauuuc aggguuuuuu uaugaagaua uuuuuacaga aauuggaaaa 240
aauaauuuua aaaaaacuuu agaaaaauuu uuagauaaga aauauaagau uaaacuagau 300
gauauauaua ucauaucuuu aaguggagug gaaaaauuug auuuagagga guuuaaacgc 360
uuuuuagaaa guacugaggc uaaagagaag gguaugggua gcgagguaaa aaaagcacuu 420
gaaaacuuag aaguuccuaa aacucaaguu ccuaguguug aaaagauccc aacuccuagu 480
guuccaaauu uagaagucaa gcaaguugaa cagcuuuuca aagauccaga ugaagaaaau 540
aaaaaugaca auggagaaau caauauagau aauuuaaaua caccuaaaau gacuccagau 600
auagaagaaa aaauuaaaag agauuuaauc gccaauccuc cacaaauauu caaagaaaau 660
aacgcaagca agccuuauca uuugccacaa acaggcuaug auauaaagcu ugaugagaau 720
ucaacgcaaa auuag 735

<210> SEQ ID NO 71
<211> LENGTH: 780
<212> TYPE: RNA
<213> ORGANISM: Campylobacter jejuni

<400> SEQUENCE: 71
augaaaaauu augguuugag uaauuuaaau ucguuuuuac uugcuuuagc aauauauauu 60
aguauaguaa uucuuguuuu uuuuagacuu guaagcgagg uugaaccugc uauacaauau 120
acugauauaa aagauaguuu uguagauauu gaacuugcug aaccaucaaa acaaguuauu 180
acucaaagca acacuccuaa agaaauacaa aaaccaacag agcaaauuga uauagaaaag 240
cuuuuugcuc agacuacaaa uaaaacaguu aaaacugaag auauugacca aaaggcaagu 300
aauuuuaaug agcuuuuugg aaauauuaaa gaaauacaag aagaaaagac uacaaaaauu 360
caaucaagug cuaaaucagg aauuucuagu gccccaaaac cucaagcuuc ugaacuugua 420
aaacaacuua augauaguuu acuucaagaa gaaaguucaa cgcaaggcga aagcacaaag 480
gcgcaaaaga uuggaauuua ugaugaauuu uuagggaaag uugugcguau uaucacucaa 540
agauggacuc aguauuaucc aaauagugaa aaaauuucug uuaagguaaa aauuuuuauu 600
gaugaaaaug gaaaauuugg cuauacuuca guugaaaaaa gugggaaucc uuuauaugau 660
gcuaaagugg cugaauuuuu agaaagucaa aaagguaaau uuauuacuua uccuccgcaa 720
aauaaaaaua uaagcauuac caugaauuua agagaugaag uaaaaguuaa aaaugauuag 780

<210> SEQ ID NO 72
<211> LENGTH: 822
<212> TYPE: RNA
<213> ORGANISM: Campylobacter jejuni

<400> SEQUENCE: 72
augaaaaaau uuucuuuagu cgcagcaacu uugauugcag guguaguuuu aaauguaaau 60
gcagcuacag uagcuacugu uaauggcaag agcauuagcg auacagaagu aagugaauuu 120
uuugccccua ugcuuagagg acaggauuuu aaaacuuugc cagauaauca aaaaaaagcu 180
cuuauucagc aauauauuau gcaagauuua auuuugcaag augcuaaaaa acaaaauuua 240
gaaaaagacc cuuuauacac aaaagaacuu gaucgugcaa aagaugcaau acuuguuaau 300
guuuaucaag agaaaauuuu aaauacuauu aaaauugaug cggcuaaagu uaaagcuuuu 360
uaugaucaaa auaaagacaa auauguaaaa ccugcaagag ugcaagcaaa acauaucuua 420
guagcgacag aaaaagaagc uaaggauauu auuaacgaac uuaaagguuu aaaagguaaa 480
gaacuagaug cuaaauuuag cgagcuugcu aaagagaaau caauugaucc agguucaaaa 540
aaccaaggug gugagcuugg uugguuugau caaucaacua ugguaaagcc uuuuacagau 600
gcugcuuucg cgcuuaaaaa ugguacuauu acuacaacuc cgguaaaaac gaauuuuggu 660
uaucauguaa ucuuaaaaga aaauucgcaa gcuaaagguc aaaucaaauu ugaugaagua 720
aaacaaggua uugaaaacgg acuuaaauuu gaagaauuua aaaaaguuau caaucaaaaa 780
ggccaagauc ucuuaaauag ugcuaaagug gaauauaaau aa 822

<210> SEQ ID NO 73
<211> LENGTH: 837
<212> TYPE: RNA
<213> ORGANISM: Campylobacter jejuni

<400> SEQUENCE: 73
auggaaaauc aaaaaaauga auuugaugau auuauuuuag aaaaaaguaa uaaaagugaa 60
aaaguaaaaa aaauucuuuu acgaguuauu gcuuuaguua uuuuguuuuu agcuaucaug 120
auaguuauga agcuuauuaa ugguaguggu gaugaaaaua cgcaaaauca aaguguauug 180
ccaagugaac cuauagcaac ucaagacaau aacaaugaua cuucuuuuga aaguaugcca 240
auuacagaua auacuucagc agaagaucaa uuugaggcau uaagaaaaca auuucaagau 300
gaacaaaaua caacucaaaa uacaacaacc ucuaguucaa auaacaauga uacuacaaau 360
uuugcuaugc cugaucaaga aguuccagca gaaccaacag caacuacuuc agcaaauacc 420
acuccacaag caaguacucc uaaacaagaa guaacacaaa cugcaaaauc uaaagaagaa 480
gcaaaaaaac aaacagcugu aaaaaaagaa aaagaaagug caaaacaaac cccuaaaaaa 540
gaacaaaaug caaaugauuu auuuaaaaau guugaugcua aaccuguaca uccaaguggu 600
uuagcaucgg guauuuaugu gcaaauuuuc ucaguaagua auuuggauca aaaaucaaaa 660
gaacuugcuu cuguaaagca aaaagguuau gauuauaaac uuuauaaaac uacaguugga 720
aguaaagaaa uuaccaaggu uuuaauagga ccauuugaaa aggcagauau ugcagcagaa 780
cuugcuaaaa uccguaagga uauugcaaaa gaugcuuuuu cuuuuacuuu aaaauga 837

<210> SEQ ID NO 74
<211> LENGTH: 1173
<212> TYPE: RNA
<213> ORGANISM: Campylobacter jejuni

<400> SEQUENCE: 74
augaaaaaga agauuguuuu aaucauuuua auugcaauac uuggaagugu uggggcuuau 60
uuuauuuuuu uuaauaauga ugaaaaaauc agcuauuuaa cucaaaaaau acaaaaaaaa 120
gauauaucuc aaaccauaga ggcaguagga aagguauaug ccaaagauca agucgaugug 180
ggugcucaag uuaguggaca aauuauaaaa cuuuauguug augugggaac ucauguaaag 240

```
caaggugauu ugaucgcuca aauugauaaa gauaaacaac aaaacgauuu agauauuaca    300
aaagcucagc uugaaagugc uaaggcuaau uuagagagua aaaaaguugc ccuugagauu    360
gcgaauaagc aauaucaaag agagcaaaaa cuuuaugcag cuaaagcaag uucucuugaa    420
aauuuagaaa cucaaaaaaa uaauuauuau acuuuaaaag ccaauguugc agagcuuaau    480
gcucaaguag uucagcuuga aaucacucuu aaaaaugcac aaaaagauuu agguuauaca    540
accauuacug cuccuaugga ugguguugug auuaauguag cuguagauga aggacaaaca    600
guuaaugcua aucaaaacac uccuacuaua guccguauag cuaauuuaga cgaaauggaa    660
guaagaaugg aaauagcaga ggcugaugug aguaagauaa aaguaggaac agagcuugau    720
uuuucuuugc uuaaugaucc ucaaaaaacu uaucaugcua agauugcaag uauagaucca    780
gcugauacug aagugaguga uucuaguaca agcucaagcu caucaaguuc gaguucuuca    840
agcucaagcu caucaaaugc uauuuauuau uacgcaaaau uuuauguagc caauaaagau    900
gauuuuuugc guauugguau gaguauacaa aaugaaauug ucguagcaag ugcaaaggcu    960
guuuuagcag ugccaacuua ugcaauuaaa agcgauccaa aaggcuauua uguugaaauu   1020
uuggaaaauc aaaaagcugu uaaaaaauau gucaaacuug gcauuaaaga uucuaucaau   1080
acucaaauuu uagaaggugu aaaugaagau gaagaauuga uaguaagcuc aagugcugau   1140
gguuuagcuc cuaaaaugaa guugagauuu uaa                                1173
```

<210> SEQ ID NO 75
<211> LENGTH: 1629
<212> TYPE: RNA
<213> ORGANISM: Campylobacter jejuni

<400> SEQUENCE: 75

```
augaaaauuu uacuuuuaaa ugaaaacccu guaguuucaa gacuuguaag ccuuagugcu     60
aaaaaaaugu cuuaugauuu ugaagaacuu aaugcuuaua gugaaaauuu ggguaauuau    120
gaugugauug uuguagauag ugauacucca gcaccuuuaa aaauucuuaa agaaaaaugc    180
gauagguuga uuuuuuuagc cccgcgaaau caaaauguag aagauauaga ugcgcaaauu    240
uuacaaaaac cuuuuuuacc uacagauuuu uuaaauuuac uuaauaauaa agaugcgaac    300
aagcauacau cuauugauuu gccaauguua agcaaugaug aaaauccuua ugcugauaua    360
agcuuggauu uagauaauuu aaauuuagau gauuugccug augaaaauuc uuuagauaua    420
aauucagagg gaauggaaga uuugaguuuu gaugaugaug cucaagauga uaaugcaaac    480
aaaacuuuag aaacucaaaa uuuagaacau gaaacaauua aagaacagac ucaagaagac    540
acucaaauug auuuagauuu aacuuuagaa gauggcgaaa gugaaaaaga agacuuaagc    600
caagaacaua cagcuuugga uacugagccu aguuuagaug agcuagauga uaaaaaaugau    660
gaagauuuag aaaucaaaga agaugauaaa aaugaagaaa uagaaaagca agaauuauua    720
gacgauucua aacaaauac auuagaaaug caagaagagc uuagcgaauc ucaagaugau    780
aauucaaaca aaacuuuaga aacucaaaau uuagaacaug acaauuuaga acaagaaaca    840
auuaaagaac agacucaaga agacacucaa auugauuuag auuuaacuuu agaagauggc    900
gaaagugaaa aagaagacuu aagccaagaa cauacagcuu uggauacuga gccuaguuua    960
gaugagcuag augauaaaaa ugaugaagau uuagaagaua auaaagaauu acaagcuaau   1020
auaagcgauu uugaugaucu uccugagguu gaagagcaag aaaaagaaau ggauuuugau   1080
gaucuuccug aggaugcuga auuuuuaggu caagcaaaau auaaugaaga aucagaggaa   1140
```

aauuuagagg aguuugcucc uguuguggaa gaagauauuc aagaugaaau agaugauuuu 1200
gcuucaaauu ugaguacuca agaucaaauc aaagaagaac uagcucaacu ugaugagcuu 1260
gauuauggua uugauaguga caauaguagc aaggucuuag aagauuuuaa agaugaacca 1320
auuuuagacg auaaagaauu aggaacaaau gaagaggaag ugguugugcc aaauuuaaau 1380
auaagugauu uugauacauu gaaagaaagu gauauacaag aagcucuugg agaggaaauc 1440
uuagaaaaaa augaagagcc uauaguaagu gauguaacua aagaugauaa uagcgaagag 1500
auaguuaaug agcuuagcca aagcauagca ggagcgauca cuucaaguau uaaagaugau 1560
accuuaaaag cugcucuuaa ggguaugaau augaauauaa auauaaacau uaguuuuaaa 1620
gaggauuga 1629

<210> SEQ ID NO 76
<211> LENGTH: 1833
<212> TYPE: RNA
<213> ORGANISM: Campylobacter jejuni

<400> SEQUENCE: 76
augaaaaaaa auauuuuacg cuuagguauu gucguuuugg uuuuacuuau agcgggaguu 60
uuauggcuaa auaaugauau caaucaaaaa aaagaagaug aagcaaauaa aaaugccauu 120
gcagcaaaug cugauuuuuc uuugcuuagc gaugaugauc caaauuuuga aaaauggggu 180
aagguuuuuc cagagcaacu aaaaauguau uuaacgguug aaaaagaaga gccuaaggcu 240
acugaauuug gugguaauuu agcuuauuca aaauuaauuc gcuuuccuca auuaaccaua 300
cuuugggcag gauauccuuu uagucuugau uucaaugaag aaagagggca uuuuuggguu 360
caaguagauc aaaugaaaac agcaagaaac aacaaagauu uucuuaaugc ccauggacuu 420
gcugcuuuua aaggucaacc ugcagcuugu augaauuguc auaguggaug gacuccaugg 480
cuuauaaaaa auguugcuaa aggagauuuu acugcuuuua acucuacaaa uuauuggacu 540
augauuaaaa auaucccagc uguugauggu auaguagaaa auucaccuga acaugcaggc 600
ccacauggug guaaaagaau ggguguaacu ugugcagauu gucacaaucc aaaugauaug 660
aguuuaagac uuacucgucc agcagcuauu aaugcuuuag uucuagagg auaugaaaaa 720 gauccaguac aaggcguaaa agcuacaaga gaagaaauga gaacuuuagu uugcucucaa 780
ugucauguug aauacuauuu uaaaccaaca ggggaaaaag uaaaaguaau gggugaaacu 840
auuguagaug auaguucuaa aaaauggugg aauggaacuc agaaaaauua ugaugaguau 900
gaguuuugga gagauggcaa uaaaguuaaa gagauugaaa ccgaugguau aguuuuaacu 960
uuuccuugga gugaguggaa aaaaggacaa ccauuuagaa uugaaaugcu agaugauuau 1020
uaugauaaag uucguggagu auuuggagcu gauuuuacuc auaaauuaac aggagcgcaa 1080
auuauuaaaa uucaacaucc agaaagugaa cuuuauagug gcggugugca ugcugcaaau 1140
ggaguaaguu gcguggauug ucauaugccu uauguuagag aaggagcuaa aaagguuacu 1200
caacacaaua ucacuucucc uuuaagagau auuaacucug cuuguaaguc uugucauaaa 1260
caaagugaag auuauuuaaa agcucaagug cuugacauac aaaacagcgu ugcacaugau 1320
caaagaacug cagaguaugc aauuguuagu uugauuaugg auacuaaaaa auuacgcgau 1380
gaacuaggca auauggaaaa auuccaaagc gauggaaaag cugaugcgaa aaaaauuagc 1440
gaagagcuaa aagaaguuuu agaacuucau cguaaagcuc aaaugagagc ggauuuuguu 1500
aaugcugaaa acucaacugg uuuccauaau ccucgcgaag cuucaagaau guuauugcaa 1560
gcuguugaua uggcaagaau gggacaaacu aaacuuguag aaauugcagc ggcaaaugga 1620
auuaaagauu uuaaaacuuc aaauuuaggu uuugaagaua uucaaaaauu uaauccagga 1680
gagcuuuauu auaaaaguaga uguuaauaau cauaaaagcug gagagcguua cuaugcagau 1740
gaaaaagaug uuaauggcaa ucccuccaaaa gaacuuuuag agcaugauaa agagcuugcu 1800
ccuuauaauu aucaagugau ugauaaaaaa uaa 1833

<210> SEQ ID NO 77
<211> LENGTH: 1980
<212> TYPE: RNA
<213> ORGANISM: Campylobacter jejuni

<400> SEQUENCE: 77
augaaaagcg uaaaauugaa gguuucgcug auugcaaauu uaaucgcagu agugguuuug 60
auaauuuuag guguuguaac auuuauauuu guaaagcaag caauuuuuca ugaaguugug 120
aaugcugaaa uaaauuaugu uaaaacggcu aaaaauucua uagagucuuu uaaggcaaga 180
aauucuuuag cucuugaaag uuuagcuaaa aguauuuuaa agcauccuau agaacaguua 240
gauagucaag augcuuuaau gcauuauguu ggaaaagauu uaaagaauuu uagagaugcu 300
ggaagauucu uagcaguuua uauugcucaa ccaaauggcg aacuuguugu aagcgaucca 360
gacucugaug cuaaaaauuu agauuuugga acuuauggaa aagcugauaa uuaugaugcu 420
agaacaagag aguauuauau agaagcaguu aaaacaaaua aacuuuauau uaccccaucu 480
uauauugaug uaacuacaaa uuuaccuugc uuuacauauu cuauuccgcu uuauaaagau 540
gguaaauuua uaggguuuuu ggcuguagau auucuugcgg cagauuugca agcugaauuu 600
gaaaauuuac cagguagaac uuuuguauuu gaugaagaaa auaaaguauu uguuucuaca 660
gacaaagcuc uuuuacaaaa agguuaugau auuagugcaa uugcaaaucu ugcuaaaacu 720
aaagaggauc uugaaccuuu ugaguauacu agaccaaaag augguaauga aagauuugcu 780
guaugcacaa agguuucugg aauuuauacu gcuugcguug gagagccaau agaacaaaua 840
gaagcuccag uuuauaaaau ugcauuuaua caaacugcga uuguuauuuu uacaaguauu 900
auuagcguca ucccuccuuua uuucaucgua ucaaaauacc ucuccccacu ugcagcuauc 960
caaacagguu uaacuucauu cuuugauuuu aucaacuaua aaacaaaaaa uguuuccacu 1020
auagaaguaa aaagcaauga ugaauuugga caaaucucaa augcuaucaa ugaaaacauu 1080
cuugcuacua aaagaggcuu agaacaagac aaucaagccg uuaaagaauc aguucaaacc 1140
guaucaguug uagaaggugg uaauuuaaca gcaagaauua cugcuaaucc aagaaaccca 1200
cagcuuauug aacuuaaaaa uguucuaaau aaacuucuug auguuuuaca agcuagagua 1260
gguucugaua ugaaugcuau ucauaaaauu uuugaagaau acaaaagcuu agacuuuaga 1320
aauaaauuag aaaaugcuag cgguagugua gaauuaacua cuaaugcuuu agguagugaa 1380
auaguuaaaa ugcuaaaaca aaguucagac uuugcuaaug cuuuagcuaa ugaaagugga 1440
aaauuacaaa cugcuguuca aagcuuaacc acuucuucaa auucucaagc ucaaucuuua 1500
gaagaaacug cagcagcuuu agaagagauc acuucuucua ugcaaaaugu uucaguuaaa 1560
acuagugaug uuaucacuca aucugaagag auuaaaaaug uuacagguau uauaggugau 1620
auugcagauc aaaucaaucu uuuagcuuua aaugcagcua uugaagcagc ucgugcugga 1680
gaacauggua gaggcuuugc agugguagcu gaugaaguua gaaaguuagc ugaaagaacu 1740
caaaagucuu uaucagaaau ugaagcuaau acuaauuuac uuguucaauc uaucaaugau 1800
auggcagaaa guauuaaaga acaaacugca gguaucacuc aaaucaauga uagcguagcu 1860

```
caaauugauc aaacuacuaa agauaauguu gaaauugcua augaaucagc uauuauuucu   1920

aguacaguaa gugauauagc uaauaauauc uuagaagaug uuaagaagaa gagguuuuaa   1980
```

<210> SEQ ID NO 78
<211> LENGTH: 1998
<212> TYPE: RNA
<213> ORGANISM: Campylobacter jejuni

<400> SEQUENCE: 78

```
augcaaucaa uaaauucagg caaauccguu ggaauuucag cuaagcuuac gcuaugggu     60

ggaauuuuag uuguauuaau uuuagcaauc acaagugcua uuaguuacuu ugauucgaga    120

aacaauacau augaauugcu aaaagacacu caguuaaaaa cuaugcaaga uguggaugcu    180

uucuuuaaaa gcuaugcuau gucaaaaaga aaugguauuc aaauacuagc caaugagcua    240

acaaaucguc cugauaugag cgaugaagag cuaaucaauc uuaucaaagu aauuaaaaaa    300

guuaaugacu acgaucuagu uuauguagga uuugauaaua caggaaaaaa uuaucaaucu    360

gaugaucaaa uuuuagaucu aucaaaaggu uaugauacua aaaaucgucc uugguauaaa    420

gcugccaaag aagcaaaaaa gcuuauagua acagaaccuu auaaauccgc cgcuagcgga    480

gagguugguu uaacuuacgc ugcuccauuu uaugauagaa auggaaauuu uagaggugu    540

guaggugggag auuaugaucu agcaaauuuu ucaaccaaug uuuuaacugu aggaaaauca    600

gacaauaccu uuacugaagu acuugauuca gaaggaacaa uacuuuuuaa ugaugaaguu    660

gcuaaaauac uaacaaaaac agaauuaagu aucaauaucg ccaaugcaau caaagcaaau    720

ccugcucuua uugauccaag aaaccaagau acuuuauuua ccgcuaaaga ucaccaaggc    780

guagauuaug cgauuaugug uaauucugcu uuuaauccuu uauuuagaau uuguacaaua    840

acagaaaaca aaguuuauac cgaagcuguu aauucuauuu uaaugaaaca aguuauaguu    900

gguauuauag cuauaaucau agcuuuaauc uugauuagau uuuuaaucag cagaagucuc    960

uccccacuug cagcuaucca aacagguuua acuucauucu uugauuuuau caacuauaaa   1020

acaaaaaaug uuuccacuau agaaguaaaa agcaaugaug aauuuggaca aaucucaaau   1080

gcuaucaaug aaaacauucu ugcuacuaaa agaggcuuag aacaagacaa ucaagccguu   1140

aaagaaucag uucaaaccgu aucaguugua gaaggugua auuuaacagc aagaauuacu   1200

gcuaauccaa gaaacccaca gcuuauugaa cuuaaaaaug uucuaaauaa acuucuugau   1260

guuuuacaag cuagaguagg uucugauaug aaugcuauuc auaaaaauuu ugaagaauac   1320

aaaagcuuag acuuuagaaa uaaauuagaa aaugcuagcg guaguguaga auuaacuacu   1380

aaugcuuuag gugaugaaau aguuaaaaug cuaaaacaaa guucagacuu ugcuaaugcu   1440

uuagcuaaug aaaguggaaa auuacaaacu gcuguucaaa gcuuaaccac uucuucaaau   1500

ucucaagcuc aaucuuuaga agaaacugca gcagcuuuag aagagaucac uucuucuaug   1560

caaaauguuu caguuaaaac uagugauguu aucacucaau cugaagagau uaaaaauguu   1620

acagguauua uaggugauau ugcagaucaa aucaaucuuu uagcuuuaaa ugcagcuauu   1680

gaagcagcuc gugcuggaga acaugguaga ggcuuugcag ugguagcuga ugaaguuaga   1740

aaguuagcug aaagaacuca aaagucuuua ucagaaauug aagcuaauac uaauuuacuu   1800

guucaaucua ucaaugauau ggcagaaagu auuaaaagaac aaacugcagg uaucacucaa   1860

aucaaugaua gcguagcuca aauugaucaa acuacuaaag auaauguuga aauugcuaau   1920

gaaucagcua uuauuucuag uacaguaagu gauauagcua auaauaucuu agaagauguu   1980

aagaagaaga gguuuuaa                                                 1998
```

<210> SEQ ID NO 79
<211> LENGTH: 2253
<212> TYPE: RNA
<213> ORGANISM: Campylobacter jejuni

<400> SEQUENCE: 79

```
augagaauua caaauaaacu uaacuucaca aauaguguga auaauucuau gggcggucaa     60
agugcuuuau aucagauauc ucaacaacuu gcuucagguu ugaaaauaca aaauucauau    120
gaagaugcaa gcacuuauau agauaauacg cgucuugaau augaaauuaa aacguuagaa    180
caaguaaaag aaucaacaag uagagcucaa gaaaugacuc aaaauaguau gaaagcuuua    240
caagauaugg uuaaacuucu ugaagauuuu aaaguuaaag uaacccaagc ugcaagcgau    300
agcaauucuc aaaccucaag agaagcuaua gcaaaagaac uagaacguau aaaagaaagc    360
auaguucagc uugcaaauac caguguuaau ggucaguauc uuuuugcggg uucucaaguu    420
gcaaacaaac cuuuugauuc uaauggaaau uauuauggag auaaaaauaa uauuaaugua    480
guaacuggag cuggaacuga aagcccauac aauauaccag guugggauuu auuuuuuaaa    540
gcagauggag acuauaaaaa acaaauaagc acuaauguua guuuuacaga uaaucguugg    600
gauuuaaaua aagacccuga uaaaacuaaa uaucucacag gagauucuaa auggcaacaa    660
cuuaucggac aaaguuaugu aaaagauaau agcuuagaug cugacaaaga cuuugaguau    720
gaugauagca aacuagauuu ucccuccaaca acucuuuaug uucaagguac aagacccgau    780
ggaacaaguu uuaaaagugc uguacucguc aaacccgaag auacuuuaga agauguaaug    840
gaaaauauug gagcucuuua ugguaauacu ccaaauaaua aaguaguaga aguaaguaug    900
aaugauagug gucaaauuca aauuacagau cuaaagcaag guaauaauaa acucgauuuu    960
caugcuguag cuuucacacc acaagcugau gauaaaacug aauuaaauaa uauuauccaa   1020
gcagcacagg augaaggcau uacaauggaa gauguuacaa acaggguuau gacugcugca   1080
cuaggaaauc ccaauaaugg agauauuaca aauuuaaaua auccuguaac cauucaaauu   1140
aacggacaaa acuuugaaau ugauuuaaaa caaacugauu uuaucaaaag uaaaaugaca   1200
gauacagaug gaaaugcugc uaauggagcu gauuacgaua auguguauuu ugaaaaaaau   1260
ggcaauacug uuuaugguaa uguuucucaa guuaucaaag gaagcaaugc uuaugccacu   1320
gauucaacca aacuuagcga gguaauggca ggagauagcc uaaaugguac uacuuuaaau   1380
uuaaaaguca auuccaaagg uggaaauucu uacgauguua cuauaaauuu acaaacuuca   1440
acuguaagcu auccugaucc uaauaaucca ggucaaacca uaagcuuucc uauuaugcau   1500
acuaauccug caacuggaaa uaguggggu guuacaggau caaaugauau uacuuauggu   1560
caaauuaaug auauuauagg uauguuugcu gcagauaaaa uuccuacaac aaccauacaa   1620
gccaauaaug gucaaauuaa uaaugcagau uauacccaaa uacaacaacu caugaaagau   1680
ucacaagcua cuguugaugu aaguauggau uauaaaggc guauuagugu uacugauaaa   1740
cuuucaucag gaaccaauau agaaauuucu cuuagugauu cucaaagugg ccaauuucca   1800
gcaccuccuu uuaccacaac uucuacugua caaaaugguc caaauuuuag uuuuagcgcg   1860
aauaauucuu uaacuauaga ugagccaaau guggauauua uuaaagauuu agauucaaug   1920
auugaugcug uuuuaaaagg caauaugaga gcagacuccg aaagugaaaa cccuagaaau   1980
acagguaugc aaggagcuuu agaaagacuu gaucauuuag cagaucaugu uagcaagcuu   2040
aauacaacua ugggagcaua ucauaauacu aucgaaggug uuaauacacg cacaucauuu   2100
```

uuaagcguua auguccaaag uauaaaauca aaugugauug auguagauua uggugaggca 2160
augaugaauu uaaugcaagu ucaacuugca uaucaagcuu cucuuaaagc uaguacaaca 2220
auuucucaac uuagcuuauu aaauuauaug uaa 2253

<210> SEQ ID NO 80
<211> LENGTH: 2598
<212> TYPE: RNA
<213> ORGANISM: Campylobacter jejuni

<400> SEQUENCE: 80
augaugagau cacuuuggucc uggcguaagc ggacuacaag cacaucaagu ugcgauggau 60
guugaaggua auaacauuuc aaauguuaau accacugguu uuaaaauauuc ucgugcagau 120 uuugggacua uguuuagcca aacugugaaa aucgcuacag cuccaacuga uggaagaggc 180
ggaucuaauc cacuucaaau cggucuuggc guuucaguaa guucuacaac uagaauucau 240
ucucaagguu caguucaaac cacagauaaa aacacugacg uugcuauaaa uggcgauggu 300
uuuuuuaugg uaagcgauga ugguggucuu acaaacuauc uuacaaggag cggggauuuu 360
aaacuagaug cuuauggaaa uuuuguuaau aaugcagguu uuguugucca agggugggaau 420 aucaacuggg augaucaaac uauagauagu ucaagaacuc cacaaaauau uuuuaucgau 480
ccagguaugc auaucccugc agcaaaaucu acugaaguug cuaucaaagc gaauuuaaau 540
agugguuuaa auauaggaac uucaaguaga aaucuuuaug cacuugauuc uguucaugga 600
uggaauacua aacccaaag agcagaagau gaaaaugaua caggaacuac ucaguuuuau 660
acgacuucua agaauucugu agaagugaca gaaaagggug uggaugcggg aucacuuuuu 720
aacgcgaaag gacaaggacu uaaucuuaga gauggacaag gaauuugggu aucuuaugca 780
gaugcaacau auucuaccaa uaaaguagga guaaaugcuu uugauccaaa uuuacagcaa 840
aaucaaacug cugcuuuuug gggaacagcu aaucaaaaag ugaauuuaga uauaacuuua 900
aaugggguua gaauucaaaa ugcugauauu caaaguauug augaugcuau ugcuuauauc 960
aauaccuuua cugcaccaac ggauacaagg gauggaacag guguaaaagc gguuaaaaau 1020
aaggauggua guggaauuga uuuugucaau gauaaugccg augguacuac agauaauaug 1080
aaaaauauca aucuugugggu ugccaauacc aauacagcag gugagcuuug gaaugcugua 1140
uggaauaaca acaaucaaac auuuacauuu aauauaaaug guaauggaca ggcuggaaca 1200
ccgacuauua auaaaaaugg uucuucuuug uggacagcua caaauauuac auuuacacca 1260
caaccuccuc aagcagcuac gaauguucag cuuacuggug gacuaaaugc acaaauaaua 1320
acagcacaua aauauauuua uaguucaaac ccugugggaua uagguccuau guauaauccu 1380 gacggugggac cagcauucca gccuggugcu aaugcaacua caagaccaac ugaaccaggu 1440
ucagcagcuu auugggaugc uguuaauggu ggacuuuuaa auacuaaugu aagaacuuuu 1500
agaaccacag aagauuuaag agaacuuuua caaagggaug cuagauaugg gguugauuau 1560
gauggaagug gaacuuuugc ugcagcugau auuaaucaaa auauaaaagu aguaguaacg 1620
gcagauggac auuuugcuau uuccaaugcu aaugaacaau caacuguucc accaaaugcu 1680 auuaaauggug uaggaaaugc cacuacaaca gauccaaaaa auaugaguuu uaauauaaca 1740
gcuuauagua acaaacaagg aacuguaagu acuaaugaug cuuucacugc uauuuuuaaa 1800
gcuuucgaug guccuuuggu uauaggaaau cagaucaaag aaagcgaaca acuuaagcuu 1860
ucugcuuuuu cggcggggcu ugaaauuuau gauucuuuag guucaaaaca cacuuuagaa 1920
gugcaguuug uuaagcaaag uaccacucaa gauggggggua augaauggca aaugaucauc 1980

```
cguguaccug aaccugcaga gauuaacacu acaggcgaag gaccaaacaa uaucaucgua   2040

ggaacagcua gauuuaacaa ugacggcucu uuagcuaguu auacaccaag aacgauaaau   2100

uucucaccaa acaauggugc cgcaccaaau caacaaauca aacuuuccuu uggaacaagu   2160

ggaagcaaug acggccuugu aagcucaaau ucugcuucaa cucuaacagg acaggcaacu   2220

gaugguuaua cuucagguaa cuuaaaaccu gaugcuaucc guguggauga uaaagguaau   2280

aucuuaggug aauuuacuaa uggcaaaacc uuugcuguag caaaaaucgc aauggcuuca   2340

guggcaaaua acucaggucu ugaggaaauu gguggaaauc uuuuuaaagu uacugcaaau   2400

agugguaaua ucgugguagg ugaagcagga acaggagguc guggugagau gaaaaccuca   2460

gcucuugaaa ugucaaaugu ggauuuaagu cguucuuuaa cagagcuuau uaucauucaa   2520

agagguuauc aagcaaacuc aaaaaccauu ucaacgagug aucaaaugcu ccaaacucua   2580

auccagcuua aacaauaa                                                  2598
```

<210> SEQ ID NO 81
<211> LENGTH: 2616
<212> TYPE: RNA
<213> ORGANISM: Campylobacter jejuni

<400> SEQUENCE: 81

```
auggcaaaga uuagaauuca ugaaaucgca aaagaauuag guuaugauag uaaggaaauu     60

auugaaaagg caaaugaauu aggacuugga auuaaaacag caucaaaugc uguagaaccu    120

gagauugcgg cagcuauuua ugaguauaua caaacaagag aaauuccaga agcuuuuaag    180

aaaaauauca aacuccuac agcaaaaaag ccuaaaaaag aaaauauaaa agaacaagaa    240

aagcuaaaug aaucugaaaa aaaagaaccu aaaaaagaag aaaagcuuaa acaagaaguu    300

aaaaaagaag aauuaaaaau ugaaaaagaa aaugcaaaag aggaagaaaa acaagaaauu    360

auugaugcuc auaagccaca aagccuugcu agugcaacuu uagccaaaag acgcggacuu    420

guuauuguua aaaagaaaaa agacgaagaa gaaauucaag uuaaaaaaga agaaguaaaa    480

aauucaaaug auauaucuau caauaaugaa gagcgcuuaa guuuaaaaac uauguuuuca    540

aaugcugaug agaguuuaaa gaaaaagaaa aaagaaaaaa aaucuuuugu ugcgaguaaa    600

aaagaaagua ccgaaaaaau gaauuuuuua gaugaacaug auuuugguga uauuucuuua    660

gaugaugaag augagguagu auuaccugau uuuaguguaa aagaacaaga aaaaccacaa    720

aauaucaaua aaaaacaacc uaauuuuaua agacaagcug uuggaaauuc ugcggguuuu    780

ggguuugaag guggaauuca aagaagaagu cguaaaaaac caucuaaaaa gauugaaaaa    840

aaggaaguag aagaaguagg uagcguugcu auuucuaaag aaauucgugu guaugaauuc    900

gcugauaaga uaggaaaaag cacuagugaa gugauuucaa aacuuuucau gcuuggaaug    960

augacaacaa aaaaugauuu cuuagaugaa gaugcgauug aaauuuuggc ugcugaauuu   1020

gguauagaga ucaauaucau uaacgaggcu gaugaguuug auuauguaaa agacuaugaa   1080

gaagagacug augaaaaaga uuuagugacu agagcaccug ugauuaccau cauggggcau   1140

guugaucaug guaaaacuuc uuuguuagau uauauuagaa aaucacgcgu ugcaaguggu   1200

gaagcagggg guauuacuca gcacgugggu gcuuauaugg uagaaaaaaa cgggcguaaa   1260

auuacuuuua ucgauacucc aggucacgaa gcuuuuacug cuaugcgugc aaggggugca   1320

aguaucacug auauuguaau caucguugua gccgcagaug augggguaaa accacaaacc   1380

aaagaagcga uaaaucaugc uaaagcagca ggugugccua uuauuauugc uauuaauaaa   1440
```

auggauaaag aagcagcaaa ucccgauaug guaaaaacuc aacucgcaga aauggaaauc 1500
augccaguag aauggggcgg aucuuaugaa uuuguaggag uuucggcuaa aacaggaaug 1560
gggauugaag auuugcuuga aaucgugcuu uuacaagcug auauuuuaga acuuaaagcc 1620
aauccaaaaa guuuugcuaa agcaagcauu auagaaaguu cugugcaaaa agggcguggu 1680
gcgguggcua cugucaucgu gcaaaaugga acacuuacug uaggaaguac cgugguugca 1740
ggcgaggcuu auggaaaagu gcgugcgaug agcgaugauc aagguaaagc cuuaaaagaa 1800
auuaaaccag gcgaaugugg gguuaucgua gggcuuagug aaguagcaga ugcaggugaa 1860
auuuuaaucg caguaaaaac cgauaaagaa gcaagagaau augcuaauaa acgccacgaa 1920
uacaaucgcc aaaaagaacu uagcaaaucc acuaaaguua gcauugauga gcuuggagcu 1980
aagaucaaag aagguaaucu aaaagccuug ccuguuauuu uaaaagcuga ugugcaagga 2040
ucuuuagaag ccuuaaaggc aaguuuagaa aaacuuagaa augaugagau uaaagugaau 2100
aucauucaua guggaguagg aggaaucacg caaagugaua uagagcuugc aagugcgagu 2160
gaaaacucua uaguacuagg uuuuaacaua cgcccaacag gggaaguuaa agagcgugcu 2220
aaggauaaag gcguagaaau uaaaacuuau aauguaauuu auaaucuuuu agacgaugua 2280
aaagccuuac uuggugguau gaugagcccg auuauuucug aagagcaauu aggacaagca 2340
gagauuagac aagugaucaa ugugccaaaa aucggacaaa ucgcagguug uaugguaacu 2400
gaagggguga uuaaucgugg agccaaaauu cgccuuaucc gugauggagu ugugguuuau 2460
gaaggaaaug uaaguucgcu uaaacgcuuu aaagaugaug cuaaagaagu ggcaaaaggc 2520
uaugagugug gcguagguau agaagggugc gaugauauga gaguggguga uuauauagaa 2580
agcuauaaag aaguagagga acaagcaagu cuauga 2616

<210> SEQ ID NO 82
<211> LENGTH: 2841
<212> TYPE: RNA
<213> ORGANISM: Campylobacter jejuni

<400> SEQUENCE: 82
augcuagcac cuggcauggg agaauggguu uacaaggcua auuuauuuuu auuuggagaa 60
uuugcguauu auuauccuuu uuucuuauuu auuuuaaauu auguuuauua uaaaagaaau 120
uacaaauuag cuaauuuuac aagaagagag cuuuuuggua uaggauuugc cuuuuucucg 180
aguuugcuuu uauuugcagu uuuuuauccu aauucaggcu auauacuaga gcuugcuuau 240
gcgauuuuuu cuacuauuuu ggggcauacu gggagcggaa uuuucgcucu uuuacuucua 300
cuauuuucuu ugguuuuauu guuuccaaaa uuugcaaaag aaauuuuaaa aauagaauua 360
gauuuuacuu auuuauuaaa aguagagcaa gcuuuuaaau cuuuacuuau gcguguauuu 420
gguggagaaa acgagaaaga agauguaggu aaaucagaac cuauaguucc aaaauuaaau 480
auuuugcaag auaguauuua uggaaauuua caaauaaaca aaaaagggga aaccaauaac 540
uuagaacaga uaauuaaaga uagcaauauc aaugcaagua aaaauucaau uaccacggcc 600
aaggaaaauu uugaaaaacu aaaaaaucaa auuuuagaug aaaccauaga gauugauaaa 660
caaaguuuaa aagaaucaag aaguuuuguu caugagcauu cucaacaagu gcgaaauuuc 720
gcacaaaagg cuaguaaaau gagcauuagu cuugaugaag auuuuaauuu uauuucagaa 780
gaagagguag auaugauucc ugaacguuuu uuaaaaccua aaaaacuuga agauauaaag 840
caaauagaua caaauaaaaa uuuagaugag ccaaguuaua aacguaaaaa uauugaaauu 900
ccaguuucua aucaagaagu uaaaccaaaa auuuuuacaa aagagcuuga acuuagagag 960

```
aauuugauaa aaaaagaaaa acuagaacaa gaauacaaag ccuaucaaaa ugaaauuuua   1020

gaaaauaaag uaaaacaaga aauuaaaaaa uuagaagaau augaugcgau aaauucaagc   1080

gauauuauag aagggaauaa auauaguuuu aauagcccaa aaacaauuaa aacagaaaca   1140

gaagaaucag acaaaauaaa ugaaaauaaa aaucuagaua aagcagacaa uaucuuugaa   1200

uuugcuccca uuguagaaga guuaaaucau ccuuauauag aaccuacucc uauaaaaaau   1260

auaaaugaaa uaguuauaga agaaaaaaau acacucgauu uuauccaaaa uacagaaacu   1320

aaaaucgaua augaaaaaac aaaugaucaa gaaauuaaac uucaaaaagc aguuuuagcc   1380

aaagaaauug cuauuaacca agcuuuauug cgugaaauag agcagggcga aauagaaaaa   1440

ccaaaagauu ucaccuugcc gccauuagau uuuuuagcua auccaaaaga acacaaacaa   1500

gaaaucaaug aaagugaaau agauaaaaaa auuuauaauc uucuugaaaa auugcgucgu   1560

uuuaaaauag gcggcgaugu uauaagcacu uauguugguc cugugguaac uacuuuugaa   1620

uuucguccua gugcagaugu gaaaguaagu cguauuuuaa auuuacaaga ugauuuaacu   1680

auggcuuuaa uggcaaaauc aauccguauu caagcuccaa uaccaggaaa agauguugua   1740

gguauagaag uuccaaauga ugaaauucaa accauuuauu uaagagaaau uuuacaaagu   1800

gaaguuuuua aaaacgcuaa aaguccuuua accauagcuu uagguaaaga uauaguaggc   1860

aaugcuuuug uaaccgaucu uaaaaaacuu ccgcauuuac ucaucgcagg aacgacaggu   1920

agugguaaaa gugugggau aaauucuaug cuuuuaaguc uuuuauaucg caacucucca   1980

aaaaccuugc guuugaugau gauagauccu aagaugcuug aauuuagcau uuauaaugac   2040

auuccucauc uuuuaacucc uguuaucaca gauccaaaaa aagcagucaa ugcgcuuuca   2100

aauaugguag cugaaaugga aagacgcuau cgcuuaaugg cugaugcaaa aaccaaaaau   2160

auagaaaauu acaaugaaaa aaugaaagaa uuaggcggag aaaaacuucc uuuuauugua   2220

guaauuaucg augaacuugc ugauuugaug augacugcgg guaaagaugu agaauuuuau   2280

auaggaagac uugcgcaaau ggcaagagca aguggaaucc acuugauugu agcuacacaa   2340

cgaccuucug uugauguugu aacaggacua auuaaagcga auuuaccaag uagaauuucu   2400

uauaaaguag ggcaaaaaau ugacucuaaa guuauuuuag augcuauggg ugcugaaagu   2460

uuacuuggaa gaggggauug uuuauuuacu ccuccuggaa caagcucuau agugcguuug   2520

caugcgccuu uugcaagcga auuugaaaua gaaaaaaucg uggauuuucu aaaggaucaa   2580

caaagcguag aauaugauga aagcuuuuua aaggaucagc aaagcguagg uguuacaaca   2640

aaugaaagcu uugaugggga agcagaugag cuuuaugaag aagcuaaaag aguaaucuua   2700

gaagauggaa aaacaagcau uucuuauuua caacgccguu uaaaaaucgg cuauaaccgc   2760

ucugcaaaua uuauugaaca acuuacgcaa aacgggauuu uaagcgaacc ugaugccaaa   2820

ggacaaaggg aaaucuugua a                                             2841
```

<210> SEQ ID NO 83
<211> LENGTH: 3126
<212> TYPE: RNA
<213> ORGANISM: Campylobacter jejuni

<400> SEQUENCE: 83

```
augaaaaaau uuuuuuguuu aacuuuaguu uguaaacuuu uugcuuuaag cgaauuugaa     60

cuucaucaua uugauaaagu acauaagcua ggguauagcg gagauacuau uauaauaggu    120

guagccgaug augcuuuuaa ucaagaucau auuaguuuaa aggauaagau uuuaaagucu    180
```

-continued

```
acuuauccua cugauacagc ugggaaacag cuuauaccug auuugaaaaa aucaacacac    240
ggaagucaug uagcagguau agcuguugga gcaaagauag gcgauagcaa accuuaugga    300
guggcuuaug gggcaaaauu uuauggagcu ggggguguuc caaauggcuc uuacacucaa    360
auuccugaua uuuauaauuu uuucaaagau gugaguauua uuaauaauag cuggggguauu   420
aauuuuuauc cuuauuuuaa ucuuaaggcu ucaaauucug gauuaguaga uuguacucaa    480
acuaaucaag ggacaagcua uaauaucugu aauacuccuu uggaauaugu uaugaaagca    540
gauaagguug cuaaugauau gaugaggcuu agcaaggaca agggaguauu aaauguauuu    600
gcugcuggua augaaggaau ucuuagcccu gcuuugcaug cgauuuuacc aaguuaugau    660
gaaucuuuaa gagcuugguu ggcuguugga gcuuuggaug caaaugagau uacuuuagaa    720
ucagauggga cuuuaauaau uaaaagucaa gguuuggcug auuuuaguaa ugguuuuaag    780
ggagcuacga auuuuucuuu aguugcugcu ggaguaaaua uuaauaaugu ugauucaagc    840
acuaaugaua aguuuacaaa aaaaagugga acuucuaugg cagcaccuau gguaagugga    900
acagcggcac uggucaagca aaauuucccc uuuuuggaug guaagcaaau ugcugauaua    960
cuauuaagua cagcaaauaa aaauuauaag gcuccaaaau uuacuguuaa acaaguaacc   1020
gauggaacaa aucaaccuaa auuucuuauu guguauauuu cgcaagaucc accugggaua   1080
gaagaugaaa uaaaacggga uuuaaaacag cuuuacaaug gaauacaagu ucaaguuaau   1140
ggacaaugga uugauuauag ugauuauauu ugggauaaua gagauagugc gcagucacaa   1200
aaacuuaaua cuuccacuau uaguucuauu aauggaguag uuagaguuga gaaagaagaa   1260
uuauuuggac aaggaauuuu agaugcacaa aaggcguuaa aaggacugag uauuuuagau   1320
gcaaacagac ucagugauca ggauguauua aaauaugagc aagaaccuaa uacagcuuau   1380
uauacuauaa acacugcagg uuaugaugcu gaauuuucua augauauuag ucaaagaaaa   1440
ugggaugaaa guacucauuu aucaagugcu auuaauaaac cuacacauuu agcuaaucuu   1500
aacauagggu uaucuaaaga aggugaaggu auuuugauua ucagugguca aaauacuuau   1560
gagggcgcaa cuuuaaucaa acaaggagaa uuaaagcuua aggaaaagu uaaaaaauau    1620
gcuuauguag aacaaaaagc aauauuaagc gguaaauggua uuguagggca aaauuuaaac  1680
aauaaaggca uaguuagacc uggaaaugaa gauuugaaug auuuaaccgu gcaaggaacu   1740
uauacucaag aaggaguuga uucuaaauug caacuugauu uugguaauua uaaaaaauucu  1800
aaacugauug caaaaacuua ugauauuaag agcgggaauu uagaauauau uccuuuaccu   1860
aaauacuaua ucuuaaauaa gccagugaaa auuaauuugg gagauuugga aaaaaguuua   1920
ucaucuuuua aucauguuuu gauacaaaau accuaugcuu uaaauuuuga uuuuguuuua   1980
agugaugauu uagugaguau uaauaaaacc uuaauaaaac cuaauuuaaa gccaaaugcu   2040
uacgaaauuc cuaauacaag cuugggaaau gcuuuaagac aauugcgauc uagggcagac   2100
uugagucaga cuuaucagga auuuuuugcu ucuuuagaua auggaauaga uguaaagacu   2160
aaauuaaaua gaauagaagg uucaggguau uuaagcacuu uuaguaauca uaaucaaucu   2220
aauuuaaugc aaaauaauau guuauuuacc cuucauccuc uuaauauuaa uaauuuugca   2280
caaaacaaua auaucuuacu ugcuaguacu uauuuaccua gaauuuuuag caaugaagaa   2340
uauuuuuggc aucuuacucc aaguuauaaa uacuauaaag auaaagauuu uucaggucaa   2400
aaaacaggug cuaauaucuc uuuaggagaa aauuucucau caggcuuuuu agcuuaugcu   2460
uuaucucuuu cuagcgcuaa auuuaauuuu aauaauggua gugauuugaa gaguuauaac   2520
auggauuuau ugcuuaauua uaaccaugau uuagauuuua uaaaaauauu aaguggauua   2580
```

```
gguauaggug uaggauuuaa uacucuuaau cguuuuguag uagagcagcc aauugaaggc   2640

aaauauaaaa cauugcaaac uucagcccag cuugguguaa cuaaagauau uauuuuaggu   2700

caagauuuua uuuuuaaucc uuuaaauguau uuuacacaua guuuuuuuua ucaagaagau   2760

uuuaaagaaa auaaaagucc uuuugcuaaa aauuaugaaa guuuaaaaca ucauagcaua   2820

aaugcaaauu uagguuuuaa ucuugcuaaa aauauagagc aagaugauua ucaagcuucu   2880

uuuucuacuu uuguaauuuu ugaaaaaaga auuuauggaa gaacuuuaga aaauaaggcu   2940

aguuuuguug auuuuccuau ugcuuuuauu caaaaauaua aauuaaaaga uaauauuuua   3000

agucaagguu uuaauucaga auuuuuauau aaaaacaaug uauuuuggca guuuauguua   3060

augaauagau uuucucauaa ugccuaugaa uugcauuuaa ugaguucagu aggaaaacgu   3120

uuuuga                                                              3126
```

<210> SEQ ID NO 84
<211> LENGTH: 3270
<212> TYPE: RNA
<213> ORGANISM: Campylobacter jejuni

<400> SEQUENCE: 84

```
augccaaaac gaacagauau uaaaagcauu uuacuuauag gaaguggucc uauugugaua     60

ggacaagcuu gugaauuuga uuauucugga acucaagccg caaagacuuu aaaagaauua    120

ggauaucgug uaguauuaau caacucaaau ccugcaacca ucaugacaga ucccgaauuu    180

gcagaugcga cuuauauaga acccauaaca aaagaaagua uuuuaaguau uauuaaaaaa    240

gaaaaaauug augcaauuuu gccaacuaug gguggacaag uagcguuaaa uguugcuaug    300

gaaguuuaug aaagcggacu uuuaggagau gugaaauuuu uaggcgcaaa uccugaggcg    360

auuaaaaaag gcgaagaucg ucagguuuuu aaagaaugua ugaaaaaaau uggcauggau    420

uugccaaaau cgauguaugc guauaauuau gacgaagcuu uaaaagccgu agaugaaauc    480

gacuuuccuu ugaugauccg ugcuucuuau acuuuagggg gugcuggaag uggugugguu    540

uacaauaugg acgaauuuaa agaacuuacc aauacugcuu uagcuuuauc accuauucau    600

gaaauuuuga uugaagaaag uuuguuaggu uggaaagaau augaaaugga aguuauacgc    660

gauagagcgg auaauuguau cauaguuugu agcauagaaa auaucgaucc uaugggaguu    720

cauacaggag auaguauuac aauagcucca gcauuaacuu ugacagauaa agaauaucaa    780

guuaugcgua augcuucuuu ugcuauuuug cgugaaauug guguagauac aggcggaagu    840

aaugugcaau uugcuaucaa cccaaaaaau ggaagaauga uaguuauaga aaugaaucca    900

agaguuucaa gaucaagugc uuuagcuucu aaggcaacgg guuauccuau agcaaagguu    960

gcgacacuuu uggcaguagg uuuuagcuua gaugagauua aaaaugauau uacaggaacu   1020

ccugcaucuu ucgagccugu gauugauuau auuguaacaa aaauuccucg cuuuaccuuu   1080

gaaaaauuuc caggagcaaa uacaacuuua gguacagcua ugaaaagugu gggugaggua   1140

auggcuauag gacgcacuuu uaaagaaagu auacaaaaag cacuuuguuc gcuugagcgu   1200

ucuuuaagug guuuugauag gguaaaauuu gaagauagaa augaucuugu uuuuaaaauu   1260

cgcaaugcca augaaaagcg uuuacuuuau guugcucaag cuuuuaggga agguuuuagc   1320

guagaagaac uuuaugagcu uuguaaaaua gauccuuggu uuuuaacaca gauuaaagaa   1380

auuguagauu uugaagaaca aauugauaug gauauuuuaa acaauaaggc ucuuuugaga   1440

aaagcaaaaa cuaugggcuu uucagauaaa augauagccu ugcuuguaaa uuugaaagau   1500
```

```
aauuuagaau uaagccaaaa ugauauuuau uauguaagaa ugaagcaaaa aaucaucgca   1560

gaauuuagug aaguggauac uugugcgggu gaauuugaag ccuuaacucc uuaucuuuau   1620

ucaaguauca auguaagcga acucacucaa aguaaaaacg augcuaagga uaaaaaagaa   1680

aaaaaaguga ugauuauagg ugggggcca aaccguauag gacaagguau agaauuugac   1740

uaugcuugcg uacaugcuuc uuuugcgcuu aaagauaugg guauuaaaac uauuauguau   1800

aauuguaauc cugaaaccgu uucgacugac uaugauacaa gugauauuuu guauuucgag   1860

ccuauugauu ucgaacauuu aagagcggug auugagcgug aaaaaccuga uggagugauu   1920

gugcauuuug guggacaaac uccuuugaaa uuugcuaagc guuuaagugc uuuuggagcu   1980

aagauuauag guacuagcgc aagaguaauu gauauggcag aagauagaaa gaaauuugcc   2040

gaauuuauua caaagcuagg uaucaaucag ccaaaaaauu cuacugcaac aagcguagaa   2100

gaagcgguuc uuaaggcuag ugauauaggg uauccugugc uuguaagacc aaguuauguu   2160

uuaggugggc gugcgaugcg cgugguaaau gaugaggcug aacuuagacu cuauaugcaa   2220

gaagcugugg auguaagcga uaaaagcccu guuuugaucg aucaguuuuu agacaaugcu   2280

acagaaauug auguugaugc gauuugugau ggcaaagaug uuuauguugc aggaauuaug   2340

gagcacauag aagaagcagg aauucauucg ggugacagug cuuguucuuu gccgccuugc   2400

aauaucgaug aaaaaaugca agaauuuauu gcacaaaaaa ccgcagauau ugcuuuaaau   2460

uugggaguug uaggacuuuu aaauauacaa uuugcuuuac auaauaaauga gcuuuauaug   2520

auagagguaa auccuagagc uagucguacc auaccuuuug uuaguaaagc uacggguauu   2580

ccuuuagcaa aaguggcaac gcgugugaug uggcaaggaa auuuaaaaga agcuuuaaaa   2640

uuuuaugaua cuuuuaaagu gguuaauuuu gauacuaaaa uuuuacgccc uaaaacucca   2700

aaauauauga gcgugaaaga agcaguauuu ccauuugcaa aacuuagugg aagugauuua   2760

gaauuagguc cugaaaugcg uucaacgggu gaaguuaugg guauaagcaa ggauuuugca   2820

aauucuuaug cgaaaaguca aauugcaucg uuuaaucauc uuccagagca aggcguggua   2880

uuuaucuccu uaaaagauaa ggauaaaaaa uauaccaaaa aaaucgcugc agaauaugua   2940

aagcuuggcu uuaagcuuau ggcaacaggg ggaacuugca aggaaauuuu agaaaguggu   3000

uuugagugcg aacuuguaca uaaaauuuca gaaggacgcc ccaauguuga agauaaauug   3060

aaaaauggag aaauucacuu aguuaucaau acaagcgaua gucacaguuu uaaaggcgau   3120

acgaaaaaaa uucgugaaaa uauuauucgu uuuaaaaauac cuuauuuuac aaauuuacga   3180

ucagcuuuag caggugcaaa aucgauuaaa gcuauacaga guaaaucuug ccuagaugua   3240

aagaguuugc aagaguggcu uaaaucuuga                                    3270
```

<210> SEQ ID NO 85
<211> LENGTH: 3365
<212> TYPE: RNA
<213> ORGANISM: Campylobacter jejuni

<400> SEQUENCE: 85

```
augaaaaaua ucacauuaac uaaaauaccu auaggagagg gcaaagaacc cuguuuaaau     60

ucuaaaaaga uaguuuuauc uuuagcuacu auuucuuuuu uggcaaguug ugcuaaugcu    120

aaauuaaauu cugaaauaaa aacuuaugau gaaguuaaua aaaauguuaa aacuagauca    180

gcaaguguuu auagcccuca agcuaagauc aauacgacua uaaauucuuu acacaaucaa    240

caaguaacua uuacuggaaa uggaacauca aauucuuuaa caaucggauc aaguggaacu    300

cuagguagca uaggcaauac agguaaaauc aucuaugccc augcuaaugg uagcaacacu    360
```

```
cuuacucuug caaaucuuac uaauaauaga acuauuaaug guaagauugg uauagaaaac    420

aaugguaauu uuacaggaac uauugcuguc aacaccuuug aaaauacagg ucaaauuaau    480

ggacaaauuu acaugggaau uuggggguaac aacucaggaa cucuuaauau agauaaauuu    540

gacaauagug gaaccauaau ugacaacaau aaaggaguuu uuuugaagga aagaauacca    600

acauacaaac cuuuaauaac agugguuuua uuagugcaaa uaagggugua gauauaggca    660

acauaggaac cauaaaaaau uuuaauaaca acggaacuau acaaggcuca gaagugggag    720

uggcuauaaa uacaaaaaua gauacuuuua cuaauaaugg uuuuauuaau uccccuggua    780

guggacaaug gaauaauggu auauggauaa guagcaaugc uaccauagaa aagcuuguua    840

acaauggcac aauaaaagga ggacauucug cuauaaaugu aacaucucag cauauaaaaa    900

cuguugaaaa uacaggaauu auacaugcug aaggagaaug ggguucuagu auauuauuag    960

aauauggugg uuuuauagag cauauaauca auacuggaac cauaaguaau aauaauguug   1020

guauagguuc agcuuaugga guauuuggaa cacuuaccau aaaagaugga gguaugguuu   1080

auggaaaaua cucggcaaua ggagugggguc gaucgcaaac ucuaggagau uuauauauag   1140

auggacguuc aaauaauggc acaguaagug gaauuuauag ugaagaacau ggaauuuuau   1200

uagagaauaa cucacgaacu caaaaaauag aacuuaaaaa uggcggcauu auaaaaggua   1260

auaucgaugg uauaagauug auaaacucgg ccucuuuaag uggagaaaug auuuuaucug   1320

gcgaagguuc uaggguagaa gguggaagag guguugguau auugaaucga aguggaaaaa   1380

uagaaggcuc uauaaaagua gaagauggag caacuguuac ggcuacuucg aaucgagcca   1440

uagcuaacuc uggcucagga aguauaacag gugguauuac uguuaguggg aaaaacacua   1500

aacuugaagg aaauauaauc aauacaggua augcuucuau agguagugau aucaagauag   1560

aagguggagc uaagguagaa gguggucuug uuaaucaagg uaauggaagu aucucaggaa   1620

guguucaagu aaguggugu agaguauug auuccauuac caaugagggu aauggagcua   1680

uuucugguuc aauuacugua uauaaagaua guaaacuuga uucuaucacu aacacuucua   1740

caucaucuac agguauaagu gguucuauua cuaacaauag ugauaauaaa cuugaaauuu   1800

cuaauucagg uaauaucggu gguaagauug aaaguacagg uagugcugau auggugauua   1860

gcaauaguaa ugguggaacu auuaguggcg guauuaguuc uucaggaagu ggaagcacua   1920

guauuuccaa uucacaaggc ucaaccauaa auaacggcau cacuguuuca ggaucagcac   1980

aaguugaaau cuccaaucaa ggcucaguag guaaagauga aaaugguaau acaguaacua   2040

acaaugguag ugguaguguu ggaaucaaag auuggcuugu uucuacagau aaaaacacag   2100

guaaauuaaa cacugugguu auaggguggaa guagagcuuu uaauguaaaa guagaaaaca   2160

ucaccguaga ucaaagcaau guugaucuug aagagcuaaa cgauauaaac aacaucaucu   2220

cagguguuaa ucaaaacaau auuggcaaua uaggaaccaa uggaagugga gaaauaucuu   2280

uaagcuuuga uccaauaaca ggaaagcuua cuacagauuu uaaucuuaau gcuuccauau   2340

caggugcaac cuuuagaucu uuaaucucua cuacuucaag aagaucaacc uuuauagaua   2400

auguuauggg uaauucuaug caaagcuuug cuuuagcuuc uucaaguaaa ucucaaagca   2460

ucgcuauguc ugaaaagggu aauuuauaug cagaugcaag ugauuauaua aagagugauu   2520

uaaauaaugg aagcuauggu ucuaauaaag aacauucuuu auucauccuu ccuuauacuu   2580

cuucacagaa uguugaacuu ucuuuaaaug aagaaaguaa aggacacacu aaaggaacca   2640

uuauagguua uucuacuuua aaagacagug gaauauaugg uguguaugca gguuaugaag   2700
```

```
auacaaaaau ggguucaacu uauuuugaua uuaauaauag aaccuauuau gcagguuuaa   2760

aauacuuuaa uaccuuauuu acuacagaaa aaggucaaga aguuuauauc aaagcucaag   2820

guaaagcugc uuugauuaaa aaugauuuaa cugaaaaaau aggaaauaau gaagcuaaag   2880

cugaaccuaa uucuuaugcu uauggaguca auacagccuu agguaugaau uuuauuucua   2940

auaaagauau auucucuccu gaaauagguc uugcuuauga aggagguuau acugaagcuu   3000

uuucuaugaa agacaccaua ggacaagcaa caguuaaagg uggagaaaga accuaugcaa   3060

acuauuuaaa ucuuuucucu acuaaaacaa gucuuacuug guuuagagau ugguugccua   3120

auuuaaaaac uucaguagaa cuuggagcua aguuuaauau caauccuaaa guagaagcug   3180

aggcuagauu ugguaauaua aaaguaagug augaguuuga uuuaccaaga guacaaaaau   3240

uuguaagcac uucuuuuauc guuccuguua augaagcuuu cuauuuuagu uuaaacuaua   3300

auggaauguu ugauaaagau ggcaauaccc auacaggauu ugcucaguuu aauuaucuuu   3360

gguaa                                                               3365
```

<210> SEQ ID NO 86
<211> LENGTH: 3436
<212> TYPE: RNA
<213> ORGANISM: Campylobacter jejuni

<400> SEQUENCE: 86

```
augaauaaaa cugcauuaac uaaaacauac acaaaagaua uacaaaauuc cuguuuaaau     60

ucuaaaaaga uaguuuuauc uuuagcuacu auuucuuuuu uggcaaguug uacucaugcu    120

acacuuacuc cugaaauaaa aacuuacgaa gagacaaaua gacaugcuaa agcuagguca    180

ggucuucaau cuagaaauuc gaauaaugag acuauaaaua auuuacaaac uuuaacuaaa    240

acuauaagug acaccggcaa uacucuaguu auagaaagua guggaacuau uacuauuucu    300

aaugaugggc aacaagcagu aaacuuucaa ccaaauucuu caacuucuac cuuuuuaaau    360

aaaggaacuc uuauaggugg aaauaauacu gcuaguguuc aacuaggagc agcaaaugga    420

aauaacggug uuagcauaga aaccuuuaau aaucaaggua ucauagguaa ugguucuucu    480

aaauuuggag uaacaguuuu uggggggggg gaguaaagau aacccuaaau cuauaaucaa    540

uaauuuuagu aauaguggaa cuauucacuc uaauacuggu gaaaguauuu auuuugguaa    600

cgccaaaaua ucaaguuuug uuaauagugg gacuauuaag aguaaacaag gugcaggagu    660

aaauauaucu caaggaacaa guauagagaa uuuuaacaau accggaaccg gaauuauuga    720

aggcaagaga augggguguaa auguucguuc aacaauaaau accuucguca augacgguuu    780

aauugcugca acgaacgaug gaauacagau aaaugcuaau guaaaaacau uaauaaauaa    840

gggaaccaua aaaggagaug cuauaucuau aagaucauua gguggaacua uagaaacauu    900

gaccaaugaa ggcauuaugu augguaaaag ugcugguauu uacaugaaca gaagucuugu    960

uaaaacucuu acaaauagcg guaccauuaa ucaaaacaau ucggcaacuu ggucugcugg   1020

uauaaaacuc gaaaauggua guaucauaga aaauaucauc aacacaggau cuauccguuc   1080

uaaugcuuuu ggaauaucug uaacuggugg uaaauuugga acacuuacca uaaaagaugg   1140

agguauggu uauggaaaau acucggcaau aggagugggu cgaucgcaaa cucuaggaga   1200

uuuauauaua gauggacguu caaauaaugg cacaguaagu ggaauuuaua gugaagaaca   1260

uggaauuuua uuagagaaua acucacgaac ucaaaaaaua gaacuuaaaa auggcggcau   1320

uauaaaaggu aauaucgaug guauaagauu gauaaacucg gccucuuuaa guggagaaau   1380

gauuuuaucu ggcgaagguu cuaggguaga agguggaaga gguguuggua uauugaaucg   1440
```

```
aaguggaaaa auagaaggcu cuauaaaagu agaagaugga gcaacuguua cggcuacuuc   1500
gaaucgagcc auagcuaacu cuggcucagg aaguauaaca ggugguauua cuguuagugg   1560
gaaaaacacu aaacuugaag gaaauauaau caauacaggu aaugcuucua uagguaguga   1620
uaucaagaua gaaggugggag cuaagguaga agguggucuu guuaaucaag guaauggaag   1680
uaucucagga aguguucaag uaaguggugg uaguaguauu gauuccauua ccaaugaggg   1740
uaauggagcu auuucugguu caauuacugu auauaaagau aguaaacuug auucuaucac   1800
uaacacuucu acaucaucua cagguauaag ugguucuauu acuaacaaua gugauaaauaa  1860
acuugaaauu ucuaauucag guaauaucgg ugguaagauu gaaaguacag guagugcuga   1920
uauggugauu agcaauagua augguggaac uauuaguggc gguauuaguu cuucaggaag   1980
uggaagcacu aguauuucca auucacaagg cucaaccaua aauaacggca ucacuguuuc   2040
aggaucagca caaguugaaa ucuccaauca aggcucagua gguaaagaug aaaaugguaa   2100
uacaguaacu aacaauggua gugguagugu uggaaucaaa gauuggcuug uuucuacaga   2160
uaaaaacaca gguaaauuaa acacuguggu uauaggugga aguagagcuu uuaauguaaa   2220
aguagaaaac aucaccguag aucaaagcaa uguugaucuu gaagagcuaa acgauauaaa   2280
caacaucauc ucagguguua aucaaaacaa uauuggcaau auaggaacca auggaagugg   2340
agaaauaucu uuaagcuuug auccaauaac aggaaagcuu acuacagauu uuaaucuuaa   2400
ugcuuccaua ucaggugcaa ccuuuagauc uuuaaucucu acuacuucaa gaagaucaac   2460
cuuuauagau aauguuaugg guaauucuau gcaaagcuuu gcuuuagcuu cuucaaguaa   2520
aucucaaagc aucgcuaugu cugaaaaggg uaauuuauau gcagaugcaa gugauuauau   2580
aaagagugau uuaaauaaug gaagcuaugg uucuaauaaa gaacauucuu uauucauccu   2640
uccuuauacu ucuucacaga auguugaacu uucuuuaaau gaagaaagua aaggacacac   2700
uaaaggaacc auuauagguu auucuacuuu aaaagacagu ggaauauaug guguguaugc   2760
agguuaugaa gauacaaaaa uggguucaac uuauuuugau auuaauaaua gaaccuauua   2820
ugcagguuua aaauacuuua auaccuuauu uacuacagaa aaaggucaag aaguuuauau   2880
caaagcucaa gguaaagcug cuuugauuaa aaaugauuua acugaaaaaa uaggaaauaa   2940
ugaagcuaaa gcugaaccua auucuuaugc uuauggaguc aauacagccu uagguaugaa   3000
uuuuauuucu aauaaaagaua uauucucucc ugaaauaggu cuugcuuaug aaggagguua  3060
uacugaagcu uuuucuauga aagacaccau aggacaagca acaguuaaag guggagaaag   3120
aaccuaugca aacuauuuaa aucuuuucuc uacuaaaaca agucuuacuu gguuuagaga   3180
uugguugccu aauuuaaaaa cuucaguaga acuuggagcu aaguuuaaua ucaauccuaa   3240
aguagaagcu gaggcuagau uugguaauau aaaaguaagu gaugaguuug auuuaccaag   3300
aguacaaaaa uuuguaagca cuucuuuuau cguuccuguu aaugaagcuu ucuauuuuag   3360
uuuaaacuau aauggaaugu uugauaaaga uggcaauacc cauacaggau uugcucaguu   3420
uaauuaucuu ugguaa                                                   3436
```

<210> SEQ ID NO 87
<211> LENGTH: 3561
<212> TYPE: RNA
<213> ORGANISM: Campylobacter jejuni

<400> SEQUENCE: 87

```
augggguaaaa uuaugaaaac uauggacgga aaugaggcug cugcauacgc ugcguaugcu   60
```

```
uuuacugaag uugcuggaau uuauccuauu acaccuaguu cuccuauggc ugauuauacc    120
gauauguggg cagcugcagg aaaaaaaaau cuuuuuggag uuccuguaaa aaucguagaa    180
augcaaagug aagcaggagc ugcagguagu gugcauggau cuuuacaagc uggggcuuug    240
acuacaacuu auacggcuuc ucaaggauua cuccuuaaaa uuccaaauau guauaaaaua    300
gcaggucaau uacuccccug uguaauccau guagcagcgc guucuuuggc ugcucaagcu    360
uugucuaucu uuggugauca ucaagauauu uaugcagcaa gacaaauugg uuuugcuaug    420
cuuuguucgc auucugugca agaaaccaug gacuuagcug guguagcaca uuuagcugca    480
auuaagggaa gagugccauu uuuacauuuu uuugaugguu uuagaacaag ccaugaaauu    540
caaaaaguug aaguaaugga uuaugcgcau uuugauagau uauuagauag agaagcuuug    600
cuugaauuua gaaauaaugc uuuaaaucca gaaaauccaa aaacacgugg aacagcacaa    660
aaugaugaua uuuauuuuca aacuagagaa guaagcaauc guuuuuacga ugcuuuaccu    720
gauguuguua augaauauau gcaagaaauu ucaaaaauua cagguagaga auacaaacca    780
uuuacuuauu auggucacaa agagccagag ugugugauug uugcuauggg uucuguaacu    840
caagcacuug aagaaguggu ggacuaucuu aaugccaagg gugaaaaggu agggauuuua    900
aaaguuuauc uuuaucgccc auuuaguuua aaauauuucu uugauguuau gccaaaauca    960
gugaaaaaaa ucgcgguuuu agauagaacc aaagaaccag gaagucucgg agaaccacuu   1020
uaucuugaug uaaaaucagc uuucuaugga agagaaaaug cuccuguuau agugggugga   1080
agauacggac uuucuucaaa ggauguugau ccugcucaaa ugauagcagu auuugaaaau   1140
cuuaaacuug auaaauccaa agauggcuuu acuguaggua uaauugauga uguaacucau   1200
acuucacuga guacuggaga gaaaauuuca cuuggagaug aaaguacgau cgaauguuua   1260
uuuuacggac uuggugcuga uggaacugug ggugcaaaua aaaacucgau uaaaaucauc   1320
ggagauaaaa cggauuuuua cgcucaagcu uauuuuugcuu augauucuaa aaaaucaggg   1380
gguuauacaa gaagccauuu aagauuuucu aaaaaaccua uccguucaac uuaucuuguu   1440
ucaacuccgc auuuuaucgc uuguucggua gcggcuuauu uggaaauuua ugauguuuua   1500
gcaggaauuc gcaaaggagg aacuuuccuu uuaaauagua uuuggaaugc ugaagaaacc   1560
auaagacaac uuccagaugc aguaaagaaa acuuuagcug aaaaagaagu aaauuuuuau   1620
aucaucaaug caaccaaacu agcucgugau auagguuugg gaaaucguac aaauaccauu   1680
augcaaucag ccuuuuucaa acuugcaaaa aucauuccuu augaagacgc acaaaaauac   1740
augaaagagc uugcguauaa aucuuauagu aaaaaaggcg augcuauugu agaaaugaau   1800
uacaaggcua uugauguggg ugcugaugga cuuguaaaag uugaagugga uccaaauugg   1860
aaaaauuuag agcuuaaaga aaaagaacaa accaaugccu auaaagguac ugaauuuguu   1920
gaaaaaaucg uaaaaccuau gaaugcggcu aagggugaug auuuaccugu uucagccuuu   1980
uuagguuaug aagauggaag uuuugaacac ggcacaaccg aauacgaaaa acgcgguguu   2040
gggguuaugg uaccaagaug gauagaggca aauuguauuc aaugcaauca augugcuuca   2100
guuuguccgc augcuguuau caggccauuu uugauuaaug augaagaaau ggcaaaugca   2160
ccucgcggug uaaaagauca ugcuuuagaa gcuaaaggaa ccaaaggaga aaaauuaagc   2220
uuuaaaauuc aaguuucucc acuugauugu acaggcugug agcuuugugu ucaugagugu   2280
ccuacuaaag aaaaaucuuu gguuauggua ccacuucaag aagagaugga uuuuggugag   2340
caagaaaaug cggauuauuu auuuaaagaa auuacuuaua aagaugauau uuuaaauaaa   2400
gaaaccacaa aaggagcgca auuugcccaa ccuuuauuug aauuccaugg ggcaugucu   2460
```

```
ggaugugggg aaacuccuua uauuacuuua auuacaagau uguucgguga aagaaugauu   2520

guggcuaaug cuacagguug uaguucuauu uaugggggu u cagcuccauc aacuccuuau   2580

agaaaaagug ugaaaaaugg acacgguccu gcuuggggaa auucacuuuu ugaagacaau   2640

gcugaguuug guuuggguau gaaaauugca acugaaaaua caagacaccg cauugaacau   2700

aucaugaaug aaaguaugca agaaguucca aaugcuuuau cagcucuuuu uaaagauugg   2760

auugcaaaua aagacaaugg ugcuaugucu guggaaauua aagauaaaau gaucccuauu   2820

uuagagcaaa auaaaaaauau uaaagcugua caagauauau uagagcuuaa acaguauuua   2880

aguaaaaaau cucacuggau uuuuggugu gaugguuggg cuuaugauau aggcuauggc   2940

ggacuugauc auguuuuagc aaguggagaa aauguaaaua uuuuagugcu ugauacagaa   3000

guuuauucua auacaggcgg ucaaaguuca aaaucuucua gaacaggagc uguagcacag   3060

uuugcagcag caggcaaacc uauacagaaa aaagaucuag gucaaauugc uaugacuuau   3120

gguuauauuu uuguagcaca aguaaauuca acggcaaauu auacucaucu uaucaaagcu   3180

aucacugcag cugaggccua ugauggacca ucuuugguga uuuguuauuc uccuuguaua   3240

gcucauggua uuaaaggugg gcuggguuac ucaggagagc aaggugagcu ugcuacaaaa   3300

ugugguuauu ggccacuuua uaccuuugau ccucguuuag aagagcaagg aaaaaauccu   3360

uuaacucuaa caggaaaaga accugauugg gauuuauaug agcaauuuuu gaugaaugaa   3420

gugcguuaua auucacuuaa aaaagcaaau ccugaacacg cugcugagcu uuuugaacgc   3480

aauaaaaaag acgcucaacg ucgcuauaga cagcuuaagc guauugcuau ggcugauuau   3540

agcaaugagg ucgaaagcug a                                              3561
```

<210> SEQ ID NO 88
<211> LENGTH: 4137
<212> TYPE: RNA
<213> ORGANISM: Campylobacter jejuni

<400> SEQUENCE: 88

```
augugcgaua uguuagauaa uaaauuagga aaucguuuaa gaguagacuu cucaaacauu     60

ucaaaacaaa uagaaauccc aaaucuucua caauuacaaa aaaagaguuu ugauuauuuu    120

uuaaaucuug auaaauggug aaguggua ua gaaaaaguuu uuaaaucaau uuuuccuauu    180

caugauccgc aaaauagauu gagucuugaa uauguuagua gugaaauagg caagccaaaa    240

uauaccauuc gcgaaugcau ggaaagaggu uugacuuauu cuguaaauuu aaaaaugaaa    300

auccgucuua cucugcauga aaaagaugaa aaaacagggg aaaaaguugg cguaaaagau    360

auuaaagaac aagaaauuua uauccgcgaa auuccuuuaa ugacagaucg uguaucuuuu    420

aucauuaacg ggguugagag agugguugua aaucaauuac auagaagccc ugguguuauu    480

uuuaaagaag aagaaaguuc aacgguugca aauaagcuug uuuauacagc acaaauuauu    540

ccugaucgug guucguggcu uuauuuugaa uacgaugcca aagauguuuu guauguaaga    600

aucaauaagc guagaaaagu uccuguaacu augcuuuuua gagcuuuagg guauaaaaaa    660

caagauauua uuaaguuguu uuauccuauu cagacuauac augugaaaaa agauaaauuu    720

uuaacagaau uuaauccaaa ugauuuuaug gauagaauag aauaugauau uaaagaugaa    780

aaaggaaaaa ucguucauca agcuggaaaa agacuuacaa agaaaaaagc agaacagcuu    840

auuaaagacg guuuaaaaug gauagaauau ccuguagaaa uuuuacuuaa ucguuauuua    900

gcaaauccua uuauugauaa agaaagugga gagguuuuau uugauucuuu aacuuuguua    960
```

```
gaugagagua agcuugcuaa gauuaaagag caaaaaaguu uugauauagc aaaugacuug   1020

gcuaauggcg uugaugcagc gauuauuaac uccuuugccc aagauggaga aacucuaaaa   1080

cuucuuaaac aaagugaaaa uaucgaugau gaaaaugauu uagcugcgau uagaauuuac   1140

aaaguuaugc gcccagguga accuguggua aaagaugcag cgaaggcuuu uguaaaugau   1200

uuauucuuca auccugaaag auacgaucuu accaagguag gucguaugaa aaugaaccau   1260

aaauuagguc uugaaguacc ugaguauguu acuguuuuga cuaaugaaga uauuauuaaa   1320

acugcaaaau auuuaauuaa aguaaaaaau gguaaaggac auauugauga uagagaucau   1380

uuaggaaauc gucguauccg uucuauaggu gaacuuuuag ccaaugaacu ucauuuaggu   1440

cuugcaaaaa ugcaaaaggc gaucagagau aaauuuacuu cuuuaaaugc ggaucuugau   1500

aaaguaaugc cuuaugauuu aaucaauccu aaaaugauua cuacaacuau cauugaauuu   1560

uuuacaggag gucagcuuuc gcaauuuaug gaucaaacca acccuuuaag cgagguuacu   1620

cauaagcguc guuugucagc gcuuggugaa gguggacuug uaaaagaaag agcagguuuu   1680

gaagugcgug auguucacgc gacacauuau gguagaauuu guccaguuga aacaccugaa   1740

ggucaaaaua uugguuugau uaacacucuu ucuacuuaug caaaaguaaa ugaacuuggc   1800

uuuguugaag cgccauauag aaaaguugua aaugguaaag ugacuaauga aguuguuuau   1860

cuuacagcga cacaagaaga aggcuuguuu aucgcaccag cuucaacuaa gguugaugcu   1920

aaaggcaaua uaguagaaga auuuguugag gcuaggcaag auggugaaac uauacuugca   1980

agacgcgaag aagugcaauu aaucgaucuu ugcucaggua ugguuguugg aguugcagcu   2040

ucuuugauuc cguuuuuaga gcacgaugau gcaaacagag cgcuaauggg uucaaacaug   2100

caacgucaag cugugccacu ucuuacugcu ucagcuccga uaguaggaac agguauggaa   2160

caaauuauug cgcgugaugc uugggaagcu guuaaagcaa agcguggcgg ugugguugag   2220

aaaguggaua auaaaagcau uuucauuuua ggugaagaug auaaaggucc auuuauugac   2280

cauuacacua uggagaaaaa uuuaagaacc aaucaaaaua caaauuauau ucaacacccu   2340

auuguuaaaa aaggugauau aguaaaagca ggacaaauua ucgcagaugg uccuucuaug   2400

gaucaaggcg aacuugcuau agguaaaaau gcuuuaaucg cuuuuaugcc uuggaauggu   2460

uauaacuaug aggaugcuau aguuguaagu gagagaauua uucgugaaga uacuuuuaca   2520

agcgugcaca uuuaugaaaa agaaauugaa gcaagagaac uaaaagacgg uauagaagaa   2580

auuaccaaag auauuccaaa uguaaaagaa gaagauguug cgcaucuuga ugagagcggu   2640

auugcaaaaa uugguaccca uaucaaacca gguaugauuu ugguggguaa gguuucucca   2700

aaaggugagg uuaaaccaac uccugaagaa agacuuuuaa gagcgauuuu uggagaaaaa   2760

gcaggacaug uugugaauaa aucccuuuau gcaaccgcuu cuuuagaggg uguuguugug   2820

gauguuaaaa uuuucacuaa aaaaggcuau gaaaaagaug aucgcgcaau aaaaucuuau   2880

gauaaagaaa aaauggcuuu agaaaaagag caucaugaua gacuuuugau gauggauaga   2940

gaagaaaugc uucguguuug ugcucuucuu uccaaagccu cuuuaaauag cgaucaaaaa   3000

auuggagaua aaaauuauaa aaaaggacaa acugcagaua uuagcgaacu ugaaaaaauc   3060

aaucguuuua cuuuaacaac uuugauuaaa gcuuauucua aagagauuca aaaagaauac   3120

gaugauuuaa aaaaucauuu ccaaaaugag aagaaaaaau uaaaagcaga acacgaugaa   3180

aagcuugaaa uuuuagaaaa agaugauauu uuaccaagug ggguaauuaa gcuuguuaaa   3240

guuuauauug cuacaaaaag aaagcuuaaa gucggugaua aaauggcagg acgucaugga   3300

aauaaaggua uaguuucaac uauaguuccu gaaguagaua ugccuuauuu gccaaauggu   3360
```

```
aagagcgugg auauugcgcu uaauccacuu ggcguuccaa gucguaugaa uauaggucaa   3420

auuuuagaaa gucauuuagg uuuaguugga cuuagacuug gggaucaaau ucaagaaauu   3480

uuugauagaa agcaaaaaga uuuucuuaaa gaauuaagag cgaaaauacu ugaaauuugu   3540

ucuauuccaa gacuugcaaa cgaaaaagaa uuuauuaaaa gcuuaagcga ugaagagcuu   3600

uuaaacuaug cuagagacug gaguaaagga guuaaauuuu cuacuccugu uuuugaaggu   3660

guaaauauag aagaauuuag caagcuuuuu aaaauggcua agauagauau ggauggcaaa   3720

acagaacuuu augauggacg cacgggggaa aaaauugcag agcguguuca uguaggaugu   3780

auguauaugc uaaaacucca ucacuugguu gaugaaaaag uucaugcaag aaguacagga   3840

ccuuauagcu ugguuaccca acaaccugug gguggguaaag cacucuuugg gggacaaaga   3900

uuuggagaaa uggaaguuug ggcacuugaa gcuuauggag cggcucacac uuuaagagaa   3960

auguuaacca uaaaaucaga ugauguagaa gguagauuua gugccuauaa agcauugaca   4020

aaaggugaaa auguuccagc aacaggaauu ccugaaacau uuuuuguauu aaccaaugag   4080

cuuaaaucuc uugcuuuaga uguugagauu uuugauaagg augaagauaa ugaguaa      4137
```

<210> SEQ ID NO 89
<211> LENGTH: 4491
<212> TYPE: RNA
<213> ORGANISM: Campylobacter jejuni

<400> SEQUENCE: 89

```
auggauuuag aaaauauccu agaaaauaau caaagcauag guuuauauca cccaaagaac     60

gaacacgaug ccugugguau cgcugcaguu gcuaauauac gcgguauugc uucuuauaag    120

guuauuugug augcuuuaga aauuuugaug aaucuugaac accgaggugg uacaggagcu    180

gaagaaaauu caggugaugg ggcggggauu uuaauccaaa uuccacauga uuuuuuuaaa    240

acucaagaau uggguuuuga acuuccuaaa aagggugauu augcuguagc acagauguuu    300

uuaucaccca auacugaugc aaaagaagaa gcaaaagaaa uauuuuuaca agguuuaaag    360

gauaaaaaac uugaauuuuu agguuuuaga gaagugccuu uuaauccuag cgauauaggu    420

gcaagugcuu uaaaagcuau gccuuauuuu uuacaagccu uuguaaaaaa accaaguaaa    480

auaagugcag gacuugaguu ugaaagagug cuuuauagua cgcgucgacu uauagaaaaa    540

agagcuauua augugccaaa auuuuauuuu ucaaguuuuu cuucacgcac cauaguuuau    600

aaaggaaugc uucuuucaac ucaauugagc gauuuuuauc uugauuuuaa agaugucaau    660

augaaaucag ccaucgcuuu ggugcauucu cgcuuuucga cuaauaccuu cccaaguugg    720

gaaagagccc auccaaaccg uuauauggug cauaauggag agauuaauac cauacgcgga    780

aauguugaua gcauaagagc uagagaaggc uugaugcaaa gugaguauuu ugaaaauuua    840

gaugaaauuu uuccuaucau agcuaagcuu agcagugauu cugcaauguu ugauaauacu    900

uuagaauuuu uagcucuaaa uggucguacu uuagaagaag cuuuuaugau gauggugcca    960

gaaccuuggc auaaaaauga aaauauggaa agcaaaaagc gugcuuuuua ugaauaucau   1020

ucuuuauuga uggagccuug ggauggaccu gcugcuauag uuuuuacuga uggagugauu   1080

augggggcga guuuggauag aaaugguuuu cguccuucaa gguauuaucu uacaaaagau   1140

gauaugcuca uacuuucaag ugaaacaggg gcuuuaaaac uugaugaaaa aaauaucaaa   1200

gcuaaaaaac gcuuagaacc uggaaaacuu uuacucguug auacagcaag agguaggguu   1260

auagcugaua augaaaucaa agagcauuau gcuaaugcua agccuuauaa aaaauggcuu   1320
```

-continued

```
aaaaauuuag uugaacuuga aaaacaaaaa agcggaguuu auaaacauca guuuuuaaaa   1380
gaagaugagg uuuuaaaacu ucaaaaagcu uuugguugga guuaugauga gcuuaaaaug   1440
agcguggcug cuauggcuca aaaugguaaa gaagcuauag cagcuauggg uguagauacu   1500
ccuuuggcua uacuuucuaa aacuuaucaa ccuuuguaua auuauuuuaa acaacuuuuu   1560
gcacaaguaa cuaauccucc ucuugaugcc auaagagaag agauuguuac uucuacaagg   1620
auuuaucuag gaagcgaagg caauuuauua aaacccgaug aaaacaaugc aaaacgcgua   1680
aaaauagccu ugccugugau aagcaaugaa gaacuuuuug aaguuaaggc uuuaaauaaa   1740
uuucaaguua aagaauuuuc uauacuuuau gauuauucua aaaaaacuuu agaaaaggcu   1800
uuagaugaac uuugcguuaa gauagaagau gagguuaaaa aaggguguuuc uauuaucauu   1860
uuaagcgaua aaggagugga ugaaaaaaac gcuuauaucc cugcuuugcu ugcuguuucu   1920
ggagugcaua aucaucuagu aagaaaaaau uuaagaacac auacaagucu uaucaucgaa   1980
agugguguaac cuagagaaau ucaucauuuu gcaugucuuu uagguuaugg ugcgacuguu   2040
auuaauccuu auuugguuua ugagaguaua caaaaacuca uugccaauaa agauuuaaau   2100
uuaaguuaug aaaaggcggu agaaaauuuc aucaaggcaa guucaagugg uauagucaaa   2160
auugcuucua aaauggggggu uucuaccuug caaaguuaua auggcucugc acuuuuugaa   2220
ugucugggcu uaagcucuaa ggugauugau aaauacuuca cuucuacaac uucacgcauu   2280
gaagguaugg auuuagaaga uuuugaaaaa gaacucauug cuuuacacaa acaugcuuuu   2340
aacgauacac auaaggcuuu agauucuaaa ggaauucaug guuuuagaag ugcuaaagaa   2400
gaacauuuaa ucgauccgcu ugugauuuuu aaucuucagc aagccugucg caacaaagac   2460
uauaaaaagcu uuaaaaaaua cucggcuuua guagaugaaa aacaaguuaa uuugcguucu   2520
uugauggaau uugauuuuag ugaagcuauc aguauagaua agguugaaag uguagaaagu   2580
auaguuaaac gcuuuagaac aggggcgaug aguuaugguu cuauuucuaa agaagcacac   2640
gaguguuuag cacaggcuau gaauaaaaua ggugcuaaau caaauucagg ugaaggugu   2700
gaggaugaag aacgcuauga aaucaaagag ggugugggaua aaaacucagc cauuaagcaa   2760
guagcaagug ggcguuuugg cguggauuua aacuacuuaa gucaugcaaa agaaauucaa   2820
aucaaagucg cucaaggugc aaaaccaggu gagggcggac aauuaauggg cuuuaaaguc   2880
uauccuugga uagcuaaggc uagacauucu acugcaggug ugacgcuuau uuccccaccu   2940
ccucaucaug auauuuauuc uauugaggau uuggcucaac ucauuuauga uuuaaaacau   3000
gcgaacaaag acgcuaaaau uucaguaaaa cuuguaagcg aaaauggcau aggaacgguu   3060
gcugcaggug uggcuaaggc aggcgcgaau uuaauccuug uuucagguua ugauggaggu   3120
acgggugcaa guccuagaac uucuauaccg caugcuggaa uuccuuggga guuaggcuua   3180
gcugaaacgc aucaaacuuu gaucuuaaau aagcuuagag auagggguaag auuagaaacu   3240
gauggaaagc uuaugaaugg gcgugauuua gccauagcag cacuuuuagg agcugaagaa   3300
uuugguuuug caaccgcucc uuugauuguu uuagguugua caaugaugag aguuugucau   3360
cuaaauaccu guccuuuugg uauagccacu caagauacag aacuuagaga ucguuucaaa   3420
ggcaaaguag augauguggau uaauuucaug uauuuuauag cugaggagcu uagagaauac   3480
auggcaaggc uugguuuuga acgccuagau gauaugauag gucgcgugga uaaacuccgc   3540
caaaaaagug ugcaagguaa agcaggaaag cuaaauuuag auaaaaauuu aaaauccuug   3600
ccuacuuaua auagaaccgc ugugcauuuu aaagauuaua aagacaauaa acuugaaaaa   3660
acgauugauu auagaauuuu acuaccacuu uguaaaaaug cuguggagaa aaaagagccu   3720
```

```
aucaaacuuu cuuuagaagu aggaaaucaa agucguacuu uugcaacuau gcuuucaagu   3780
gaaauuuuaa aaacuuaugg aaaagaugcu uuagaugaag auaguaucca uaucaaagcu   3840
auaggcaaug caggcaauag cuuuggagcg uuuuuguuaa aggguauuaa acuugagauu   3900
auaggcgaua gcaaugauua uuuaggcaag gguuuaagug gugguaaaau cauagcaaaa   3960
auuucaaaug aagccacuuu uucaccugaa gaaaauauca ucgcaggaaa ugcuuguuua   4020
uacggagcua caaaagguga aguguauuua gaugguauag caggggaaag auuuugugua   4080
agaaauucag gggcuuuggc ugugguuuua ggaacaggcg ugcaugguug ugaauauaug   4140
acagguggac aaguuguagu ucuuggagau gugggugcga auuucgcugc ugguaugagu   4200
gggggcguug uuuauaucuu uggaagacac aaugaagcuc auguaaaauc cgagcuugug   4260
gauauuaaag aucuuaaugc uaaggaugaa aaagaauuaa aagcugugau agaaaaacau   4320
aucacuuaua cagauucuaa aaaggcuaaa gauauuuuag aaaaauucga uaaaaaagac   4380
uuuuuuaaag ucaugccaag agauuaugaa aagauguuaa aaaugcuuga ucuuuguaaa   4440
aaugaaaaag auccaaauuu agcagcauuu uugaaaauca cacaaaaaua a            4491
```

```
<210> SEQ ID NO 90
<211> LENGTH: 4554
<212> TYPE: RNA
<213> ORGANISM: Campylobacter jejuni

<400> SEQUENCE: 90

augaguaaau uuaaaguaau agaaauuaaa gaagaugcaa gaccuagaga uuuugaagca     60
uuucaacuaa gacuugcaag uccugaaaaa aucaaaucau ggucuuaugg agaaguaaaa    120
aaaccagaaa cuauuaauua uagaaccuua aagccugaaa gagaugggcu uuuuugugca    180
aagauuuuug gaccuauaag agauuaugag ugucuuugug guaaauacaa aaaaaugcgu    240
uuuaaaggcg uuaaguguga aaaaugnggu guugaaguag caaauucaaa agugcgucgu    300
ucuagaaugg ggcauaucga gcuuguaacu ccuguggcuc auauuuggua uguuaauucu    360
cuuccaagcc guauaggaac gcuuuugggu guuaagauga aagaucuuga gcgcgugcuu    420
uauuaugaag cuuauauugu ugaaaaccca ggugaugcuu ucuaugauaa ugaaaguacu    480
aaaaaagugg aauauugcga uguuuugaac gaagagcaau aucaaaauuu aaugcaacgc    540
uaugaaaaua gcggcuuuaa agcaagaaug gguggagaag uuguucguga uuuacuugca    600
aauuuagauc uuguagcgcu uuuaaaucag cuuaaagaag aaaugggggc uacaaauuca    660
gaggcuaaga aaaaaacuau cauuaaacgc uuaaaaguug uagaaaauuu cuuaaauuca    720
aauuuaaacg ccaauaccga uagcgacgaa gcuguaccaa aucguccuga auggaugaug    780
auuacaaauc uuccaguuuu accgccagau uugcguccuu uaguggcuuu agaugguggg    840
aaauuugcag uuucugaugu gaaugacuua uaucgucgug uuaucaauag aaauacacgu    900
cuuaaaaaac uuauggaacu ugaugcaccu gaaaucauua ucagaaauga aaaaagaaug    960
cuucaagagg cuguugaugc gcuuuuugac aacggucguc gugcuaaugc uguaaaagga   1020
gcaaauaaac gcccauugaa aucuuuaagu gaaaucauca aagggaaaca aggacguuuu   1080
agacaaaauc uacuagguaa aaggguggau uucucagguc guagcguuau uguuguaggu   1140
ccaaaacuua gaauggauca augcgguuua ccuaaaaaaa uggcuuuaga gcuuuuuaag   1200
ccacaucuuu uagcuaagcu ugaagaaaaa gguuaugcaa ccacaguaaa acaagcuaaa   1260
aaaaugauag aaaauaaaac caaugaaguu ugggaauguu uagaagaggu aguaaaggga   1320
```

```
cauccuguua ugcuaaaccg ugcaccuacu uugcauaagc uuucuaucca agcuuuucau   1380
ccuguuuuag uggaagguaa ggcuauacaa cuucauccuu ugguuugugc agcauuuaac   1440
gcagacuuug auggggauca aauggcagug cauguaccgc uuucucaaga ggcuauugca   1500
gaauguaaag ugcuuaugcu uucaucaaug aauauucuuu uaccagcaag cgguaagucu   1560
guaaccguuc caucgcaaga uaugguuuua ggaauuuauu aucuuucguu ggaaaaagca   1620
ggugcuaaag guucgcauaa aauuuguaca ggcauugaug aagugaugau ggcacuugaa   1680
agcaaguguu uggauauuca ugcgagcaua caaacuaugg uagaugguag aaagauuacc   1740
acuacagcag gaagauugau uguuaaaucc aucuugccug auuuugugcc ugaaaauagu   1800
uggaauaaag ucuuaaagaa aaaagacauu gcugcgcuug uagauuaugu uuauaaacaa   1860
gguggguuuag agauuacagc aaguuucuua gauagacuua aaaauuuagg uuuugaauau   1920
gcaacuaaag cagguauuuc aauuucgauu gcagauauua uuguuccuaa ugauaaacaa   1980
aaagcuaucg augaagcaaa aaaacaagua agagaaauuc aaaauucuua uaaucucggu   2040
uugauuacuu caggggaaag auacaauaaa aucauugaua uuuggaaaag uacaaacaau   2100
guucuuucaa aagaaaugau gaagcuugua gaaaaagaua aagaagguuu uaacucuauu   2160
uauaugaugg cagauucugg ugcuaggggu agugcagcuc aaauuucuca gcuugcugcg   2220
augagaggac uuaugaccaa accugauggu ucuauuaucg aaacgccuau uauuucaaau   2280
uuccgugaag ggcuaaaugu ucuugaauac uuuauuucaa cucacggugc uagaaaaggu   2340
cuugcagaua ccgcucuuaa aacagcaaau gcggguuauu ugacaagaaa acucaucgau   2400
guugcacaaa auguaaaaau uaccauugaa gauuguggaa cacaugaggg uguugaaauc   2460
aaugaaauua ccgcagauag uucuauuaua gaaacuuuag aagaaagaau uuuaggcagg   2520
guuuuagcug aggaugugau ugauccuauu acaaauucug ugcuuuuugc ggaagguacu   2580
uuaauggaug aggaaaaagc aaaaauucuu ggcgaaagcg guauaaaaag ugucaauauc   2640
cgcacuccua uuaccugcaa agcuaaaaaa ggaauuugug caaaauguua ugguaucaau   2700
cuuggugaag guaaauuagu aaaaccaggc gaagcagugg gaauuauuuc cgcucaaucu   2760
aucggugaac caggaacgca gcuaacucua agaacuuucc auagcggggg aacugcaagu   2820
acggauuuac aagauagaca aguaagcgca caaaaagaag guuuuauaag auuuuauaau   2880
cuuaaaacuu auaaaaacaa agaagguaaa aauaucguag caaaucguag aaaugcggcg   2940
guuuuacuug uggagccaaa aaucaaaacu ccauuuaaag gugugauuaa uauagaaaau   3000
auucaugaag augugauugu uucuauuaaa gauaaaaaac aagaaguaaa auacauauua   3060
agaaaauacg aucuugcuaa accaaaugaa uuagcaggug uaaguggcag uauagaugga   3120
aaacuuuauu ugccauauca aagcggcaug caaguagaag aaaaugaaag uaucguagaa   3180
gugauuaaag aggguuggaa uguaccaaau cguauuccuu uugcgaguga aauuuuagua   3240
gaagauggcg agccuguagu ucaaaauauc aaagcaggcg aaaaaggaac acucaaauuu   3300
uacauccuua aaggcgaugg uuuagauaga guaaaaaaug uuaaaaaagg ugauauuguu   3360
aaagaaaaag gauucuuugu agugauugcu gaugaaaaug auagagaagc aaaaagacac   3420
uauauucccaa gagaaucuaa gauagaauuu aacgauagug aaaaaaucga ugacgcaaau   3480
acuaucauug caagugcucc uaaaaaagaa agaaaaguga uugcagaaug ggaugcuuau   3540
aauaauacua ucauugcaga aauugauggu guuguaagcu uugaggauau ugaagcaggu   3600
uauagugccg augagcaaau ugaugaagcu acagguaagc guucuuuagu aauuaaugag   3660
uauuuaccua gcggaguuag accaacuuug guaauugcag gaaaaggga uaaagcugug   3720
```

```
cguuaucacc uugaaccaaa aaccguuauu uuuguucaug auggcgauaa aauugcucaa   3780

gcagauauuu uagcaaaaac uccaaaagca gcagcuaaau caaaggauau uacaggaggu   3840

cuuccaagag uuucugaacu uuuugaagca agaaaaccaa aaaaugcggc ugugauugca   3900

gaaauugaug guguuguucg uuuugauaag ccuuugcguu cuaaagaaag aauuauuauc   3960

caagcagaag auggaacaag ugcugaguau uuaaucgaca aaucaaaaca uauucaagua   4020

agagauggag aguuuauuca ugcaggugaa aaacuuacag auggaguugu uucgagucau   4080

gaugugcuua aaauuuuagg ugaaaaagcc uugcauuauu auuugauuuc ugaaauucag   4140

caaguuuauc gcggacaagg uguugugauu ucugauaaac auauagaagu uaucguuucu   4200

caaaugcuaa gacaaguaaa aguuguagau aguggacaua cgaaauuuau ugaaggugau   4260

uugguuucaa gacguaaauu ccgugaagaa aaugaaagaa ucauuagaau ggguggagaa   4320

ccagcuauug ccgagccugu gcuuuuaggu guaacaagag cagcgauugg aagugauagu   4380

gugauuucug cggcuucauu ccaagaaacu accaaaguuu uaacugaagc aaguauagca   4440

gguaaauuug acuacuuaga agauuuaaaa gaaaauguua uucuagguag aaugauuccu   4500

guuggaacag ggcuuuaugg cgaacaaaau uuaaaacuua aagaacaaga auaa         4554


<210> SEQ ID NO 91
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 91

gctatcccac aaattgataa                                                 20
```

PEPTIDES DERIVED FROM *CAMPYLOBACTER JEJUNI* AND THEIR USE IN VACCINATION

FIELD OF THE INVENTION

The present invention relates to the field of antimicrobial prophylaxis and therapy. In particular the present invention relates to novel proteins and polynucleotides derived from *Campylobacter jejuni*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

*C. jejuni* is a bacterium commonly associated with poultry, since it naturally colonises the digestive tract of many bird species. Contaminated drinking water and unpasteurized milk provide an efficient means for distribution in human populations. Contaminated food is a major source of isolated *C. jejuni* infections, with incorrectly prepared meat and poultry normally being the source of the bacteria.

Infection with *C. jejuni* usually results in enteritis, which is characterised by abdominal pain, diarrhea, fever, and malaise. The symptoms usually persist for between 24 hours and a week, but may be longer. Diarrhea can vary in severity from loose stools to bloody stools. The disease is usually self-limiting. However, it does respond to antibiotics. Severe (accompanying fevers, blood in stools) or prolonged cases may require ciprofloxacin, erythromycin, azithromycin or norfloxacin. The drug of choice is usually erythromycin. About 90% of cases respond to ciprofloxacin treatment. Fluid and electrolyte replacement may be required for serious cases.

The first full-genome sequence of *C. jejuni* was performed in 2000 (strain NCTC11168) with a circular chromosome of 1,641,481 base pairs As mentioned, *C. jejuni* infections may successfully be treated by administration of antibiotics to patients in need thereof, but that would not prevent acute illness. Further, due to careless or thoughtless use of powerful antibiotics, many pathological germs, including *C. jejuni* become resistant against antibiotics over time. In particular in hospitals, treatment with antibiotics can prove inadequate: not only will a *C. jejuni* infection be life-threatening for patients that already suffer from other health problems meaning that treatment with antibiotics may simply be non-effective within the relevant time-span, but in addition antibiotic-resistant *C. jejuni* strains will also withstand treatment with those antibiotics used as the initial choice in treatment. There is thus a need to provide alternatives to current treatment regimens. Also, infection with *C. jejuni* is associated with reactive arthritis and Guillain-Barré Syndrome.

Vaccination is considered to be a very effective method of preventing infectious diseases in human and veterinary health care. Vaccination is the administration of immunogenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immuno-protective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *C. jejuni* derived antigenic polypeptides that may serve as constituents in vaccines against *C. jejuni* infections and in diagnosis of *C. jejuni* infections. It is also an object to provide nucleic acids, vectors, transformed cells, vaccine compositions, and other useful means for molecular cloning as well as for therapy and diagnosis with relevance for *C. jejuni*.

SUMMARY OF THE INVENTION

It has been found by the present inventor(s) that *C. jejuni*, in particular drug resistant *C. jejuni*, expresses a number of hitherto unknown putatively surface exposed proteins which are candidates as vaccine targets as well as candidates as immunizing agents for preparation of antibodies that target *C. jejuni*. One of these putatively surface exposed antigens (cj0404; SEQ ID NO: 13) has now been tested for suitability as a vaccine agent and has as the only candidate among 25 randomly isolated *C. jejuni* proteins been found to be a capable of providing protection against challenge infection. The remaining 29 variants are currently being investigated in a similar setup. So, in a first aspect the present invention relates to a polypeptide comprising a) an amino acid sequence selected from the group consisting of any one of SEQ ID NOs: 1-30, orb) an amino acid sequence consisting of at least 5 contiguous amino acid residues from any one of SEQ ID NOs: 1-30, orc) an amino acid sequence having a sequence identity of at least 60% with the amino acid sequence of a), d) an amino acid sequence having a sequence identity of at least 60% with the amino acid sequence of b), ore) an assembly of amino acids derived from any one of SEQ ID NOs: 1-30 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or ii) a nucleotide sequence consisting of any one of SEQ ID NOs: 31-90. iii) a nucleotide sequence consisting of at least 10 consecutive nucleotides in any one of SEQ ID NOs: 31-90, iv) a nucleotide sequence having a sequence identity of at least 60% with the nucleotide sequence in i) or ii), v) a nucleotide sequence having a sequence identity of at least 60% with the nucleotide sequence in iii), vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *C. jejuni* in the animal.

In a seventh and eighth aspect, the invention relates to 1) a polyclonal antibody in which the antibodies specifically bind to at least one polypeptide of the invention, and which is essentially free from antibodies binding specifically to other *C. jejuni* polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with *C. jejuni*, in particular infection with multi-resistant *C. jejuni*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *C. jejuni*, in particular the presence of multi-resistant *C. jejuni*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *C. jejuni*, in particular the presence of antibodies specific for multi-resistant *C. jejuni*, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *C. jejuni*, in particular the presence of a nucleic acid characteristic of multi-resistant *C. jejuni*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising—culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or—preparing said polypeptide by means of solid or liquid phase peptide synthesis.

In a $15^{th}$ aspect, the invention relates to a method for determining whether a substance, such as an antibody, is potentially useful for treating infection with *C. jejuni*, the method comprising contacting the polypeptide of the invention with the substance and subsequently establishing whether the substance has at least one of the following characteristics: 1) the ability to bind specifically to said polypeptide, 2) the ability to compeed with said polypeptide for specific binding to a ligand/receptor, and 3) the ability to specifically inactivate said polypeptide.

Finally, in a $16^{th}$ aspect, the invention relates to a method for determining whether a substance, such as a nucleic acid, is potentially useful for treating infection with *C. jejuni*, the method comprising contacting the substance with the nucleic acid fragment of claim of the invention and subsequently establishing whether the substance has either the ability to 1) bind specifically to the nucleic acid fragment, or 2) bind specifically to a nucleic acid that hybridizes specifically with the nucleic acid fragment.

LEGENDS TO THE FIGURE

FIG. 1: Gels showing the expression of 14 proteins of *C. jejuni* genes cloned in *E. coli* BL21.X: presence of expression product in BL21 after induction. O: No induction of protein expression.

Figure 2:
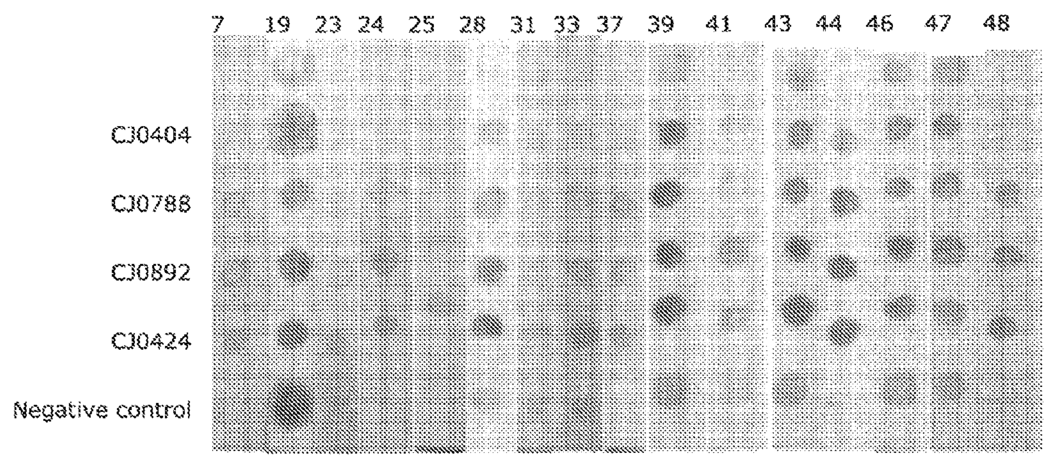
Figure 2:
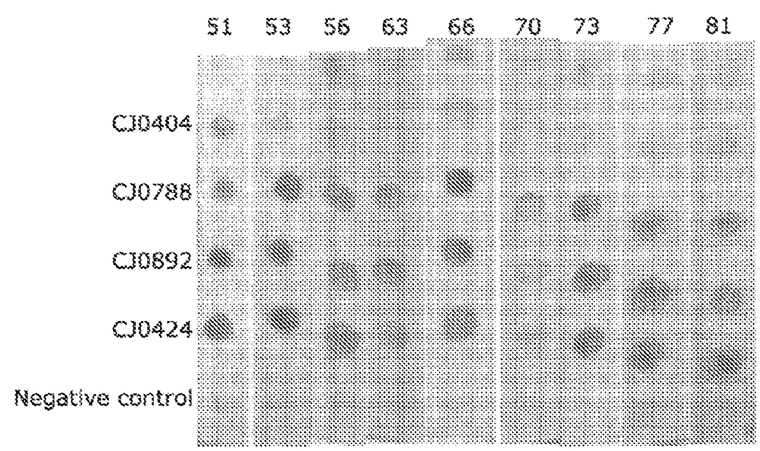

FIG. 2: *C. jejuni* transformed clones were tested for antibody recognition in a dot blot assay. Four clones were tested for expression and antigenicity. The dot blots are showing reactivity of 4 *C. jejuni* antigens with antiserea from rabbits immunized with five different *C. jejuni* strains from five different isolates. All clones reacted to all sera.

Figure 3:
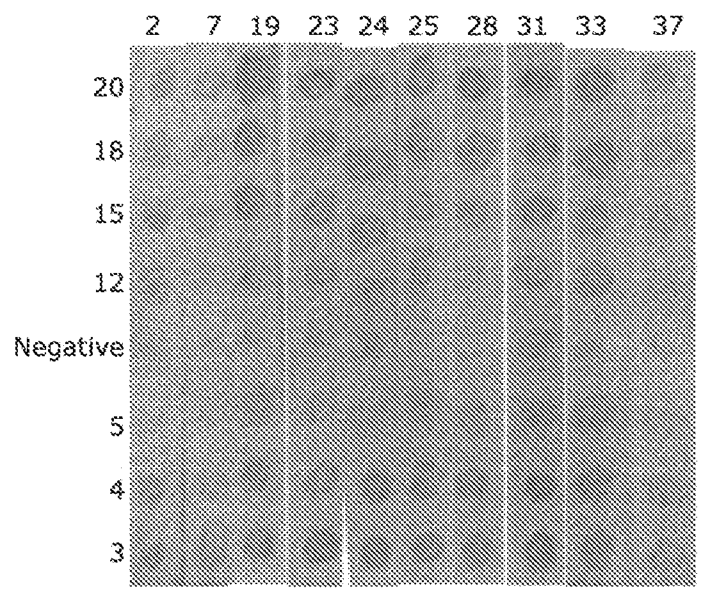
Figure 3:
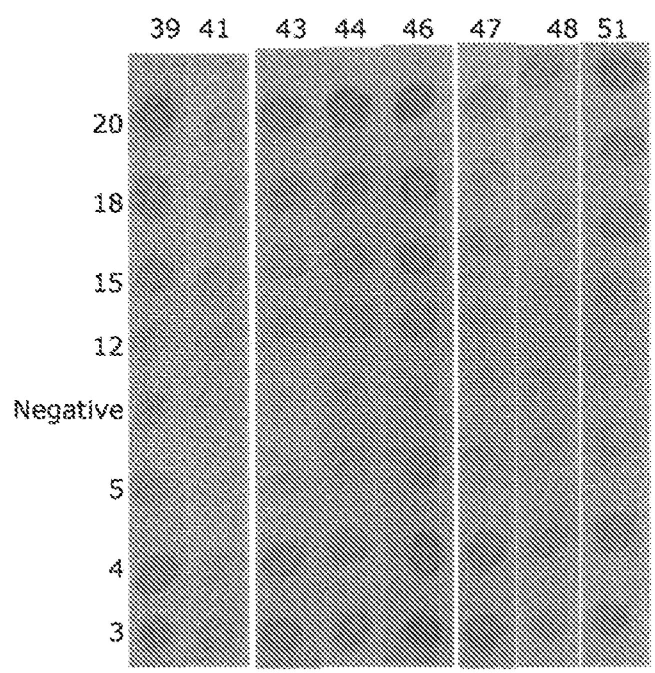

FIG. 3: Dot blots showing reactivity of 7 *C. jejuni* antigens against human sera.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least amino acids or, when relevant, of at least 3 nucleotides, derived directly from a naturally occurring amino acid sequence or nucleic acid sequence, respectively The term “amino acid sequence” s the order in which amino acid residues, connected by peptide bonds, lie in the chain in peptides and proteins.

The term “adjuvant” has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

“Sequence identity” is in the context of the present invention determined by comparing 2 optimally aligned sequences of equal length (e.g. DNA, RNA or amino acid) according to the following formula: $(N_{ref}-N_{thf})\cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAAC-3' and 5'-ATACGGGAC-3' will provide the sequence identity 77.78% ($N_{ref}$=9 and $N_{dif}$=2).

An “assembly of amino acids” means two or more amino acids bound together by physical or chemical means.

The “3D conformation” is the 3 dimensional structure of a biomolecule such as a protein. In monomeric polypeptides/proteins, the 3D conformation is also termed “the tertiary structure” and denotes the relative locations in 3 dimensional space of the amino acid residues forming the polypeptide.

“An immunogenic carrier” is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immungon by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A “T-helper lymphocyte response” is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule prese An “immunogen” is a substance of matter which is capable of inducing an adaptive immune response in a host, whose immune system is confronted with the immunogen. As such, immunogens are a subset of the larger genus “antigens”, which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A “hapten” is a small molecule, which can neither induce or elicit an immune response, but if conjugated to an immunogenic carrier, antibodies or TCRs that recognize the hapten can be induced upon confrontation of the immune system with the hapten carrier conjugate.

An “adaptive immune response” is an immune response in response to confrontation with an antigen or immunogen, where the immune response is specific for antigen determinants of the antigen/immunogen—examples of adaptive immune responses are induction of antigen specific antibody production or antigen specific induction/activation of T helper lymphocytes or cytotoxic lymphocytes.

A “protective, adaptive immune response” is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

“Stimulation of the immune system” means that a substance or composition of matter exhibits a general, non-specific immunostimulatory effect. A number of adjuvants and putative adjuvants (such as certain cytokines) share the ability to stimulate the immune system. The result of using an immunostimulating agent is an increased “alertness” of the immune system meaning that simultaneous or subsequent immunization with an immunogen induces a significantly more effective immune response compared to isolated use of the immunogen.

Hybridization under “stringent conditions” is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term “animal” is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterelogous nucleic acid sequence The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

Specific Embodiments of the Invention

The Polypeptides of the Invention

In some embodiments the at least 5 contiguous amino acids referred to in option b) in the definition of the first aspect of the invention constitute at least 6, such as at least 7, at least 8, at least 9, at least 10, at least 11, at least 12, at least 13, at least 14, at least 15, at least 16, at least 17, at least 18; at least 19, at least 20, at least 21, at least 22, at least 23, at least 24, at least 25, at least 26, at least 27 at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, and at least 51 contiguous amino acid residues.

The number may, where applicable, be higher, such as at least 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, at least 124, and at least 125 contiguous amino acid residues. Another way to phrase this is that for each of SEQ ID NOs: 1-30, the number of the contiguous amino acid residues is at least N−n, where N is the length of the sequence ID in question and n is any integer between 6 and N−1; that is, the at least 5 contiguous amino acids can be at least any number between 5 and the length of the reference sequence minus one, in increments of one.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47 in any one of SEQ ID NOs: 1-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 48, 49, 50, 51, 52, 53, 54, 55, 56, 57, 58, 59, 60, and 61 in any on of SEQ ID NOs: 2-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, and 112 in any one of SEQ ID NOs: 3-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 113, 114, 115, 116, 117, 118, 119, 120, 121, 122, 123, 124, 125, 126, 127, 128, 129, 130, 131, 132, 133, and 134 in any one of SEQ ID NOs: 4-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 135, 136, and 137 in any one of SEQ ID NOs: 5-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 138, 139, and 140 in any one of SEQ ID NOs: 6-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 141, 142, 143, 144, 145, 146, 147, 148, 149, 150, 151, 152, 153, 154, 155, 156, 157, 158, 159, 160, 161, 162, 163, 164, 165, 166, 167, 168, 169, and 170 in any one of SEQ ID NOs: 7-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 171, 172, 173, 174, 175, 176, 177, 178, 179, 180, 181, 182, 183, 184, 185, 186, 187, 188, 189, 190, 191, 192, 193, 194, 195, 196, and 197 in any one of SEQ ID NOs: 8-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 198, 199, 200, 201, 202, 203, 204, 205, and 206 in any one of SEQ ID NOs: 9-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, and 240 in any one of SEQ ID NOs: 10-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 241, 242, 243, 244, 245, 246, 247, 248, 249, 250, 251, 252, 253, 254, and 255 in any one of SEQ ID NOs: 11-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 256, 257, 258, 259, 260, 261, 262, 263, 264, 265, 266, 267, 268, and 269 in any one of SEQ ID NOs: 12-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 270, 271, 272, 273, and 274 in any one of SEQ ID NOs: 13-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, and 386 in any one of SEQ ID NOs: 14-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, and 538 in any one of SEQ ID NOs: 15-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, and 606 in any one of SEQ ID NOs: 16-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655 in any one of SEQ ID NOs: 17-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 656, 657, 658, 659, 660, 661 in any one of SEQ ID NOs: 18-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, and 746 in any one of SEQ ID NOs: 19-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, and 861 in any one of SEQ ID NOs: 20-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 862, 863, 864, 865, 866, and 867 in any one of SEQ ID NOs: 21-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, and 942 in any one of SEQ ID NOs: 22-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, and 1037 in any one of SEQ ID NOs: 23-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, and 1085 in any one of SEQ ID NOs: 24-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, and 1116 in any one of SEQ ID NOs: 25-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, and 1140 in any one of SEQ ID NOs: 26-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, and 1182 in any one of SEQ ID NOs: 27-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, and 1374 in any one of SEQ ID NOs: 28-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, and 1492 in SEQ ID NO: 29 or 30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1493, 1494, 1495, 1496, 1497, 1498, 1499, 1500, 1501, 1502, 1503, 1504, 1505, 1506, 1507, 1508, 1509, 1510, 1511, 1512, 1513 in SEQ ID NO: 30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-30. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *C. jejuni*, in particular multi-resistant *C. jejuni*. The polypeptide may in these cases induce a humeral and/or a cellular immune response.

Epitopes

SEQ ID NOs: 1-30 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised against *C. jejuni* or *C. jejuni* derived proteins disclosed herein are tested for binding to overlapping oligomeric peptides derived from any one of SEQ ID NO: 1-30. Thereby, the regions of the *C. jejuni* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-30 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 31-60) or an RNA fragment (such as SEQ ID NOs 61-90).

The nucleic acid fragment of the invention typically consists of at least 11, such as at least 12, at least 13, at least 14, at least 15, at least 16, at least 17 at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, and at least 153 consecutive nucleotides in any one of SEQ ID NOs: 31-90. Longer fragments are contemplated, i.e. fragments having at least 200, at least 300 at least 400, at least 500, at least 600, at least 700, at least 800, at least 900, at least 1000, at least 1500, at least 2000, at least 2500, at least 3000, at least 3500, and at least 4000 nucleotides from those of SEQ ID NOs: 31-90 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in *E coli*. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain (Banerji et al, 1983; Gilles et al, 1983; Grosschedl et al, 1985; Atchinson et al, 1986, 1987; toiler et al, 1987; Weinberger et al, 1984; Kiledjian et al, 1988; Porton et al; 1990), Immunoglobulin Light Chain (Queen et al, 1983; Picard et al, 1984), T Cell Receptor (Luria et al, 1987; Winoto et al, 1989; Redondo et al; 1990), HLA DQα and/or DQβ (Sullivan et al, 1987), β-Interferon (Goodbourn et al, 1986; Fujita et al, 1987; Goodbourn et al, 1988), Interleukin-2 (Greene et al, 1989), Interleukin-2 Receptor (Greene et al, 1989; Lin et al, 1990), MHC Class II 5 (Koch et al, 1989), MHC Class II HLA-DRα (Sherman et al, 1989), 13-Actin (Kawamoto et al, 1988; Ng et al; 1989), Muscle Creatine Kinase (MCK) (Jaynes et al, 1988; Horlick et al, 1989; Johnson et al, 1989), Prealbumin (Transthyretin) (Costa et al, 1988), Elastase I (Omitz et al, 1987), Metallothionein (MTII) (Karin et al, 1987; Culotta et al, 1989), Collagenase (Pinkert et al, 1987; Angel et al, 1987), Albumin (Pinkert et al, 1987; Tranche et al, 1989, 1990), α-Fetoprotein (Godbout et al, 1988; Campere et al, 1989), γ-Globin (Bodine et al, 1987; Perez-Stable et al, 1990), β-Globin (Trudel et al, 1987), c-fos (Cohen et al, 1987), c-HA-ras (Triesman, 1986; Deschamps et al, 1985), Insulin (Edlund et al, 1985), Neural Cell Adhesion Molecule (NCAM) (Hirsh et al, 1990), αl-Antitrypain (Larimer et al, 1990), H2B (TH2B) Histone (Hwang et al, 1990), Mouse and/or Type I Collagen (Ripe et al, 1989), Glucose-Regulated Proteins (GRP94 and GRP78) (Chang et al, 1989), Rat Growth Hormone (Larsen et al, 1986), Human Serum Amyloid A (SAA) (Edbrooke et al, 1989), Troponin I (TN I) (Yutzey et al, 1989), Platelet-Derived Growth Factor (PDGF) (Pech et al, 1989), Duchenne Muscular Dystrophy (Klamut et al, 1990), SV40 (Banerji et al, 1981; Moreau et al, 1981; Sleigh et al, 1985; Firak et al, 1986; Herr et al, 1986; Imbra et al, 1986; Kadesch et al, 1986; Wang et al, 1986; Ondek et al, 1987; Kuhl et al, 1987; Schaffner et al, 1988), Polyoma (Swartzendruber et al, 1975; Vasseur et al, 1980; Katinka et al, 1980, 1981; Tyndell et al, 1981; Dandolo et al, 1983; de Villiers et al, 1984; Hen et al, 1986; Satake et al, 1988; Campbell et al, 1988), Retroviruses (Kriegler et al, 1982, 1983; Levinson et al, 1982; Kriegler et al, 1983, 1984a, b, 1988; Bosze et al, 1986; Miksicek et al, 1986; Celander et al, 1987; Thiesen et al, 1988; Celander et al, 1988; Choi et al, 1988; Reisman et al, 1989), Papilloma Virus (Campo et al, 1983; Lusky et al, 1983; Spandidos and Wilkie, 1983; Spalholz et al, 1985; Lusky et al, 1986; Cripe et al, 1987; Gloss et al, 1987; Hirochika et al, 1987; Stephens et al, 1987), Hepatitis B Virus (Bulla et al, 1986; Jameel et al, 1986; Shaul et al, 1987; Spandau et al, 1988; Vannice et al, 1988), Human Immunodeficiency Virus (Muesing et al, 1987; Hauber et al, 1988; Jakobovits et al, 1988; Feng et al, 1988; Takebe et al, 1988; Rosen et al, 1988; Berkhout et al, 1989; Laspia et al, 1989; Sharp et al, 1989; Braddock et al, 1989), Cytomegalovirus (CMV) IE (Weber et al, 1984; Boshart et al, 1985; Foecking et al, 1986), Gibbon Ape Leukemia Virus (Holbrook et al, 1987; Quinn et al, 1989).

Inducible Elements include, but are not limited to MT II-Phorbol Ester (TFA)/Heavy metals (Palmiter et al, 1982; Haslinger et al, 1985; Searle et al, 1985; Stuart et al, 1985; Imagawa et al, 1987, Karin et al, 1987; Angel et al, 1987b; McNeall et al, 1989); MMTV (mouse mammary tumor virus)-Glucocorticoids (Huang et al, 1981; Lee et al, 1981; Majors et al, 1983; Chandler et al, 1983; Lee et al, 1984; Ponta et al, 1985; Sakai et al, 1988); β-Interferon-poly(rl)x/poly(rc) (Tavernier et al, 1983); Adenovirus 5 E2-E1A (Imperiale et al, 1984); Collagenase-Phorbol Ester (TPA) (Angel et al, 1987a); Stromelysin-Phorbol Ester (TPA) (Angel et al, 1987b); SV40-Phorbol Ester (TPA) (Angel et al, 1987b); Murine MX Gene-Interferon, Newcastle Disease Virus (Hug et al, 1988); GRP78 Gene-A23187 (Resendez et al, 1988); α-2-Macroglobulin-IL-6 (Kunz et al, 1989); Vimentin-Serum (Rittling et al, 1989); MHC Class I Gene H-2κb-Interferon (Blanar et al, 1989); HSP70-E1A/SV40 Large T Antigen (Taylor et al, 1989, 1990a, 1990b); Proliferin-Phorbol Ester/TPA (Mordacq et al, 1989); Tumor Necrosis Factor-PMA (Hensel et al, 1989); and Thyroid Stimulating Hormoneα Gene-Thyroid Hormone (Chatterjee et al, 1989).

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "on"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention. Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli.*), *Bacillus*, (e.g. *Bacillus subtilis*) *Salmonella*, and *Mycobacterium* [preferably non-pathogenic, (e.g. *M. bovis* BCG)].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these inter alia allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JMl 09, and KC8, as well as a number of commercially available bacterial hosts such as SURE® Competent Cells and SOLOP ACK™ Gold Cells (STRATAGENE®, La Jolla, Calif.). Alternatively, bacterial cells such as (*E. coli* LE392) could be used as host cells for phage viruses. Appropriate yeast cells include *Saccharomyces cerevisiae, Saccharomyces pombe*, and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast (*Pichia methanolica*). One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al, 1993; U.S. Pat. Nos. 4,684,611 and 4,952,500, each incorporated herein by reference); by desiccation/inhibition mediated DNA uptake (Potrykus et al, 1985). Through the application of techniques such as these, organelle(s), cell(s), tissue(s) or organism(s) may be stably or transiently transformed.

The Antibodies of the Invention—and their Production/Isolation

Antibodies directed against the proteins of the invention are useful for affinity chromatography, immunoassays, and for distinguishing/identifying *staphylococcus* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4 C for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective 1 aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 125I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 1151 may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 125I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an $F(ab')_2$, an scFV; cf. also the definition of the term "antibody" presented above.

Compositions of the Invention; Vaccines

Pharmaceutical compositions, in particular vaccines, according to the invention may either be prophylactic (ie. to prevent infection) or therapeutic (ie, to treat disease after infection).

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP
(see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. non-human primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 μg and 500 mg (however, often not higher than 5,000 μg), and very often in the range between 10 and 200 μg.

The immunogenic compositions are conventionally administered parenterally, eg, by injection, either subcutaneously, intramuscularly, or transdermally/transcutaneously (eg. WO98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Immunol 9: 271-283; Donnelly et al. (1997) Annu Rev Immunol 15: 617-648; later herein].

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 μg of the polypeptide of the invention per administration.

In preferred embodiments of the sixth aspect, the immunisation scheme includes that the animal (e.g. the human) receives a priming administration and one or more booster administrations.

Preferred embodiments of the 6$^{th}$ aspect of the invention comprise that the administration is for the purpose of inducing protective immunity against *C. jejuni*. In this embodiment it is particularly preferred that the protective immunity is effective in reducing the risk of attracting infection with *C. jejuni* or is effective in treating or ameliorating infection with *C. jejuni*.

As mentioned herein, the preferred vaccines of the invention induce humoral immunity, so it is preferred that the administration is for the purpose of inducing antibodies specific for *C. jejuni* and wherein said antibodies or B-lymphocytes producing said antibodies are subsequently recovered from the animal.

But, as also mentioned the method of the 6$^{th}$ aspect may also be useful in antibody production, so in other embodiments the administration is for the purpose of inducing antibodies specific for *C. jejuni* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claim, the invention also relates to related embodiments to the treatment and prophylaxis disclosed herein: the invention also includes embodiments where

- the polypeptide of the invention is for use as a pharmaceutical, in particular for use as a pharmaceutical in the treatment, prophylaxis or amelioration of infection with *C. jejuni;*
- the nucleic acid fragment of the invention or the vector of the invention is for use as a pharmaceutical, in particular for use as a pharmaceutical in the treatment, prophylaxis or amelioration of infection with *C. jejuni;*
- the transformed cell of the invention is for use as a pharmaceutical, in particular for use as a pharmaceutical in the treatment, prophylaxis or amelioration of infection with *C. jejuni*.
- the antibody, antibody fragment or antibody analogue of the invention is for use as a pharmaceutical, in particular for use as a pharmaceutical in the treatment, prophylaxis or amelioration of infection with *C. jejuni*.

Examples

Material and Methods

Bacterial Strains and Plasmid

The bacterial strains used in this study included *E. coli* SURE (Stratagene) and *E. coli* BL21 (DE3) (Stratagene) and the plasmid was pTLJ03. Strains and plasmid originates from a NCTC 11168 *C. jejuni* ORF library (Parrish et al., 2004) available from Geneservice. The expression clone set comprises >1,600 *C. jejuni* ORF's and the expression vector pTLJ03 generates N-terminal GST-His-tagged fusion proteins.

Strains were grown in LB media or the expression media MagicMedia (Invitrogen) at 37° C. pTLJ03 containing strains were grown in media containing 50 μg/mL ampicillin unless otherwise specified. *C. jejuni* 11168H is a stable motile variant of the reference strain *C. jejuni* NCTC 11168; its preparation is described infra in the section headed "recombinant DNA techniques". *C. jejuni* strains (NCTC 11168 and 11168H) were grown at 37° C. microaerophilic on blood plates (Basell and 5% blood) in BHI broth or biphasic (blood plates and BHI broth) with antibiotic when needed (30 μg/mL kanamycin or/and 50 μg/mL streptomycin).

Expression Library

The library was originally created in *E. coli* SURE for optimal storage. This strain does not contain the T7 polymerase and for that reason the library was transformed to the *E. coli* BL21 (DE3) expression strain. The clones were grown separately overnight in microtiter plates in 200 μl LB media containing ampicillin and subsequently the plasmids were purified as a pool and transformed to the chemocompetent *E. coli* BL21 (DE3) strain. This revealed an expression library consisting of 2304 clones (24 microtiter plates).

Immunoblot Assay

Individual clones were grown 16-20 hrs in microtiter plates in MagicMedia for optimal expression. 2 μl of the culture was spotted on nitrocellulose membranes. The membranes were blocked in blocking buffer 30 min., washed in PBS Tween and then incubated in primary antibody (1:1000) at 4° C. for 16-20 hrs. The membranes were then washed in PBS Tween and incubated in secondary antibody (Polyclonal goat anti-rabbit immunoglobulins/HRP, Dako) for 1 hr. The reaction was visualised by chemoluminescence (chemoluminescent substrate, Invitrogen). The primary antibody was raised in rabbit immunised with a boiled-treated (100° C. for 1 h) *C. jejuni* Penner serotype 2 originally isolated from a human patient. Rabbit serum from immunisations with the Penner serotype 2 was chosen since it corresponds to the serotype used for creating the commercial library (NCTC 11168). The serum was preincubated with *E. coli* BL21 (DE3) before use to minimise background reaction. To verify that the antigens also reacted against human serum, a dot blot with 10 selected clones expressing antigens and serum isolated from a patient infected with *C. jejuni* Penner serotype 2 (Strid M A et al. 2001, "Antibody responses to *Campylobacter* infections determined by an enzyme-linked immunosorbent assay: 2-year follow-up study of 210 patients", Clin. Diag. Lab. Immunol. 183:2553-9.) was carried out as described above.

Clone Sequencing

Plasmid DNA was isolated from 100 ml *E. coli* BL21 (DE3) cultures using MidiPrep (Qiagen). Sequencing was conducted by Macrogen Inc. and the primer 5"GCT ATC CCA CAA ATT GAT AA 3" (SEQ ID NO: 91).

Recombinant DNA Techniques

*C. jejuni* 11168H knock-out mutants were kindly provided by Brendan Wren from the London School of Hygiene and Tropical Medicine, University of London. Mutants were constructed via insertion of the Km cassette into unique sites present in pUC18-based recombinant plasmids containing random 1-2 kb fragments from the *C. jejuni* NCTC 11168 genome library (Garénaux A et al. 2008, "Role of the Cj1371 periplasmic protein and the Cj0355c two-component regulator in the *Campylobacter jejuni* NCTC 11168 response to oxidative stress caused by paraquat", Res Microbiol. 159: 718-26 and Parkhill J et al. 2000, "The genome sequence of the food-borne pathogen *Campylobacter jejuni* reveals hypervariable sequences", Nature 10; 403(6770):665-8). The 11168H knock out mutant provided for this study is: Cj0034c. Subsequently the gene knock-outs were transferred from the *C. jejuni* 11168H strain to the *C. jejuni* 11168 strain to restore motility and spiral morfology. Natural transformation was performed as described previously (Wang Y and Taylor D E 1990, "Natural transformation in *Campylobacter* species", J Bacteriol. 172: 949-55) with some modifications. *C. jejuni* cultures grown overnight on BHI agar plates were collected and resuspended in 12 ml BHI broth to $OD_{600}$ of 0.001. Bacterial suspensions in three dilutions were transferred to sterilized Petri dishes, incubated at 37° C. with no shaking under micro aerobic conditions over night. 200 µg cultures with $OD_{600}$ 0.2-0.3 were transferred to sterilized tube with 1 ml BHI and incubated at 37° C. with shaking under micro aerobic conditions 2 h. Then 10 ng of genomic DNA, purified with Qiagen blood and tissue kit, of the mutants, was added each tube. After additional incubation for 3 h, bacterial cultures were serially diluted and plated on Basell agar plates with antibiotics (50 mg/l kanamycin). The agar plates were incubated at 37° C. under microaerobic conditions 3 days. The mutants were checked for curved shape and motility before tested in assays.

INT407 Adhesion Assay

INT407 cells (representing intestinal cell line) were grown in MEM (+glutamax) media (Invitrogen) added 25 µg/ml gentamycin and 10% heat inactivated fetal bovine serum in 5% $CO_2$. Cells were seeded at $2.5\times10^5$pr well in 24 well plates, incubated overnight and checked for 100% confluent monolayer. The *E. coli* clones were grown overnight in MagicMedia broth at 37° C. and *C. jejuni* on blood agar plates microaerophilic at 37° C. Immediately before assay, the $OD_{600}$ of the bacteria was adjusted to 1 in PBS and 1 ml bacteria culture was added the INT407 cells and cells were incubated with bacteria for 2 hours at 37° C., then resuspended and diluted in PBS and spotted on agar plates with appropriate antibiotics.

Electron Microscopy

To investigate, whether the *C. jejuni* mutant strain differed morphologically from the wild type strain, a transmission electron microscopy analysis was conducted. Initially, the bacterial cultures were fixated in 1% glutaraldehyde (EMS, Hatfield, USA) for 30 minutes. To improve the adhesion of the bacteria, formvar coated 400-mesh copper grids were treated for minutes with alcian blue (Sigma-Aldrich). The alcian blue treated grids were placed on top of cultures of *C. jejuni* NCTC11168 and *C. jejuni* NCTC11168Δ0034 (Cj0034c), respectively, and after 5 minutes of incubation, most of the suspensions were removed from the grids with filter paper and the grids were stained for 30 seconds with phosphotungstic acid (BDH Chemicals). The grids were allowed to air-dry, and then they were viewed in a Morgagni 268D transmission electron microscope, and pictures were taken using a Mega-view III digital camera.

Motility Assay

A motility assay was carried out to ensure no altered motility for the 11168Δ0034 mutant. 0.25% soft agar plates were supplied with 1 gi bacterial culture ($OD_{600}$ adjusted to 0.1) in the middle of the plate and diameter was measured over a time period.

Serum Resistance Assay

Serum sensitivity assays were performed by modification of the method of Blaser et al (Blaser M J et al. 1985, "Susceptibility of *Campylobacter* isolates to the bactericidal activity of human serum", J Infect Dis. 151: 227-235.) *C. jejuni* strains were grown overnight in *Brucella* biphasic cultures at 37° C., washed in PBS, pH 7.4, and adjusted to a concentration of $10^3$ CFU/ml. *C. jejuni* cells (10-µl aliquots) were incubated in 240-µl pools of whole human blood (venous blood), human serum (whole blood incubated at 25° C. 30 min, centrifuged 1000×g 10 min at 4° C. and supernatant isolated) and heat inactivated human serum (56° C. for 30 min) respectively for 30, 60, 90 and 120 min. Following the incubation period, CFU was enumerated on BHI agar.

Biofilm and Autoagglutination

Cell-to-cell autoagglutination was assayed in PBS as described by Misawa and Blaser (Misawa N and Blaser M J 2000, "Detection and characterization of autoagglutination activity by *Campylobacter jejuni*", Infect. Immun. 68: 6168-6175.) Biofilm assay was made in 50 ml centrifuge tubes containing 25 ml inoculated *Brucella* broth with NCTC 11168 and the knock out mutants in Cj0034c. A glass slide was added each tube and incubated micro aerobic for 48 h. Then the slides were stained with crystal violet and biofilm formation visualised.

Predictions of Protein Localization

Prediction of protein localization and amount of transmembrane helixes was made by TMHMM 2.0 server (Moller S et al. 2001, "Evaluation of methods for the prediction of membrane spanning regions", Bioinformatics, 17: 646-653).

The SignalP 3.0 server predicts the presence and location of signal peptide cleavage sites in amino acid sequences. The method incorporates a prediction of cleavage sites and a signal peptide/non-signal peptide prediction based on a combination of several artificial neural networks and hidden Markov models. The LipoP 1.0 server produces predictions of lipoproteins and discriminates between lipoprotein signal peptides, other signal peptides and N-terminal membrane helices in Gram-negative bacteria (Juncker A S et al. 2003, "Prediction of lipoprotein signal peptides in Gram-negative bacteria", Protein Sci. 12:1652-62).

Protein Purification

His-tag purification was made with the already GST-His-tagged constructed vector from Geneservice. An overnight pre-culture of *E. coli* BL21(DE3) containing the vectors was 50-fold diluted to inoculate 1000 ml LB medium containing appropriate antibiotics. The cultures were incubated with shaking at 37° C. to an $OD_{600}$ of 0.5, then induced with 10 mM IPTG and incubated with shaking for 16 hours at 30° C. After induction, cells were lysed on ice in 20 ml lysis buffer (50 mM $NaH_2PO_4$, 300 mMNaCl, 10 mM imidazole 10% glycerol) by addition of 1 mg/ml lysozyme followed by sonication. Lysates were cleared by centrifugation at 15,000×g for 30 min. Proteins were purified by nickel affinity chromatography using the Ni-NTA resin (Qiagen) equilibrated with lysis buffer and eluted with 250 mM imidazole. Eluted proteins were concentrated and dialyzed against 25 mM HEPES pH 7.5, 50 mMNaCl, 10% glycerol.

Mouse Vaccination and Challenge Studies

To study ability of the proteins to protection against infection, immunization of mice were carried out. Cj0404 (SEQ ID NO: 13) was tested together with other putative vaccine candidates for its ability to protect against *C. jejuni* infection. Mice (10 in each group) were immunized with 5 pg/dose, except one with 1.6 μg/dose (Cj1371c), along with adjuvant (GNE, Intervet, NL). Four weeks later, the mice (Balb/c for colonization and CH3/HeN for invasion) were treated for three days with streptomycin (5 g/l in drinking water) and challenged orally one day later with *C. jejuni* 81116 ($6\times10^5$ CFU, colonization study) and 72Dz/92 ($5\times10^7$ CFU, invasion study) respectively. Balb/c mice 6-8 weeks (female) were used in groups of three. One fresh faecal dropping was collected and weighted from each animal and dilutions were made in order to determine CFU/gram faeces. Faecal samples were collected from the Balb/c mice regularly in 23 days. Necropsy was prepared one week after challenge of the CH3/HeN mice, spleen and liver were collected and CFU/organ were detected.

Results

Identification of *C. jejuni* Antigens

With the aim of identifying immuno-reactive *C. jejuni* proteins plasmid DNA was isolated from a pooled mixture of commercial library clones established by Parrish et al (Parrish J R et al. 2004, "High-throughput cloning of *Campylobacter jejuni* ORFs by in vivo recombination in *Escherichia coli*", J Proteome Res. 3: 582-6.) with *C. jejuni* NCTC11168 ORFs in the plasmid pTLJ03 (Parrish J R et al. 2004). Plasmid DNA was transformed into *E. coli* BL21 to allow expression from the T7 promoter. The resulting transformants were individually spotted on a nitrocellulose membrane and reacted with serum isolated from a rabbit infected with a *C. jejuni* human clinical isolate (serotype 2). The screening revealed several immunogenic *E. coli* clones that selectively reacted with the serum. Inserts in plasmids isolated from the transformants that repeatedly proved as most immunogenic were selected for sequencing and from a total of 2304 clones, 52 inserts were sequenced representing 25 genes encoding potential antigens. The identified *C. jejuni* genes were classified according to their predicted function.

To confirm that the identified antigens also are functional in humans we reacted 10 of the 25 clones (Cj0034, Cj0203, Cj0404 (SEQ ID NO: 13), Cj0525c, Cj0645, Cj0917c, Cj1094c, Cj1371, Cj1382c, Cj1632c) with human antiserum obtained from a patient infected with a *C. jejuni* Penner serotype 2 and found in all cases a positive reaction. This result supports that the antigens reacting with the mouse antiserum also are antigens in humans.

Prediction of Protein Localization

Prediction of localization of the proteins and amount of transmembrane helixes was made: 14 out of 25 proteins are predicted to contain one or more membrane helixes, two of them further with a signal peptide. Other ten of the proteins are predicted to be located externally, where three of them harbor a signal peptide. None of the proteins were predicted to contain a lipoprotein signal peptidase.

Several Antigens Support Host Cell Adhesion

Adhesion of *C. jejuni* to host cells forms the first important step in the infection process. With the aim of addressing whether the identified antigens contribute to host cell invasion a selection of 10 *E. coli* clones expressing *C. jejuni* antigens were investigated for their ability to adhere to the intestinal epithelial cell line, INT407. Interestingly, expression of three of the *C. jejuni* antigens enhanced the ability of *E. coli* BL21 to adhere to INT407 cells, Cj0034c, Cj0404 (SEQ ID NO: 13) and Cj1371. Subsequently, gene-specific *C. jejuni* mutations were constructed in the corresponding genes, and the resulting mutants were examined in the same cell adhesion assay. While the absence of Cj0404 and Cj1371 did not affect the ability of *C. jejuni* to adhere to INT407 cells, inactivation of Cj0034 dramatically reduced adhesion suggesting that Cj0034 may contribute to establishment of *C. jejuni* in host organisms. Further characterization of the Cj0034 mutant *C. jejuni* strain revealed, that the mutation does not result in major structural changes of the bacterial cell morphology as visualized by electron microscopy. Also, the inactivation of Cj0034 did not influence serum resistance, motility, auto-agglutination and biofilm formation, when compared to wild type strain.

Antigens as Vaccine Candidates

Five identified antigens were selected to test as vaccine candidates in two *Campylobacter* oral challenge mouse models; one in C3H/HeN mice in which invasion in liver and spleen was measured and the other in Balb/c mice in which shedding faecal was determined. The challenge study showed a reduced invasion into spleen and liver for at least two of the proteins; Cj0525c and Cj0404 (SEQ ID NO: 13). No decreased colonization for any of the proteins was observed.

Further Examples

*C. jejuni* Antigen Expression 30 genes encoding potentially antigenic *C. jejuni* proteins were identified and checked in NCBI and presence in the clone library. Of the 30 suggested gene sequences, 19 were commercially available and purchased from Life Sciences. All 19 were used for cloning in expression plasmid (with his-tag) and transformation into the expression strain *E. coli* BL21. Two of the constructs were not transferred to *E. coli* BL21 and after several attempts we did not proceed, which left 17 successful transformants.

We also separately PCR-cloned from *Campylobacter jejuni* 11168. Thus Cj0404, Cj0788, Cj0892 and Cj0424 were cloned into plasmid with his-tag and transformed into *E. coli* BL21. Previous work suggested that Cj0404 was antigenic (Clin Vaccine Immunol. 2012 February; 19(2):113-9) whereas Cj0424 was identified by us.

Preliminary tests were performed with the 4 *C. jejuni* genes transformed in BL21.

Further, several inductions were made with the 17 *C. jejuni* genes transformed in *E. coli* BL21. Media and induction protocols were tested. "Magic media" was seen to induce relevant sized proteins as can be seen from the SDS gels shown in FIG. 1. It was demonstrated that 7 *C. jejuni* clones were induced (circle markings). Overnight cultures were run on the 12% SDS gel. All experiments were performed at least twice with essentially the same results.

Protein Purification and Verification of Immunogenicity

The *C. jejuni* transformed clones were tested for antibody recognition in a dot blot assay.

The four selected clones produced from PCR cloning were tested for expression and antibody antigenicity in a dot blot assay against human sera (dot blot 1 shown in FIG. 2).

The 7 *E. coli* clones that could be induced to produce *C. jejuni* proteins were tested for reaction with antisera from rabbits immunised with five different *Campylobacter* strains of five different isolates. All clones reacted to all sera.

All experiments were performed at least twice with essentially the same results.

Since all antigens were recognised by rabbit antisera, they were subsequently tested with sera from patients that were shown to have antibodies against *Campylobacter jejuni* tested in the diagnostic test that runs at the Danish State Serum Institute (Strid et al. Clin Diagn Lab Immunol. 2001 March; 8(2):314-9).

The sera were randomly picked but all exhibited antibodies against *Campylobacter jejuni*. Patients with no antibodies to *C. jejuni* by ELISA are not expected to react in the dot blot assay (data not shown). Examples of the dot blots are seen in FIG. 2.

From the dot blots it is seen that all patients found to have antibodies against *C. jejuni* by a diagnostic ELISA react also react with colonies of *E. coli* BL21 that express *C. jejuni* antigens. In many cases the negative control being an *E. coli* BL21 without a plasmid is seen to also react with the sera This is expected since humans have encountered *E. coli* infections and are colonised in the gut.

IN CONCLUSION

We have identified 30 *C. jejuni* genes that are be potentially antigenic and recognised by antibodies against *Campylobacter*. We have been able to show that 7 of these are indeed able to be recognised by antibodies raised in humans after a natural infection with *Campylobacter jejuni* (diarrhea).

Sequences of Proteins of the Invention:

The protein sequences of the invention mentioned in the above examples are related to the sequences in the sequence listing as follows:

| Aa sequence | Designation |
|---|---|
| SEQ ID NO: 1: | Cj0251c |
| SEQ ID NO: 2: | Cj1464 |
| SEQ ID NO: 3: | Cj1406c |
| SEQ ID NO: 4: | Cj0579c |
| SEQ ID NO: 5: | Cj0158c |
| SEQ ID NO: 6: | Cj0592c |
| SEQ ID NO: 7: | Cj0783 |
| SEQ ID NO: 8: | Cj0371 |
| SEQ ID NO: 9: | Cj0424 |
| SEQ ID NO: 10: | Cj0944c |
| SEQ ID NO: 11: | Cj0111 |
| SEQ ID NO: 12: | Cj0596 |
| SEQ ID NO: 13: | Cj0404 |
| SEQ ID NO: 14: | Cj0606 |
| SEQ ID NO: 15: | Cj1178c |
| SEQ ID NO: 16: | Cj1357c |
| SEQ ID NO: 17: | Cj0144 |
| SEQ ID NO: 18: | Cj0262c |
| SEQ ID NO: 19: | Cj0887c |
| SEQ ID NO: 20: | Cj1729c |
| SEQ ID NO: 21: | Cj0136 |
| SEQ ID NO: 22: | Cj0886c |
| SEQ ID NO: 23: | Cj1365c |
| SEQ ID NO: 24: | Cj0279 |
| SEQ ID NO: 25: | Cj1677 |
| SEQ ID NO: 26: | Cj0628 |
| SEQ ID NO: 27: | Cj1476c |
| SEQ ID NO: 28: | Cj0478 |
| SEQ ID NO: 29: | Cj0007 |
| SEQ ID NO: 30: | Cj0479 |

For easy reference, the protein sequences of the invention are set forth in one-letter amino acid code in the following:

```
                                                        SEQ ID NO: 1
MAYEDEEDLN YDDYENEDEE YPQNHHKNYN YDDDDYEYDD DNNDDDFYEM D          51

                                                        SEQ ID NO: 2
MINPIQQSYV ANTALNTNRI DKETKTNDTQ KTENDKASKI AEQIKNGTYK IDTKATAAAI   60

ADSLI                                                              65

                                                        SEQ ID NO: 3
MKKILILLTL CAFAFGASEC DRKIDRINKE ISFSKAHNDT ARTLSLELAL KQVQNDCAKD   60

PMFYDKKLEA KKLKEQEVEK IEKELDALKE QKDYMSKAEY KAKKEALKEQ KEKIKK     116

                                                        SEQ ID NO: 4
MSFGEIIVIL VVAILVLGPD KLPEAIVQIA KILKAVKRNI DDAKSSIEKE IRINDLKEEA   60

KKYKDEFSST NENIRKKLSF EEFDDLKRDI LDKTKVDLTF DSRDDKVKNN LSGQNLNTEE  120

KPNLSKLETQ DKNGKINV                                               138

                                                        SEQ ID NO: 5
MQKAKILIAL SFFLLVLSAC SNDEKNISKT QNTDQEVVQI EQNDEKTELS DSNLPLPVDD   60

EAQSSNDEHE VNPSIINSLY KQKCATCHGE KGELKPKNST AIKTLSNKIF IQKIKTIKDK  120

NHSFLSDEQI QNLADFINKG K                                           141
```

-continued

SEQ ID NO: 6

```
MRRLSILLAI LIVINITACD SKTENYYKNL PSEAKEKAKE CKESGTLSED CINALKVGVK     60

PTNEEGKYSP NTPKKSDNQI LEALKQNDLK KEKTTKDINQ SSENNESIII PPIAETPSEI    120

YPSKTTENNQ SSIFSDDVNM TQEK                                           144
```

SEQ ID NO: 7

```
MMKKKLVLLG SAAVVFFAAC AMNSGVSSEQ IGLRKASLEN ENKVNLVEAN FTTLQPGEST     60

RFERSYENAP PLIPHAIEDL LPITKDNNMC LSCHDKAIAA DAGATPLPAS HYYDFRHNKT    120

TGDMISDSRF NCTQCHVPQS DAKPLVGNSF KPEFKNEQLK SRSNLIDVIN EGVK          174
```

SEQ ID NO: 8

```
MKKIKKIIQI GMIGGLAAVA GGALAGCGSN NDNADTLNQA ANAQGAFVII EETAPGQYKI     60

KDQYPSDETR VVLKDLNGTE RILSKEEMDA LIKEEAAKID NGTSNLTKDN GQISSGGLSL    120

GETLLASAAG AILGSWIGSK LFNNQNFANQ QRGAFSNQSA YQRSVNSFNK AGTTSSASSA    180

KKSGFFGGGS KATSSSSSFG S                                              201
```

SEQ ID NO: 9

```
MTKFLSICSL IAMLLSGCGS DFPGQPSDVA RVQQNKYPNG NLKKEIPYNK DSRIHGLKRA     60

FYDNGQLRAE ENYKNGKKDG ISREYSRNGQ LLEEVHFKDN RGYGDFASYY ENGNMRAKGK    120

LLGYNEDGMP EFEGNYKEYY ENGTLMCDYN FDNKGKFDGV QKRYDENGAL EDEENYKNGL    180

KNGVFREYKK GEIVREEEYK NGILVAKPKN                                     210
```

SEQ ID NO: 10

```
MKKIFLSVFL VLSLNAQNLE IDKIRTDLYS KSGANVLKKV EISLEFDGNN LKENENKLID     60

AVNTVISGFF YEDIFTEIGK NNFKKTLEKF LDKKYKIKLD DIYIISLSGV EKFDLEEFKR    120

FLESTEAKEK GMGSEVKKAL ENLEVPKTQV PSVEKIPTPS VPNLEVKQVE QLFKDPDEEN    180

KNDNGEINID NLNTPKMTPD IEEKIKRDLI ANPPQIFKEN NASKPYHLPQ TGYDIKLDEN    240

STQN                                                                 244
```

SEQ ID NO: 11

```
MKNYGLSNLN SFLLALAIYI SIVILVFFRL VSEVEPAIQY TDIKDSFVDI ELAEPSKQVI     60

TQSNTPKEIQ KPTEQIDIEK LFAQTTNKTV KTEDIDQKAS NFNELFGNIK EIQEEKTTKI    120

QSSAKSGISS APKPQASELV KQLNDSLLQE ESSTQGESTK AQKIGIYDEF LGKVVRIITQ    180

RWTQYYPNSE KISVKVKIFI DENGKFGYTS VEKSGNPLYD AKVAEFLESQ KGKFITYPPQ    240

NKNISITMNL RDEVKVKND                                                 259
```

SEQ ID NO: 12

```
MKKFSLVAAT LIAGVVLNVN AATVATVNGK SISDTEVSEF FAPMLRGQDF KTLPDNQKKA     60

LIQQYIMQDL ILQDAKKQNL EKDPLYTKEL DRAKDAILVN VYQEKILNTI KIDAAKVKAF    120

YDQNKDKYVK PARVQAKHIL VATEKEAKDI INELKGLKGK ELDAKFSELA KEKSIDPGSK    180

NQGGELGWFD QSTMVKPFTD AAFALKNGTI TTTPVKTNFG YHVILKENSQ AKGQIKFDEV    240

KQGIENGLKF EEFKKVINQK GQDLLNSAKV EYK                                 273
```

SEQ ID NO: 13

```
MENQKNEFDD IILEKSNKSE KVKKILLRVI ALVILFLAIM IVMKLINGSG DENTQNQSVL     60

PSEPIATQDN NNDTSFESMP ITDNTSAEDQ FEALRKQFQD EQNTTQNTTT SSSNNNDTTN    120

FAMPDQEVPA EPTATTSANT TPQASTPKQE VTQTAKSKEE AKKQTAVKKE KESAKQTPKK    180

EQNANDLFKN VDAKPVHPSG LASGIYVQIF SVSNLDQKSK ELASVKQKGY DYKLYKTTVG    240

SKEITKVLIG PFEKADIAAE LAKIRKDIAK DAFSFTLK                            278
```

SEQ ID NO: 14

```
MKKKIVLIIL IAILGSVGAY FIFFNNDEKI SYLTQKIQKK DISQTIEAVG KVYAKDQVDV     60

GAQVSGQIIK LYVDVGTHVK QGDLIAQIDK DKQQNDLDIT KAQLESAKAN LESKKVALEI    120
```

-continued

```
ANKQYQREQK LYAAKASSLE NLETQKNNYY TLKANVAELN AQVVQLEITL KNAQKDLGYT      180

TITAPMDGVV INVAVDEGQT VNANQNTPTI VRIANLDEME VRMEIAEADV SKIKVGTELD      240

FSLLNDPQKT YHAKIASIDP ADTEVSDSST SSSSSSSSSS SSSSSNAIYY YAKFYVANKD      300

DFLRIGMSIQ NEIVVASAKA VLAVPTYAIK SDPKGYYVEI LENQKAVKKY VKLGIKDSIN      360

TQILEGVNED EELIVSSSAD GLAPKMKLRF                                       390

                                                          SEQ ID NO: 15
MKILLLNENP VVSRLVSLSA KKMSYDFEEL NAYSENLGNY DVIVVDSDTP APLKILKEKC       60

DRLIFLAPRN QNVEDIDAQI LQKPFLPTDF LNLLNNKDAN KHTSIDLPML SNDENPYADI      120

SLDLDNLNLD DLPDENSLDI NSEGMEDLSF DDDAQDDNAN KTLETQNLEH ETIKEQTQED      180

TQIDLDLTLE DGESEKEDLS QEHTALDTEP SLDELDDKND EDLEIKEDDK NEEIEKQELL      240

DDSKTNTLEM QEELSESQDD NSNKTLETQN LEHDNLEQET IKEQTQEDTQ IDLDLTLEDG      300

ESEKEDLSQE HTALDTEPSL DELDDKNDED LEDNKELQAN ISDFDDLPEV EEQEKEMDFD      360

DLPEDAEFLG QAKYNEESEE NLEEFAPVVE EDIQDEIDDF ASNLSTQDQI KEELAQLDEL      420

DYGIDSDNSS KVLEDFKDEP ILDDKELGTN EEEVVVPNLN ISDFDTLKES DIQEALGEEI      480

LEKNEEPIVS DVTKDDNSEE IVNELSQSIA GAITSSIKDD TLKAALKGMN MNININISFK      540

ED                                                                     542

                                                          SEQ ID NO: 16
MKKNILRLGI VVLVLLIAGV LWLNNDINQK KEDEANKNAI AANADFSLLS DDDPNFEKWG       60

KVFPEQLKMY LTVEKEEPKA TEFGGNLAYS KLIRFPQLTI LWAGYPFSLD FNEERGHFWV      120

QVDQMKTARN NKDFLNAHGL AAFKGQPAAC MNCHSGWTPW LIKNVAKGDF TAFNSTNYWT      180

MIKNIPAVDG IVENSPEHAG PHGGKRMGVT CADCHNPNDM SLRLTRPAAI NALVSRGYEK      240

DPVQGVKATR EEMRTLVCSQ CHVEYYFKPT GEKVKVMGET IVDDSSKKWW NGTQKNYDEY      300

EFWRDGNKVK EIETDGIVLT FPWSEWKKGQ PFRIEMLDDY YDKVRGVFGA DFTHKLTGAQ      360

IIKIQHPESE LYSGGVHAAN GVSCVDCHMP YVREGAKKVT QHNITSPLRD INSACKSCHK      420

QSEDYLKAQV LDIQNSVAHD QRTAEYAIVS LIMDTKKLRD ELGNMEKFQS DGKADAKKIS      480

EELKEVLELH RKAQMRADFV NAENSTGFHN PREASRMLLQ AVDMARMGQT KLVEIAAANG      540

IKDFKTSNLG FEDIQKFNPG ELYYKVDVNN HKAGERYYAD EKDVNGNPPK ELLEHDKELA      600

PYNYQVIDKK                                                             610

                                                          SEQ ID NO: 17
MKSVKLKVSL IANLIAVVCL IILGVVTFIF VKQAIFHEVV NAEINYVKTA KNSIESFKAR       60

NSLALESLAK SILKHPIEQL DSQDALMHYV GKDLKNFRDA GRFLAVYIAQ PNGELVVSDP      120

DSDAKNLDFG TYGKADNYDA RTREYYIEAV KTNKLYITPS YIDVTTNLPC FTYSIPLYKD      180

GKFIGVLAVD ILAADLQAEF ENLPGRTFVF DEENKVFVST DKALLQKGYD ISAIANLAKT      240

KEDLEPFEYT RPKDGNERFA VCTKVSGIYT ACVGEPIEQI EAPVYKIAFI QTAIVIFTSI      300

ISVILLYFIV SKYLSPLAAI QTGLTSFFDF INYKTKNVST IEVKSNDEFG QISNAINENI      360

LATKRGLEQD NQAVKESVQT VSVVEGGNLT ARITANPRNP QLIELKNVLN KLLDVLQARV      420

GSDMNAIHKI FEEYKSLDFR NKLENASGSV ELTTNALGDE IVKMLKQSSD FANALANESG      480

KLQTAVQSLT TSSNSQAQSL EETAAALEEI TSSMQNVSVK TSDVITQSEE IKNVTGIIGD      540

IADQINLLAL NAAIEAARAG EHGRGFAVVA DEVRKLAERT QKSLSEIEAN TNLLVQSIND      600

MAESIKEQTA GITQINDSVA QIDQTTKDNV EIANESAIIS STVSDIANNI LEDVKKKRF       659

                                                          SEQ ID NO: 18
MQSINSGKSV GISAKLTLWV GILVVLILAI TSAISYFDSR NNTYELLKDT QLKTMQDVDA       60

FFKSYAMSKR NGIQILANEL TNRPDMSDEE LINLIKVIKK VNDYDLVYVG FDNTGKNYQS      120
```

-continued

```
DDQILDLSKG YDTKNRPWYK AAKEAKKLIV TEPYKSAASG EVGLTYAAPF YDRNGNFRGV      180

VGGDYDLANF STNVLTVGKS DNTFTEVLDS EGTILFNDEV AKILTKTELS INIANAIKAN      240

PALIDPRNQD TLFTAKDHQG VDYAIMCNSA FNPLFRICTI TENKVYTEAV NSILMKQVIV      300

GIIAIIIALI LIRFLISRSL SPLAAIQTGL TSFFDFINYK TKNVSTIEVK SNDEFGQISN      360

AINENILATK RGLEQDNQAV KESVQTVSVV EGGNLTARIT ANPRNPQLIE LKNVLNKLLD      420

VLQARVGSDM NAIHKIFEEY KSLDFRNKLE NASGSVELTT NALGDEIVKM LKQSSDFANA      480

LANESGKLQT AVQSLTTSSN SQAQSLEETA AALEEITSSM QNVSVKTSDV ITQSEEIKNV      540

TGIIGDIADQ INLLALNAAI EAARAGEHGR GFAVVADEVR KLAERTQKSL SEIEANTNLL      600

VQSINDMAES IKEQTAGITQ INDSVAQIDQ TTKDNVEIAN ESAIISSTVS DIANNILEDV      660

KKKRF                                                                 665

                                                            SEQ ID NO: 19
MRITNKLNFT NSVNNSMGGQ SALYQISQQL ASGLKIQNSY EDASTYIDNT RLEYEIKTLE       60

QVKESTSRAQ EMTQNSMKAL QDMVKLLEDF KVKVTQAASD SNSQTSREAI AKELERIKES      120

IVQLANTSVN GQYLFAGSQV ANKPFDSNGN YYGDKNNINV VTGAGTESPY NIPGWDLFFK      180

ADGDYKKQIS TNVSFTDNRW DLNKDPDKTK YLTGDSKWQQ LIGQSYVKDN SLDADKDFEY      240

DDSKLDFPPT TLYVQGTRPD GTSFKSAVLV KPEDTLEDVM ENIGALYGNT PNNKVVEVSM      300

NDSGQIQITD LKQGNNKLDF HAVAFTPQAD DKTELNNIIQ AAQDEGITME DVTNRVMTAA      360

LGNPNNGDIT NLNNPVTIQI NGQNFEIDLK QTDFIKSKMT DTDGNAANGA DYDNVYFEKN      420

GNTVYGNVSQ VIKGSNAYAT DSTKLSEVMA GDSLNGTTLN LKVNSKGGNS YDVTINLQTS      480

TVSYPDPNNP GQTISFPIMH TNPATGNSGV VTGSNDITYG QINDIIGMFA ADKIPTTTIQ      540

ANNGQINNAD YTQIQQLMKD SQATVDVSMD YKGRISVTDK LSSGTNIEIS LSDSQSGQFP      600

APPFTTTSTV QNGPNFSFSA NNSLTIDEPN VDIIKDLDSM IDAVLKGNMR ADSESENPRN      660

TGMQGALERL DHLADHVSKL NTTMGAYHNT IEGVNTRTSF LSVNVQSIKS NVIDVDYGEA      720

MMNLMQVQLA YQASLKASTT ISQLSLLNYM                                      750

                                                            SEQ ID NO: 20
MMRSLWSGVS GLQAHQVAMD VEGNNISNVN TTGFKYSRAD FGTMFSQTVK IATAPTDGRG       60

GSNPLQIGLG VSVSSTTRIH SQGSVQTTDK NTDVAINGDG FFMVSDDGGL TNYLTRSGDF      120

KLDAYGNFVN NAGFVVQGWN INWDDQTIDS SRTPQNIFID PGMHIPAAKS TEVAIKANLN      180

SGLNIGTSSR NLYALDSVHG WNTKTQRAED ENDTGTTQFY TTSKNSVEVT EKGVDAGSLF      240

NAKGQGLNLR DGQGIWVSYA DATYSTNKVG VNAFDPNLQQ NQTAAFWGTA NQKVNLDITL      300

NGVRIQNADI QSIDDAIAYI NTFTAPTDTR DGTGVKAVKN KDGSGIDFVN DNADGTTDNM      360

KNINLVVANT NTAGELWNAV WNNNNQTFTF NNNGNGQAGT PTINKNGSSL WTATNITFTP      420

QPPQAATNVQ LTGGLNAQII TAHKYIYSSN PVDIGPMYNP DGGPAFQPGA NATTRPTEPG      480

SAAYWDAVNG GLLNTNVRTF RTTEDLRELL QRDARYGVDY DGSGTFAAAD INQNIKVVVT      540

ADGHFAISNA NEQSTVPPNA INGVGNATTT DPKNMSFNIT AYSNKQGTVS TNDAFTAIFK      600

AFDGPLVIGN QIKESEQLKL SAFSAGLEIY DSLGSKHTLE VQFVKQSTTQ DGGNEWQMII      660

RVPEPAEINT TGEGPNNIIV GTARFNNDGS LASYTPRTIN FSPNNGAAPN QQIKLSFGTS      720

GSNDGLVSSN SASTLTGQAT DGYTSGNLKP DAIRVDDKGN ILGEFTNGKT FAVAKIAMAS      780

VANNSGLEEI GGNLFKVTAN SGNIVVGEAG TGGRGEMKTS ALEMSNVDLS RSLTELIIIQ      840

RGYQANSKTI STSDQMLQTL IQLKQ                                           865
```

-continued

SEQ ID NO: 21

```
MAKIRIHEIA KELGYDSKEI IEKANELGLG IKTASNAVEP EIAAAIYEYI QTREIPEAFK      60
KNIKTPTAKK PKKENIKEQE KLNESEKKEP KKEEKLKQEV KKEELKIEKE NAKEEEKQEI     120
IDAHKPQSLA SATLAKRRGL VIVKKKKDEE EIQVKKEEVK NSNDISINNE ERLSLKTMFS     180
NADESLKKKK KEKKSFVASK KESTEKMNFL DEHDFGDISL DDEDEVVLPD FSVKEQEKPQ     240
NINKKQPNFI RQAVGNSAGF GFEGGIQRRS RKKPSKKIEK KEVEEVGSVA ISKEIRVYEF     300
ADKIGKSTSE VISKLFMLGM MTTKNDFLDE DAIEILAAEF GIEINIINEA DEFDYVKDYE     360
EETDEKDLVT RAPVITIMGH VDHGKTSLLD YIRKSRVASG EAGGITQHVG AYMVEKNGRK     420
ITFIDTPGHE AFTAMRARGA SITDIVIIVV AADDGVKPQT KEAINHAKAA GVPIIIAINK     480
MDKEAANPDM VKTQLAEMEI MPVEWGGSYE FVGVSAKTGM GIEDLLEIVL LQADILELKA     540
NPKSFAKASI IESSVQKGRG AVATVIVQNG TLTVGSTVVA GEAYGKVRAM SDDQGKALKE     600
IKPGECGVIV GLSEVADAGE ILIAVKTDKE AREYANKRHE YNRQKELSKS TKVSIDELGA     660
KIKEGNLKAL PVILKADVQG SLEALKASLE KLRNDEIKVN IIHSGVGGIT QSDIELASAS     720
ENSIVLGFNI RPTGEVKERA KDKGVEIKTY NVIYNLLDDV KALLGGMMSP IISEEQLGQA     780
EIRQVINVPK IGQIAGCMVT EGVINRGAKI RLIRDGVVVY EGNVSSLKRF KDDAKEVAKG     840
YECGVGIEGC DDMRVGDYIE SYKEVEEQAS L                                 871
```

SEQ ID NO: 22

```
MLAPGMGEWV YKANLFLFGE FAYYYPFFLF ILNYVYYKRN YKLANFTRRE LFGIGFAFFS      60
SLLLFAVFYP NSGYILELAY AIFSTILGHT GSGIFALLLL LFSLVLLFPK FAKEILKIEL     120
DFTYLLKVEQ AFKSLLMRVF GGENEKEDVG KSEPIVPKLN ILQDSIYGNL QINKKGETNN     180
LEQIIKDSNI NASKNSITTA KENFEKLKNQ ILDETIEIDK QSLKESRSFV HEHSQQVRNF     240
AQKASKMSIS LDEDFNFISE EEVDMIPERF LKPKKLEDIK QIDTNKNLDE PSYKRKNIEI     300
PVSNQEVKPK IFTKELELRE NLIKKEKLEQ EYKAYQNEIL ENKVKQEIKK LEEYDAINSS     360
DIIEGNKYSF NSPKTIKTET EESDKINENK NLDKADNIFE FAPIVEELNH PYIEPTPIKN     420
INEIVIEEKN TLDFIQNTET KIDNEKTNDQ EIKLQKAVLA KEIAINQALL REIEQGEIEK     480
PKDFTLPPLD FLANPKEHKQ EINESEIDKK IYNLLEKLRR FKIGGDVIST YVGPVVTTFE     540
FRPSADVKVS RILNLQDDLT MALMAKSIRI QAPIPGKDVV GIEVPNDEIQ TIYLREILQS     600
EVFKNAKSPL TIALGKDIVG NAFVTDLKKL PHLLIAGTTG SGKSVGINSM LLSLLYRNSP     660
KTLRLMMIDP KMLEFSIYND IPHLLTPVIT DPKKAVNALS NMVAEMERRY RLMADAKTKN     720
IENYNEKMKE LGGEKLPFIV VIIDELADLM MTAGKDVEFY IGRLAQMARA SGIHLIVATQ     780
RPSVDVVTGL IKANLPSRIS YKVGQKIDSK VILDAMGAES LLGRGDCLFT PPGTSSIVRL     840
HAPFASEFEI EKIVDFLKDQ QSVEYDESFL KDQQSVGVTT NESFDGEADE LYEEAKRVIL     900
EDGKTSISYL QRRLKIGYNR SANIIEQLTQ NGILSEPDAK GQREIL                 946
```

SEQ ID NO: 23

```
MKKFFCLTLV CKLFALSEFE LHHIDKVHKL GYSGDTIIIG VADDAFNQDH ISLKDKILKS      60
TYPTDTAGKQ LIPDLKKSTH GSHVAGIAVG AKIGDSKPYG VAYGAKFYGA GVFPNGSYTQ     120
IPDIYNFFKD VSIINNSWGI NFYPYFNLKA SNSGLVDCTQ TNQGTSYNIC NTPLEYVMKA     180
DKVANDMMRL SKDKGVLNVF AAGNEGILSP ALHAILPSYD ESLRAWLAVG ALDANEITLE     240
SDGTLIIKSQ GLADFSNGFK GATNFSLVAA GVNINNVDSS TNDKFTKKSG TSMAAPMVSG     300
TAALVKQNFP FLDGKQIADI LLSTANKNYK APKFTVKQVT DGTNQPKFLI VYISQDPPGI     360
EDEIKRDLKQ LYNGIQVQVN GQWIDYSDYI WDNRDSAQSQ KLNTSTISSI NGVVRVEKEE     420
LFGQGILDAQ KALKGLSILD ANRLSDQDVL KYEQEPNTAY YTINTAGYDA EFSNDISQRK     480
```

-continued

```
WDESTHLSSA INKPTHLANL NIGLSKEGEG ILIISGQNTY EGATLIKQGE LKLKGKVKNN      540

AYVEQKAILS GNGIVGQNLN NKGIVRPGNE DLNDLTVQGT YTQEGVDSKL QLDFGNYKNS      600

KLIAKTYDIK SGNLEYIPLP KYYILNKPVK INLGDLEKSL SSFNHVLIQN TYALNFDFVL      660

SDDLVSINKT LIKPNLKPNA YEIPNTSLGN ALRQLRSRAD LSQTYQEFFA SLDNGIDVKT      720

KLNRIEGSGY LSTFSNHNQS NLMQNNMLFT LHPLNINNFA QNNNILLAST YLPRIFSNEE      780

YFWHLTPSYK YYKDKDFSGQ KTGANISLGE NFSSGFLAYA LSLSSAKFNF NNGSDLKSYN      840

MDLLLNYNHD LDFIKILSGL GIGVGFNTLN RFVVEQPIEG KYKTLQTSAQ LGVTKDIILG      900

QDFIFNPLMY FTHSFFYQED FKENKSPFAK NYESLKHHSI NANLGFNLAK NIEQDDYQAS      960

FSTFVIFEKR IYGRTLENKA SFVDFPIAFI QKYKLKDNIL SQGFNSEFLY KNNVFWQFML     1020

MNRFSHNAYE LHLMSSVGKR F                                               1041

                                                          SEQ ID NO: 24
MPKRTDIKSI LLIGSGPIVI GQACEFDYSG TQAAKTLKEL GYRVVLINSN PATIMTDPEF       60

ADATYIEPIT KESILSIIKK EKIDAILPTM GGQVALNVAM EVYESGLLGD VKFLGANPEA      120

IKKGEDRQVF KECMKKIGMD LPKSMYAYNY DEALKAVDEI DFPLMIRASY TLGGAGSGVV      180

YNMDEFKELT NTALALSPIH EILIEESLLG WKEYEMEVIR DRADNCIIVC SIENIDPMGV      240

HTGDSITIAP ALTLTDKEYQ VMRNASFAIL REIGVDTGGS NVQFAINPKN GRMIVIEMNP      300

RVSRSSALAS KATGYPIAKV ATLLAVGFSL DEIKNDITGT PASFEPVIDY IVTKIPRFTF      360

EKFPGANTTL GTAMKSVGEV MAIGRTFKES IQKALCSLER SLSGFDRVKF EDRNDLVFKI      420

RNANEKRLLY VAQAFREGFS VEELYELCKI DPWFLTQIKE IVDFEEQIDM DILNNKALLR      480

KAKTMGFSDK MIALLVNLKD NLELSQNDIY YVRMKQKIIA EFSEVDTCAG EFEALTPYLY      540

SSINVSELTQ SKNDAKDKKE KKVMIIGGGP NRIGQGIEFD YACVHASFAL KDMGIKTIMY      600

NCNPETVSTD YDTSDILYFE PIDFEHLRAV IEREKPDGVI VHFGGQTPLK FAKRLSAFGA      660

KIIGTSARVI DMAEDRKKFA EFITKLGINQ PKNSTATSVE EAVLKASDIG YPVLVRPSYV      720

LGGRAMRVVN DEAELRLYMQ EAVDVSDKSP VLIDQFLDNA TEIDVDAICD GKDVYVAGIM      780

EHIEEAGIHS GDSACSLPPC NIDEKMQEFI AQKTADIALN LGVVGLLNIQ FALHNNELYM      840

IEVNPRASRT IPFVSKATGI PLAKVATRVM WQGNLKEALK FYDTFKVVNF DTKILRPKTP      900

KYMSVKEAVF PFAKLSGSDL ELGPEMRSTG EVMGISKDFA NSYAKSQIAS FNHLPEQGVV      960

FISLKDKDKK YTKKIAAEYV KLGFKLMATG GTCKEILESG FECELVHKIS EGRPNVEDKL     1020

KNGEIHLVIN TSDSHSFKGD TKKIRENIIR FKIPYFTNLR SALAGAKSIK AIQSKSCLDV     1080

KSLQEWLKS                                                             1089

                                                          SEQ ID NO: 25
MKNITLTKIP IGEGKEPCLN SKKIVLSLAT ISFLASCANA KLNSEIKTYD EVNKNVKTRS       60

ASVYSPQAKI NTTINSLHNQ QVTITGNGTS NSLTIGSSGT LGSIGNTGKI IYAHANGSNT      120

LTLANLTNNR TINGKIGIEN NGNFTGTIAV NTFENTGQIN GQIYMGIWGN NSGTLNIDKF      180

DNSGTIIDNN KGVFEGKNTN IQTFNNSGFI SANKGVDIGN IGTIKNFNNN GTIQGSEVGV      240

AINTKIDTFT NNGFINSPGS GQWNNGIWIS SNATIEKLVN NGTIKGGHSA IMVTSQHIKT      300

VENTGIIHAE GEWGSSILLE YGGFIEHIIN TGTISNNNVG IGSAYGVFGT LTIKDGGMVY      360

GKYSAIGVGR SQTLGDLYID GRSNNGTVSG IYSEEHGILL ENNSRTQKIE LKNGGIIKGN      420

IDGIRLINSA SLSGEMILSG EGSRVEGGRG VGILNRSGKI EGSIKVEDGA TVTATSNRAI      480

ANSGSGSITG GITVSGKNTK LEGNIINTGN ASIGSDIKIE GGAKVEGGLV NQGNGSISGS      540

VQVSGGSSID SITNEGNGAI SGSITVYKDS KLDSITNTST SSTGISGSIT NNSDNKLEIS      600
```

-continued

```
NSGNIGGKIE STGSADMVIS NSNGGTISGG ISSSGSGSTS ISNSQGSTIN NGITVSGSAQ      660

VEISNQGSVG KDENGNTVTN NGSGSVGIKD WLVSTDKNTG KLNTVVIGGS RAFNVKVENI      720

TVDQSNVDLE ELNDINNIIS GVNQNNIGNI GTNGSGEISL SFDPITGKLT TDFNLNASIS      780

GATFRSLIST TSRRSTFIDN VMGNSMQSFA LASSSKSQSI AMSEKGNLYA DASDYIKSDL      840

NNGSYGSNKE HSLFILPYTS SQNVELSLNE ESKGHTKGTI IGYSTLKDSG IYGVYAGYED      900

TKMGSTYFDI NNRTYYAGLK YFNTLFTTEK GQEVYIKAQG KAALIKNDLT EKIGNNEAKA      960

EPNSYAYGVN TALGMNFISN KDIFSPEIGL AYEGGYTEAF SMKDTIGQAT VKGGERTYAN     1020

YLNLFSTKTS LTWFRDWLPN LKTSVELGAK FNINPKVEAE ARFGNIKVSD EFDLPRVQKF     1080

VSTSFIVPVN EAFYFSLNYN GMFDKDGNTH TGFAQFNYLW                           1120

                                                               SEQ ID NO: 26
MNKTALTKTY TKDIQNSCLN SKKIVLSLAT ISFLASCTHA TLTPEIKTYE ETNRHAKARS       60

GLQSRNSNNE TINNLQTLTK TISDTGNTLV IESSGTITIS NDGQQAVNFQ PNSSTSTFLN      120

KGTLIGGNNT ASVQLGAANG NNGVSIETFN NQGIIGNGSS KFGVTVFGGG SKDNPKSIIN      180

NFSNSGTIHS NTGESIYFGN AKISSFVNSG TIKSKQGAGV NISQGTSIEN FNNTGTGIIE      240

GKRMGVNVRS TINTFVNDGL IAATNDGIQI NANVKTLINK GTIKGDAISI RSLGGTIETL      300

TNEGIMYGKS AGIYMNRSLV KTLTNSGTIN QNNSATWSAG IKLENGSIIE NIINTGSIRS      360

NAFGISVTGG KFGTLTIKDG GMVYGKYSAI GVGRSQTLGD LYIDGRSNNG TVSGIYSEEH      420

GILLENNSRT QKIELKNGGI IKGNIDGIRL INSASLSGEM ILSGEGSRVE GGRGVGILNR      480

SGKIEGSIKV EDGATVTATS NRAIANSGSG SITGGITVSG KNTKLEGNII NTGNASIGSD      540

IKIEGGAKVE GGLVNQGNGS ISGSVQVSGG SSIDSITNEG NGAISGSITV YKDSKLDSIT      600

NTSTSSTGIS GSITNNSDNK LEISNSGNIG GKIESTGSAD MVISNSNGGT ISGGISSSGS      660

GSTSISNSQG STINNGITVS GSAQVEISNQ GSVGKDENGN TVTNNGSGSV GIKDWLVSTD      720

KNTGKLNTVV IGGSRAFNVK VENITVDQSN VDLEELNDIN NIISGVNQNN IGNIGTNGSG      780

EISLSFDPIT GKLTTDFNLN ASISGATFRS LISTTSRRST FIDNVMGNSM QSFALASSSK      840

SQSIAMSEKG NLYADASDYI KSDLNNGSYG SNKEHSLFIL PYTSSQNVEL SLNEESKGHT      900

KGTIIGYSTL KDSGIYGVYA GYEDTKMGST YFDINNRTYY AGLKYFNTLF TTEKGQEVYI      960

KAQGKAALIK NDLTEKIGNN EAKAEPNSYA YGVNTALGMN FISNKDIFSP EIGLAYEGGY     1020

TEAFSMKDTI GQATVKGGER TYANYLNLFS TKTSLTWFRD WLPNLKTSVE LGAKFNINPK     1080

VEAEARFGNI KVSDEFDLPR VQKFVSTSFI VPVNEAFYFS LNYNGMFDKD GNTHTGFAQF     1140

NYLW                                                                  1144

                                                               SEQ ID NO: 27
MGKIMKTMDG NEAAAYAAYA FTEVAGIYPI TPSSPMADYT DMWAAAGKKN LFGVPVKIVE       60

MQSEAGAAGS VHGSLQAGAL TTTYTASQGL LLKIPNMYKI AGQLLPCVIH VAARSLAAQA      120

LSIFGDHQDI YAARQIGFAM LCSHSVQETM DLAGVAHLAA IKGRVPFLHF FDGFRTSHEI      180

QKVEVMDYAH FDRLLDREAL LEFRNNALNP ENPKTRGTAQ NDDIYFQTRE VSNRFYDALP      240

DVVNEYMQEI SKITGREYKP FTYYGHKEPE CVIVAMGSVT QALEEVVDYL NAKGEKVGIL      300

KVYLYRPFSL KYFFDVMPKS VKKIAVLDRT KEPGSLGEPL YLDVKSAFYG RENAPVIVGG      360

RYGLSSKDVD PAQMIAVFEN LKLDNPKDGF TVGIIDDVTH TSLSTGEKIS LGDESTIECL      420

FYGLGADGTV GANKNSIKII GDKTDFYAQA YFAYDSKKSG GYTRSHLRFS KKPIRSTYLV      480

STPHFIACSV AAYLEIYDVL AGIRKGGTFL LNSIWNAEET IRQLPDAVKK TLAEKEVNFY      540

IINATKLARD IGLGNRTNTI MQSAFFKLAK IIPYEDAQKY MKELAYKSYS KKGDAIVEMN      600

YKAIDVGADG LVKVEVDPNW KNLELKEKEQ TNAYKGTEFV EKIVKPMNAA KGDDLPVSAF      660
```

-continued

```
LGYEDGSFEH GTTEYEKRGV GVMVPRWIEA NCIQCNQCAS VCPHAVIRPF LINDEEMANA   720

PRGVKDHALE AKGTKGEKLS FKIQVSPLDC TGCELCVHEC PTKEKSLVMV PLQEEMDFGE   780

QENADYLFKE ITYKDDILNK ETTKGAQFAQ PLFEFHGACP GCGETPYITL ITRLFGERMI   840

VANATGCSSI YGGSAPSTPY RKSVKNGHGP AWGNSLFEDN AEFGLGMKIA TENTRHRIEH   900

IMNESMQEVP NALSALFKDW IANKDNGAMS VEIKDKMIPI LEQNKNIKAV QDILELKQYL   960

SKKSHWIFGG DGWAYDIGYG GLDHVLASGE NVNILVLDTE VYSNTGGQSS KSSRTGAVAQ  1020

FAAAGKPIQK KDLGQIAMTY GYIFVAQVNS TANYTHLIKA ITAAEAYDGP SLVICYSPCI  1080

AHGIKGGLGY SGEQGELATK CGYWPLYTFD PRLEEQGKNP LTLTGKEPDW DLYEQFLMNE  1140

VRYNSLKKAN PEHAAELFER NKKDAQRRYR QLKRIAMADY SNEVES                 1186
```

SEQ ID NO: 28

```
MCDMLDNKLG NRLRVDFSNI SKQIEIPNLL QLQKKSFDYF LNLDNGESGI EKVFKSIFPI    60

HDPQNRLSLE YVSSEIGKPK YTIRECMERG LTYSVNLKMK IRLTLHEKDE KTGEKVGVKD   120

IKEQEIYIRE IPLMTDRVSF IINGVERVVV NQLHRSPGVI FKEEESSTVA NKLVYTAQII   180

PDRGSWLYFE YDAKDVLYVR INKRRKVPVT MLFRALGYKK QDIIKLFYPI QTIHVKKDKF   240

LTEFNPNDFM DRIEYDIKDE KGKIVHQAGK RLTKKKAEQL IKDGLKWIEY PVEILLNRYL   300

ANPIIDKESG EVLFDSLTLL DESKLAKIKE QKSFDIANDL ANGVDAAIIN SFAQDGETLK   360

LLKQSENIDD ENDLAAIRIY KVMRPGEPVV KDAAKAFVND LFFNPERYDL TKVGRMKMNH   420

KLGLEVPEYV TVLTNEDIIK TAKYLIKVKN GKGHIDDRDH LGNRRIRSIG ELLANELHLG   480

LAKMQKAIRD KFTSLNADLD KVMPYDLINP KMITTTIIEF FTGGQLSQFM DQTNPLSEVT   540

HKRRLSALGE GGLVKERAGF EVRDVHATHY GRICPVETPE GQNIGLINTL STYAKVNELG   600

FVEAPYRKVV NGKVTNEVVY LTATQEEGLF IAPASTKVDA KGNIVEEFVE ARQDGETILA   660

RREEVQLIDL CSGMVVGVAA SLIPFLEHDD ANRALMGSNM QRQAVPLLTA SAPIVGTGME   720

QIIARDAWEA VKAKRGGVVE KVDNKSIFIL GEDDKGPFID HYTMEKNLRT NQNTNYIQHP   780

IVKKGDIVKA GQIIADGPSM DQGELAIGKN ALIAFMPWNG YNYEDAIVVS ERIIREDTFT   840

SVHIYEKEIE ARELKDGIEE ITKDIPNVKE EDVAHLDESG IAKIGTHIKP GMILVGKVSP   900

KGEVKPTPEE RLLRAIFGEK AGHVVNKSLY ATASLEGVVV DVKIFTKKGY EKDDRAIKSY   960

DKEKMALEKE HHDRLLMMDR EEMLRVCALL SKASLNSDQK IGDKNYKKGQ TADISELEKI  1020

NRFTLTTLIK AYSKEIQKEY DDLKNHFQNE KKKLKAEHDE KLEILEKDDI LPSGVIKLVK  1080

VYIATKRKLK VGDKMAGRHG NKGIVSTIVP EVDMPYLPNG KSVDIALNPL GVPSRMNIGQ  1140

ILESHLGLVG LRLGDQIQEI FDRKQKDFLK ELRAKILEIC SIPRLANEKE FIKSLSDEEL  1200

LNYARDWSKG VKFSTPVFEG VNIEEFSKLF KMAKIDMDGK TELYDGRTGE KIAERVHVGC  1260

MYMLKLHHLV DEKVHARSTG PYSLVTQQPV GGKALFGGQR FGEMEVWALE AYGAAHTLRE  1320

MLTIKSDDVE GRFSAYKALT KGENVPATGI PETFFVLTNE LKSLALDVEI FDKDEDNE    1378
```

SEQ ID NO: 29

```
MDLENILENN QSIGLYHPKN EHDACGIAAV ANIRGIASYK VICDALEILM NLEHRGGTGA    60

EENSGDGAGI LIQIPHDFFK TQELGFELPK KGDYAVAQMF LSPNTDAKEE AKEIFLQGLK   120

DKKLEFLGFR EVPFNPSDIG ASALKAMPYF LQAFVKKPSK ISAGLEFERV LYSTRRLIEK   180

RAINVPKFYF SSFSSRTIVY KGMLLSTQLS DFYLDFKDVN MKSAIALVHS RFSTNTFPSW   240

ERAHPNRYMV HNGEINTIRG NVDSIRAREG LMQSEYFENL DEIFPIIAKL SSDSAMFDNT   300

LEFLALNGRT LEEAFMMMVP EPWHKNENME SKKRAFYEYH SLLMEPWDGP AAIVFTDGVI   360

MGASLDRNGF RPSRYYLTKD DMLILSSETG ALKLDEKNIK AKKRLEPGKL LLVDTARGRV   420
```

-continued

```
IADNEIKEHY ANAKPYKKWL KNLVELEKQK SGVYKHQFLK EDEVLKLQKA FGWSYDELKM     480

SVAAMAQNGK EAIAAMGVDT PLAILSKTYQ PLYNYFKQLF AQVTNPPLDA IREEIVTSTR     540

IYLGSEGNLL KPDENNAKRV KIALPVISNE ELFEVKALNK FQVKEFSILY DYSKKTLEKA     600

LDELCVKIED EVKKGVSIII LSDKGVDEKN AYIPALLAVS GVHNHLVRKN LRTHTSLIIE     660

SGEPREIHHF ACLLGYGATV INPYLVYESI QKLIANKDLN LSYEKAVENF IKASSSGIVK     720

IASKMGVSTL QSYNGSALFE CLGLSSKVID KYFTSTTSRI EGMDLEDFEK ELIALHKHAF     780

NDTHKALDSK GIHGFRSAKE EHLIDPLVIF NLQQACRNKD YKSFKKYSAL VDEKQVNLRS     840

LMEFDFSEAI SIDKVESVES IVKRFRTGAM SYGSISKEAH ECLAQAMNKI GAKSNSGEGG     900

EDEERYEIKE GVDKNSAIKQ VASGRFGVDL NYLSHAKEIQ IKVAQGAKPG EGGQLMGFKV     960

YPWIAKARHS TAGVTLISPP PHHDIYSIED LAQLIYDLKH ANKDAKISVK LVSENGIGTV    1020

AAGVAKAGAN LILVSGYDGG TGASPRTSIP HAGIPWELGL AETHQTLILN KLRDRVRLET    1080

DGKLMNGRDL AIAALLGAEE FGFATAPLIV LGCTMMRVCH LNTCPFGIAT QDTELRDRFK    1140

GKVDDVINFM YFIAEELREY MARLGFERLD DMIGRVDKLR QKSVQGKAGK LNLDKILKSL    1200

PTYNRTAVHF KDYKDNKLEK TIDYRILLPL CKNAVEKKEP IKLSLEVGNQ SRTFATMLSS    1260

EILKTYGKDA LDEDSIHIKA IGNAGNSFGA FLLKGIKLEI IGDSNDYLGK GLSGGKIIAK    1320

ISNEATFSPE ENIIAGNACL YGATKGEVYL DGIAGERFCV RNSGALAVVL GTGVHGCEYM    1380

TGGQVVVLGD VGANFAAGMS GGVVYIFGRH NEAHVNTELV DIKDLNAKDE KELKAVIEKH    1440

ITYTDSKKAK DILEKFDKKD FFKVMPRDYE KMLKMLDLCK NEKDPNLAAF LKITQK        1496

                                                          SEQ ID NO: 30
MSKFKVIEIK EDARPRDFEA FQLRLASPEK IKSWSYGEVK KPETINYRTL KPERDGLFCA      60

KIFGPIRDYE CLCGKYKKMR FKGVKCEKCG VEVANSKVRR SRMGHIELVT PVAHIWYVNS     120

LPSRIGTLLG VKMKDLERVL YYEAYIVENP GDAFYDNEST KKVEYCDVLN EEQYQNLMQR     180

YENSGFKARM GGEVVRDLLA NLDLVALLNQ LKEEMGATNS EAKKKTIIKR LKVVENFLNS     240

NLNANTDSDE AVPNRPEWMM ITNLPVLPPD LRPLVALDGG KFAVSDVNDL YRRVINRNTR     300

LKKLMELDAP EIIIRNEKRM LQEAVDALFD NGRRANAVKG ANKRPLKSLS EIIKGKQGRF     360

RQNLLGKRVD FSGRSVIVVG PKLRMDQCGL PKKMALELFK PHLLAKLEEK GYATTVKQAK     420

KMIENKTNEV WECLEEVVKG HPVMLNRAPT LHKLSIQAFH PVLVEGKAIQ LHPLVCAAFN     480

ADFDGDQMAV HVPLSQEAIA ECKVLMLSSM NILLPASGKS VTVPSQDMVL GIYYLSLEKA     540

GAKGSHKICT GIDEVMMALE SKCLDIHASI QTMVDGRKIT TTAGRLIVKS ILPDFVPENS     600

WNKVLKKKDI AALVDYVYKQ GGLEITASFL DRLKNLGFEY ATKAGISISI ADIIVPNDKQ     660

KAIDEAKKQV REIQNSYNLG LITSGERYNK IIDIWKSTNN VLSKEMMKLV EKDKEGFNSI     720

YMMADSGARG SAAQISQLAA MRGLMTKPDG SIIETPIISN FREGLNVLEY FISTHGARKG     780

LADTALKTAN AGYLTRKLID VAQNVKITIE DCGTHEGVEI NEITADSSII ETLEERILGR     840

VLAEDVIDPI TNSVLFAEGT LMDEEKAKIL GESGIKSVNI RTPITCKAKK GICAKCYGIN     900

LGEGKLVKPG EAVGIISAQS IGEPGTQLTL RTFHSGGTAS TDLQDRQVSA QKEGFIRFYN     960

LKTYKNKEGK NIVANRRNAA VLLVEPKIKT PFKGVINIEN IHEDVIVSIK DKKQEVKYIL    1020

RKYDLAKPNE LAGVSGSIDG KLYLPYQSGM QVEENESIVE VIKEGWNVPN RIPFASEILV    1080

EDGEPVVQNI KAGEKGTLKF YILKGDGLDR VKNVKKGDIV KEKGFFVVIA DENDREAKRH    1140

YIPRESKIEF NDSEKIDDAN TIIASAPKKE RKVIAEWDAY NNTIIAEIDG VVSFEDIEAG    1200

YSADEQIDEA TGKRSLVINE YLPSGVRPTL VIAGKGDKAV RYHLEPKTVI FVHDGDKIAQ    1260

ADILAKTPKA AAKSKDITGG LPRVSELFEA RKPKNAAVIA EIDGVVRFDK PLRSKERIII    1320
```

-continued

```
QAEDGTSAEY LIDKSKHIQV RDGEFIHAGE KLTDGVVSSH DVLKILGEKA LHYYLISEIQ     1380

QVYRGQGVVI SDKHIEVIVS QMLRQVKVVD SGHTKFIEGD LVSRRKFREE NERIIRMGGE     1440

PAIAEPVLLG VTRAAIGSDS VISAASFQET TKVLTEASIA GKFDYLEDLK ENVILGRMIP     1500

VGTGLYGEQN LKLKEQE                                                    1517
```

LIST OF REFERENCES CITED IN APPLICATION

Angel et al., Cell, 49:729, 1987b.
Angel et al., Mol. Cell. Biol., 7:2256, 1987a.
Arap et al., Cancer Res., 55:1351-1354, 1995.
Atchison and Perry, Cell, 46:253, 1986.
Atchison and Perry, Cell, 48:121, 1987.
Ausubel, ed., Current protocols in molecular biology, New York, John Wiley & Sons, 1996.
Banerji et al., Cell, 27:299, 1981.
Banerji et al., Cell, 35:729, 1983.
Berkhout et al., Cell, 59:273, 1989.
Blanar et al, EMBO J, 8:1139, 1989.
Bodine and Ley, EMBO J, 6:2997, 1987.
Boshart et al., Cell, 41:521, 1985.
Bosze et al., EMBO J, 5:1615, 1986.
Braddock et al., Cell, 58:269, 1989.
Bulla et al., J. Virol., 62:1437, 1986.
Campbell et al., Mol. Cell. Biol., 8:1993, 1988.
Campo et al., Nature, 303:77, 1983.
Carbonelli et al. FEMS Microbiol Lett. 177(1):75-82, 1999.
Celander and Haseltine, J. Virology, 61:269, 1987.
Celander et al., J Virology, 62:1314, 1988.
Chandler et al., Cell, 33:489, 1983.
Chang et al., Mol. Cell. Biol., 9:2153, 1989.
Chatterjee et al, Proc. Nat'l Acad. Sci. USA., 86:9114, 1989.
Chen and Okayama, Mol. Cell. Biol., 7:2745-2752, 1987.
Choi et al., Cell, 53:519, 1988.
Cohen et al, J. Cell. Physiol, 5:75, 1987.
Costa et al, Mol. Cell. Biol., 8:81, 1988.
Cripe et al., EMBO J, 6:3745, 1987.
Culotta and Hamer, Mol. Cell. Biol., 9:1376, 1989.
Dandolo et al., J. Virology, 47:55, 1983.
De Villiers et al., Nature, 312:242, 1984.
Deschamps et al., Science, 230:1174, 1985.
Edbrooke et al., Mol. Cell. Biol., 9:1908, 1989.
Edlund et al., Science, 230:912, 1985.
Feng et al., Nature, 334:6178, 1988.
Firak and Subramanian, Mol. Cell. Biol., 6:3667, 1986.
Foecking and Hofstetter, Gene, 45(1):101-5, 1986.
Fraley et al., Proc. Nat'l Acad. Sci. USA, 76:3348-3352, 1979.
Fujita et al., Cell, 49:357, 1987.
Gilles et al., Cell, 33:717, 1983.
Gloss et al., EMBO J, 6:3735, 1987.
Godbout et al., Mol. Cell. Biol., 8:1169, 1988.
Goodbourn et al., Proc. Nat'l Acad. Sci. USA, 85:1447, 1988.
Goodbourn et al., Cell, 45:601, 1986.
Greene et al., Immunology Today, 10:272, 1989.
Grosschedl et al., Cell, 41:885, 1985.
Haslinger and Karin, Proc. Nat'l Acad. Sci. USA., 82:8572, 1985.
Hauber and Cullen, J. Virology, 62:673, 1988.
Hen et al., Nature, 321:249, 1986.
Hensel et al., Lymphokine Res., 8:347, 1989.
Herr et al., Cell, 45:461, 1986.
Hirochika et al., J. Virol., 61:2599, 1987.
Hirsch et al., Mol. Cell. Biol., 10: 1959, 1990.
Holbrook et al., Virology, 157:211, 1987.
Horlick and Benfield, Mol. Cell. Biol., 9:2396, 1989.
Huang et al., Cell, 27:245, 1981.
Hug et al., Mol Cell Biol., 8:3065, 1988.
Hwang et al., Mol. Cell. Biol., 10:585, 1990.
Imagawa et al., Cell, 51:251, 1987.
Imbra and Karin, Nature, 323:555, 1986.
Imperiale and Nevins, Mol. Cell. Biol., 4:875, 1984.
Innis et al., Proc Natl Acad Sci USA. 85(24):9436-9440, 1988.
Inouye et al., Nucleic Acids Res., 13:3101-3109, 1985.
Jakobovits et al., Mol. Cell. Biol., 8:2555, 1988.
Jameel and Siddiqui, Mol. Cell. Biol., 6:710, 1986.
Jaynes et al, Mol. Cell. Biol., 8:62, 1988.
Johnson et al., Mol. Cell. Biol., 9:3393, 1989.
Kadesch et al., Mol. Cell. Biol., 6:2593, 1986.
Kaeppler et al., Plant Cell Reports 9: 415-418, 1990.
Kaneda et al., Science, 243:375-378, 1989.
Karin et al., Mol. Cell. Biol., 7:606, 1987.
Katinka et al., Cell, 20:393, 1980.
Katinka et al., Nature, 290:720, 1981.
Kato et al, J. Biol. Chem., 266:3361-3364, 1991.
Kawamoto et al., Mol. Cell. Biol., 8:267, 1988.
Kiledjian et al., Mol. Cell. Biol., 8:145, 1988.
Klamut et al., Mol. Cell. Biol., 10:193, 1990.
Koch et al., Mol. Cell. Biol., 9:303, 1989.
Kriegler et al, In: Eukaryotic Viral Vectors, Y. Gluzman, ed., Cold Spring Harbor: Cold Spring Harbor Laboratory, NY, 1982.
Kriegler and Botchan, Mol. Cell. Biol., 3:325, 1983.
Kriegler et al., Cell, 38:483, 1984a. Kriegler et al., Cell, 53:45, 1988.
Kriegler et al., In: Cancer Cells 2/Oncogenes and Viral Genes, Van de Woude et al. eds, Cold Spring Harbor, Cold Spring Harbor Laboratory, 1984b.
Kriegler et al., In: Gene Expression, D. Hamer and M. Rosenberg, eds., New York: Alan R. Liss, 1983.
Kuhl et al., Cell, 50:1057, 1987.
Kunz et al., Nucl. Acids Res., 17:1121, 1989.
Larsen et al., Proc. Nat'l Acad. Sci. USA., 83:8283, 1986.
Latimer et al., Mol. Cell. Biol., 10:760, 1990.
Lee et al., Nature, 294:228, 1981.
Lee et al., Nucleic Acids Res., 12:4191-206, 1984.
Levenson et al., Hum Gene Ther. 20; 9(8):1233-1236, 1998.
Levinson et al., Nature, 295:79, 1982.
Lin et al., Mol. Cell. Biol., 10:850, 1990.
Luria et al, EMBO J., 6:3307, 1987.
Lusky et al., Proc. Nat'l Acad. Sci. USA., 83:3609, 1986.
Lusky et al., Mol. Cell. Biol., 3:1108, 1983.
Majors and Vannus, Proc. Nat'l Acad. Sci. USA., 80:5866, 1983.
McNeall et al., Gene, 76:81, 1989.
Miksicek et al., Cell, 46:203, 1986.
Mordacq and Linzer, Genes and Dev., 3:760, 1989.
Moreau et al., Nucl. Acids Res., 9:6047, 1981.
Muesing et al., Cell, 48:691, 1987.
Ng et al, Nuc. Acids Res., 17:601, 1989.
Nicolau et al., Methods Enzymol., 149:157-176, 1987.

Omirulleh et al., Plant Mol. Biol., 21:415-28, 1993.
Ondek et al., EMBO J., 6:1017, 1987
Ornitz et al., Mol. Cell. Biol., 7:3466, 1987.
Palmiter et al., Nature, 300:611, 1982.
Pech et al., Mol. Cell. Biol., 9:396, 1989.
Perez-Stable and Constantini, Mol. Cell. Biol., 10:1116, 1990.
Picard and Schaffner, Nature, 307:83, 1984.
Pietras et al., Oncogene, 17(17):2235-49, 1998.
Pinkert et al., Genes and Dev., 1:268, 1987.
Ponta et al., Proc. Nat'l Acad. Sci. USA., 82:1020, 1985.
Porton et al., Mol. Cell. Biol., 10:1076, 1990.
Potrykus et al., Mol. Gen. Genet., 199:183-188, 1985.
Queen et al., Cell, 35:741, 1983.
Quinn et al., Mol. Cell. Biol., 9:4713, 1989.
Redondo et al., Science, 247:1225, 1990.
Reisman and Rotter, Mol. Cell. Biol., 9:3571, 1989.
Resendez Jr. et al., Mol. Cell. Biol., 8:4579, 1988.
Ripe et al., Mol. Cell. Biol., 9:2224, 1989.
Rippe et al., Mol. Cell. Biol., 10:689-695, 1990.
Rittling et al., Nucl. Acids Res., 17:1619, 1989.
Roselli et al., In Vivo 1993; 7:615-21, 1993.
Rosen et al., Cell, 41:813, 1988.
Sakai et al., Genes and Dev., 2:1144, 1988.
Sambrook et al., In: Molecular Cloning: A Laboratory Manual, 2nd Ed., Cold Spring Harbor Press, Cold Spring Harbor, N. Y., 1989.
Satake et al., J. Virology, 62:970, 1988.
Schaffner et al., J. Mol. Biol., 201:81, 1988.
Searle et al, Mol. Cell. Biol., 5:1480, 1985.
Sharp et al., Cell, 59:229, 1989.
Shaul et al, EMBO J, 6:1913, 1987.
Sherman et al., Mol. Cell. Biol., 9:50, 1989.
Sleigh et al., J. EMBO, 4:3831, 1985.
Spalholz et al., Cell, 42:183, 1985.
Spandau and Lee, J. Virology, 62:427, 1988.
Spandidos and Wilkie, EMBO J., 2:1193, 1983.
Stephens et al, Biochem. J, 248:1, 1987.
Stuart et al., Nature, 317:828, 1985.
Sullivan and Peterlin, Mol. Cell. Biol., 7:3315, 1987.
Swartzendruber and Lehman, J. Cell. Physiology, 85:179, 1975.
Takebe et al., Mol. Cell. Biol., 8:466, 1988.
Tavernier et al., Nature, 301:634, 1983.
Taylor et al., Mol. Cell. Biol., 10:165, 1990a.
Taylor et al., Mol. Cell. Biol., 10:176, 1990b.
Taylor et al., J. Biol. Chem., 264:15160, 1989.
Thiesen et al., J. Virology, 62:614, 1988.
Triesman, Cell, 46:567-74, 1986.
Toiler et al., Mol. Cell. Biol., 7:2558, 1987.
Tranche et al., Mol. Biol. Med., 7:173, 1990.
Tranche et al., Mol. Cell. Biol., 9:4759, 1989.
Tyndell et al., Nuc. Acids. Res., 9:6231, 1981.
Vannice and Levinson, J. Virology, 62:1305, 1988.
Vasseur et al., Proc. Nat'l Acad. Sci. USA., 77:1068, 1980.
Wang and Calame, Cell, 47:241, 1986.
Weber et al., Cell, 36:983, 1984.
Weinberger et al. Mol. Cell. Biol., 8:988, 1984.
Winoto and Baltimore, Cell, 59:649, 1989.
Wong et al., Gene, 10:87-94, 1980.
Yutzey et al. Mol. Cell. Biol., 9:1397, 1989.

The invention claimed is:

1. A polypeptide which is fused or conjugated to an immunogenic carrier molecule, wherein said polypeptide comprises:

a) an amino acid sequence selected from the group consisting of any one of SEQ ID NOs: 1-4, 6-11, 13-16, 18, 21-28, and 30, or b) an amino acid sequence consisting of at least 35 contiguous amino acid residues from any one of SEQ ID NOs: 1-4, 6-11, 13-16, 18, 21-28, and 30, or c) an amino acid sequence having a sequence identity of at least 60% with the amino acid sequence of any one of SEQ ID NOs: 1-4, 6-11, 13-16, 18, 21-28, and 30, or d) an amino acid sequence having a sequence identity of at least 60% with the amino acid sequence of at least 35 contiguous amino acid residues from any one of SEQ ID NOs: 1-4, 6-11, 13-16, 18, 21-28, and 30, said polypeptide being antigenic in a mammal.

2. The polypeptide according to claim 1, wherein the at least 35 contiguous amino acid residues have, as their N-terminal amino acid residue, amino acid residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47 in any one of SEQ ID NOs: 1-4, 6-11, 13-16, 18, 21-28 and 30.

3. The polypeptide according to claim 1, wherein the at least 35 contiguous amino acid residues have, as their N-terminal amino acid residue, amino acid residue 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, and 243 in any one of SEQ ID NOs: 1-4, 6-11, 13-16, 18, 21-28 and 30.

4. The polypeptide according to claim 1, wherein the immunogenic carrier molecule is a polypeptide that induces T-helper lymphocyte responses in a majority of humans.

5. A pharmaceutical composition comprising a polypeptide and a pharmaceutically acceptable carrier, vehicle or diluent, and which further comprises an immunological adjuvant, wherein said polypeptide comprises:

a) an amino acid sequence selected from the group consisting of any one of SEQ ID NOs: 1-4, 6-11, 13-16, 18, 21-28, and 30, or b) an amino acid sequence consisting of at least 35 contiguous amino acid residues from any one of SEQ ID NOs: 1-4, 6-11, 13-16, 18, 21-28, and 30, or c) an amino acid sequence having a sequence identity of at least 60% with the amino acid sequence of any one of SEQ ID NOs: 1-4, 6-11, 13-16, 18, 21-28, and 30, or d) an amino acid sequence having a sequence identity of at least 60% with the amino acid sequence of at least 35 contiguous amino acid residues from any one of SEQ ID NOs: 1-4, 6-11, 13-16, 18, 21-28, and 30, said polypeptide being antigenic in a mammal, or wherein said polypeptide is according to claim 1.

6. The pharmaceutical composition according to claim 5, wherein the adjuvant is an aluminum based adjuvant.

7. A method for inducing immunity in an animal by administering at least once an immunogenically effective amount of a polypeptide or a pharmaceutical composition according to claim 5 or 6 so as to induce adaptive immunity against *C. jejuni* in the animal, wherein said polypeptide comprises:

a) an amino acid sequence selected from the group consisting of any one of SEQ ID NOs: 1-4, 6-11, 13-16, 18, 21-28, and 30, or b) an amino acid sequence consisting of at least 35 contiguous amino acid residues from any one of SEQ ID NOs: 1-4, 6-11, 13-16, 18, 21-28, and 30, or c) an amino acid sequence having a sequence identity of at least 60% with the amino acid sequence of any one of SEQ ID NOs: 1-4, 6-11, 13-16, 18, 21-28, and 30, or d) an amino acid sequence having a sequence identity of at least 60% with the amino acid sequence of at least 35 contiguous amino acid residues from any one of SEQ ID NOs: 1-4, 6-11, 13-16, 18, 21-28, and 30, said polypeptide being antigenic in a mammal.

8. The method according to claim 7, wherein the animal receives between 0.5 and 5,000 μg of the polypeptide according to claim 1 per administration.

9. The method according to claim 7, wherein the animal receives a priming administration and one or more booster administrations of said polypeptide or pharmaceutical composition.

10. The method according to claim 7, wherein the animal is a human being.

11. The method according to claim 7, wherein the adaptive immunity is effective in reducing the risk of contracting infection with *C. jejuni* or is effective in treating or ameliorating infection with *C. jejuni*.

12. The method according to claim 7, wherein the administration is for the purpose of inducing antibodies specific for *C. jejuni* and wherein said antibodies or B-lymphocytes producing said antibodies are subsequently recovered from the animal.

13. The method according to claim 7, wherein the administration is for the purpose of inducing antibodies specific for *C. jejuni* and wherein B-lymphocytes producing said antibodies are subsequently recovered from the animal and used for preparation of monoclonal antibodies.

* * * * *